(12) United States Patent
Steelman et al.

(10) Patent No.: US 11,643,650 B2
(45) Date of Patent: May 9, 2023

(54) COMPOSITIONS AND METHODS FOR LABELING OF AGENTS

(71) Applicant: The Broad Institute, Inc., Cambridge, MA (US)

(72) Inventors: Scott Steelman, Cambridge, MA (US); Robert Nicol, Cambridge, MA (US); Robert E. Lintner, Cambridge, MA (US)

(73) Assignee: The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 16/793,680

(22) Filed: Feb. 18, 2020

(65) Prior Publication Data

US 2020/0277596 A1    Sep. 3, 2020

Related U.S. Application Data

(63) Continuation of application No. 14/664,356, filed on Mar. 20, 2015, now Pat. No. 10,738,299, which is a continuation-in-part of application No. PCT/US2013/061189, filed on Sep. 23, 2013.

(60) Provisional application No. 61/779,999, filed on Mar. 13, 2013, provisional application No. 61/731,021, filed on Nov. 29, 2012, provisional application No. 61/703,884, filed on Sep. 21, 2012.

(51) Int. Cl.
  *C12Q 1/6855* (2018.01)
  *C12N 15/10* (2006.01)
  *C12Q 1/6869* (2018.01)

(52) U.S. Cl.
  CPC ....... *C12N 15/1065* (2013.01); *C12Q 1/6855* (2013.01); *C12Q 1/6869* (2013.01)

(58) Field of Classification Search
  CPC ................ C12Q 1/6855; C12Q 1/6869; C12Q 2525/191; C12Q 2563/179
  See application file for complete search history.

(56) References Cited

U.S. PATENT DOCUMENTS

| | | |
|---|---|---|
| 8,753,391 B2 | 6/2014 | Lu et al. |
| 2002/0142313 A1 | 10/2002 | Wolber et al. |
| 2004/0005609 A1 | 1/2004 | Wolber et al. |
| 2004/0110191 A1 | 6/2004 | Winkler et al. |
| 2012/0010091 A1 | 1/2012 | Linnarson |
| 2012/0122714 A1 | 5/2012 | Samuels et al. |
| 2013/0225418 A1 | 8/2013 | Watson |

FOREIGN PATENT DOCUMENTS

| | | |
|---|---|---|
| EP | 1024201 A1 | 8/2000 |
| WO | WO-2004/094664 A1 | 11/2004 |
| WO | WO-2006/040549 A2 | 4/2006 |
| WO | WO-2006/086210 A2 | 8/2006 |
| WO | WO-2008/007951 A1 | 1/2008 |
| WO | WO-2012/037882 A1 | 3/2012 |
| WO | WO-2012048341 A1 | 4/2012 |
| WO | WO-2012083225 A2 | 6/2012 |
| WO | WO-2013/134261 A1 | 9/2013 |

OTHER PUBLICATIONS

Tabuchi, I. et al., Multi-line split DNA synthesis: a novel combinatorial method to make high quality peptide libraries, BMC Biotech., vol. 4:19, pp. 1-8 (Year: 2004).*
Horspool, D.R. et al., Efficient assembly of very short oligonucleotides using T4 DNA ligase, BMC Res. Notes, vol. 3:291, pp. 1-9 (Year: 2010).*
Lashkari, D.A. et al., An automated multiplex oligonucleotide synthesizer: Development of high-throughput, low-cost DNA synthesis PNAS USA, vol. 92, pp. 7912-7915 (Year: 1995).*
Empodocles et al., "Three-dimensional orientation measurements of symmetric single chromophores using polarization microscopy," Nature, 399:126-130 (1999).
Extended European Search Report issued by the European Patent Office in corresponding Application No. EP 13838452.4 dated Jun. 16, 2016.
International Preliminary Report on Patentability for International Application No. PCT/US13/060990 dated Sep. 24, 2015.
International Preliminary Report on Patentability for International Application No. PCT/US13/061000 dated Sep. 24, 2015.
International Search Report and Written Opinion for International Application No. PCT/US13/060990 dated Jan. 23, 2014.
International Search Report and Written Opinion for International Application No. PCT/US13/061000 dated Feb. 4, 2014.
International Search Report and Written Opinion for International Application No. PCT/US13/061182 dated Jan. 23, 2014.
International Search Report and Written Opinion for International Application No. PCT/US13/061189 dated Jan. 20, 2014.
Lacoste et al., "Ultrahigh-resolution multicolor colocalization of single fluorescent probes," PNAS, 97(17):9461-9466 (2000).
Lu et al., "Tracking single hematopoietic stem cells in vivo using high-throughput sequencing in conjunction with viral genetic barcoding," Nat Biotechnol, 29(10):928-933 (2011).
Meyer et al., "Targeted high-throughput sequencing of tagged nucleic acid samples," Nucleic Acids Research, 35(15):e971-e976 (2007).
Reichert et al., "Chip-Based Optical Detection of DNA Hybridization by Means of Nanobead Labeling," Anal Chem, 72:6025-6029 (2000).
Sibson et al., "Molecular indexing of human genomic DNA," Nucleic Acids Res, 29(19):E95 (2001).
Zhu et al., "Single-Molecule Emulsion PCR in Microfluidic Droplets," Anal Bioanal Chem, 403:2127-2143 (2012).

* cited by examiner

*Primary Examiner* — Teresa E Strzelecka
(74) *Attorney, Agent, or Firm* — Foley Hoag LLP

(57) ABSTRACT

The invention provides, inter alia, methods for uniquely labeling populations of agents of interest using random combinations of oligonucleotides. The oligonucleotides may comprise a unique nucleotide sequence and/or one or more non-nucleic acid detectable moieties.

17 Claims, 46 Drawing Sheets

Specification includes a Sequence Listing.

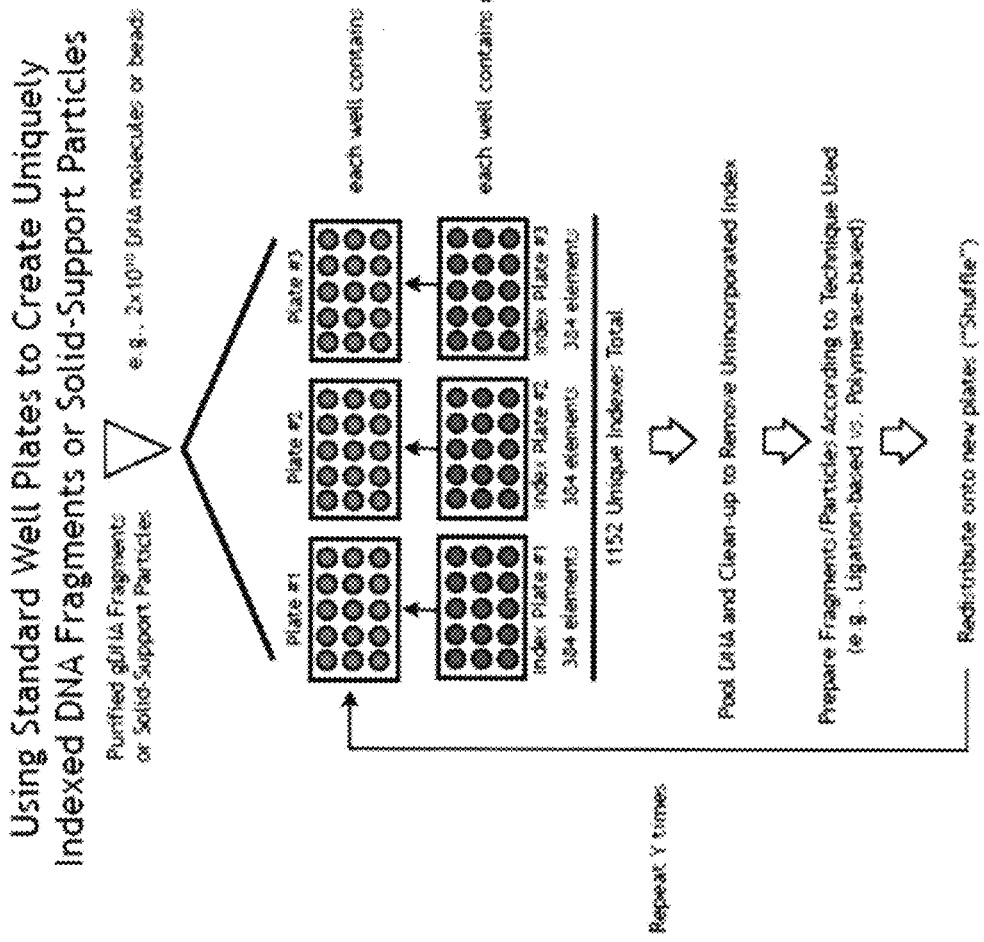

Although many molecules/particles receive the same index in any given round of addition, the probability that any two identically indexed molecules/particles will travel together in a subsequent round of index addition is extremely low. Essentially, we create the capacity to distinguish $X^Y$ molecules/particles, where X=size of the index array and Y=the number of rounds of addition. For Example, 3 rounds of index addition using a 1152 element array creates >1x10$^9$ unique combinations.

- Ultimately, need PCR-based assay to detect ligation
  - Designed small (34bp) adapter
  - Biotinylated and A-tailed (to force directionality)
  - Can use primers to adapter for sequencing (still needs to be confirmed)
  - For these experiments, use lambda DNA as template since it is unlikely to form circles/concatamers Symmetric Ligation-Mediated Index Addition

Figure 21

Determine Optimal Molar Ratio of Index:gDNA

| Molar Ratio Index:gDNA | % of Indexed Reads |
|---|---|
| 25:1 | 46% |
| 50:1 | 47% |
| 75:1 | 47% |
| 100:1 | 56% |
| 1000:1 | 58% |

Using Emulsion Droplets to Create Uniquely Symmetrically Indexed DNA Fragments

5' Overhanging Index Strategy

Note: The 5' ends of all oligos used to create the Cap and Index duplexes are phosphorylated Comparing Blunt Ended and Cohesive Ended Indexes

Figure 36

Transposome-based Selection and Amplification of Ends

Ligate P7-SP1 adapter to ends of construct

P7-SP1-Idx-Cap ———————— Cap-Idx-SP1-P7

Treat with P5-SP2 transposome (might only want to use SP2 and put P5 on later via PCR)

P7-SP1-Idx-Cap ———————— Tnp-Sp2-P5   +   Tnp-SP2-P5 ———————— Tnp-SP2-P5

PCR amplify using P5/P7 primers

P7-SP1-Idx-Cap ———————— Tnp-SP2-P5

Figure 37A

Enrichment of Ends via *In Vitro* Transcription

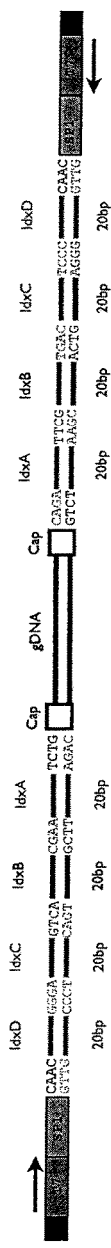

Synthesize double stranded T7-SP1 adapter designed to attach to the end of the "D" index series Ligate to indexed genomic construct Amplify ends of each molecule via *in vitro* transcription (anticipate 100-1000x amplification); creates population of varying length RNA copies of each "parent" molecule Trim RNA to more uniform length?
Ligate SP1 site to 3' ends of RNA?

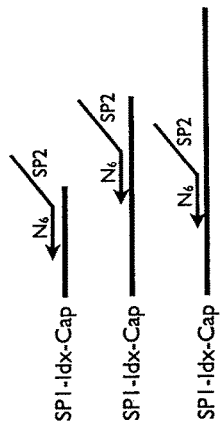

Reverse transcription using random hexamer (for example) joined to SP2 seqeuence PCR using P5-SP1 and P7-SP2 primers

Figure 38

Amplification of Ends via Anchored PCR

Ligate P7-SP1 adapter to ends of construct

P7-SP1-Idx-Cap ─────────── Cap-Idx-SP1-P7

Treat with Fragmentase or RE cocktail

P7-SP1-Idx-Cap ─────

Add 3' tail via TdT

P7-SP1-Idx-Cap ───────── CCC

PCR with P7 and GGG-SP2-P5 primers

P7-SP1-Idx-Cap ───────── CCC
                          GGG-SP2-P5

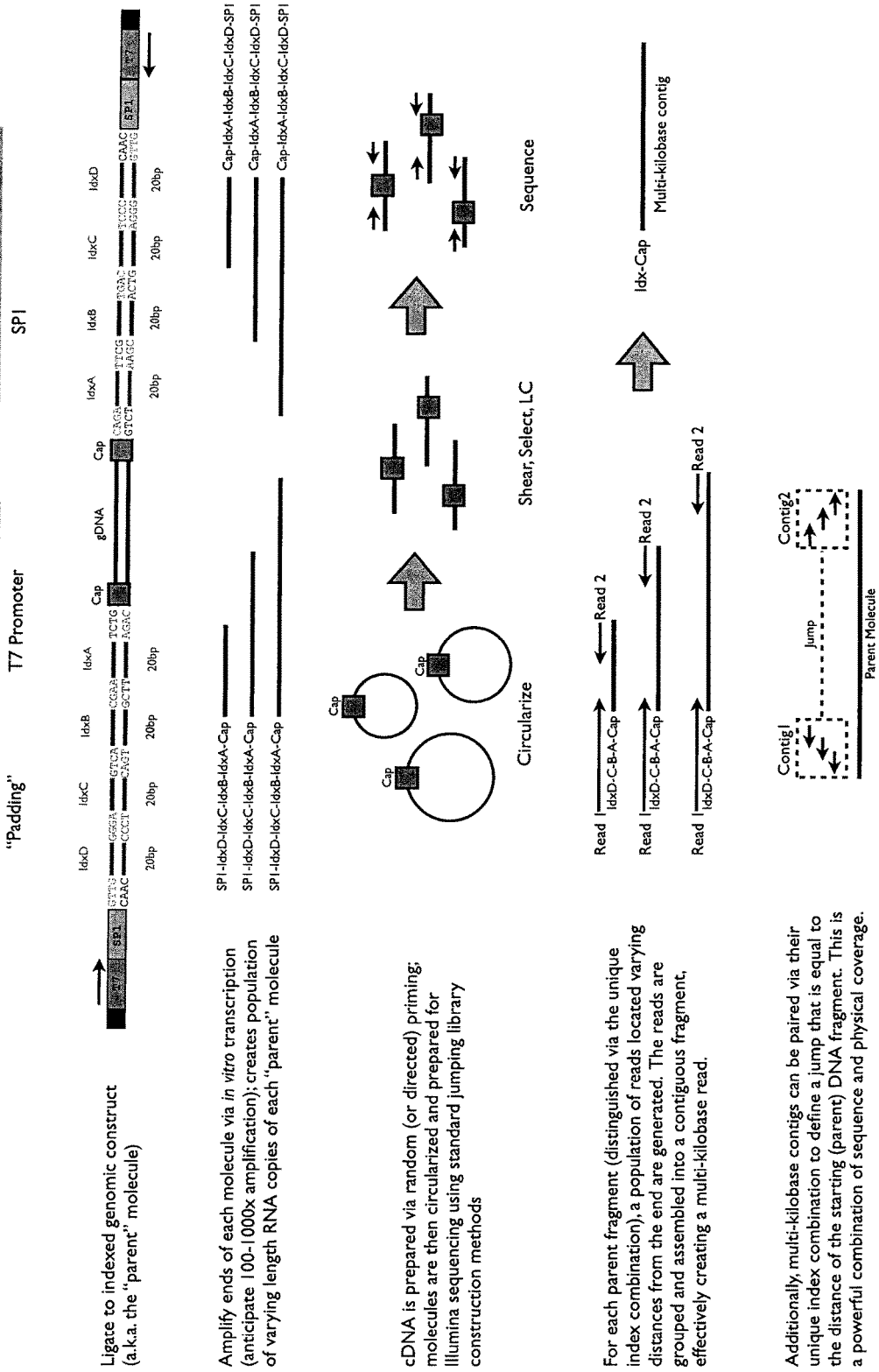

US 11,643,650 B2

COMPOSITIONS AND METHODS FOR LABELING OF AGENTS

RELATED APPLICATIONS AND INCORPORATION BY REFERENCE

This application is a continuation-in-part application of international patent application Serial No. PCT/US2013/061189 filed Sep. 23, 2013, which published as PCT Publication No. WO 2014/047561 on Mar. 27, 2014, which claims the benefit of and priority to U.S. Provisional Application Ser. No. 61/779,999, filed Mar. 13, 2013; 61/731,021, filed Nov. 29, 2012; and 61/703,884, filed Sep. 21, 2012. This application is related to U.S. Provisional Application Ser. No. 61/779,999, filed Mar. 13, 2013.

The foregoing application, and all documents cited therein ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention is directed to methods for labeling populations of agents of interest using random combinations of oligonucleotides. All documents cited to or relied upon below are expressly incorporated by reference herein.

BACKGROUND OF INVENTION

The ability to label and distinguish agents of interest (e.g., DNA, proteins, chemicals, cells, etc.) serves multiple purposes in research and industry. However, several limitations exist in current labeling technologies. These limitations include the limited number of distinguishable detectable moieties currently in existence, the amount of time required to uniquely label a plurality of agents, the requirement, in some instances, for specialized equipment, and the cost involved.

SUMMARY OF INVENTION

The invention provides, in part, methods for uniquely labeling agents in a dynamic manner. The methods allow a plurality of agents, ranging from 2 to millions of agents, to be uniquely labeled without the need to manually generate the same number of unique labels. The agents may be of diverse nature. In some important embodiments, the agents are nucleic acids such as genomic DNA fragments. The invention contemplates that agents may be labeled in order to identify them, identify their source, identify their relationship to other agents, and/or identify one or more conditions to which the agents have been subject.

The methods of the invention also provide for amplifying nucleic acids to increase the number of read pairs properly mated via their unique index combination. In a further embodiment, the method of the invention allows for each end-labeled nucleic acid to be identically labeled at its 5' and 3' ends.

The unique labels provided herein are at least partly nucleic acid in nature. The invention contemplates that the labels are prepared by sequentially attaching randomly selected oligonucleotides (referred to interchangeably as oligonucleotide tags) to each other. The order in which the oligonucleotides attach to each other is random and in this way the resultant label is unique from other labels so generated. The invention is based, in part, on the appreciation by the inventors that a limited number of oligonucleotides can be used to generate a much larger number of unique labels. The invention therefore allows a large number of labels to be generated (and thus a large number of agents to be uniquely labeled) using a relatively small number of oligonucleotides.

BRIEF DESCRIPTION OF DRAWINGS

Non-limiting embodiments of the present invention will be described by way of example with reference to the accompanying Figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

FIG. 3C is a schematic illustrating index addition to either beads or DNA using multi-well plates.

FIG. 5 shows various end products from a labeling synthesis as well as the frequency of each end product, including desired and spurious end products.

FIG. 21 shows a determination of the optimal ratio of genomic Index:genomic DNA.

FIG. 36 shows amplification of fragment ends via transposome-based selection.

FIGS. 37a and 37b illustrate enrichment of ends via in vitro transcription.

FIG. 38 shows amplification of ends via anchored PCR.

FIG. 39 shows producing multi-kilobase fragment reads from indexed DNA ends.

DETAILED DESCRIPTION OF INVENTION

Figure 1:
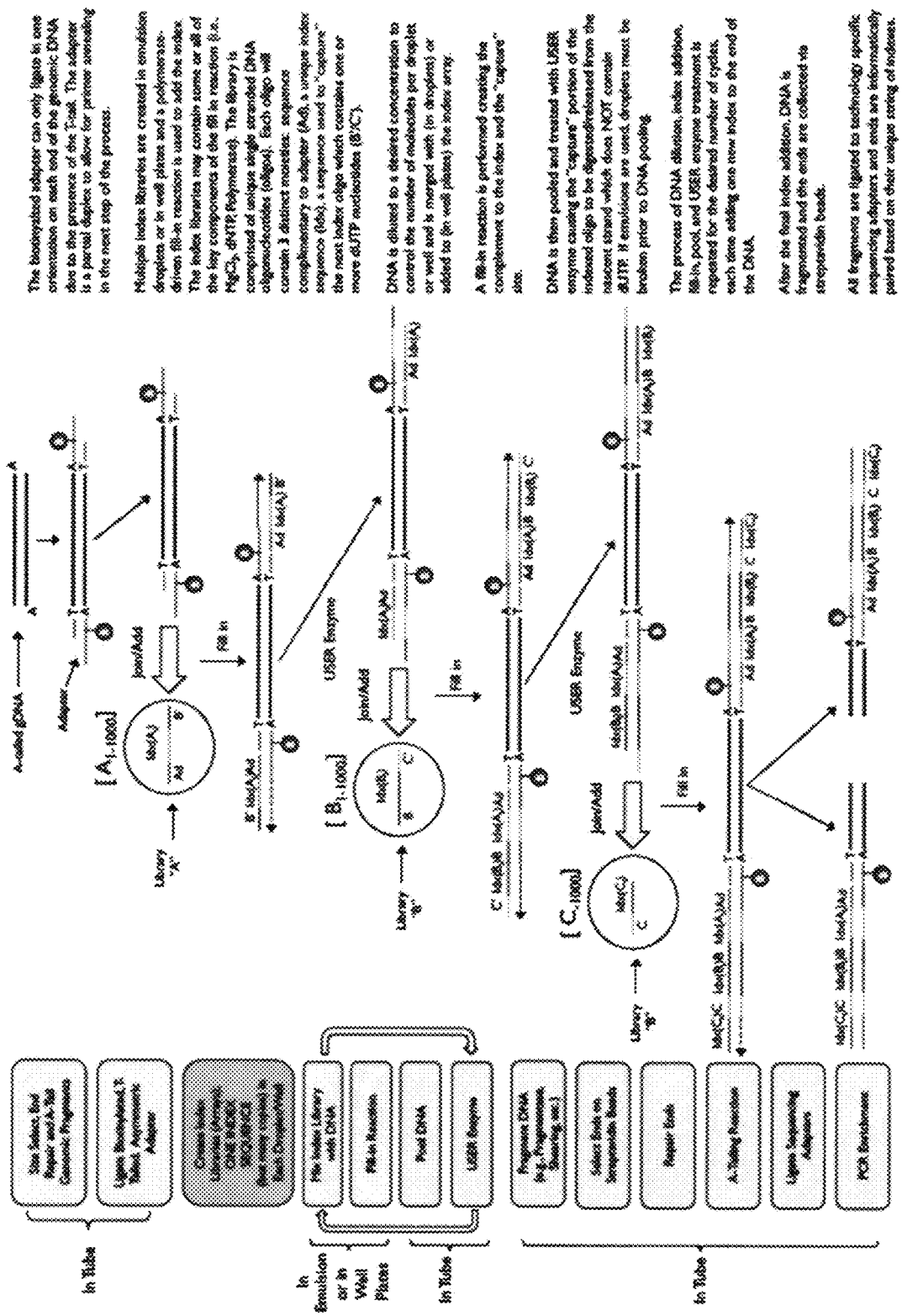
FIG. 1 is a schematic of a mate pair synthesis using droplets or multi-well plates and oligonucleotides tags which may comprise unique sequences (such unique sequences referred to as "index sequences" or "Idx"). The oligonucleotides are attached to each other, to form a unique label, using polymerase fill-in reactions. It is to be understood that a droplet or well may typically comprise an oligonucleotide tag of a single type, although it may contain (and most likely does contain) multiple copies of the same oligonucleotide tag.

The invention provides methods and compositions for uniquely labeling agents of interest including for example nucleic acids, such as DNA, peptides or proteins, cells, chemicals, etc. The ability to uniquely label agents has a number of applications, as contemplated by the invention, including but not limited to genomic sequencing, genomic assembly, screening of putative drugs and biologics, analysis of environmental samples to discover new organisms, labeling of individual elements of synthetic biology constructs, quality control analysis of reagents to verify purity, and analysis of downstream effects of various conditions on cells or cell components, etc. One of the major limitations of prior art labeling techniques is the limited number of available unique labels. Typically the number of agents to be labeled in any given application far exceeds the number of unique labels that are available. The methods of the invention can be used to synthesize essentially an infinite number of unique labels. Moreover, because of their nature, the labels can be easily detected and distinguished from each other, making them suitable for many applications and uses.

The methods of the invention easily and efficiently generate libraries of unique labels. Such libraries may be of any size, and are preferably large libraries including hundreds of thousands to billions of unique labels. The libraries of unique labels may be synthesized separately from agents and then associated with agents post-synthesis. Alternatively, unique labels may be synthesized in real-time (e.g., while in the presence of the agent) and in some instances the label synthesis is a function of the history of the agent. This means, in some instances, that synthesis of the label may occur while an agent is being exposed to one or more conditions. The invention therefore contemplates that the resultant label may store (or code) within it information about the agent (i.e., agent-specific information) including the origin or source of the agent, the relatedness of the agent to other agents, the genomic distance between two agents (e.g., in the case of genomic fragments), conditions to which the agent may have been exposed, and the like.

Some methods of the invention may comprise determining information about an agent based on the unique label associated with the agent. In some instances, determining information about the agent may comprise obtaining the nucleotide sequence of the unique label (i.e., sequencing the unique label). In other instances, determining information about the agent may comprise determining the presence, number and/or order of non-nucleic acid detectable moieties. In still other instances, determining information about the agent may comprise obtaining the nucleotide sequence of the unique label and determining the presence, number and/or order of non-nucleic acid detectable moieties. Methods for nucleic acid sequencing and detection of non-nucleic acid detectable moieties are known in the art and are described herein.

As used herein, "agent" or "agents" refers to any moiety or entity that can be associated with, including attached to, a unique label. An agent may be a single entity or it may be a plurality of entities. An agent may be a nucleic acid, a peptide, a protein, a cell, a cell lysate, a solid support, a polymer, a chemical, and the like, or an agent may be a plurality of any of the foregoing, or it may be a mixture of any of the foregoing. As an example, an agent may be nucleic acids (e.g., mRNA transcripts and/or genomic DNA fragments), solid supports such as beads or polymers, and/or proteins from a single cell or from a single cell population (e.g., a tumor or non-tumor tissue sample).

In some important embodiments, an agent is a nucleic acid. The nucleic acid agent may be single-stranded (ss) or double-stranded (ds), or it may be partially single-stranded and partially double-stranded. Nucleic acid agents include but are not limited to DNA such as genomic DNA fragments, PCR and other amplification products, RNA, cDNA, and the like. Nucleic acid agents may be fragments of larger nucleic acids such as but not limited to genomic DNA fragments.

Association of Labels and Agents

An agent of interest may be associated with a unique label. As used herein, "associated" refers to a relationship between the agent and the unique label such that the unique label may be used to identify the agent, identify the source or origin of the agent, identify one or more conditions to which the agent has been exposed, etc. A label that is associated with an agent may be, for example, physically attached to the agent, either directly or indirectly, or it may be in the same defined, typically physically separate, volume as the agent. A defined volume may be an emulsion droplet, a well (of for example a multiwell plate), a tube, a container, and the like. It is to be understood that the defined volume will typically contain only one agent and the label with which it is associated, although a volume containing multiple agents with multiple copies of the label is also contemplated depending on the application.

An agent may be associated with a single copy of a unique label or it may be associated with multiple copies of the same unique label including for example 2, 3, 4, 5, 6, 7, 8, 9, 10, 100, 1000, 10,000, 100,000 or more copies of the same unique label. In this context, the label is considered unique because it is different from labels associated with other, different agents.

Attachment of labels to agents may be direct or indirect. The attachment chemistry will depend on the nature of the agent and/or any derivatisation or functionalisation applied to the agent. For example, labels can be directly attached through covalent attachment. The label may include a moiety, which may be a non-nucleotide chemical modification, to facilitate attachment. By way of non-limiting example, the label may include methylated nucleotides, uracil bases, phosphorothioate groups, ribonucleotides, diol linkages, disulphide linkages, etc., to enable covalent attachment to an agent.

In another example, a label can be attached to an agent via a linker or in another indirect manner. Examples of linkers, include, but are not limited to, carbon-containing chains, polyethylene glycol (PEG), nucleic acids, monosaccharide units, and peptides. The linkers may be cleavable under certain conditions. Cleavable linkers are discussed in greater detail herein.

Methods for attaching nucleic acids to each other, as for example attaching nucleic acid labels to nucleic acid agents, are known in the art. Such methods include but are not limited to ligation, such as blunt end ligation or cohesive overhang ligation, and polymerase-mediated attachment methods (see, e.g., U.S. Pat. Nos. 7,863,058 and 7,754,429; Green and Sambrook. Molecular Cloning: A Laboratory Manual, Fourth Edition, 2012; Current Protocols in Molecular Biology, and Current Protocols in Nucleic Acid Chemistry, all of which are incorporated herein by reference).

In some embodiments, oligonucleotide adapters are used to attach a unique label to an agent or to a solid support. In some embodiments, an oligonucleotide adapter may comprise one or more known sequences, e.g., an amplification sequence, a capture sequence, a primer sequence, and the like. In some embodiments, the adapter may comprise a thymidine (T) tail overhang. Methods for producing a thymidine tail overhang are known in the art, e.g., using terminal deoxynucleotide transferase (TdT) or a polymerase that adds a thymidine overhang at the termination of polymerization. In some embodiments, the oligonucleotide adapter may comprise a region that is forked. Examples of forked oligonucleotide adapters are described in Example 6.

In some embodiments, the adapter may comprise a capture or detection moiety. Examples of such moieties include, but are not limited to, fluorophores, microparticles such as quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, and other moieties known to those skilled in the art. In some embodiments, the moiety is biotin.

A label and/or an agent may be attached to a solid support. In some instances, a label (or multiple copies of the same label) and the agent are attached to the same solid support. Examples of suitable solid supports include, but are not limited to, inert polymers (preferably non-nucleic acid polymers), beads, glass, or peptides. In some embodiments, the solid support is an inert polymer or a bead. The solid support may be functionalised to permit covalent attachment of the agent and/or label. Such functionalisation may comprise placing on the solid support reactive groups that permit covalent attachment to an agent and/or a label.

Labels and/or agents may be attached to each other or to solid supports using cleavable linkers. Cleavable linkers are known in the art and include, but are not limited to, TEV, trypsin, thrombin, cathepsin B, cathespin D, cathepsin K, caspase lumatrix metalloproteinase sequences, phosphodiester, phospholipid, ester,β-galactose, dialkyl dialkoxysilane, cyanoethyl group, sulfone, ethylene glycolyl disuccinate, 2-N-acyl nitrobenzenesulfonamide, a-thiophenylester, unsaturated vinyl sulfide, sulfonamide after activation, malondialdehyde (MDA)-indole derivative, levulinoyl ester, hydrazone, acylhydrazone, alkyl thioester, disulfide bridges, azo compounds, 2-Nitrobenzyl derivatives, phenacyl ester, 8-quinolinyl benzenesulfonate, coumarin, phosphotriester, bis-arylhydrazone, bimane bi-thiopropionic acidderivative, paramethoxybenzyl derivative, tert-butylcarbamate analogue, dialkyl or diaryl dialkoxysilane, orthoester, acetal, aconityl, hydrazone, b-thiopropionate, phosphoramidate, imine, trityl, vinyl ether, polyketal, alkyl 2-(diphenylphosphino)benzoate derivatives, allyl ester, 8-hydroxyquinoline ester, picolinate ester, vicinal diols, and selenium compounds (see, e.g. Leriche G, Chisholm L, Wagner A. Cleavable Linkers in Chemical Biology. Bioorg Med Chem. 15; 20(2):571-82. 2012, which is incorporated herein by reference). Cleavage conditions and reagents include, but are not limited to, enzymes, nucleophilic/basic reagents, reducing agents, photo-irradiation, electrophilic/acidic reagents, organometallic and metal reagents, and oxidizing reagents.

Detectable Oligonucleotide Tags

The unique labels of the invention are, at least in part, nucleic acid in nature, and are generated by sequentially attaching two or more detectable oligonucleotide tags to each other. As used herein, a detectable oligonucleotide tag is an oligonucleotide that can be detected by sequencing of its nucleotide sequence and/or by detecting non-nucleic acid detectable moieties it may be attached to.

The oligonucleotide tags are typically randomly selected from a diverse plurality of oligonucleotide tags. In some instances, an oligonucleotide tag may be present once in a plurality or it may be present multiple times in a plurality. In the latter instance, the plurality of tags may be comprised of a number of subsets each which may comprise a plurality of identical tags. In some important embodiments, these subsets are physically separate from each other. Physical separation may be achieved by providing the subsets in separate wells of a multiwell plate or separate droplets from an emulsion. It is the random selection and thus combination of oligonucleotide tags that results in a unique label. Accordingly, the number of distinct (i.e., different) oligonucleotide tags required to uniquely label a plurality of agents can be far less than the number of agents being labeled. This is particularly advantageous when the number of agents is large (e.g., when the agents are members of a library).

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the non-nucleic acid detectable moiety.

As used herein, the term "oligonucleotide" refers to a nucleic acid such as deoxyribonucleic acid (DNA), ribonucleic acid (RNA), or DNA/RNA hybrids and includes analogs of either DNA or RNA made from nucleotide analogs known in the art (see, e.g. U.S. Patent or Patent Application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference). Oligonucleotides may be single-stranded (such as sense or antisense oligonucleotides), double-stranded, or partially single-stranded and partially double-stranded.

In some embodiments, a detectable oligonucleotide tag may comprise one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags may comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide which may comprise a nucleotide sequence complementary to a capture sequence, e.g. a second detectable oligonucleotide tag or an oligonucleotide attached to a bead. A capture entity may also be any other entity capable of binding to the capture sequence, e.g. an antibody or peptide. An index sequence is a sequence which may comprise a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

Table 1 below provides examples of certain oligonucleotide tags of the invention:

TABLE 1

| Tag | Full Oligo Sequence (Top) | Full Oligo Sequence (Bot) |
|---|---|---|
| GGATATCTGTGGATATCTGT | /5Phos/CAGAGGATATCTGTGGATATCTGT | /5Phos/CGAAACAGATATCCACAGATATCC |
| GGCTGCCATAGGCTGCCATA | /5Phos/CAGAGGCTGCCATAGGCTGCCATA | /5Phos/CGAATATGGCAGCCTATGGCAGCC |
| GGTATGTCAAGGTATGTCAA | /5Phos/CAGAGGTATGTCAAGGTATGTCAA | /5Phos/CGAATTGACATACCTTGACATACC |
| GGTGAAGGACGGTGAAGGAC | /5Phos/CAGAGGTGAAGGACGGTGAAGGAC | /5Phos/CGAAGTCCTTCACCGTCCTTCACC |
| GTACCAGCATGTACCAGCAT | /5Phos/CAGAGTACCAGCATGTACCAGCAT | /5Phos/CGAAATGCTGGTACATGCTGGTAC |
| GTATACATCCGTATACATCC | /5Phos/CAGAGTATACATCCGTATACATCC | /5Phos/CGAAGGATGTATACGGATGTATAC |
| GTATCGCTCAGTATCGCTCA | /5Phos/CAGAGTATCGCTCAGTATCGCTCA | /5Phos/CGAATGAGCGATACTGAGCGATAC |
| GTCCGATGGAGTCCGATGGA | /5Phos/CAGAGTCCGATGGAGTCCGATGGA | /5Phos/CGAATCCATCGGACTCCATCGGAC |
| GTGTGGAATTGTGTGGAATT | /5Phos/CAGAGTGTGGAATTGTGTGGAATT | /5Phos/CGAAAATTCCACACAATTCCACAC |
| GTGTGGCAGAGTGTGGCAGA | /5Phos/CAGAGTGTGGCAGAGTGTGGCAGA | /5Phos/CGAATCTGCCACACTCTGCCACAC |
| GTTACGGTGAGTTACGGTGA | /5Phos/CAGAGTTACGGTGAGTTACGGTGA | /5Phos/CGAATCACCGTAACTCACCGTAAC |

TABLE 1 -continued

| Tag | Full Oligo Sequence (Top) | Full Oligo Sequence (Bot) |
|---|---|---|
| GTTCGTACATGTTCGTACAT | /5Phos/CAGAGTTCGTACATGTTCGTACAT | /5Phos/CGAAATGTACGAACATGTACGAAC |
| TAACCGGTAATAACCGGTAA | /5Phos/CAGATAACCGGTAATAACCGGTAA | /5Phos/CGAATTACCGGTTATTACCGGTTA |
| TACAGAGTCATACAGAGTCA | /5Phos/CAGATACAGAGTCATACAGAGTCA | /5Phos/CGAATGACTCTGTATGACTCTGTA |
| TACCGAGATATACCGAGATA | /5Phos/CAGATACCGAGATATACCGAGATA | /5Phos/CGAATATCTCGGTATATCTCGGTA |
| TACGCATCGCTACGCATCGC | /5Phos/CAGATACGCATCGCTACGCATCGC | /5Phos/CGAAGCGATGCGTAGCGATGCGTA |
| TACGCGCTTGTACGCGCTTG | /5Phos/CAGATACGCGCTTGTACGCGCTTG | /5Phos/CGAACAAGCGCGTACAAGCGCGTA |
| TAGACTTCACTAGACTTCAC | /5Phos/CAGATAGACTTCACTAGACTTCAC | /5Phos/CGAAGTGAAGTCTAGTGAAGTCTA |
| TATCGCTTAGTATCGCTTAG | /5Phos/CAGATATCGCTTAGTATCGCTTAG | /5Phos/CGAACTAAGCGATACTAAGCGATA |
| TCACGATCCGTCACGATCCG | /5Phos/CAGATCACGATCCGTCACGATCCG | /5Phos/CGAACGGATCGTGACGGATCGTGA |
| TCAGCTTCGCTCAGCTTCGC | /5Phos/CAGATCAGCTTCGCTCAGCTTCGC | /5Phos/CGAAGCGAAGCTGAGCGAAGCTGA |
| TCCGGACTTCTCCGGACTTC | /5Phos/CAGATCCGGACTTCTCCGGACTTC | /5Phos/CGAAGAAGTCCGGAAGAAGTCCGGA |
| TCCGGTATGGTCCGGTATGG | /5Phos/CAGATCCGGTATGGTCCGGTATGG | /5Phos/CGAACCATACCGGACCATACCGGA |
| TCCGTGGTGATCCGTGGTGA | /5Phos/CAGATCCGTGGTGATCCGTGGTGA | /5Phos/CGAATCACCACGGATCACCACGGA |
| TCCTCATCCATCCTCATCCA | /5Phos/CAGATCCTCATCCATCCTCATCCA | /5Phos/CGAATGGATGAGGATGGATGAGGA |
| TCCTTCTGGATCCTTCTGGA | /5Phos/CAGATCCTTCTGGATCCTTCTGGA | /5Phos/CGAATCCAGAAGGATCCAGAAGGA |
| TCGCTGTTGCTCGCTGTTGC | /5Phos/CAGATCGCTGTTGCTCGCTGTTGC | /5Phos/CGAAGCAACAGCGAGCAACAGCGA |
| TCGGAGCTTGTCGGAGCTTG | /5Phos/CAGATCGGAGCTTGTCGGAGCTTG | /5Phos/CGAACAAGCTCCGACAAGCTCCGA |
| TCGGCATGAGTCGGCATGAG | /5Phos/CAGATCGGCATGAGTCGGCATGAG | /5Phos/CGAACTCATGCCGACTCATGCCGA |
| TCGGTGGAACTCGGTGGAAC | /5Phos/CAGATCGGTGGAACTCGGTGGAAC | /5Phos/CGAAGTTCCACCGAGTTCCACCGA |
| TCGGTTGTAATCGGTTGTAA | /5Phos/CAGATCGGTTGTAATCGGTTGTAA | /5Phos/CGAATTACAACCGATTACAACCGA |
| TCGTGTGGCATCGTGTGGCA | /5Phos/CAGATCGTGTGGCATCGTGTGGCA | /5Phos/CGAATGCCACACGATGCCACACGA |
| TCTGTTCCGCTCTGTTCCGC | /5Phos/CAGATCTGTTCCGCTCTGTTCCGC | /5Phos/CGAAGCGGAACAGAGCGGAACAGA |
| TCTTGGCGTCTTGGCGTC | /5Phos/CAGATCTTGGCGTCTCTTGGCGTC | /5Phos/CGAAGACGCCAAGAGACGCCAAGA |
| TGATTGAGTCTGATTGAGTC | /5Phos/CAGATGATTGAGTCTGATTGAGTC | /5Phos/CGAAGACTCAATCAGACTCAATCA |
| TGCGTTGGCATGCGTTGGCA | /5Phos/CAGATGCGTTGGCATGCGTTGGCA | /5Phos/CGAATGCCAACGCATGCCAACGCA |
| TGGACATGCGTGGACATGCG | /5Phos/CAGATGGACATGCGTGGACATGCG | /5Phos/CGAACGCATGTCCACGCATGTCCA |
| TGGCAAGCCATGGCAAGCCA | /5Phos/CAGATGGCAAGCCATGGCAAGCCA | /5Phos/CGAATGGCTTGCCATGGCTTGCCA |
| TGGTTAACTGTGGTTAACTG | /5Phos/CAGATGGTTAACTGTGGTTAACTG | /5Phos/CGAACAGTTAACCACAGTTAACCA |
| TGTACCTGAGTGTACCTGAG | /5Phos/CAGATGTACCTGAGTGTACCTGAG | /5Phos/CGAACTCAGGTACACTCAGGTACA |
| TGTACTACAGTGTACTACAG | /5Phos/CAGATGTACTACAGTGTACTACAG | /5Phos/CGAACTGTAGTACACTGTAGTACA |
| TGTCGGTTGCTGTCGGTTGC | /5Phos/CAGATGTCGGTTGCTGTCGGTTGC | /5Phos/CGAAGCAACCGACAGCAACCGACA |
| TGTCTGTCGGTCTGTCGG | /5Phos/CAGATGTCTGTCGGTCTGTCGG | /5Phos/CGAACCGACAGACACCGACAGACA |
| TGTGACTATCTGTGACTATC | /5Phos/CAGATGTGACTATCTGTGACTATC | /5Phos/CGAAGATAGTCACAGATAGTCACA |
| TGTGAGTGCGTGTGAGTGCG | /5Phos/CAGATGTGAGTGCGTGTGAGTGCG | /5Phos/CGAACGCACTCACACGCACTCACA |
| TGTGGTTCGCTGTGGTTCGC | /5Phos/CAGATGTGGTTCGCTGTGGTTCGC | /5Phos/CGAAGCGAACCACAGCGAACCACA |
| TGTTCTACTGTTCTCTAC | /5Phos/CAGATGTTCTCTACTGTTCTCTAC | /5Phos/CGAAGTAGAGAACAGTAGAGAACA |
| TTAGCCAGTCTTAGCCAGTC | /5Phos/CAGATTAGCCAGTCTTAGCCAGTC | /5Phos/CGAAGACTGGCTAAGACTGGCTAA |
| TTCGCGAATATTCGCGAATA | /5Phos/CAGATTCGCGAATATTCGCGAATA | /5Phos/CGAATATTCGCGAATATTCGCGAA |
| TTCGCGGTACTTCGCGGTAC | /5Phos/CAGATTCGCGGTACTTCGCGGTAC | /5Phos/CGAAGTACCGCGAAGTACCGCGAA |
| TTCTATGCAGTTCTATGCAG | /5Phos/CAGATTCTATGCAGTTCTATGCAG | /5Phos/CGAACTGCATAGAACTGCATAGAA |
| TTCTTACCGATTCTTACCGA | /5Phos/CAGATTCTTACCGATTCTTACCGA | /5Phos/CGAATCGGTAAGAATCGGTAAGAA |
| TTGCTCTGGATTGCTCTGGA | /5Phos/CAGATTGCTCTGGATTGCTCTGGA | /5Phos/CGAATCCAGAGCAATCCAGAGCAA |
| TTGTAACACCTTGTAACACC | /5Phos/CAGATTGTAACACCTTGTAACACC | /5Phos/CGAAGGTGTTACAAGGTGTTACAA |
| AACAAGTTCCAACAAGTTCC | /5Phos/CAGAAACAAGTTCCAACAAGTTCC | /5Phos/CGAAGGAACTTGTTGGAACTTGTT |
| AACAGCACGCAACAGCACGC | /5Phos/CAGAAACAGCACGCAACAGCACGC | /5Phos/CGAAGCGTGCTGTTGCGTGCTGTT |
| AACGTGCGGTAACGTGCGGT | /5Phos/CAGAAACGTGCGGTAACGTGCGGT | /5Phos/CGAAACCGCACGTTACCGCACGTT |
| AAGAGCGATGAAGAGCGATG | /5Phos/CAGAAAGAGCGATGAAGAGCGATG | /5Phos/CGAACATCGCTCTTCATCGCTCTT |
| AAGGAATTCCAAGGAATTCC | /5Phos/CAGAAAGGAATTCCAAGGAATTCC | /5Phos/CGAAGGAATTCCTTGGAATTCCTT |
| AAGTGAGGCGAAGTGAGGCG | /5Phos/CAGAAAGTGAGGCGAAGTGAGGCG | /5Phos/CGAACGCCTCACTTCGCCTCACTT |
| AATACGCGATAATACGCGAT | /5Phos/CAGAAATACGCGATAATACGCGAT | /5Phos/CGAAATCGCGTATTATCGCGTATT |
| AATAGGTTGGAATAGGTTGG | /5Phos/CAGAAATAGGTTGGAATAGGTTGG | /5Phos/CGAACCAACCTATTCCAACCTATT |
| AATCGAAGCTAATCGAAGCT | /5Phos/CAGAAATCGAAGCTAATCGAAGCT | /5Phos/CGAAAGCTTCGATTAGCTTCGATT |
| ACACTACGATACACTACGAT | /5Phos/CAGAACACTACGATACACTACGAT | /5Phos/CGAAATCGTAGTGTATCGTAGTGT |
| ACACTCAGCCACACTCAGCC | /5Phos/CAGAACACTCAGCCACACTCAGCC | /5Phos/CGAAGGCTGAGTGTGGCTGAGTGT |
| ACATCGAGCCACATCGAGCC | /5Phos/CAGAACATCGAGCCACATCGAGCC | /5Phos/CGAAGGCTCGATGTGGCTCGATGT |
| ACATTATGCGACATTATGCG | /5Phos/CAGAACATTATGCGACATTATGCG | /5Phos/CGAACGCATAATGTCGCATAATGT |
| ACCAGCAACTACCAGCAACT | /5Phos/CAGAACCAGCAACTACCAGCAACT | /5Phos/CGAAAGTTGCTGGTAGTTGCTGGT |
| ACCGAACACGACCGAACACG | /5Phos/CAGAACCGAACACGACCGAACACG | /5Phos/CGAACGTGTTCGGTCGTGTTCGGT |
| ACCGAACGGTACCGAACGGT | /5Phos/CAGAACCGAACGGTACCGAACGGT | /5Phos/CGAAACCGTTCGGTACCGTTCGGT |
| ACGAGTGGCTACGAGTGGCT | /5Phos/CAGAACGAGTGGCTACGAGTGGCT | /5Phos/CGAAAGCCACTCGTAGCCACTCGT |
| ACGGTTACGGACGGTTACGG | /5Phos/CAGAACGGTTACGGACGGTTACGG | /5Phos/CGAACCGTAACCGTCCGTAACCGT |
| ACGTAAGCGCACGTAAGCGC | /5Phos/CAGAACGTAAGCGCACGTAAGCGC | /5Phos/CGAAGCGCTTACGTGCGCTTACGT |
| ACTATGTGCTACTATGTGCT | /5Phos/CAGAACTATGTGCTACTATGTGCT | /5Phos/CGAAAGCACATAGTAGCACATAGT |
| ACTGGAGTCCACTGGAGTCC | /5Phos/CAGAACTGGAGTCCACTGGAGTCC | /5Phos/CGAAGGACTCCAGTGGACTCCAGT |
| ACTGTACTTCACTGTACTTC | /5Phos/CAGAACTGTACTTCACTGTACTTC | /5Phos/CGAAGAAGTACAGTGAAGTACAGT |
| AGAAGTCTGCAGAAGTCTGC | /5Phos/CAGAAGAAGTCTGCAGAAGTCTGC | /5Phos/CGAAGCAGACTTCTGCAGACTTCT |
| AGACGCGAGTAGACGCGAGT | /5Phos/CAGAAGACGCGAGTAGACGCGAGT | /5Phos/CGAACTCGCGTCTACTCGCGTCT |
| AGACTGTGCTAGACTGTGCT | /5Phos/CAGAAGACTGTGCTAGACTGTGCT | /5Phos/CGAAAGCACAGTCTAGCACAGTCT |
| AGAGTACGCCAGAGTACGCC | /5Phos/CAGAAGAGTACGCCAGAGTACGCC | /5Phos/CGAAGGCGTACTCTGGCGTACTCT |
| AGATCGACTGAGATCGACTG | /5Phos/CAGAAGATCGACTGAGATCGACTG | /5Phos/CGAACAGTCGATCTCAGTCGATCT |
| AGATTCGGCCAGATTCGGCC | /5Phos/CAGAAGATTCGGCCAGATTCGGCC | /5Phos/CGAAGGCCGAATCTGGCCGAATCT |
| AGCAAGTGCTAGCAAGTGCT | /5Phos/CAGAAGCAAGTGCTAGCAAGTGCT | /5Phos/CGAAAGCACTTGCTAGCACTTGCT |
| AGCCATTGCGAGCCATTGCG | /5Phos/CAGAAGCCATTGCGAGCCATTGCG | /5Phos/CGAACGCAATGGCTCGCAATGGCT |
| AGCGGACAGTAGCGGACAGT | /5Phos/CAGAAGCGGACAGTAGCGGACAGT | /5Phos/CGAAACTGTCCGCTACTGTCCGCT |
| AGCGTAAGCGAGCGTAAGCG | /5Phos/CAGAAGCGTAAGCGAGCGTAAGCG | /5Phos/CGAAGCGCTTACGCTCGCTTACGCT |
| AGCTATTCTCAGCTATTCTC | /5Phos/CAGAAGCTATTCTCAGCTATTCTC | /5Phos/CGAAGAGAATAGCTGAGAATAGCT |
| AGCTTATACGAGCTTATACG | /5Phos/CAGAAGCTTATACGAGCTTATACG | /5Phos/CGAACGTATAAGCTCGTATAAGCT |
| AGGACAGATGAGGACAGATG | /5Phos/CAGAAGGACAGATGAGGACAGATG | /5Phos/CGAACATCTGTCCTCATCTGTCCT |

TABLE 1 -continued

| Tag | Full Oligo Sequence (Top) | Full Oligo Sequence (Bot) |
|---|---|---|
| AGGATCAGATAGGATCAGAT | /5Phos/CAGAAGGATCAGATAGGATCAGAT | /5Phos/CGAAATCTGATCCTATCTGATCCT |
| AGGCTGAAGGAGGCTGAAGG | /5Phos/CAGAAGGCTGAAGGAGGCTGAAGG | /5Phos/CGAACCTTCAGCCTCCTTCAGCCT |
| AGGTACGAGGAGGTACGAGG | /5Phos/CAGAAGGTACGAGGAGGTACGAGG | /5Phos/CGAACCTCGTACCTCCTCGTACCT |
| AGGTAGGCTCAGGTAGGCTC | /5Phos/CAGAAGGTAGGCTCAGGTAGGCTC | /5Phos/CGAAGAGCCTACCTGAGCCTACCT |
| AGGTGAACGGAGGTGAACGG | /5Phos/CAGAAGGTGAACGGAGGTGAACGG | /5Phos/CGAACCGTTCACCTCCGTTCACCT |
| AGGTGCCAATAGGTGCCAAT | /5Phos/CAGAAGGTGCCAATAGGTGCCAAT | /5Phos/CGAAATTGGCACCTATTGGCACCT |
| AGGTTCAACGAGGTTCAACG | /5Phos/CAGAAGGTTCAACGAGGTTCAACG | /5Phos/CGAACGTTGAACCTCGTTGAACCT |
| AGTCACTCGCAGTCACTCGC | /5Phos/CAGAAGTCACTCGCAGTCACTCGC | /5Phos/CGAAGCGAGTGACTGCGAGTGACT |
| AGTCGTGGTGAGTCGTGGTG | /5Phos/CAGAAGTCGTGGTGAGTCGTGGTG | /5Phos/CGAACACCACGACTCACCACGACT |
| AGTGGAGGAGAGTGGAGGAG | /5Phos/CAGAAGTGGAGGAGAGTGGAGGAG | /5Phos/CGAACTCCTCCACTCTCCTCCACT |
| AGTTGAGCGCAGTTGAGCGC | /5Phos/CAGAAGTTGAGCGCAGTTGAGCGC | /5Phos/CGAAGCGCTCAACTGCGCTCAACT |
| AGTTGATGGTAGTTGATGGT | /5Phos/CAGAAGTTGATGGTAGTTGATGGT | /5Phos/CGAAACCATCAACTACCATCAACT |
| ATAACACAGCATAACACAGC | /5Phos/CAGAATAACACAGCATAACACAGC | /5Phos/CGAAGCTGTGTTATGCTGTGTTAT |
| ATAAGGTCCGATAAGGTCCG | /5Phos/CAGAATAAGGTCCGATAAGGTCCG | /5Phos/CGAACGGACCTTATCGGACCTTAT |
| ATACAGTCAGATACAGTCAG | /5Phos/CAGAATACAGTCAGATACAGTCAG | /5Phos/CGAACTGACTGTATCTGACTGTAT |
| ATACCGGCCTATACCGGCCT | /5Phos/CAGAATACCGGCCTATACCGGCCT | /5Phos/CGAAAGGCCGGTATAGGCCGGTAT |
| ATAGCAGGATATAGCAGGAT | /5Phos/CAGAATAGCAGGATATAGCAGGAT | /5Phos/CGAAATCCTGCTATATCCTGCTAT |
| ATAGCGTTACATAGCGTTAC | /5Phos/CAGAATAGCGTTACATAGCGTTAC | /5Phos/CGAAGTAACGCTATGTAACGCTAT |
| ATAGTCCAACATAGTCCAAC | /5Phos/CAGAATAGTCCAACATAGTCCAAC | /5Phos/CGAAGTTGGACTATGTTGGACTAT |
| ATATCGGCGGATATCGGCGG | /5Phos/CAGAATATCGGCGGATATCGGCGG | /5Phos/CGAACCGCCGATATCCGCCGATAT |
| ATCCGTGATGATCCGTGATG | /5Phos/CAGAATCCGTGATGATCCGTGATG | /5Phos/CGAACATCACGGATCATCACGGAT |
| ATCGTACCGGATCGTACCGG | /5Phos/CAGAATCGTACCGGATCGTACCGG | /5Phos/CGAACCGGTACGATCCGGTACGAT |
| ATCGTTACTGATCGTTACTG | /5Phos/CAGAATCGTTACTGATCGTTACTG | /5Phos/CGAACAGTAACGATCAGTAACGAT |
| ATGAAGATGCATGAAGATGC | /5Phos/CAGAATGAAGATGCATGAAGATGC | /5Phos/CGAAGCATCTTCATGCATCTTCAT |
| ATGGCGTGGTATGGCGTGGT | /5Phos/CAGAATGGCGTGGTATGGCGTGGT | /5Phos/CGAAACCACGCCATACCACGCCAT |
| ATGTTGAGCGATGTTGAGCG | /5Phos/CAGAATGTTGAGCGATGTTGAGCG | /5Phos/CGAACGCTCAACATCGCTCAACAT |
| ATTAGCTGTCATTAGCTGTC | /5Phos/CAGAATTAGCTGTCATTAGCTGTC | /5Phos/CGAAGACAGCTAATGACAGCTAAT |
| ATTCGCGTGCATTCGCGTGC | /5Phos/CAGAATTCGCGTGCATTCGCGTGC | /5Phos/CGAAGCACGCGAATGCACGCGAAT |
| ATTGCGCTCCATTGCGCTCC | /5Phos/CAGAATTGCGCTCCATTGCGCTCC | /5Phos/CGAAGGAGCGCAATGGAGCGCAAT |
| ATTGTGTTGCATTGTGTTGC | /5Phos/CAGAATTGTGTTGCATTGTGTTGC | /5Phos/CGAAGCAACACAATGCAACACAAT |
| CAAGACGAATCAAGACGAAT | /5Phos/CAGACAAGACGAATCAAGACGAAT | /5Phos/CGAAATTCGTCTTGATTCGTCTTG |
| CACGCACTGTCACGCACTGT | /5Phos/CAGACACGCACTGTCACGCACTGT | /5Phos/CGAAACAGTGCGTGACAGTGCGTG |
| CACGGAGTAGCACGGAGTAG | /5Phos/CAGACACGGAGTAGCACGGAGTAG | /5Phos/CGAACTACTCCGTGCTACTCCGTG |
| CACGGTATCGCACGGTATCG | /5Phos/CAGACACGGTATCGCACGGTATCG | /5Phos/CGAACGATACCGTGCGATACCGTG |
| CACTCGGATTCACTCGGATT | /5Phos/CAGACACTCGGATTCACTCGGATT | /5Phos/CGAAAATCCGAGTGAATCCGAGTG |
| CACTTGAGTACACTTGAGTA | /5Phos/CAGACACTTGAGTACACTTGAGTA | /5Phos/CGAATACTCAAGTGTACTCAAGTG |
| CAGCCTCAGTCAGCCTCAGT | /5Phos/CAGACAGCCTCAGTCAGCCTCAGT | /5Phos/CGAAACTGAGGCTGACTGAGGCTG |
| CAGCTCCAAGCAGCTCCAAG | /5Phos/CAGACAGCTCCAAGCAGCTCCAAG | /5Phos/CGAACTTGGAGCTGCTTGGAGCTG |
| CATCGAGGAGCATCGAGGAG | /5Phos/CAGACATCGAGGAGCATCGAGGAG | /5Phos/CGAACTCCTCGATGCTCCTCGATG |
| CATTGGCCGTCATTGGCCGT | /5Phos/CAGACATTGGCCGTCATTGGCCGT | /5Phos/CGAAACGGCCAATGACGGCCAATG |
| CCAGAACTGGCCAGAACTGG | /5Phos/CAGACCAGAACTGGCCAGAACTGG | /5Phos/CGAACCAGTTCTGGCCAGTTCTGG |
| CCAGATACGGCCAGATACGG | /5Phos/CAGACCAGATACGGCCAGATACGG | /5Phos/CGAACCGTATCTGGCCGTATCTGG |
| CCAGGATCCACCAGGATCCA | /5Phos/CAGACCAGGATCCACCAGGATCCA | /5Phos/CGAATGGATCCTGGTGGATCCTGG |
| CCAGGATGTTCCAGGATGTT | /5Phos/CAGACCAGGATGTTCCAGGATGTT | /5Phos/CGAAAACATCCTGGAACATCCTGG |
| CCGAGCATGTCCGAGCATGT | /5Phos/CAGACCGAGCATGTCCGAGCATGT | /5Phos/CGAAACATGCTCGGACATGCTCGG |
| CCGGAGTGTTCCGGAGTGTT | /5Phos/CAGACCGGAGTGTTCCGGAGTGTT | /5Phos/CGAAAACACTCCGGAACACTCCGG |
| CCGGTACCATCCGGTACCAT | /5Phos/CAGACCGGTACCATCCGGTACCAT | /5Phos/CGAAATGGTACCGGATGGTACCGG |
| CCGTCTAAGGCCGTCTAAGG | /5Phos/CAGACCGTCTAAGGCCGTCTAAGG | /5Phos/CGAACCTTAGACGGCCTTAGACGG |
| CCTCCATTAACCTCCATTAA | /5Phos/CAGACCTCCATTAACCTCCATTAA | /5Phos/CGAATTAATGGAGGTTAATGGAGG |
| CCTCCTGACTCCTCCTGACT | /5Phos/CAGACCTCCTGACTCCTCCTGACT | /5Phos/CGAAAGTCAGGAGGAGTCAGGAGG |
| CCTCTGCTCCTCCTCTGCTCT | /5Phos/CAGACCTCTGCTCTCCTCTGCTCT | /5Phos/CGAAAGAGCAGAGGAGAGCAGAGG |
| CCTGCCTTGTCCTGCCTTGT | /5Phos/CAGACCTGCCTTGTCCTGCCTTGT | /5Phos/CGAACAAGGCAGGACAAGGCAGG |
| CCTGGCCATTCCTGGCCATT | /5Phos/CAGACCTGGCCATTCCTGGCCATT | /5Phos/CGAAAATGGCCAGGAATGGCCAGG |
| CCTTAACGCGCCTTAACGCG | /5Phos/CAGACCTTAACGCGCCTTAACGCG | /5Phos/CGAACGCGTTAAGGCGCGTTAAGG |
| CGACCTGTCTCGACCTGTCT | /5Phos/CAGACGACCTGTCTCGACCTGTCT | /5Phos/CGAAAGACAGGTCGAGACAGGTCG |
| CGCGTTACGTCGCGTTACGT | /5Phos/CAGACGCGTTACGTCGCGTTACGT | /5Phos/CGAAACGTAACGCGACGTAACGCG |
| CGGCAGTTCACGGCAGTTCA | /5Phos/CAGACGGCAGTTCACGGCAGTTCA | /5Phos/CGAATGAACTGCCGTGAACTGCCG |
| CGGCCATTAGCGGCCATTAG | /5Phos/CAGACGGCCATTAGCGGCCATTAG | /5Phos/CGAACTAATGGCCGCTAATGGCCG |
| CGTATTGCATCGTATTGCAT | /5Phos/CAGACGTATTGCATCGTATTGCAT | /5Phos/CGAAATGCAATACGATGCAATACG |
| CTACGACCGTCTACGACCGT | /5Phos/CAGACTACGACCGTCTACGACCGT | /5Phos/CGAAACGGTCGTAGACGGTCGTAG |
| CTAGGAAGGTCTAGGAAGGT | /5Phos/CAGACTAGGAAGGTCTAGGAAGGT | /5Phos/CGAAACCTTCCTAGACCTTCCTAG |
| CTAGTCCTGTCTAGTCCTGT | /5Phos/CAGACTAGTCCTGTCTAGTCCTGT | /5Phos/CGAAACAGGACTAGACAGGACTAG |
| CTAGTGGAGGCTAGTGGAGG | /5Phos/CAGACTAGTGGAGGCTAGTGGAGG | /5Phos/CGAACCTCCACTAGCCTCCACTAG |
| CTCGCAGAGTCTCGCAGAGT | /5Phos/CAGACTCGCAGAGTCTCGCAGAGT | /5Phos/CGAAACTCTGCGAGACTCTGCGAG |
| CTCGCTTCGTCTCGCTTCGT | /5Phos/CAGACTCGCTTCGTCTCGCTTCGT | /5Phos/CGAAACGAAGCGAGACGAAGCGAG |
| CTCGTTAGCGCTCGTTAGCG | /5Phos/CAGACTCGTTAGCGCTCGTTAGCG | /5Phos/CGAACGCTAACGAGCGCTAACGAG |
| CTCTTCCAAGCTCTTCCAAG | /5Phos/CAGACTCTTCCAAGCTCTTCCAAG | /5Phos/CGAACTTGGAAGAGCTTGGAAGAG |
| CTGCTTCAATCTGCTTCAAT | /5Phos/CAGACTGCTTCAATCTGCTTCAAT | /5Phos/CGAAATTGAAGCAGATTGAAGCAG |
| CTGGTATCAACTGGTATCAA | /5Phos/CAGACTGGTATCAACTGGTATCAA | /5Phos/CGAATTGATACCAGTTGATACCAG |
| CTGTCTTCGGCTGTCTTCGG | /5Phos/CAGACTGTCTTCGGCTGTCTTCGG | /5Phos/CGAACCGAAGACAGCCGAAGACAG |
| CTTCATGACGCTTCATGACG | /5Phos/CAGACTTCATGACGCTTCATGACG | /5Phos/CGAACGTCATGAAGCGTCATGAAG |
| CTTCGGCAGTCTTCGGCAGT | /5Phos/CAGACTTCGGCAGTCTTCGGCAGT | /5Phos/CGAAACTGCCGAAGACTGCCGAAG |
| CTTGACCGGTCTTGACCGGT | /5Phos/CAGACTTGACCGGTCTTGACCGGT | /5Phos/CGAAACCGGTCAAGACCGGTCAAG |
| CTTGCCTATTCTTGCCTATT | /5Phos/CAGACTTGCCTATTCTTGCCTATT | /5Phos/CGAAAATAGGCAAGAATAGGCAAG |
| GAACTTGTGAGAACTTGTGA | /5Phos/CAGAGAACTTGTGAGAACTTGTGA | /5Phos/CGAATCACAAGTTCTCACAAGTTC |
| GAAGCATTCTGAAGCATTCT | /5Phos/CAGAGAAGCATTCTGAAGCATTCT | /5Phos/CGAAAGAATGCTTCAGAATGCTTC |
| GAATCCATTCGAATCCATTC | /5Phos/CAGAGAATCCATTCGAATCCATTC | /5Phos/CGAAGAATGGATTCGAATGGATTC |
| GACGCCTGTTGACGCCTGTT | /5Phos/CAGAGACGCCTGTTGACGCCTGTT | /5Phos/CGAAAACAGGCGTCAACAGGCGTC |

TABLE 1 -continued

| Tag | Full Oligo Sequence (Top) | Full Oligo Sequence (Bot) |
| --- | --- | --- |
| GACGTAGGACGACGTAGGAC | /5Phos/CAGAGACGTAGGACGACGTAGGAC | /5Phos/CGAAGTCCTACGTCGTCCTACGTC |
| GACTAATGGTGACTAATGGT | /5Phos/CAGAGACTAATGGTGACTAATGGT | /5Phos/CGAAACCATTAGTCACCATTAGTC |
| GAGCCTCCTTGAGCCTCCTT | /5Phos/CAGAGAGCCTCCTTGAGCCTCCTT | /5Phos/CGAAAAGGAGGCTCAAGGAGGCTC |
| GAGCGTCTACGAGCGTCTAC | /5Phos/CAGAGAGCGTCTACGAGCGTCTAC | /5Phos/CGAAGTAGACGCTCGTAGACGCTC |
| GAGGATAGGCGAGGATAGGC | /5Phos/CAGAGAGGATAGGCGAGGATAGGC | /5Phos/CGAAGCCTATCCTCGCCTATCCTC |
| GAGTGCCATCGAGTGCCATC | /5Phos/CAGAGAGTGCCATCGAGTGCCATC | /5Phos/CGAAGATGGCACTCGATGGCACTC |
| GAGTGGATCTGAGTGGATCT | /5Phos/CAGAGAGTGGATCTGAGTGGATCT | /5Phos/CGAAAGATCCACTCAGATCCACTC |
| GAGTGGTAGCGAGTGGTAGC | /5Phos/CAGAGAGTGGTAGCGAGTGGTAGC | /5Phos/CGAAGCTACCACTCGCTACCACTC |
| GAGTTAGAGAGAGTTAGAGA | /5Phos/CAGAGAGTTAGAGAGAGTTAGAGA | /5Phos/CGAATCTCTAACTCTCTCTAACTC |
| GCACATCTGCGCACATCTGC | /5Phos/CAGAGCACATCTGCGCACATCTGC | /5Phos/CGAAGCAGATGTGCGCAGATGTGC |
| GCACCATTACGCACCATTAC | /5Phos/CAGAGCACCATTACGCACCATTAC | /5Phos/CGAAGTAATGGTGCGTAATGGTGC |
| GCAGCCTATTGCAGCCTATT | /5Phos/CAGAGCAGCCTATTGCAGCCTATT | /5Phos/CGAAAATAGGCTGCAATAGGCTGC |
| GCAGTATCAAGCAGTATCAA | /5Phos/CAGAGCAGTATCAAGCAGTATCAA | /5Phos/CGAATTGATACTGCTTGATACTGC |
| GCCGTCGTTAGCCGTCGTTA | /5Phos/CAGAGCCGTCGTTAGCCGTCGTTA | /5Phos/CGAATAACGACGGCTAACGACGGC |
| GCCTGAGCTAGCCTGAGCTA | /5Phos/CAGAGCCTGAGCTAGCCTGAGCTA | /5Phos/CGAATAGCTCAGGCTAGCTCAGGC |
| GCGCAAGCAAGCGCAAGCAA | /5Phos/CAGAGCGCAAGCAAGCGCAAGCAA | /5Phos/CGAATTGCTTGCGCTTGCTTGCGC |
| GCGTTACGACGCGTTACGAC | /5Phos/CAGAGCGTTACGACGCGTTACGAC | /5Phos/CGAAGTCGTAACGCGTCGTAACGC |
| GCGTTGGATCGCGTTGGATC | /5Phos/CAGAGCGTTGGATCGCGTTGGATC | /5Phos/CGAAGATCCAACGCGATCCAACGC |
| GCTAGTCGCAGCTAGTCGCA | /5Phos/CAGAGCTAGTCGCAGCTAGTCGCA | /5Phos/CGAATGCGACTAGCTGCGACTAGC |
| GCTCACTACCGCTCACTACC | /5Phos/CAGAGCTCACTACCGCTCACTACC | /5Phos/CGAAGGTAGTGAGCGGTAGTGAGC |
| GCTCGAATTAGCTCGAATTA | /5Phos/CAGAGCTCGAATTAGCTCGAATTA | /5Phos/CGAATAATTCGAGCTAATTCGAGC |
| GCTCGATTCCGCTCGATTCC | /5Phos/CAGAGCTCGATTCCGCTCGATTCC | /5Phos/CGAAGGAATCGAGCGGAATCGAGC |
| GCTGAGGATCGCTGAGGATC | /5Phos/CAGAGCTGAGGATCGCTGAGGATC | /5Phos/CGAAGATCCTCAGCGATCCTCAGC |
| GCTTCATTCTGCTTCATTCT | /5Phos/CAGAGCTTCATTCTGCTTCATTCT | /5Phos/CGAAAGAATGAAGCAGAATGAAGC |
| GCTTGCTATTGCTTGCTATT | /5Phos/CAGAGCTTGCTATTGCTTGCTATT | /5Phos/CGAAAATAGCAAGCAATAGCAAGC |
| GCTTGGTTGCGCTTGGTTGC | /5Phos/TTCGGCTTGGTTGCGCTTGGTTGC | /5Phos/GTCAGCAACCAAGCGCAACCAAGC |
| GGAGTGGTTCGGAGTGGTTC | /5Phos/TTCGGGAGTGGTTCGGAGTGGTTC | /5Phos/GTCAGAACCACTCCGAACCACTCC |
| GGATAATACCGGATAATACC | /5Phos/TTCGGGATAATACCGGATAATACC | /5Phos/GTCAGGTATTATCCGGTATTATCC |
| GGATCGTGGTGGATCGTGGT | /5Phos/TTCGGGATCGTGGTGGATCGTGGT | /5Phos/GTCAACCACGATCCACCACGATCC |
| GGATGATTGTGGATGATTGT | /5Phos/TTCGGGATGATTGTGGATGATTGT | /5Phos/GTCAACAATCATCCACAATCATCC |
| GGATGCGTTCGGATGCGTTC | /5Phos/TTCGGGATGCGTTCGGATGCGTTC | /5Phos/GTCAGAACGCATCCGAACGCATCC |
| GGCGAATGTCGGCGAATGTC | /5Phos/TTCGGGCGAATGTCGGCGAATGTC | /5Phos/GTCAGACATTCGCCGACATTCGCC |
| GGCGATTGGTGGCGATTGGT | /5Phos/TTCGGGCGATTGGTGGCGATTGGT | /5Phos/GTCAACCAATCGCCACCAATCGCC |
| GGCGGTATCAGGCGGTATCA | /5Phos/TTCGGGCGGTATCAGGCGGTATCA | /5Phos/GTCATGATACCGCCTGATACCGCC |
| GGCTATCCACGGCTATCCAC | /5Phos/TTCGGGCTATCCACGGCTATCCAC | /5Phos/GTCAGTGGATAGCCGTGGATAGCC |
| GGCTATTACAGGCTATTACA | /5Phos/TTCGGGCTATTACAGGCTATTACA | /5Phos/GTCATGTAATAGCCTGTAATAGCC |
| GGCTGAACTCGGCTGAACTC | /5Phos/TTCGGGCTGAACTCGGCTGAACTC | /5Phos/GTCAGAGTTCAGCCGAGTTCAGCC |
| GGTACAGTCAGGTACAGTCA | /5Phos/TTCGGGTACAGTCAGGTACAGTCA | /5Phos/GTCATGACTGTACCTGACTGTACC |
| GGTCGAACCTGGTCGAACCT | /5Phos/TTCGGGTCGAACCTGGTCGAACCT | /5Phos/GTCAAGGTTCGACCAGGTTCGACC |
| GGTCTCTCGTGGTCTCTCGT | /5Phos/TTCGGGTCTCTCGTGGTCTCTCGT | /5Phos/GTCAACGAGAGACCACGAGAGACC |
| GGTGCTTGTCGGTGCTTGTC | /5Phos/TTCGGGTGCTTGTCGGTGCTTGTC | /5Phos/GTCAGACAAGCACCGACAAGCACC |
| GGTTCCACTTGGTTCCACTT | /5Phos/TTCGGGTTCCACTTGGTTCCACTT | /5Phos/GTCAAAGTGGAACCAAGTGGAACC |
| GGTTGCATCCGGTTGCATCC | /5Phos/TTCGGGTTGCATCCGGTTGCATCC | /5Phos/GTCAGGATGCAACCGGATGCAACC |
| GGTTGGACGTGGTTGGACGT | /5Phos/TTCGGGTTGGACGTGGTTGGACGT | /5Phos/GTCAACGTCCAACCACGTCCAACC |
| GTAAGAGCAAGTAAGAGCAA | /5Phos/TTCGGTAAGAGCAAGTAAGAGCAA | /5Phos/GTCATTGCTCTTACTTGCTCTTAC |
| GTAAGGCTTAGTAAGGCTTA | /5Phos/TTCGGTAAGGCTTAGTAAGGCTTA | /5Phos/GTCATAAGCCTTACTAAGCCTTAC |
| GTAGTCCTCAGTAGTCCTCA | /5Phos/TTCGGTAGTCCTCAGTAGTCCTCA | /5Phos/GTCATGAGGACTACTGAGGACTAC |
| GTCCGGTTCTGTCCGGTTCT | /5Phos/TTCGGTCCGGTTCTGTCCGGTTCT | /5Phos/GTCAAGAACCGGACAGAACCGGAC |
| GTCCTACAGCGTCCTACAGC | /5Phos/TTCGGTCCTACAGCGTCCTACAGC | /5Phos/GTCAGCTGTAGGACGCTGTAGGAC |
| GTCGGATTAAGTCGGATTAA | /5Phos/TTCGGTCGGATTAAGTCGGATTAA | /5Phos/GTCATTAATCCGACTTAATCCGAC |
| GTGAACAGAAGTGAACAGAA | /5Phos/TTCGGTGAACAGAAGTGAACAGAA | /5Phos/GTCATTCTGTTCACTTCTGTTCAC |
| GTGCCTACACGTGCCTACAC | /5Phos/TTCGGTGCCTACACGTGCCTACAC | /5Phos/GTCAGTGTAGGCACGTGTAGGCAC |
| GTGTATCGGAGTGTATCGGA | /5Phos/TTCGGTGTATCGGAGTGTATCGGA | /5Phos/GTCATCCGATACACTCCGATACAC |
| GTGTCCATGAGTGTCCATGA | /5Phos/TTCGGTGTCCATGAGTGTCCATGA | /5Phos/GTCATCATGGACACTCATGGACAC |
| GTGTCTAATCGTGTCTAATC | /5Phos/TTCGGTGTCTAATCGTGTCTAATC | /5Phos/GTCAGATTAGACACGATTAGACAC |
| GTGTTCCTGCGTGTTCCTGC | /5Phos/TTCGGTGTTCCTGCGTGTTCCTGC | /5Phos/GTCAGCAGGAACACGCAGGAACAC |
| GTGTTCTGCTGTGTTCTGCT | /5Phos/TTCGGTGTTCTGCTGTGTTCTGCT | /5Phos/GTCAAGCAGAACACAGCAGAACAC |
| GTTAAGAGGAGTTAAGAGGA | /5Phos/TTCGGTTAAGAGGAGTTAAGAGGA | /5Phos/GTCATCCTCTTAACTCCTCTTAAC |
| GTTAATGCGTGTTAATGCGT | /5Phos/TTCGGTTAATGCGTGTTAATGCGT | /5Phos/GTCAACGCATTAACACGCATTAAC |
| GTTAGGCTGTGTTAGGCTGT | /5Phos/TTCGGTTAGGCTGTGTTAGGCTGT | /5Phos/GTCAACAGCCTAACACAGCCTAAC |
| GTTCATTGGAGTTCATTGGA | /5Phos/TTCGGTTCATTGGAGTTCATTGGA | /5Phos/GTCATCCAATGAACTCCAATGAAC |
| GTTCGGACCAGTTCGGACCA | /5Phos/TTCGGTTCGGACCAGTTCGGACCA | /5Phos/GTCATGGTCCGAACTGGTCCGAAC |
| GTTGGCCAGTGTTGGCCAGT | /5Phos/TTCGGTTGGCCAGTGTTGGCCAGT | /5Phos/GTCAACTGGCCAACACTGGCCAAC |
| GTTGGTAGTTGTTGGTAGTT | /5Phos/TTCGGTTGGTAGTTGTTGGTAGTT | /5Phos/GTCAAACTACCAACAACTACCAAC |
| TAACACGACATAACACGACA | /5Phos/TTCGTAACACGACATAACACGACA | /5Phos/GTCATGTCGTGTTATGTCGTGTTA |
| TAAGAGCATAAGAGAGCA | /5Phos/TTCGTAAGAGCATAAGAGAGCA | /5Phos/GTCATGCTCTTATGCTCTCTTA |
| TAAGAGGCGGTAAGAGGCGG | /5Phos/TTCGTAAGAGGCGGTAAGAGGCGG | /5Phos/GTCACCGCCTCTTACCGCCTCTTA |
| TAAGGAATGGTAAGGAATGG | /5Phos/TTCGTAAGGAATGGTAAGGAATGG | /5Phos/GTCACCATTCCTTACCATTCCTTA |
| TAATGAGCACTAATGAGCAC | /5Phos/TTCGTAATGAGCACTAATGAGCAC | /5Phos/GTCAGTGCTCATTAGTGCTCATTA |
| TACACTGGTCTACACTGGTC | /5Phos/TTCGTACACTGGTCTACACTGGTC | /5Phos/GTCAGACCAGTGTAGACCAGTGTA |
| TACAGCGCAATACAGCGCAA | /5Phos/TTCGTACAGCGCAATACAGCGCAA | /5Phos/GTCATTGCGCTGTATTGCGCTGTA |
| TACAGGTTAGTACAGGTTAG | /5Phos/TTCGTACAGGTTAGTACAGGTTAG | /5Phos/GTCACTAACCTGTACTAACCTGTA |
| TACATTACCGTACATTACCG | /5Phos/TTCGTACATTACCGTACATTACCG | /5Phos/GTCACGGTAATGTACGGTAATGTA |
| TACCAATCTCTACCAATCTC | /5Phos/TTCGTACCAATCTCTACCAATCTC | /5Phos/GTCAGAGATTGGTAGAGATTGGTA |
| TACCGGAGAGTACCGGAGAG | /5Phos/TTCGTACCGGAGAGTACCGGAGAG | /5Phos/GTCACTCTCCGGTACTCTCCGGTA |
| TACCGGCTTCTACCGGCTTC | /5Phos/TTCGTACCGGCTTCTACCGGCTTC | /5Phos/GTCAGAAGCCGGTAGAAGCCGGTA |
| TACCTACATGTACCTACATG | /5Phos/TTCGTACCTACATGTACCTACATG | /5Phos/GTCACATGTAGGTACATGTAGGTA |
| TACGATTACGTACGATTACG | /5Phos/TTCGTACGATTACGTACGATTACG | /5Phos/GTCACGTAATCGTACGTAATCGTA |

TABLE 1 -continued

| Tag | Full Oligo Sequence (Top) | Full Oligo Sequence (Bot) |
| --- | --- | --- |
| TACGCAGAGGTACGCAGAGG | /5Phos/TTCGTACGCAGAGGTACGCAGAGG | /5Phos/GTCACCTCTGCGTACCTCTGCGTA |
| TACTCAACGATACTCAACGA | /5Phos/TTCGTACTCAACGATACTCAACGA | /5Phos/GTCATCGTTGAGTATCGTTGAGTA |
| TAGACCAACCTAGACCAACC | /5Phos/TTCGTAGACCAACCTAGACCAACC | /5Phos/GTCAGGTTGGTCTAGGTTGGTCTA |
| TAGACCTCCGTAGACCTCCG | /5Phos/TTCGTAGACCTCCGTAGACCTCCG | /5Phos/GTCACGGAGGTCTACGGAGGTCTA |
| TAGCAGTTGATAGCAGTTGA | /5Phos/TTCGTAGCAGTTGATAGCAGTTGA | /5Phos/GTCATCAACTGCTATCAACTGCTA |
| TAGCGCAAGCTAGCGCAAGC | /5Phos/TTCGTAGCGCAAGCTAGCGCAAGC | /5Phos/GTCAGCTTGCGCTAGCTTGCGCTA |
| TAGCTATACCTAGCTATACC | /5Phos/TTCGTAGCTATACCTAGCTATACC | /5Phos/GTCAGGTATAGCTAGGTATAGCTA |
| TAGCTTGCGCTAGCTTGCGC | /5Phos/TTCGTAGCTTGCGCTAGCTTGCGC | /5Phos/GTCAGCGCAAGCTAGCGCAAGCTA |
| TAGGAATCCATAGGAATCCA | /5Phos/TTCGTAGGAATCCATAGGAATCCA | /5Phos/GTCATGGATTCCTATGGATTCCTA |
| TAGGCCGTTCTAGGCCGTTC | /5Phos/TTCGTAGGCCGTTCTAGGCCGTTC | /5Phos/GTCAGAACGGCCTAGAACGGCCTA |
| TAGGTCACTATAGGTCACTA | /5Phos/TTCGTAGGTCACTATAGGTCACTA | /5Phos/GTCATAGTGACCTATAGTGACCTA |
| TAGTCGCGTCTAGTCGCGTC | /5Phos/TTCGTAGTCGCGTCTAGTCGCGTC | /5Phos/GTCAGACGCGACTAGACGCGACTA |
| TATACGGCTATATACGGCTA | /5Phos/TTCGTATACGGCTATATACGGCTA | /5Phos/GTCATAGCCGTATATAGCCGTATA |
| TATCGCGGCATATCGCGGCA | /5Phos/TTCGTATCGCGGCATATCGCGGCA | /5Phos/GTCATGCCGCGATATGCCGCGATA |
| TATGGAGCAATATGGAGCAA | /5Phos/TTCGTATGGAGCAATATGGAGCAA | /5Phos/GTCATTGCTCCATATTGCTCCATA |
| TATGGCGTGGTATGGCGTGG | /5Phos/TTCGTATGGCGTGGTATGGCGTGG | /5Phos/GTCACCACGCCATACCACGCCATA |
| TATGTTCAGGTATGTTCAGG | /5Phos/TTCGTATGTTCAGGTATGTTCAGG | /5Phos/GTCACCTGAACATACCTGAACATA |
| TATTCCTGTCTATTCCTGTC | /5Phos/TTCGTATTCCTGTCTATTCCTGTC | /5Phos/GTCAGACAGGAATAGACAGGAATA |
| TCAAGAGATCTCAAGAGATC | /5Phos/TTCGTCAAGAGATCTCAAGAGATC | /5Phos/GTCAGATCTCTTGAGATCTCTTGA |
| TCACTACCAATCACTACCAA | /5Phos/TTCGTCACTACCAATCACTACCAA | /5Phos/GTCATTGGTAGTGATTGGTAGTGA |
| TCAGTCTGCGTCAGTCTGCG | /5Phos/TTCGTCAGTCTGCGTCAGTCTGCG | /5Phos/GTCACGCAGACTGACGCAGACTGA |
| TCAGTTAAGCTCAGTTAAGC | /5Phos/TTCGTCAGTTAAGCTCAGTTAAGC | /5Phos/GTCAGCTTAACTGAGCTTAACTGA |
| TCCAGAGTGGTCCAGAGTGG | /5Phos/TTCGTCCAGAGTGGTCCAGAGTGG | /5Phos/GTCACCACTCTGGACCACTCTGGA |
| TCCAGTCGTCTCCAGTCGTC | /5Phos/TTCGTCCAGTCGTCTCCAGTCGTC | /5Phos/GTCAGACGACTGGAGACGACTGGA |
| TCCGACGTTGTCCGACGTTG | /5Phos/TTCGTCCGACGTTGTCCGACGTTG | /5Phos/GTCACAACGTCGGACAACGTCGGA |
| TCCTACCGACTCCTACCGAC | /5Phos/TTCGTCCTACCGACTCCTACCGAC | /5Phos/GTCAGTCGGTAGGAGTCGGTAGGA |
| TCCTTCCTCCTTCCTCC | /5Phos/TTCGTCCTTCCTCCTTCCTCC | /5Phos/GTCAGGAGGAAGGAGGAGGAAGGA |
| TCGAGAGCCATCGAGAGCCA | /5Phos/TTCGTCGAGAGCCATCGAGAGCCA | /5Phos/GTCATGGCTCTCGATGGCTCTCGA |
| TCGCACAGACTCGCACAGAC | /5Phos/TTCGTCGCACAGACTCGCACAGAC | /5Phos/GTCAGTCTGTGCGAGTCTGTGCGA |
| TCGCCGTTAGTCGCCGTTAG | /5Phos/TTCGTCGCCGTTAGTCGCCGTTAG | /5Phos/GTCACTAACGGCGACTAACGGCGA |
| TCGGCACAACTCGGCACAAC | /5Phos/TTCGTCGGCACAACTCGGCACAAC | /5Phos/GTCAGTTGTGCCGAGTTGTGCCGA |
| TCGGCAGTTGTCGGCAGTTG | /5Phos/TTCGTCGGCAGTTGTCGGCAGTTG | /5Phos/GTCACAACTGCCGACAACTGCCGA |
| TCGGTCACACTCGGTCACAC | /5Phos/TTCGTCGGTCACACTCGGTCACAC | /5Phos/GTCAGTGTGACCGAGTGTGACCGA |
| TCGTGCTAGCTCGTGCTAGC | /5Phos/TTCGTCGTGCTAGCTCGTGCTAGC | /5Phos/GTCAGCTAGCACGAGCTAGCACGA |
| TCTAGCCTAATCTAGCCTAA | /5Phos/TTCGTCTAGCCTAATCTAGCCTAA | /5Phos/GTCATTAGGCTAGATTAGGCTAGA |
| TCTCACTGCGTCTCACTGCG | /5Phos/TTCGTCTCACTGCGTCTCACTGCG | /5Phos/GTCACGCAGTGAGACGCAGTGAGA |
| TCTCCGGCAATCTCCGGCAA | /5Phos/TTCGTCTCCGGCAATCTCCGGCAA | /5Phos/GTCATTGCCGGAGATTGCCGGAGA |
| TCTCGCTCTCTCGCTCTC | /5Phos/TTCGTCTCGCTCTCTCGCTCTC | /5Phos/GTCAGAGAGCGAGAGAGAGCGAGA |
| TCTGTCGCAATCTGTCGCAA | /5Phos/TTCGTCTGTCGCAATCTGTCGCAA | /5Phos/GTCATTGCGACAGATTGCGACAGA |
| TCTTAACCTCTCTTAACCTC | /5Phos/TTCGTCTTAACCTCTCTTAACCTC | /5Phos/GTCAGAGGTTAAGAGAGGTTAAGA |
| TGACACATGATGACACATGA | /5Phos/TTCGTGACACATGATGACACATGA | /5Phos/GTCATCATGTGTCATCATGTGTCA |
| TGAGAGTGAATGAGAGTGAA | /5Phos/TTCGTGAGAGTGAATGAGAGTGAA | /5Phos/GTCATTCACTCTCATTCACTCTCA |
| TGAGTGGCTGTGAGTGGCTG | /5Phos/TTCGTGAGTGGCTGTGAGTGGCTG | /5Phos/GTCACAGCCACTCACAGCCACTCA |
| TGATTGACCATGATTGACCA | /5Phos/TTCGTGATTGACCATGATTGACCA | /5Phos/GTCATGGTCAATCATGGTCAATCA |
| TGCAGTCGCATGCAGTCGCA | /5Phos/TTCGTGCAGTCGCATGCAGTCGCA | /5Phos/GTCATGCGACTGCATGCGACTGCA |
| TGCCATGAGGTGCCATGAGG | /5Phos/TTCGTGCCATGAGGTGCCATGAGG | /5Phos/GTCACCTCATGGCACCTCATGGCA |
| TGCCTAACGCTGCCTAACGC | /5Phos/TTCGTGCCTAACGCTGCCTAACGC | /5Phos/GTCAGCGTTAGGCAGCGTTAGGCA |
| TGCCTATAACTGCCTATAAC | /5Phos/TTCGTGCCTATAACTGCCTATAAC | /5Phos/GTCAGTTATAGGCAGTTATAGGCA |
| TGCGAGAGAGTGCGAGAGAG | /5Phos/TTCGTGCGAGAGAGTGCGAGAGAG | /5Phos/GTCACTCTCTCGCACTCTCTCGCA |
| TGCGCGATCATGCGCGATCA | /5Phos/TTCGTGCGCGATCATGCGCGATCA | /5Phos/GTCATGATCGCGCATGATCGCGCA |
| TGCGGAGTGATGCGGAGTGA | /5Phos/TTCGTGCGGAGTGATGCGGAGTGA | /5Phos/GTCATCACTCCGCATCACTCCGCA |
| TGCGGATTCCTGCGGATTCC | /5Phos/TTCGTGCGGATTCCTGCGGATTCC | /5Phos/GTCAGGAATCCGCAGGAATCCGCA |
| TGCGGCTACATGCGGCTACA | /5Phos/TTCGTGCGGCTACATGCGGCTACA | /5Phos/GTCATGTAGCCGCATGTAGCCGCA |
| TGCGTAACAATGCGTAACAA | /5Phos/TTCGTGCGTAACAATGCGTAACAA | /5Phos/GTCATTGTTACGCATTGTTACGCA |
| TGCGTCCTCATGCGTCCTCA | /5Phos/TTCGTGCGTCCTCATGCGTCCTCA | /5Phos/GTCATGAGGACGCATGAGGACGCA |
| TGCGTTCAGCTGCGTTCAGC | /5Phos/TTCGTGCGTTCAGCTGCGTTCAGC | /5Phos/GTCAGCTGAACGCAGCTGAACGCA |
| TGCTTCAGCGTGCTTCAGCG | /5Phos/TTCGTGCTTCAGCGTGCTTCAGCG | /5Phos/GTCACGCTGAAGCACGCTGAAGCA |
| TGCTTGCCTCTGCTTGCCTC | /5Phos/TTCGTGCTTGCCTCTGCTTGCCTC | /5Phos/GTCAGAGGCAAGCAGAGGCAAGCA |
| TGGAACTGGCTGGAACTGGC | /5Phos/TTCGTGGAACTGGCTGGAACTGGC | /5Phos/GTCAGCCAGTTCCAGCCAGTTCCA |
| TGTATTGGAGTGTATTGGAG | /5Phos/TTCGTGTATTGGAGTGTATTGGAG | /5Phos/GTCACTCCAATACACTCCAATACA |
| TGTGGAACGTGTGTGGAACG | /5Phos/TTCGTGTGGAACGTGTGTGGAACG | /5Phos/GTCACCGTTCCACACCGTTCCACA |
| TGTGGAGTCGTGTGGAGTCG | /5Phos/TTCGTGTGGAGTCGTGTGGAGTCG | /5Phos/GTCAGACTCCACACGACTCCACA |
| TGTGTGGCCATGTGTGGCCA | /5Phos/TTCGTGTGTGGCCATGTGTGGCCA | /5Phos/GTCATGGCCACACATGGCCACACA |
| TGTTAAGAGGTGTTAAGAGG | /5Phos/TTCGTGTTAAGAGGTGTTAAGAGG | /5Phos/GTCACCTCTTAACACCTCTTAACA |
| TGTTACTCACTGTTACTCAC | /5Phos/TTCGTGTTACTCACTGTTACTCAC | /5Phos/GTCAGTGAGTAACAGTGAGTAACA |
| TGTTCGCAGCTGTTCGCAGC | /5Phos/TTCGTGTTCGCAGCTGTTCGCAGC | /5Phos/GTCAGCTGCGAACAGCTGCGAACA |
| TGTTGGCATATGTTGGCATA | /5Phos/TTCGTGTTGGCATATGTTGGCATA | /5Phos/GTCATATGCCAACATATGCCAACA |
| TTAAGTGCAGTTAAGTGCAG | /5Phos/TTCGTTAAGTGCAGTTAAGTGCAG | /5Phos/GTCACTGCACTTAACTGCACTTAA |
| TTAGAGATCCTTAGAGATCC | /5Phos/TTCGTTAGAGATCCTTAGAGATCC | /5Phos/GTCAGGATCTCTAAGGATCTCTAA |
| TTAGGTCAGATTAGGTCAGA | /5Phos/TTCGTTAGGTCAGATTAGGTCAGA | /5Phos/GTCATCTGACCTAATCTGACCTAA |
| TTATCTCCTGTTATCTCCTG | /5Phos/TTCGTTATCTCCTGTTATCTCCTG | /5Phos/GTCACAGGAGATAACAGGAGATAA |
| TTCAGTGTCGTTCAGTGTCG | /5Phos/TTCGTTCAGTGTCGTTCAGTGTCG | /5Phos/GTCACGACACTGAACGACACTGAA |
| TTCAAGAAGTTCAAGAAGT | /5Phos/TTCGTTCAAGAAGTTCAAGAAGT | /5Phos/GTCACTTCTTGGAACTTCTTGGAA |
| TTCCACCGCATTCCACCGCA | /5Phos/TTCGTTCCACCGCATTCCACCGCA | /5Phos/GTCATGCGGTGGAATGCGGTGGAA |
| TTCCACTATCTTCCACTATC | /5Phos/TTCGTTCCACTATCTTCCACTATC | /5Phos/GTCAGATAGTGGAAGATAGTGGAA |
| TTCCACTTGATTCCACTTGA | /5Phos/TTCGTTCCACTTGATTCCACTTGA | /5Phos/GTCATCAAGTGGAATCAAGTGGAA |
| TTCCGAGAGCTTCCGAGAGC | /5Phos/TTCGTTCCGAGAGCTTCCGAGAGC | /5Phos/GTCAGCTCTCGGAAGCTCTCGGAA |
| TTCCTGAGCCTTCCTGAGCC | /5Phos/TTCGTTCCTGAGCCTTCCTGAGCC | /5Phos/GTCAGGCTCAGGAAGGCTCAGGAA |

TABLE 1 -continued

| Tag | Full Oligo Sequence (Top) | Full Oligo Sequence (Bot) |
|---|---|---|
| TTCGAGTCGCTTCGAGTCGC | /5Phos/TTCGTTCGAGTCGCTTCGAGTCGC | /5Phos/GTCAGCGACTCGAAGCGACTCGAA |
| TTCGTGCCAGTTCGTGCCAG | /5Phos/TTCGTTCGTGCCAGTTCGTGCCAG | /5Phos/GTCACTGGCACGAACTGGCACGAA |
| TTCTACACCATTCTACACCA | /5Phos/TTCGTTCTACACCATTCTACACCA | /5Phos/GTCATGGTGTAGAATGGTGTAGAA |
| TTCTCGCTCCTTCTCGCTCC | /5Phos/TTCGTTCTCGCTCCTTCTCGCTCC | /5Phos/GTCAGGAGCGAGAAGGAGCGAGAA |
| TTCTGGCCACTTCTGGCCAC | /5Phos/TTCGTTCTGGCCACTTCTGGCCAC | /5Phos/GTCAGTGGCCAGAAGTGGCCAGAA |
| TTGAATGGTGTTGAATGGTG | /5Phos/TTCGTTGAATGGTGTTGAATGGTG | /5Phos/GTCACACCATTCAACACCATTCAA |
| TTGAGCCGACTTGAGCCGAC | /5Phos/TTCGTTGAGCCGACTTGAGCCGAC | /5Phos/GTCAGTCGGCTCAAGTCGGCTCAA |
| TTGCGCCAAGTTGCGCCAAG | /5Phos/TTCGTTGCGCCAAGTTGCGCCAAG | /5Phos/GTCACTTGGCGCAACTTGGCGCAA |
| TTGCTCTTAGTTGCTCTTAG | /5Phos/TTCGTTGCTCTTAGTTGCTCTTAG | /5Phos/GTCACTAAGAGCAACTAAGAGCAA |
| TTGGCAAGGCTTGGCAAGGC | /5Phos/TTCGTTGGCAAGGCTTGGCAAGGC | /5Phos/GTCAGCCTTGCCAAGCCTTGCCAA |
| TTGGCTCACGTTGGCTCACG | /5Phos/TTCGTTGGCTCACGTTGGCTCACG | /5Phos/GTCACGTGAGCCAACGTGAGCCAA |
| TTGGCTTCCATTGGCTTCCA | /5Phos/TTCGTTGGCTTCCATTGGCTTCCA | /5Phos/GTCATGGAAGCCAATGGAAGCCAA |
| TTGTGGATACTTGTGGATAC | /5Phos/TTCGTTGTGGATACTTGTGGATAC | /5Phos/GTCAGTATCCACAAGTATCCACAA |
| AACACGGATGAACACGGATG | /5Phos/TTCGAACACGGATGAACACGGATG | /5Phos/GTCACATCCGTGTTCATCCGTGTT |
| AACAGACCGGACAGACCGG | /5Phos/TTCGAACAGACCGGACAGACCGG | /5Phos/GTCACCGGTCTGTTCCGGTCTGTT |
| AACAGTGATCAACAGTGATC | /5Phos/TTCGAACAGTGATCAACAGTGATC | /5Phos/GTCAGATCACTGTTGATCACTGTT |
| AACCATCTTGAACCATCTTG | /5Phos/TTCGAACCATCTTGAACCATCTTG | /5Phos/GTCACAAGATGGTTCAAGATGGTT |
| AACGGTGACGAACGGTGACG | /5Phos/TTCGAACGGTGACGAACGGTGACG | /5Phos/GTCACGTCACCGTTCGTCACCGTT |
| AACTACGCGGAACTACGCGG | /5Phos/TTCGAACTACGCGGAACTACGCGG | /5Phos/GTCACCGCGTAGTTCCGCGTAGTT |
| AACTAGGCTTAACTAGGCTT | /5Phos/TTCGAACTAGGCTTAACTAGGCTT | /5Phos/GTCAAAGCCTAGTTAAGCCTAGTT |
| AACTGGCGTGAACTGGCGTG | /5Phos/TTCGAACTGGCGTGAACTGGCGTG | /5Phos/GTCACACGCCAGTTCACGCCAGTT |
| AAGACAGGATAAGACAGGAT | /5Phos/TTCGAAGACAGGATAAGACAGGAT | /5Phos/GTCAATCCTGTCTTATCCTGTCTT |
| AAGAGCCAGTAAGAGCCAGT | /5Phos/TTCGAAGAGCCAGTAAGAGCCAGT | /5Phos/GTCAACTGGCTCTTACTGGCTCTT |
| AAGAGTATCGAAGAGTATCG | /5Phos/TTCGAAGAGTATCGAAGAGTATCG | /5Phos/GTCACGATACTCTTCGATACTCTT |
| AAGGAACACTAAGGAACACT | /5Phos/TTCGAAGGAACACTAAGGAACACT | /5Phos/GTCAAGTGTTCCTTAGTGTTCCTT |
| AAGTCGCAGGAAGTCGCAGG | /5Phos/TTCGAAGTCGCAGGAAGTCGCAGG | /5Phos/GTCACCTGCGACTTCCTGCGACTT |
| AATCACAGTCAATCACAGTC | /5Phos/TTCGAATCACAGTCAATCACAGTC | /5Phos/GTCAGACTGTGATTGACTGTGATT |
| AATCGCCATTAATCGCCATT | /5Phos/TTCGAATCGCCATTAATCGCCATT | /5Phos/GTCAAATGGCGATTAATGGCGATT |
| AATTGCGGCCAATTGCGGCC | /5Phos/TTCGAATTGCGGCCAATTGCGGCC | /5Phos/GTCAGGCCGCAATTGGCCGCAATT |
| ACAACTCGCGACAACTCGCG | /5Phos/TTCGACAACTCGCGACAACTCGCG | /5Phos/GTCACGCGAGTTGTCGCGAGTTGT |
| ACAAGCTGCGACAAGCTGCG | /5Phos/TTCGACAAGCTGCGACAAGCTGCG | /5Phos/GTCACGCAGCTTGTCGCAGCTTGT |
| ACACCAATTCACACCAATTC | /5Phos/TTCGACACCAATTCACACCAATTC | /5Phos/GTCAGAATTGGTGTGAATTGGTGT |
| ACACGAAGGTACACGAAGGT | /5Phos/TTCGACACGAAGGTACACGAAGGT | /5Phos/GTCAACCTTCGTGTACCTTCGTGT |
| ACAGAATGTGACAGAATGTG | /5Phos/TTCGACAGAATGTGACAGAATGTG | /5Phos/GTCACACATTCTGTCACATTCTGT |
| ACATAGTGGTACATAGTGGT | /5Phos/TTCGACATAGTGGTACATAGTGGT | /5Phos/GTCAACCACTATGTACCACTATGT |
| ACCACCACGTACCACCACGT | /5Phos/TTCGACCACCACGTACCACCACGT | /5Phos/GTCAACGTGGTGGTACGTGGTGGT |
| ACCGACAGCTACCGACAGCT | /5Phos/TTCGACCGACAGCTACCGACAGCT | /5Phos/GTCAAGCTGTCGGTAGCTGTCGGT |
| ACCGGCTAGTACCGGCTAGT | /5Phos/TTCGACCGGCTAGTACCGGCTAGT | /5Phos/GTCAACTAGCCGGTACTAGCCGGT |
| ACCGTAGATTACCGTAGATT | /5Phos/TTCGACCGTAGATTACCGTAGATT | /5Phos/GTCAAATCTACGGTAATCTACGGT |
| ACCGTGACTTACCGTGACTT | /5Phos/TTCGACCGTGACTTACCGTGACTT | /5Phos/GTCAAAAGTCACGGTAAGTCACGGT |
| ACCTCACAACACCTCACAAC | /5Phos/TTCGACCTCACAACACCTCACAAC | /5Phos/GTCAGTTGTGAGGTGTTGTGAGGT |
| ACCTTGTCCTACCTTGTCCT | /5Phos/TTCGACCTTGTCCTACCTTGTCCT | /5Phos/GTCAAGGACAAGGTAGGACAAGGT |
| ACGAAGCAGGACGAAGCAGG | /5Phos/TTCGACGAAGCAGGACGAAGCAGG | /5Phos/GTCACCTGCTTCGTCCTGCTTCGT |
| ACGACTGGACACGACTGGAC | /5Phos/TTCGACGACTGGACACGACTGGAC | /5Phos/GTCAGTCCAGTCGTGTCCAGTCGT |
| ACGAGAGCAGACGAGAGCAG | /5Phos/TTCGACGAGAGCAGACGAGAGCAG | /5Phos/GTCACTGCTCTCGTCTGCTCTCGT |
| ACGCCTGTTGACGCCTGTTG | /5Phos/TTCGACGCCTGTTGACGCCTGTTG | /5Phos/GTCACAACAGGCGTCAACAGGCGT |
| ACGCGACTTCACGCGACTTC | /5Phos/TTCGACGCGACTTCACGCGACTTC | /5Phos/GTCAGAAGTCGCGTGAAGTCGCGT |
| ACGGATTGATACGGATTGAT | /5Phos/TTCGACGGATTGATACGGATTGAT | /5Phos/GTCAATCAATCCGTATCAATCCGT |
| ACGGCTCATGACGGCTCATG | /5Phos/TTCGACGGCTCATGACGGCTCATG | /5Phos/GTCACATGAGCCGTCATGAGCCGT |
| ACGGTAAGATACGGTAAGAT | /5Phos/TTCGACGGTAAGATACGGTAAGAT | /5Phos/GTCAATCTTACCGTATCTTACCGT |
| ACGGTAGCACACGGTAGCAC | /5Phos/TTCGACGGTAGCACACGGTAGCAC | /5Phos/GTCAGTGCTACCGTGTGCTACCGT |
| ACGGTGTTCGACGGTGTTCG | /5Phos/TTCGACGGTGTTCGACGGTGTTCG | /5Phos/GTCACGAACACCGTCGAACACCGT |
| ACGTCGATGGACGTCGATGG | /5Phos/TTCGACGTCGATGGACGTCGATGG | /5Phos/GTCACCATCGACGTCCATCGACGT |
| ACGTGCAGACACGTGCAGAC | /5Phos/TTCGACGTGCAGACACGTGCAGAC | /5Phos/GTCAGTCTGCACGTGTCTGCACGT |
| ACGTTCCAGCACGTTCCAGC | /5Phos/TTCGACGTTCCAGCACGTTCCAGC | /5Phos/GTCAGCTGGAACGTGCTGGAACGT |
| ACTAGCTTGTACTAGCTTGT | /5Phos/TTCGACTAGCTTGTACTAGCTTGT | /5Phos/GTCAACAAGCTAGTACAAGCTAGT |
| ACTAGGACGCACTAGGACGC | /5Phos/TTCGACTAGGACGCACTAGGACGC | /5Phos/GTCAGCGTCCTAGTGCGTCCTAGT |
| ACTCACCTGGACTCACCTGG | /5Phos/TTCGACTCACCTGGACTCACCTGG | /5Phos/GTCACCAGGTGAGTCCAGGTGAGT |
| ACTCATATCGACTCATATCG | /5Phos/TTCGACTCATATCGACTCATATCG | /5Phos/GTCACGATATGAGTCGATATGAGT |
| ACTGACCGTGACTGACCGTG | /5Phos/TTCGACTGACCGTGACTGACCGTG | /5Phos/GTCACACGGTCAGTCACGGTCAGT |
| ACTTCTAACCACTTCTAACC | /5Phos/TTCGACTTCTAACCACTTCTAACC | /5Phos/GTCAGGTTAGAAGTGGTTAGAAGT |
| ACTTGGCGCTACTTGGCGCT | /5Phos/TGACACTTGGCGCTACTTGGCGCT | /5Phos/GGGAAGCGCCAAGTAGCGCCAAGT |
| AGAACGCTCCAGAACGCTCC | /5Phos/TGACAGAACGCTCCAGAACGCTCC | /5Phos/GGGAGGAGCGTTCTGGAGCGTTCT |
| AGAACTTAGGAGAACTTAGG | /5Phos/TGACAGAACTTAGGAGAACTTAGG | /5Phos/GGGACCTAAGTTCTCCTAAGTTCT |
| AGAAGCGATAGAAGCGCAT | /5Phos/TGACAGAAGCGATAGAAGCGCAT | /5Phos/GGGAATGCGCTTCTATGCGCTTCT |
| AGACAATAGCAGACAATAGC | /5Phos/TGACAGACAATAGCAGACAATAGC | /5Phos/GGGAGCTATTGTCTGCTATTGTCT |
| AGACCGAGACAGACCGAGAC | /5Phos/TGACAGACCGAGACAGACCGAGAC | /5Phos/GGGAGTCTCGGTCTGTCTCGGTCT |
| AGACGCTGTCAGACGCTGTC | /5Phos/TGACAGACGCTGTCAGACGCTGTC | /5Phos/GGGAGACAGCGTCTGACAGCGTCT |
| AGACGTAGCGAGACGTAGCG | /5Phos/TGACAGACGTAGCGAGACGTAGCG | /5Phos/GGGAGCGCTACGTCTCGCTACGCT |
| AGAGAGCTCTAGAGAGCTCT | /5Phos/TGACAGAGAGCTCTAGAGAGCTCT | /5Phos/GGGAAGAGCTCTCTAGAGCTCTCT |
| AGAGGCCACTAGAGGCCACT | /5Phos/TGACAGAGGCCACTAGAGGCCACT | /5Phos/GGGAAGTGGCCTCTAGTGGCCTCT |
| AGATTGCCGCAGATTGCCGC | /5Phos/TGACAGATTGCCGCAGATTGCCGC | /5Phos/GGGAGCGGCAATCTGCGGCAATCT |
| AGCACGATGCAGCACGATGC | /5Phos/TGACAGCACGATGCAGCACGATGC | /5Phos/GGGAGCATCGTGCTGCATCGTGCT |
| AGCAGAATAGCAGAGAAT | /5Phos/TGACAGCAGAATAGCAGAGAAT | /5Phos/GGGAATTCTCTGCTATTCTCTGCT |
| AGCCACAAGGAGCCACAAGG | /5Phos/TGACAGCCACAAGGAGCCACAAGG | /5Phos/GGGACCTTGTGGCTCCTTGTGGCT |
| AGCCAGGAAGAGCCAGGAAG | /5Phos/TGACAGCCAGGAAGAGCCAGGAAG | /5Phos/GGGACTTCCTGGCTCTTCCTGGCT |
| AGCTCTGGAGAGCTCTGGAG | /5Phos/TGACAGCTCTGGAGAGCTCTGGAG | /5Phos/GGGACTCCAGAGCTCTCCAGAGCT |
| AGCTTGGCAGAGCTTGGCAG | /5Phos/TGACAGCTTGGCAGAGCTTGGCAG | /5Phos/GGGACTGCCAAGCTCTGCCAAGCT |

TABLE 1 -continued

| Tag | Full Oligo Sequence (Top) | Full Oligo Sequence (Bot) |
|---|---|---|
| AGGAATAACGAGGAATAACG | /5Phos/TGACAGGAATAACGAGGAATAACG | /5Phos/GGGACGTTATTCCTCGTTATTCCT |
| AGGAATTGACAGGAATTGAC | /5Phos/TGACAGGAATTGACAGGAATTGAC | /5Phos/GGGAGTCAATTCCTGTCAATTCCT |
| AGGAGGAATTAGGAGGAATT | /5Phos/TGACAGGAGGAATTAGGAGGAATT | /5Phos/GGGAAATTCCTCCTAATTCCTCCT |
| AGGATAGGCCAGGATAGGCC | /5Phos/TGACAGGATAGGCCAGGATAGGCC | /5Phos/GGGAGGCCTATCCTGGCCTATCCT |
| AGGTGGCCTTAGGTGGCCTT | /5Phos/TGACAGGTGGCCTTAGGTGGCCTT | /5Phos/GGGAAAGGCCACCTAAGGCCACCT |
| AGGTGTTGCGAGGTGTTGCG | /5Phos/TGACAGGTGTTGCGAGGTGTTGCG | /5Phos/GGGACGCAACACCTCGCAACACCT |
| AGGTTAGGTGAGGTTAGGTG | /5Phos/TGACAGGTTAGGTGAGGTTAGGTG | /5Phos/GGGACACCTAACCTCACCTAACCT |
| AGTCCGTCCTAGTCCGTCCT | /5Phos/TGACAGTCCGTCCTAGTCCGTCCT | /5Phos/GGGAAGGACGGACTAGGACGGACT |
| AGTCGATCCGAGTCGATCCG | /5Phos/TGACAGTCGATCCGAGTCGATCCG | /5Phos/GGGACGGATCGACTCGGATCGACT |
| AGTCGCTGCTAGTCGCTGCT | /5Phos/TGACAGTCGCTGCTAGTCGCTGCT | /5Phos/GGGAAGCAGCGACTAGCAGCGACT |
| AGTCGTCCTCAGTCGTCCTC | /5Phos/TGACAGTCGTCCTCAGTCGTCCTC | /5Phos/GGGAGAGGACGACTGAGGACGACT |
| AGTGTTCCGTAGTGTTCCGT | /5Phos/TGACAGTGTTCCGTAGTGTTCCGT | /5Phos/GGGAACGGAACACTACGGAACACT |
| AGTTGCTCATAGTTGCTCAT | /5Phos/TGACAGTTGCTCATAGTTGCTCAT | /5Phos/GGGAATGAGCAACTATGAGCAACT |
| ATAACGTGAGATAACGTGAG | /5Phos/TGACATAACGTGAGATAACGTGAG | /5Phos/GGGACTCACGTTATCTCACGTTAT |
| ATACGCAGGCATACGCAGGC | /5Phos/TGACATACGCAGGCATACGCAGGC | /5Phos/GGGAGCCTGCGTATGCCTGCGTAT |
| ATACTGATGCATACTGATGC | /5Phos/TGACATACTGATGCATACTGATGC | /5Phos/GGGAGCATCAGTATGCATCAGTAT |
| ATAGTTCGTCATAGTTCGTC | /5Phos/TGACATAGTTCGTCATAGTTCGTC | /5Phos/GGGAGACGAACTATGACGAACTAT |
| ATATCTTCGCATATCTTCGC | /5Phos/TGACATATCTTCGCATATCTTCGC | /5Phos/GGGAGCGAAGATATGCGAAGATAT |
| ATATGCCTTCATATGCCTTC | /5Phos/TGACATATGCCTTCATATGCCTTC | /5Phos/GGGAGAAGGCATATGAAGGCATAT |
| ATCAGATCACATCAGATCAC | /5Phos/TGACATCAGATCACATCAGATCAC | /5Phos/GGGAGTGATCTGATGTGATCTGAT |
| ATCCAATCTGATCCAATCTG | /5Phos/TGACATCCAATCTGATCCAATCTG | /5Phos/GGGACAGATTGGATCAGATTGGAT |
| ATCCACAGCGATCCACAGCG | /5Phos/TGACATCCACAGCGATCCACAGCG | /5Phos/GGGACGCTGTGGATCGCTGTGGAT |
| ATCCGGAACGATCCGGAACG | /5Phos/TGACATCCGGAACGATCCGGAACG | /5Phos/GGGACGTTCCGGATCGTTCCGGAT |
| ATCGGCTTCCATCGGCTTCC | /5Phos/TGACATCGGCTTCCATCGGCTTCC | /5Phos/GGGAGGAAGCCGATGGAAGCCGAT |
| ATCGTCGGAGATCGTCGGAG | /5Phos/TGACATCGTCGGAGATCGTCGGAG | /5Phos/GGGACTCCGACGATCTCCGACGAT |
| ATCTCTCACGATCTCTCACG | /5Phos/TGACATCTCTCACGATCTCTCACG | /5Phos/GGGACGTGAGAGATCGTGAGAGAT |
| ATGCACCTGCATGCACCTGC | /5Phos/TGACATGCACCTGCATGCACCTGC | /5Phos/GGGAGCAGGTGCATGCAGGTGCAT |
| ATGCAGTCGCATGCAGTCGC | /5Phos/TGACATGCAGTCGCATGCAGTCGC | /5Phos/GGGAGCGACTGCATGCGACTGCAT |
| ATGCCGTAGGATGCCGTAGG | /5Phos/TGACATGCCGTAGGATGCCGTAGG | /5Phos/GGGACCTACGGCATCCTACGGCAT |
| ATGCGCGATCATGCGCGATC | /5Phos/TGACATGCGCGATCATGCGCGATC | /5Phos/GGGAGATCGCGCATGATCGCGCAT |
| ATGTGGTGATATGTGGTGAT | /5Phos/TGACATGTGGTGATATGTGGTGAT | /5Phos/GGGAATCACCACATATCACCACAT |
| ATTACGAGCCATTACGAGCC | /5Phos/TGACATTACGAGCCATTACGAGCC | /5Phos/GGGAGGCTCGTAATGGCTCGTAAT |
| ATTCCACGGCATTCCACGGC | /5Phos/TGACATTCCACGGCATTCCACGGC | /5Phos/GGGAGCCGTGGAATGCCGTGGAAT |
| ATTCGGCGTCATTCGGCGTC | /5Phos/TGACATTCGGCGTCATTCGGCGTC | /5Phos/GGGAGACGCCGAATGACGCCGAAT |
| ATTGGAAGCCATTGGAAGCC | /5Phos/TGACATTGGAAGCCATTGGAAGCC | /5Phos/GGGAGGCTTCCAATGGCTTCCAAT |
| ATTGTCGGCCATTGTCGGCC | /5Phos/TGACATTGTCGGCCATTGTCGGCC | /5Phos/GGGAGGCCGACAATGGCCGACAAT |
| CAACCGCTTGCAACCGCTTG | /5Phos/TGACCAACCGCTTGCAACCGCTTG | /5Phos/GGGACAAGCGGTTGCAAGCGGTTG |
| CAACTGGTGGCAACTGGTGG | /5Phos/TGACCAACTGGTGGCAACTGGTGG | /5Phos/GGGACCACCAGTTGCCACCAGTTG |
| CAAGATGGTGCAAGATGGTG | /5Phos/TGACCAAGATGGTGCAAGATGGTG | /5Phos/GGGACACCATCTTGCACCATCTTG |
| CAAGATTCGACAAGATTCGA | /5Phos/TGACCAAGATTCGACAAGATTCGA | /5Phos/GGGATCGAATCTTGTCGAATCTTG |
| CAAGCACGAGCAAGCACGAG | /5Phos/TGACCAAGCACGAGCAAGCACGAG | /5Phos/GGGACTCGTGCTTGCTCGTGCTTG |
| CAAGCCTGTGCAAGCCTGTG | /5Phos/TGACCAAGCCTGTGCAAGCCTGTG | /5Phos/GGGACACAGGCTTGCACAGGCTTG |
| CAAGCTCACGCAAGCTCACG | /5Phos/TGACCAAGCTCACGCAAGCTCACG | /5Phos/GGGACGTGAGCTTGCGTGAGCTTG |
| CAAGGTTGCGCAAGGTTGCG | /5Phos/TGACCAAGGTTGCGCAAGGTTGCG | /5Phos/GGGACGCAACCTTGCGCAACCTTG |
| CAAGTCGACGCAAGTCGACG | /5Phos/TGACCAAGTCGACGCAAGTCGACG | /5Phos/GGGACGTCGACTTGCGTCGACTTG |
| CACCACGAAGCACCACGAAG | /5Phos/TGACCACCACGAAGCACCACGAAG | /5Phos/GGGACTTCGTGGTGCTTCGTGGTG |
| CACCGATATTCACCGATATT | /5Phos/TGACCACCGATATTCACCGATATT | /5Phos/GGGAAATATCGGTGAATATCGGTG |
| CACCGTCGAACACCGTCGAA | /5Phos/TGACCACCGTCGAACACCGTCGAA | /5Phos/GGGATTCGACGGTGTTCGACGGTG |
| CACCGTGACACACCGTGACA | /5Phos/TGACCACCGTGACACACCGTGACA | /5Phos/GGGATGTCACGGTGTGTCACGGTG |
| CACCTGCTGACACCTGCTGA | /5Phos/TGACCACCTGCTGACACCTGCTGA | /5Phos/GGGATCAGCAGGTGTCAGCAGGTG |
| CACGCACATACACGCACATA | /5Phos/TGACCACGCACATACACGCACATA | /5Phos/GGGATATGTGCGTGTATGTGCGTG |
| CACGCTAAGGCACGCTAAGG | /5Phos/TGACCACGCTAAGGCACGCTAAGG | /5Phos/GGGACCTTAGCGTGCCTTAGCGTG |
| CACGTAATCTCACGTAATCT | /5Phos/TGACCACGTAATCTCACGTAATCT | /5Phos/GGGAAGATTACGTGAGATTACGTG |
| CACGTGGAGTCACGTGGAGT | /5Phos/TGACCACGTGGAGTCACGTGGAGT | /5Phos/GGGAACTCCACGTGACTCCACGTG |
| CACTCGAGAGCACTCGAGAG | /5Phos/TGACCACTCGAGAGCACTCGAGAG | /5Phos/GGGACTCTCGAGTGCTCTCGAGTG |
| CACTCTGACACTCTCTGA | /5Phos/TGACCACTCTCTGACACTCTCTGA | /5Phos/GGGATCAGAGAGTGTCAGAGAGTG |
| CACTCTGGCTCACTCTGGCT | /5Phos/TGACCACTCTGGCTCACTCTGGCT | /5Phos/GGGAAGCCAGAGTGAGCCAGAGTG |
| CACTGCCATGCACTGCCATG | /5Phos/TGACCACTGCCATGCACTGCCATG | /5Phos/GGGACATGGCAGTGCATGGCAGTG |
| CACTTGAACTCACTTGAACT | /5Phos/TGACCACTTGAACTCACTTGAACT | /5Phos/GGGAAGTTCAAGTGAGTTCAAGTG |
| CAGACCTGAGCAGACCTGAG | /5Phos/TGACCAGACCTGAGCAGACCTGAG | /5Phos/GGGACTCAGGTCTGCTCAGGTCTG |
| CAGCGAGCATCAGCGAGCAT | /5Phos/TGACCAGCGAGCATCAGCGAGCAT | /5Phos/GGGAATGCTCGCTGATGCTCGCTG |
| CAGGAAGAGGCAGGAAGAGG | /5Phos/TGACCAGGAAGAGGCAGGAAGAGG | /5Phos/GGGACCTCTTCCTGCCTCTTCCTG |
| CAGTCTCATACAGTCTCATA | /5Phos/TGACCAGTCTCATACAGTCTCATA | /5Phos/GGGATATGAGACTGTATGAGACTG |
| CAGTTATCGACAGTTATCGA | /5Phos/TGACCAGTTATCGACAGTTATCGA | /5Phos/GGGATCGATAACTGTCGATAACTG |
| CATACACGCATACACGCG | /5Phos/TGACCATACACGCGCATACACGCG | /5Phos/GGGACGCGTGTATGCGCGTGTATG |
| CATACCGACGCATACCGACG | /5Phos/TGACCATACCGACGCATACCGACG | /5Phos/GGGACGTCGGTATGCGTCGGTATG |
| CATCAATGGTCATCAATGGT | /5Phos/TGACCATCAATGGTCATCAATGGT | /5Phos/GGGAACCATTGATGACCATTGATG |
| CATGACACCGCATGACACCG | /5Phos/TGACCATGACACCGCATGACACCG | /5Phos/GGGACGGTGTCATGCGGTGTCATG |
| CATGGTTCGGCATGGTTCGG | /5Phos/TGACCATGGTTCGGCATGGTTCGG | /5Phos/GGGACCGAACCATGCCGAACCATG |
| CATTGGAGCGCATTGGAGCG | /5Phos/TGACCATTGGAGCGCATTGGAGCG | /5Phos/GGGACGCTCCAATGCGCTCCAATG |
| CCAACGAGAGCCAACGAGAG | /5Phos/TGACCCAACGAGAGCCAACGAGAG | /5Phos/GGGACTCTCGTTGGCTCTCGTTGG |
| CCAAGACCAGCCAAGACCAG | /5Phos/TGACCCAAGACCAGCCAAGACCAG | /5Phos/GGGACTGGTCTTGGCTGGTCTTGG |
| CCAATCACGGCCAATCACGG | /5Phos/TGACCCAATCACGGCCAATCACGG | /5Phos/GGGACCGTGATTGGCCGTGATTGG |
| CCACCGTTGTCCACCGTTGT | /5Phos/TGACCCACCGTTGTCCACCGTTGT | /5Phos/GGGAACAACGGTGGACAACGGTGG |
| CCAGATCGGACCAGATCGGA | /5Phos/TGACCCAGATCGGACCAGATCGGA | /5Phos/GGGATCCGATCTGGTCCGATCTGG |
| CCGAAGTCAGCCGAAGTCAG | /5Phos/TGACCCGAAGTCAGCCGAAGTCAG | /5Phos/GGGACTGACTTCGGCTGACTTCGG |
| CCGCTGAAGTCCGCTGAAGT | /5Phos/TGACCCGCTGAAGTCCGCTGAAGT | /5Phos/GGGAACTTCAGCGGACTTCAGCGG |
| CCGGACCATACCGGACCATA | /5Phos/TGACCCGGACCATACCGGACCATA | /5Phos/GGGATATGGTCCGGTATGGTCCGG |

TABLE 1 -continued

| Tag | Full Oligo Sequence (Top) | Full Oligo Sequence (Bot) |
| --- | --- | --- |
| CCGTTCTAGGCCGTTCTAGG | /5Phos/TGACCCGTTCTAGGCCGTTCTAGG | /5Phos/GGGACCTAGAACGGCCTAGAACGG |
| CCTAATGCGGCCTAATGCGG | /5Phos/TGACCCTAATGCGGCCTAATGCGG | /5Phos/GGGACCGCATTAGGCCGCATTAGG |
| CCTATGACGACCTATGACGA | /5Phos/TGACCCTATGACGACCTATGACGA | /5Phos/GGGATCGTCATAGGTCGTCATAGG |
| CCTCACCAGTCCTCACCAGT | /5Phos/TGACCCTCACCAGTCCTCACCAGT | /5Phos/GGGAACTGGTGAGGACTGGTGAGG |
| CCTGAAGACGCCTGAAGACG | /5Phos/TGACCCTGAAGACGCCTGAAGACG | /5Phos/GGGACGTCTTCAGGCGTCTTCAGG |
| CCTGACTCCTCCTGACTCCT | /5Phos/TGACCCTGACTCCTCCTGACTCCT | /5Phos/GGGAAGGAGTCAGGAGGAGTCAGG |
| CGAAGAGTGGCGAAGAGTGG | /5Phos/TGACCGAAGAGTGGCGAAGAGTGG | /5Phos/GGGACCACTCTTCGCCACTCTTCG |
| CGAAGGTGGTCGAAGGTGGT | /5Phos/TGACCGAAGGTGGTCGAAGGTGGT | /5Phos/GGGAACCACCTTCGACCACCTTCG |
| CGACTAGCAGCGACTAGCAG | /5Phos/TGACCGACTAGCAGCGACTAGCAG | /5Phos/GGGACTGCTAGTCGCTGCTAGTCG |
| CGACTCGAGACGACTCGAGA | /5Phos/TGACCGACTCGAGACGACTCGAGA | /5Phos/GGGATCTCGAGTCGTCTCGAGTCG |
| CGACTTACAACGACTTACAA | /5Phos/TGACCGACTTACAACGACTTACAA | /5Phos/GGGATTGTAAGTCGTTGTAAGTCG |
| CGAGGATTAACGAGGATTAA | /5Phos/TGACCGAGGATTAACGAGGATTAA | /5Phos/GGGATTAATCCTCGTTAATCCTCG |
| CGAGGCATGTCGAGGCATGT | /5Phos/TGACCGAGGCATGTCGAGGCATGT | /5Phos/GGGAACATGCCTCGACATGCCTCG |
| CGAGTCTGCTCGAGTCTGCT | /5Phos/TGACCGAGTCTGCTCGAGTCTGCT | /5Phos/GGGAAGCAGACTCGAGCAGACTCG |
| CGAGTGAGCACGAGTGAGCA | /5Phos/TGACCGAGTGAGCACGAGTGAGCA | /5Phos/GGGATGCTCACTCGTGCTCACTCG |
| CGATCGGAAGCGATCGGAAG | /5Phos/TGACCGATCGGAAGCGATCGGAAG | /5Phos/GGGACTTCCGATCGCTTCCGATCG |
| CGATCTACCGCGATCTACCG | /5Phos/TGACCGATCTACCGCGATCTACCG | /5Phos/GGGACGGTAGATCGCGGTAGATCG |
| CGCCAAGCTTCGCCAAGCTT | /5Phos/TGACCGCCAAGCTTCGCCAAGCTT | /5Phos/GGGAAAGCTTGGCGAAGCTTGGCG |
| CGCCAGAATTCGCCAGAATT | /5Phos/TGACCGCCAGAATTCGCCAGAATT | /5Phos/GGGAAATTCTGGCGAATTCTGGCG |
| CGCGAATGGACGCGAATGGA | /5Phos/TGACCGCGAATGGACGCGAATGGA | /5Phos/GGGATCCATTCGCGTCCATTCGCG |
| CGCTCATCCTCGCTCATCCT | /5Phos/TGACCGCTCATCCTCGCTCATCCT | /5Phos/GGGAAGGATGAGCGAGGATGAGCG |
| CGCTCGAATGCGCTCGAATG | /5Phos/TGACCGCTCGAATGCGCTCGAATG | /5Phos/GGGACATTCGAGCGCATTCGAGCG |
| CGCTTACTATCGCTTACTAT | /5Phos/TGACCGCTTACTATCGCTTACTAT | /5Phos/GGGAATAGTAAGCGATAGTAAGCG |
| CGCTTAGCGTCGCTTAGCGT | /5Phos/TGACCGCTTAGCGTCGCTTAGCGT | /5Phos/GGGAACGTAAGCGACGCGTAAGCG |
| CGGACTTAAGCGGACTTAAG | /5Phos/TGACCGGACTTAAGCGGACTTAAG | /5Phos/GGGACTTAAGTCCGCTTAAGTCCG |
| CGGCGAACAACGGCGAACAA | /5Phos/TGACCGGCGAACAACGGCGAACAA | /5Phos/GGGATTGTTCGCCGTTGTTCGCCG |
| CGGCTTGGAACGGCTTGGAA | /5Phos/TGACCGGCTTGGAACGGCTTGGAA | /5Phos/GGGATTCCAAGCCGTTCCAAGCCG |
| CGGTAGTGCTCGGTAGTGCT | /5Phos/TGACCGGTAGTGCTCGGTAGTGCT | /5Phos/GGGAAGCACTACCGAGCACTACCG |
| CGGTTACACACGGTTACACA | /5Phos/TGACCGGTTACACACGGTTACACA | /5Phos/GGGATGTGTAACCGTGTGTAACCG |
| CGTACCGTGTCGTACCGTGT | /5Phos/TGACCGTACCGTGTCGTACCGTGT | /5Phos/GGGAACACGGTACGACACGGTACG |
| CGTAGAGCCACGTAGAGCCA | /5Phos/TGACCGTAGAGCCACGTAGAGCCA | /5Phos/GGGATGGCTCTACGTGGCTCTACG |
| CGTAGGACTGCGTAGGACTG | /5Phos/TGACCGTAGGACTGCGTAGGACTG | /5Phos/GGGACAGTCCTACGCAGTCCTACG |
| CGTATCACAACGTATCACAA | /5Phos/TGACCGTATCACAACGTATCACAA | /5Phos/GGGATTGTGATACGTTGTGATACG |
| CGTGTTGCGACGTGTTGCGA | /5Phos/TGACCGTGTTGCGACGTGTTGCGA | /5Phos/GGGATCGCAACACGTCGCAACACG |
| CGTTGGTCCACGTTGGTCCA | /5Phos/TGACCGTTGGTCCACGTTGGTCCA | /5Phos/GGGATGGACCAACGTGGACCAACG |
| CTACAGCCGACTACAGCCGA | /5Phos/TGACCTACAGCCGACTACAGCCGA | /5Phos/GGGATCGGCTGTAGTCGGCTGTAG |
| CTACGCAAGGCTACGCAAGG | /5Phos/TGACCTACGCAAGGCTACGCAAGG | /5Phos/GGGACCTTGCGTAGCCTTGCGTAG |
| CTACGGTGTGCTACGGTGTG | /5Phos/TGACCTACGGTGTGCTACGGTGTG | /5Phos/GGGACACACCGTAGCACACCGTAG |
| CTACGTTCCTCTACGTTCCT | /5Phos/TGACCTACGTTCCTCTACGTTCCT | /5Phos/GGGAAGGAACGTAGAGGAACGTAG |
| CTAGAGGCAGCTAGAGGCAG | /5Phos/TGACCTAGAGGCAGCTAGAGGCAG | /5Phos/GGGACTGCCTCTAGCTGCCTCTAG |
| CTAGGTCCAGCTAGGTCCAG | /5Phos/TGACCTAGGTCCAGCTAGGTCCAG | /5Phos/GGGACTGGACCTAGCTGGACCTAG |
| CTAGGTCGCTCTAGGTCGCT | /5Phos/TGACCTAGGTCGCTCTAGGTCGCT | /5Phos/GGGAAGCGACCTAGAGCGACCTAG |
| CTATCGCCGTCTATCGCCGT | /5Phos/TGACCTATCGCCGTCTATCGCCGT | /5Phos/GGGAACGGCGATAGACGGCGATAG |
| CTATGGATCTCTATGGATCT | /5Phos/TGACCTATGGATCTCTATGGATCT | /5Phos/GGGAAGATCCATAGAGATCCATAG |
| CTCGCGAGTTCTCGCGAGTT | /5Phos/TGACCTCGCGAGTTCTCGCGAGTT | /5Phos/GGGAAACTCGCGAGAACTCGCGAG |
| CTCGTGGCAACTCGTGGCAA | /5Phos/TGACCTCGTGGCAACTCGTGGCAA | /5Phos/GGGATTGCCACGAGTTGCCACGAG |
| CTCTACAACTCTCTACAACT | /5Phos/TGACCTCTACAACTCTCTACAACT | /5Phos/GGGAAGTTGTAGAGAGTTGTAGAG |
| CTCTATATCGCTCTATATCG | /5Phos/TGACCTCTATATCGCTCTATATCG | /5Phos/GGGACGATATAGAGCGATATAGAG |
| CTCTCCTTCACTCTCCTTCA | /5Phos/TGACCTCTCCTTCACTCTCCTTCA | /5Phos/GGGATGAAGGAGAGTGAAGGAGAG |
| CTCTCTTGCGCTCTCTTGCG | /5Phos/TGACCTCTCTTGCGCTCTCTTGCG | /5Phos/GGGACGCAAGAGAGCGCAAGAGAG |
| CTCTGCGTTGCTCTGCGTTG | /5Phos/TGACCTCTGCGTTGCTCTGCGTTG | /5Phos/GGGACAACGCAGAGCAACGCAGAG |
| CTGAATCCAGCTGAATCCAG | /5Phos/TGACCTGAATCCAGCTGAATCCAG | /5Phos/GGGACTGGATTCAGCTGGATTCAG |
| CTGAGCTTGGCTGAGCTTGG | /5Phos/TGACCTGAGCTTGGCTGAGCTTGG | /5Phos/GGGACCAAGCTCAGCCAAGCTCAG |
| CTGGATCCGACTGGATCCGA | /5Phos/TGACCTGGATCCGACTGGATCCGA | /5Phos/GGGATCGGATCCAGTCGGATCCAG |
| CTGGTCTGATCTGGTCTGAT | /5Phos/TGACCTGGTCTGATCTGGTCTGAT | /5Phos/GGGAATCAGACCAGATCAGACCAG |
| CTGTCCACAGCTGTCCACAG | /5Phos/TGACCTGTCCACAGCTGTCCACAG | /5Phos/GGGACTGTGGACAGCTGTGGACAG |
| CTGTCCTCCTCTGTCCTCCT | /5Phos/TGACCTGTCCTCCTCTGTCCTCCT | /5Phos/GGGAAGGAGGACAGAGGAGGACAG |
| CTGTCGGATGCTGTCGGATG | /5Phos/TGACCTGTCGGATGCTGTCGGATG | /5Phos/GGGACATCCGACAGCATCCGACAG |
| CTTCATCTGACTTCATCTGA | /5Phos/TGACCTTCATCTGACTTCATCTGA | /5Phos/GGGATCAGATGAAGTCAGATGAAG |
| CTTCCTGCGTCTTCCTGCGT | /5Phos/TGACCTTCCTGCGTCTTCCTGCGT | /5Phos/GGGAACGCAGGAAGACGCAGGAAG |
| CTTCGGCTAGCTTCGGCTAG | /5Phos/TGACCTTCGGCTAGCTTCGGCTAG | /5Phos/GGGACTAGCCGAAGCTAGCCGAAG |
| CTTCTTATGGCTTCTTATGG | /5Phos/TGACCTTCTTATGGCTTCTTATGG | /5Phos/GGGACCATAAGAAGCCATAAGAAG |
| CTTCTTGGATCTTCTTGGAT | /5Phos/TGACCTTCTTGGATCTTCTTGGAT | /5Phos/GGGAATCCAAGAAGATCCAAGAAG |
| CTTGCGATGGCTTGCGATGG | /5Phos/TGACCTTGCGATGGCTTGCGATGG | /5Phos/GGGACCATCGCAAGCCATCGCAAG |
| GAACCTCAGCGAACCTCAGC | /5Phos/TGACGAACCTCAGCGAACCTCAGC | /5Phos/GGGAGCTGAGGTTCGCTGAGGTTC |
| GAACGGATTAGAACGGATTA | /5Phos/TGACGAACGGATTAGAACGGATTA | /5Phos/GGGATAATCCGTTCTAATCCGTTC |
| GAACGTCATTGAACGTCATT | /5Phos/TGACGAACGTCATTGAACGTCATT | /5Phos/GGGAAATGACGTTCAATGACGTTC |
| GAACTGATCCGAACTGATCC | /5Phos/TGACGAACTGATCCGAACTGATCC | /5Phos/GGGAGGATCAGTTCGGATCAGTTC |
| GACAGCAGTCGACAGCAGTC | /5Phos/TGACGACAGCAGTCGACAGCAGTC | /5Phos/GGGAGACTGCTGTCGACTGCTGTC |
| GACCGAATGTGACCGAATGT | /5Phos/TGACGACCGAATGTGACCGAATGT | /5Phos/GGGAACATTCGGTCACATTCGGTC |
| GACGCCATCAGACGCCATCA | /5Phos/TGACGACGCCATCAGACGCCATCA | /5Phos/GGGATGATGGCGTCTGATGGCGTC |
| GACGCGATACGACGCGATAC | /5Phos/TGACGACGCGATACGACGCGATAC | /5Phos/GGGAGTATCGCGTCGTATCGCGTC |
| GACGCTGTGAGACGCTGTGA | /5Phos/TGACGACGCTGTGAGACGCTGTGA | /5Phos/GGGATCACAGCGTCTCACAGCGTC |
| GACGGACCTTGACGGACCTT | /5Phos/TGACGACGGACCTTGACGGACCTT | /5Phos/GGGAAAGGTCCGTCAAGGTCCGTC |
| GACGGAGTCTGACGGAGTCT | /5Phos/TGACGACGGAGTCTGACGGAGTCT | /5Phos/GGGAAGACTCCGTCAGACTCCGTC |
| GAGCACAACCGAGCACAACC | /5Phos/TGACGAGCACAACCGAGCACAACC | /5Phos/GGGAGGTTGTGCTCGGTTGTGCTC |
| GAGGAAGACCGAGGAAGACC | /5Phos/TGACGAGGAAGACCGAGGAAGACC | /5Phos/GGGAGGTCTTCCTCGGTCTTCCTC |
| GAGGCACGATGAGGCACGAT | /5Phos/TGACGAGGCACGATGAGGCACGAT | /5Phos/GGGAATCGTGCCTCATCGTGCCTC |

TABLE 1 -continued

| Tag | Full Oligo Sequence (Top) | Full Oligo Sequence (Bot) |
| --- | --- | --- |
| GAGGTGAAGCGAGGTGAAGC | /5Phos/TGACGAGGTGAAGCGAGGTGAAGC | /5Phos/GGGAGCTTCACCTCGCTTCACCTC |
| GAGTCACACCGAGTCACACC | /5Phos/TGACGAGTCACACCGAGTCACACC | /5Phos/GGGAGGTGTGACTCGGTGTGACTC |
| GAGTCCAGACGAGTCCAGAC | /5Phos/TGACGAGTCCAGACGAGTCCAGAC | /5Phos/GGGAGTCTGGACTCGTCTGGACTC |
| GATAACCTGTGATAACCTGT | /5Phos/TGACGATAACCTGTGATAACCTGT | /5Phos/GGGAACAGGTTATCACAGGTTATC |
| GATCCAAGGCGATCCAAGGC | /5Phos/TGACGATCCAAGGCGATCCAAGGC | /5Phos/GGGAGCCTTGGATCGCCTTGGATC |
| GATCGAGCCAGATCGAGCCA | /5Phos/TGACGATCGAGCCAGATCGAGCCA | /5Phos/GGGATGGCTCGATCTGGCTCGATC |
| GATGGCAATCGATGGCAATC | /5Phos/TGACGATGGCAATCGATGGCAATC | /5Phos/GGGAGATTGCCATCGATTGCCATC |
| GATTACCAACGATTACCAAC | /5Phos/TGACGATTACCAACGATTACCAAC | /5Phos/GGGAGTTGGTAATCGTTGGTAATC |
| GATTCGTCTTGATTCGTCTT | /5Phos/TGACGATTCGTCTTGATTCGTCTT | /5Phos/GGGAAAGACGAATCAAGACGAATC |
| GATTGTTGGAGATTGTTGGA | /5Phos/TGACGATTGTTGGAGATTGTTGGA | /5Phos/GGGATCCAACAATCTCCAACAATC |
| GCAACACGGAGCAACACGGA | /5Phos/TGACGCAACACGGAGCAACACGGA | /5Phos/GGGATCCGTGTTGCTCCGTGTTGC |
| GCAATGGTACGCAATGGTAC | /5Phos/TGACGCAATGGTACGCAATGGTAC | /5Phos/GGGAGTACCATTGCGTACCATTGC |
| GCACCACATTGCACCACATT | /5Phos/TGACGCACCACATTGCACCACATT | /5Phos/GGGAAATGTGGTGCAATGTGGTGC |
| GCAGATTGGCGCAGATTGGC | /5Phos/TGACGCAGATTGGCGCAGATTGGC | /5Phos/GGGAGCCAATCTGCGCCAATCTGC |
| GCAGGATAGCGCAGGATAGC | /5Phos/TGACGCAGGATAGCGCAGGATAGC | /5Phos/GGGAGCTATCCTGCGCTATCCTGC |
| GCATTAATCCGCATTAATCC | /5Phos/TGACGCATTAATCCGCATTAATCC | /5Phos/GGGAGGATTAATGCGGATTAATGC |
| GCCACCATCTGCCACCATCT | /5Phos/TGACGCCACCATCTGCCACCATCT | /5Phos/GGGAAGATGGTGGCAGATGGTGGC |
| GCCAGATACCGCCAGATACC | /5Phos/TGACGCCAGATACCGCCAGATACC | /5Phos/GGGAGGTATCTGGCGGTATCTGGC |
| GCCATAGATAGCCATAGATA | /5Phos/TGACGCCATAGATAGCCATAGATA | /5Phos/GGGATATCTATGGCTATCTATGGC |
| GCCATTGGACGCCATTGGAC | /5Phos/TCCCGCCATTGGACGCCATTGGAC | /5Phos/GTTGGTCCAATGGCGTCCAATGGC |
| GCCGAATCCTGCCGAATCCT | /5Phos/TCCCGCCGAATCCTGCCGAATCCT | /5Phos/GTTGAGGATTCGGCAGGATTCGGC |
| GCCGTGTCTAGCCGTGTCTA | /5Phos/TCCCGCCGTGTCTAGCCGTGTCTA | /5Phos/GTTGTAGACACGGCTAGACACGGC |
| GCCTTATCTCGCCTTATCTC | /5Phos/TCCCGCCTTATCTCGCCTTATCTC | /5Phos/GTTGGAGATAAGGCGAGATAAGGC |
| GCCTTCGCTTGCCTTCGCTT | /5Phos/TCCCGCCTTCGCTTGCCTTCGCTT | /5Phos/GTTGAAGCGAAGGCAAGCGAAGGC |
| GCGAAGTGGTGCGAAGTGGT | /5Phos/TCCCGCGAAGTGGTGCGAAGTGGT | /5Phos/GTTGACCACTTCGCACCACTTCGC |
| GCGAATATCTGCGAATATCT | /5Phos/TCCCGCGAATATCTGCGAATATCT | /5Phos/GTTGAGATATTCGCAGATATTCGC |
| GCGCTGATACGCGCTGATAC | /5Phos/TCCCGCGCTGATACGCGCTGATAC | /5Phos/GTTGGTATCAGCGCGTATCAGCGC |
| GCGGACTTCTGCGGACTTCT | /5Phos/TCCCGCGGACTTCTGCGGACTTCT | /5Phos/GTTGAGAAGTCCGCAGAAGTCCGC |
| GCGGATAAGTGCGGATAAGT | /5Phos/TCCCGCGGATAAGTGCGGATAAGT | /5Phos/GTTGACTTATCCGCACTTATCCGC |
| GCGGTCCATTGCGGTCCATT | /5Phos/TCCCGCGGTCCATTGCGGTCCATT | /5Phos/GTTGAATGGACCGCAATGGACCGC |
| GCTCAGTTAAGCTCAGTTAA | /5Phos/TCCCGCTCAGTTAAGCTCAGTTAA | /5Phos/GTTGTTAACTGAGCTTAACTGAGC |
| GCTCATTCTAGCTCATTCTA | /5Phos/TCCCGCTCATTCTAGCTCATTCTA | /5Phos/GTTGTAGAATGAGCTAGAATGAGC |
| GCTCCTAAGCGCTCCTAAGC | /5Phos/TCCCGCTCCTAAGCGCTCCTAAGC | /5Phos/GTTGGCTTAGGAGCGCTTAGGAGC |
| GCTGGAAGGAGCTGGAAGGA | /5Phos/TCCCGCTGGAAGGAGCTGGAAGGA | /5Phos/GTTGTCCTTCCAGCTCCTTCCAGC |
| GGAACAATGTGGAACAATGT | /5Phos/TCCCGGAACAATGTGGAACAATGT | /5Phos/GTTGACATTGTTCCACATTGTTCC |
| GGAACATCGGAACATCTC | /5Phos/TCCCGGAACATCTCGGAACATCTC | /5Phos/GTTGGAGATGTTCCGAGATGTTCC |
| GGAACCAGTAGGAACCAGTA | /5Phos/TCCCGGAACCAGTAGGAACCAGTA | /5Phos/GTTGTACTGGTTCCTACTGGTTCC |
| GGAACGACTTGGAACGACTT | /5Phos/TCCCGGAACGACTTGGAACGACTT | /5Phos/GTTGAAGTCGTTCCAAGTCGTTCC |
| GGAAGATGATGGAAGATGAT | /5Phos/TCCCGGAAGATGATGGAAGATGAT | /5Phos/GTTGATCATCTTCCATCATCTTCC |
| GGAAGGAGACGAAGGAGAC | /5Phos/TCCCGGAAGGAGACGAAGGAGAC | /5Phos/GTTGGTCTCCTTCCGTCTCCTTCC |
| GGAAGTGGTAGGAAGTGGTA | /5Phos/TCCCGGAAGTGGTAGGAAGTGGTA | /5Phos/GTTGTACCACTTCCTACCACTTCC |
| GGAATCAGGTGGAATCAGGT | /5Phos/TCCCGGAATCAGGTGGAATCAGGT | /5Phos/GTTGACCTGATTCCACCTGATTCC |
| GGAATGTGTAGGAATGTGTA | /5Phos/TCCCGGAATGTGTAGGAATGTGTA | /5Phos/GTTGTACATTCCTACACATTCC |
| GGAGATAGGAGAGATAGGA | /5Phos/TCCCGGAGATAGGAGAGATAGGA | /5Phos/GTTGTCCTATCTCCTATCTCC |
| GGAGCAATCCGGAGCAATCC | /5Phos/TCCCGGAGCAATCCGGAGCAATCC | /5Phos/GTTGGGATTGCTCCGGATTGCTCC |
| GGAGGACATCGGAGGACATC | /5Phos/TCCCGGAGGACATCGGAGGACATC | /5Phos/GTTGGATGTCCTCCGATGTCCTCC |
| GGCAATAGCCGGCAATAGCC | /5Phos/TCCCGGCAATAGCCGGCAATAGCC | /5Phos/GTTGGGCTATTGCCGGCTATTGCC |
| GGCAGAAGGAGGCAGAAGGA | /5Phos/TCCCGGCAGAAGGAGGCAGAAGGA | /5Phos/GTTGTCCTTCTGCCTCCTTCTGCC |
| GGCAGGAATAGGCAGGAATA | /5Phos/TCCCGGCAGGAATAGGCAGGAATA | /5Phos/GTTGTATTCCTGCCTATTCCTGCC |
| GGCATACACCGGCATACACC | /5Phos/TCCCGGCATACACCGGCATACACC | /5Phos/GTTGGGTGTATGCCGGTGTATGCC |
| GGCCGTTGTAGGCCGTTGTA | /5Phos/TCCCGGCCGTTGTAGGCCGTTGTA | /5Phos/GTTGTACAACGGCCTACAACGGCC |
| GGCCTGCTTAGGCCTGCTTA | /5Phos/TCCCGGCCTGCTTAGGCCTGCTTA | /5Phos/GTTGTAAGCAGGCCTAAGCAGGCC |
| GGCGAGGTAAGGCGAGGTAA | /5Phos/TCCCGGCGAGGTAAGGCGAGGTAA | /5Phos/GTTGTTACCTCGCCTTACCTCGCC |
| GGCGTGACATGGCGTGACAT | /5Phos/TCCCGGCGTGACATGGCGTGACAT | /5Phos/GTTGATGTCACGCCATGTCACGCC |
| GGCTCCAAGAGGCTCCAAGA | /5Phos/TCCCGGCTCCAAGAGGCTCCAAGA | /5Phos/GTTGTCTTGGAGCCTCTTGGAGCC |
| GGCTGCTCAAGGCTGCTCAA | /5Phos/TCCCGGCTGCTCAAGGCTGCTCAA | /5Phos/GTTGTTGAGCAGCCTTGAGCAGCC |
| GGCTGTGCTTGGCTGTGCTT | /5Phos/TCCCGGCTGTGCTTGGCTGTGCTT | /5Phos/GTTGAAGCACAGCCAAGCACAGCC |
| GGCTTCGTCGGCTTCGTC | /5Phos/TCCCGGCTTCGTCGGCTTCGTC | /5Phos/GTTGGACAGAAGCCGACAGAAGCC |
| GGTATCGCTTGGTATCGCTT | /5Phos/TCCCGGTATCGCTTGGTATCGCTT | /5Phos/GTTGAAGCGATACCAAGCGATACC |
| GGTCCTTCCAGGTCCTTCCA | /5Phos/TCCCGGTCCTTCCAGGTCCTTCCA | /5Phos/GTTGTGGAAGGACCTGGAAGGACC |
| GGTCGGTTATGGTCGGTTAT | /5Phos/TCCCGGTCGGTTATGGTCGGTTAT | /5Phos/GTTGATAACCGACCATAACCGACC |
| GGTCTGACGAGGTCTGACGA | /5Phos/TCCCGGTCTGACGAGGTCTGACGA | /5Phos/GTTGTCGTCAGACCTCGTCAGACC |
| GGTGACCACTGGTGACCACT | /5Phos/TCCCGGTGACCACTGGTGACCACT | /5Phos/GTTGAGTGGTCACCAGTGGTCACC |
| GGTGAGTCCAGGTGAGTCCA | /5Phos/TCCCGGTGAGTCCAGGTGAGTCCA | /5Phos/GTTGTGGACTCACCTGGACTCACC |
| GGTGGCAATGGGTGGCAAT | /5Phos/TCCCGGTGGCAATGGTGGCAAT | /5Phos/GTTGATTCGCCACCATTGCCACC |
| GGTGTATATCGGTGTATATC | /5Phos/TCCCGGTGTATATCGGTGTATATC | /5Phos/GTTGGATATACACCGATATACACC |
| GGTTCCTTAAGGTTCCTTAA | /5Phos/TCCCGGTTCCTTAAGGTTCCTTAA | /5Phos/GTTGTTAAGGAACCTTAAGGAACC |
| GGTTCTACAAGGTTCTACAA | /5Phos/TCCCGGTTCTACAAGGTTCTACAA | /5Phos/GTTGTTGTAGAACCTTGTAGAACC |
| GGTTGGCGTTGGTTGGCGTT | /5Phos/TCCCGGTTGGCGTTGGTTGGCGTT | /5Phos/GTTGAACGCCAACCAACGCCAACC |
| GTAACACGCTGTAACACGCT | /5Phos/TCCCGTAACACGCTGTAACACGCT | /5Phos/GTTGAGCGTGTTACAGCGTGTTAC |
| GTAGAGCGACGTAGAGCGAC | /5Phos/TCCCGTAGAGCGACGTAGAGCGAC | /5Phos/GTTGGTCGCTCTACGTCGCTCTAC |
| GTAGCTGCTCGTAGCTGCTC | /5Phos/TCCCGTAGCTGCTCGTAGCTGCTC | /5Phos/GTTGGAGCAGCTACGAGCAGCTAC |
| GTAGGTGGATGTAGGTGGAT | /5Phos/TCCCGTAGGTGGATGTAGGTGGAT | /5Phos/GTTGATCCACCTACATCCACCTAC |
| GTAGTCAGCCGTAGTCAGCC | /5Phos/TCCCGTAGTCAGCCGTAGTCAGCC | /5Phos/GTTGGGCTGACTACGGCTGACTAC |
| GTCCTTCCACGTCCTTCCAC | /5Phos/TCCCGTCCTTCCACGTCCTTCCAC | /5Phos/GTTGGTGGAAGGACGTGGAAGGAC |
| GTCGAGCAGTGTCGAGCAGT | /5Phos/TCCCGTCGAGCAGTGTCGAGCAGT | /5Phos/GTTGACTGCTCGACACTGCTCGAC |
| GTCGCACAGAGTCGCACAGA | /5Phos/TCCCGTCGCACAGAGTCGCACAGA | /5Phos/GTTGTCTGTGCGACTCTGTGCGAC |
| GTCGCACTTCGTCGCACTTC | /5Phos/TCCCGTCGCACTTCGTCGCACTTC | /5Phos/GTTGGAAGTGCGACGAAGTGCGAC |

TABLE 1 -continued

| Tag | Full Oligo Sequence (Top) | Full Oligo Sequence (Bot) |
|---|---|---|
| GTCTGGTGGTGTCTGGTGGT | /5Phos/TCCCGTCTGGTGGTGTCTGGTGGT | /5Phos/GTTGACCACCAGACACCACCAGAC |
| GTGAACTGTTGTGAACTGTT | /5Phos/TCCCGTGAACTGTTGTGAACTGTT | /5Phos/GTTGAACAGTTCACAACAGTTCAC |
| GTGCCATCCTGTGCCATCCT | /5Phos/TCCCGTGCCATCCTGTGCCATCCT | /5Phos/GTTGAGGATGGCACAGGATGGCAC |
| GTGCGTGAACGTGCGTGAAC | /5Phos/TCCCGTGCGTGAACGTGCGTGAAC | /5Phos/GTTGGTTCACGCACGTTCACGCAC |
| GTGGAGATGTGTGGAGATGT | /5Phos/TCCCGTGGAGATGTGTGGAGATGT | /5Phos/GTTGACATCTCCACACATCTCCAC |
| GTGGTGCAACGTGGTGCAAC | /5Phos/TCCCGTGGTGCAACGTGGTGCAAC | /5Phos/GTTGGTTGCACCACGTTGCACCAC |
| GTGTCGTTAAGTGTCGTTAA | /5Phos/TCCCGTGTCGTTAAGTGTCGTTAA | /5Phos/GTTGTTAACGACACTTAACGACAC |
| GTGTCTCAATGTGTCTCAAT | /5Phos/TCCCGTGTCTCAATGTGTCTCAAT | /5Phos/GTTGATTGAGACACATTGAGACAC |
| GTGTGATGACGTGTGATGAC | /5Phos/TCCCGTGTGATGACGTGTGATGAC | /5Phos/GTTGGTCATCACACGTCATCACAC |
| GTTAGATCGCGTTAGATCGC | /5Phos/TCCCGTTAGATCGCGTTAGATCGC | /5Phos/GTTGGCGATCTAACGCGATCTAAC |
| TAAGCCGATATAAGCCGATA | /5Phos/TCCCTAAGCCGATATAAGCCGATA | /5Phos/GTTGTATCGGCTTATATCGGCTTA |
| TAAGGACACCTAAGGACACC | /5Phos/TCCCTAAGGACACCTAAGGACACC | /5Phos/GTTGGGTGTCCTTAGGTGTCCTTA |
| TAAGGCCAAGTAAGGCCAAG | /5Phos/TCCCTAAGGCCAAGTAAGGCCAAG | /5Phos/GTTGCTTGGCCTTACTTGGCCTTA |
| TAATAGCGAGTAATAGCGAG | /5Phos/TCCCTAATAGCGAGTAATAGCGAG | /5Phos/GTTGCTCGCTATTACTCGCTATTA |
| TAATGGCCGGTAATGGCCGG | /5Phos/TCCCTAATGGCCGGTAATGGCCGG | /5Phos/GTTGCCGGCCATTACCGGCCATTA |
| TACCATTGGATACCATTGGA | /5Phos/TCCCTACCATTGGATACCATTGGA | /5Phos/GTTGTCCAATGGTATCCAATGGTA |
| TACGACCACCTACGACCACC | /5Phos/TCCCTACGACCACCTACGACCACC | /5Phos/GTTGGGGTGGTCGTAGGTGGTCGTA |
| TACGACCTTATACGACCTTA | /5Phos/TCCCTACGACCTTATACGACCTTA | /5Phos/GTTGTAAGGTCGTATAAGGTCGTA |
| TACGTGATTCTACGTGATTC | /5Phos/TCCCTACGTGATTCTACGTGATTC | /5Phos/GTTGGAATCACGTAGAATCACGTA |
| TACTAGTCAGTACTAGTCAG | /5Phos/TCCCTACTAGTCAGTACTAGTCAG | /5Phos/GTTGCTGACTAGTACTGACTAGTA |
| TACTGACAAGTACTGACAAG | /5Phos/TCCCTACTGACAAGTACTGACAAG | /5Phos/GTTGCTTGTCAGTACTTGTCAGTA |
| TACTGCTGGCTACTGCTGGC | /5Phos/TCCCTACTGCTGGCTACTGCTGGC | /5Phos/GTTGGCCAGCAGTAGCCAGCAGTA |
| TAGACCGTAATAGACCGTAA | /5Phos/TCCCTAGACCGTAATAGACCGTAA | /5Phos/GTTGTTACGGTCTATTACGGTCTA |
| TAGACGAAGATAGACGAAGA | /5Phos/TCCCTAGACGAAGATAGACGAAGA | /5Phos/GTTGTCTTCGTCTATCTTCGTCTA |
| TAGCCTAGCCTAGCCTAGCC | /5Phos/TCCCTAGCCTAGCCTAGCCTAGCC | /5Phos/GTTGGGCTAGGCTAGGCTAGGCTA |
| TAGCGAATTCTAGCGAATTC | /5Phos/TCCCTAGCGAATTCTAGCGAATTC | /5Phos/GTTGGAATTCGCTAGAATTCGCTA |
| TAGCTGCCACTAGCTGCCAC | /5Phos/TCCCTAGCTGCCACTAGCTGCCAC | /5Phos/GTTGGTGGCAGCTAGTGGCAGCTA |
| TAGGTAGGCATAGGTAGGCA | /5Phos/TCCCTAGGTAGGCATAGGTAGGCA | /5Phos/GTTGTGCCTACCTATGCCTACCTA |
| TAGTCGTTACTAGTCGTTAC | /5Phos/TCCCTAGTCGTTACTAGTCGTTAC | /5Phos/GTTGGTAACGACTAGTAACGACTA |
| TAGTGCGAAGTAGTGCGAAG | /5Phos/TCCCTAGTGCGAAGTAGTGCGAAG | /5Phos/GTTGCTTCGCACTACTTCGCACTA |
| TAGTGGACGCTAGTGGACGC | /5Phos/TCCCTAGTGGACGCTAGTGGACGC | /5Phos/GTTGGCGTCCACTAGCCGTCCACTA |
| TATAACGGTGTATAACGGTG | /5Phos/TCCCTATAACGGTGTATAACGGTG | /5Phos/GTTGCACCGTTATACACCGTTATA |
| TATAGAACCGTATAGAACCG | /5Phos/TCCCTATAGAACCGTATAGAACCG | /5Phos/GTTGCGGTTCTATACGGTTCTATA |
| TATCCGAAGGTATCCGAAGG | /5Phos/TCCCTATCCGAAGGTATCCGAAGG | /5Phos/GTTGCCTTCGGATACCTTCGGATA |
| TATCGGAGCCTATCGGAGCC | /5Phos/TCCCTATCGGAGCCTATCGGAGCC | /5Phos/GTTGGGCTCCGATAGGCTCCGATA |
| TATCGGCCTGTATCGGCCTG | /5Phos/TCCCTATCGGCCTGTATCGGCCTG | /5Phos/GTTGCAGGCCGATACAGGCCGATA |
| TATCGTCGGCTATCGTCGGC | /5Phos/TCCCTATCGTCGGCTATCGTCGGC | /5Phos/GTTGGCCGACGATAGCCGACGATA |
| TATGCGCCACTATGCGCCAC | /5Phos/TCCCTATGCGCCACTATGCGCCAC | /5Phos/GTTGGTGGCGCATAGTGGCGCATA |
| TATGGCCGTCTATGGCCGTC | /5Phos/TCCCTATGGCCGTCTATGGCCGTC | /5Phos/GTTGGACGGCCATAGACGGCCATA |
| TATTCTTCCGTATTCTTCCG | /5Phos/TCCCTATTCTTCCGTATTCTTCCG | /5Phos/GTTGCGGAAGAATACGGAAGAATA |
| TCAAGCAACGTCAAGCAACG | /5Phos/TCCCTCAAGCAACGTCAAGCAACG | /5Phos/GTTGCGTTGCTTGACGTTGCTTGA |
| TCAAGCAGTCTCAAGCAGTC | /5Phos/TCCCTCAAGCAGTCTCAAGCAGTC | /5Phos/GTTGGACTGCTTGAGACTGCTTGA |
| TCAAGTCCGATCAAGTCCGA | /5Phos/TCCCTCAAGTCCGATCAAGTCCGA | /5Phos/GTTGTCGGACTTGATCGGACTTGA |
| TCAATCGAGATCAATCGAGA | /5Phos/TCCCTCAATCGAGATCAATCGAGA | /5Phos/GTTGTCTCGATTGATCTCGATTGA |
| TCAATGTCGATCAATGTCGA | /5Phos/TCCCTCAATGTCGATCAATGTCGA | /5Phos/GTTGTCGACATTGATCGACATTGA |
| TCACTGAGGCTCACTGAGGC | /5Phos/TCCCTCACTGAGGCTCACTGAGGC | /5Phos/GTTGGCCTCAGTGAGCCTCAGTGA |
| TCAGCGAGACTCAGCGAGAC | /5Phos/TCCCTCAGCGAGACTCAGCGAGAC | /5Phos/GTTGGTCTCGCTGAGTCTCGCTGA |
| TCAGGAGGAATCAGGAGGAA | /5Phos/TCCCTCAGGAGGAATCAGGAGGAA | /5Phos/GTTGTTCCTCCTGATTCCTCCTGA |
| TCAGGCACAGTCAGGCACAG | /5Phos/TCCCTCAGGCACAGTCAGGCACAG | /5Phos/GTTGCTGTGCCTGACTGTGCCTGA |
| TCAGGCTTCCTCAGGCTTCC | /5Phos/TCCCTCAGGCTTCCTCAGGCTTCC | /5Phos/GTTGGGAAGCCTGAGGAAGCCTGA |
| TCCACACTCGTCCACACTCG | /5Phos/TCCCTCCACACTCGTCCACACTCG | /5Phos/GTTGCGAGTGTGGACGAGTGTGGA |
| TCCACAGCGATCCACAGCGA | /5Phos/TCCCTCCACAGCGATCCACAGCGA | /5Phos/GTTGTCGCTGTGGATCGCTGTGGA |
| TCCAGCTGCATCCAGCTGCA | /5Phos/TCCCTCCAGCTGCATCCAGCTGCA | /5Phos/GTTGTGCAGCTGGATGCAGCTGGA |
| TCCATAATCCTCCATAATCC | /5Phos/TCCCTCCATAATCCTCCATAATCC | /5Phos/GTTGGGATTATGGAGGATTATGGA |
| TCCGGACCAATCCGGACCAA | /5Phos/TCCCTCCGGACCAATCCGGACCAA | /5Phos/GTTGTTGGTCCGGATTGGTCCGGA |
| TCCGTAACGGTCCGTAACGG | /5Phos/TCCCTCCGTAACGGTCCGTAACGG | /5Phos/GTTGCCGTTACGGACCGTTACGGA |
| TCCGTAGGTCTCCGTAGGTC | /5Phos/TCCCTCCGTAGGTCTCCGTAGGTC | /5Phos/GTTGGACCTACGGAGACCTACGGA |
| TCCGTCCAAGTCCGTCCAAG | /5Phos/TCCCTCCGTCCAAGTCCGTCCAAG | /5Phos/GTTGCTTGGACGGACTTGGACGGA |
| TCCTGAACCGTCCTGAACCG | /5Phos/TCCCTCCTGAACCGTCCTGAACCG | /5Phos/GTTGCGGTTCAGGACGGTTCAGGA |
| TCCTGGCATGTCCTGGCATG | /5Phos/TCCCTCCTGGCATGTCCTGGCATG | /5Phos/GTTGCATGCCAGGACATGCCAGGA |
| TCGCGCTACATCGCGCTACA | /5Phos/TCCCTCGCGCTACATCGCGCTACA | /5Phos/GTTGTGTAGCGCGATGTAGCGCGA |
| TCGGTTACCATCGGTTACCA | /5Phos/TCCCTCGGTTACCATCGGTTACCA | /5Phos/GTTGTGGTAACCGATGGTAACCGA |
| TCGTCCGTCATCGTCCGTCA | /5Phos/TCCCTCGTCCGTCATCGTCCGTCA | /5Phos/GTTGTGACGGACGATGACGGACGA |
| TCGTCCTCAGTCGTCCTCAG | /5Phos/TCCCTCGTCCTCAGTCGTCCTCAG | /5Phos/GTTGCTGAGGACGACTGAGGACGA |
| TCTACCGCTCTCTACCGCTC | /5Phos/TCCCTCTACCGCTCTCTACCGCTC | /5Phos/GTTGGAGCGGTAGAGAGCGGTAGA |
| TCTAGCTCGGTCTAGCTCGG | /5Phos/TCCCTCTAGCTCGGTCTAGCTCGG | /5Phos/GTTGCCGAGCTAGACCGAGCTAGA |
| TCTCGGCTGATCTCGGCTGA | /5Phos/TCCCTCTCGGCTGATCTCGGCTGA | /5Phos/GTTGTCAGCCGAGATCAGCCGAGA |
| TCTCGGTCAGTCTCGGTCAG | /5Phos/TCCCTCTCGGTCAGTCTCGGTCAG | /5Phos/GTTGCTGACCGAGACTGACCGAGA |
| TCTCTAGATCTCTCTAGATC | /5Phos/TCCCTCTCTAGATCTCTCTAGATC | /5Phos/GTTGGATCTAGAGATCTAGAGA |
| TCTGACCGCATCTGACCGCA | /5Phos/TCCCTCTGACCGCATCTGACCGCA | /5Phos/GTTGTGCGGTCAGATGCGGTCAGA |
| TCTGGACAGATCTGGACAGA | /5Phos/TCCCTCTGGACAGATCTGGACAGA | /5Phos/GTTGTCTGTCCAGATCTGTCCAGA |
| TCTGGATAAGTCTGGATAAG | /5Phos/TCCCTCTGGATAAGTCTGGATAAG | /5Phos/GTTGCTTATCCAGACTTATCCAGA |
| TCTTACGGCCTCTTACGGCC | /5Phos/TCCCTCTTACGGCCTCTTACGGCC | /5Phos/GTTGGGCCGTAAGAGGCCGTAAGA |
| TCTTGCATACTCTTGCATAC | /5Phos/TCCCTCTTGCATACTCTTGCATAC | /5Phos/GTTGTATGCAAGAGTATGCAAGA |
| TGAACTTGGATGAACTTGGA | /5Phos/TCCCTGAACTTGGATGAACTTGGA | /5Phos/GTTGTCCAAGTTCATCCAAGTTCA |
| TGACACAGCGTGACACAGCG | /5Phos/TCCCTGACACAGCGTGACACAGCG | /5Phos/GTTGCGCTGTGTCACGCTGTGTCA |
| TGACAGGTCCTGACAGGTCC | /5Phos/TCCCTGACAGGTCCTGACAGGTCC | /5Phos/GTTGGGACCTGTCAGGACCTGTCA |
| TGACCTTCCGTGACCTTCCG | /5Phos/TCCCTGACCTTCCGTGACCTTCCG | /5Phos/GTTGCGGAAGGTCACGGAAGGTCA |

TABLE 1 -continued

| Tag | Full Oligo Sequence (Top) | Full Oligo Sequence (Bot) |
|---|---|---|
| TGACGTCGGATGACGTCGGA | /5Phos/TCCCTGACGTCGGATGACGTCGGA | /5Phos/GTTGTCCGACGTCATCCGACGTCA |
| TGACTATCTCTGACTATCTC | /5Phos/TCCCTGACTATCTCTGACTATCTC | /5Phos/GTTGGAGATAGTCAGAGATAGTCA |
| TGACTCCAGGTGACTCCAGG | /5Phos/TCCCTGACTCCAGGTGACTCCAGG | /5Phos/GTTGCCTGGAGTCACCTGGAGTCA |
| TGAGAGCAGGTGAGAGCAGG | /5Phos/TCCCTGAGAGCAGGTGAGAGCAGG | /5Phos/GTTGCCTGCTCTCACCTGCTCTCA |
| TGAGCCTCCATGAGCCTCCA | /5Phos/TCCCTGAGCCTCCATGAGCCTCCA | /5Phos/GTTGTGGAGGCTCATGGAGGCTCA |
| TGAGTATGGATGAGTATGGA | /5Phos/TCCCTGAGTATGGATGAGTATGGA | /5Phos/GTTGTCCATACTCATCCATACTCA |
| TGCAACATACTGCAACATAC | /5Phos/TCCCTGCAACATACTGCAACATAC | /5Phos/GTTGGTATGTTGCAGTATGTTGCA |
| TGCGCTGTAGTGCGCTGTAG | /5Phos/TCCCTGCGCTGTAGTGCGCTGTAG | /5Phos/GTTGCTACAGCGCACTACAGCGCA |
| TGCTAACCGGTGCTAACCGG | /5Phos/TCCCTGCTAACCGGTGCTAACCGG | /5Phos/GTTGCCGGTTAGCACCGGTTAGCA |
| TGCTCCACTGTGCTCCACTG | /5Phos/TCCCTGCTCCACTGTGCTCCACTG | /5Phos/GTTGCAGTGGAGCACAGTGGAGCA |
| TGGAAGGAGCTGGAAGGAGC | /5Phos/TCCCTGGAAGGAGCTGGAAGGAGC | /5Phos/GTTGGCTCCTTCCAGCTCCTTCCA |
| TGGCAGTGACTGGCAGTGAC | /5Phos/TCCCTGGCAGTGACTGGCAGTGAC | /5Phos/GTTGGTCACTGCCAGTCACTGCCA |
| TGGCATCAGCTGGCATCAGC | /5Phos/TCCCTGGCATCAGCTGGCATCAGC | /5Phos/GTTGGCTGATGCCAGCTGATGCCA |
| TGGCCTTATATGGCCTTATA | /5Phos/TCCCTGGCCTTATATGGCCTTATA | /5Phos/GTTGTATAAGGCCATATAAGGCCA |
| TGGCGAAGCATGGCGAAGCA | /5Phos/TCCCTGGCGAAGCATGGCGAAGCA | /5Phos/GTTGTGCTTCGCCATGCTTCGCCA |
| TGGCTTAAGATGGCTTAAGA | /5Phos/TCCCTGGCTTAAGATGGCTTAAGA | /5Phos/GTTGTCTTAAGCCATCTTAAGCCA |
| TGGTCAGCTCTGGTCAGCTC | /5Phos/TCCCTGGTCAGCTCTGGTCAGCTC | /5Phos/GTTGGAGCTGACCAGAGCTGACCA |
| TGGTTCCAACTGGTTCCAAC | /5Phos/TCCCTGGTTCCAACTGGTTCCAAC | /5Phos/GTTGGTTGGAACCAGTTGGAACCA |
| TGGTTGGTAATGGTTGGTAA | /5Phos/TCCCTGGTTGGTAATGGTTGGTAA | /5Phos/GTTGTTACCAACCATTACCAACCA |
| TGTACGCGCATGTACGCGCA | /5Phos/TCCCTGTACGCGCATGTACGCGCA | /5Phos/GTTGTGCGCGTACATGCGCGTACA |
| TGTACGCTGGTGTACGCTGG | /5Phos/TCCCTGTACGCTGGTGTACGCTGG | /5Phos/GTTGCCAGCGTACACCAGCGTACA |
| TGTAGCATTGTGTAGCATTG | /5Phos/TCCCTGTAGCATTGTGTAGCATTG | /5Phos/GTTGCAATGCTACACAATGCTACA |
| TGTAGTGCCGTGTAGTGCCG | /5Phos/TCCCTGTAGTGCCGTGTAGTGCCG | /5Phos/GTTGCGGCACTACACGGCACTACA |
| TGTGAATCTGTGTGAATCTG | /5Phos/TCCCTGTGAATCTGTGTGAATCTG | /5Phos/GTTGCAGATTCACACAGATTCACA |
| TGTTCCGTGGTGTTCCGTGG | /5Phos/TCCCTGTTCCGTGGTGTTCCGTGG | /5Phos/GTTGCCACGGAACACCACGGAACA |
| TTAGCGCGTGTTAGCGCGTG | /5Phos/TCCCTTAGCGCGTGTTAGCGCGTG | /5Phos/GTTGCACGCGCTAACACGCGCTAA |
| TTAGTTGGACTTAGTTGGAC | /5Phos/TCCCTTAGTTGGACTTAGTTGGAC | /5Phos/GTTGGTCCAACTAAGTCCAACTAA |
| TTCCAACTTCTTCCAACTTC | /5Phos/TCCCTTCCAACTTCTTCCAACTTC | /5Phos/GTTGGAAGTTGGAAGAAGTTGGAA |
| TTCCGTCAGGTTCCGTCAGG | /5Phos/TCCCTTCCGTCAGGTTCCGTCAGG | /5Phos/GTTGCCTGACGGAACCTGACGGAA |
| TTCCTCACCGTTCCTCACCG | /5Phos/TCCCTTCCTCACCGTTCCTCACCG | /5Phos/GTTGCGGTGAGGAACGGTGAGGAA |
| TTCCTCCGACTTCCTCCGAC | /5Phos/TCCCTTCCTCCGACTTCCTCCGAC | /5Phos/GTTGGTCGGAGGAAGTCGGAGGAA |
| TTCGACCTGGTTCGACCTGG | /5Phos/TCCCTTCGACCTGGTTCGACCTGG | /5Phos/GTTGCCAGGTCGAACCAGGTCGAA |
| TTCGCGTGGATTCGCGTGGA | /5Phos/TCCCTTCGCGTGGATTCGCGTGGA | /5Phos/GTTGTCCACGCGAATCCACGCGAA |
| TTCGGAAGCGTTCGGAAGCG | /5Phos/TCCCTTCGGAAGCGTTCGGAAGCG | /5Phos/GTTGCGCTTCCGAACGCTTCCGAA |
| TTCTCGATTGTTCTCGATTG | /5Phos/TCCCTTCTCGATTGTTCTCGATTG | /5Phos/GTTGCAATCGAGAACAATCGAGAA |
| TTCTCTCTAGTTCTCTCTAG | /5Phos/TCCCTTCTCTCTAGTTCTCTCTAG | /5Phos/GTTGCTAGAGAGAACTAGAGAGAA |
| TTCTTGCGCGTTCTTGCGCG | /5Phos/TCCCTTCTTGCGCGTTCTTGCGCG | /5Phos/GTTGCGCGCAAGAACGCGCAAGAA |
| TTGAGGTCGGTTGAGGTCGG | /5Phos/TCCCTTGAGGTCGGTTGAGGTCGG | /5Phos/GTTGCCGACCTCAACCGACCTCAA |
| TTGCACACGCTTGCACACGC | /5Phos/TCCCTTGCACACGCTTGCACACGC | /5Phos/GTTGGCGTGTGCAAGCGTGTGCAA |
| TTGCGCTCTGTTGCGCTCTG | /5Phos/TCCCTTGCGCTCTGTTGCGCTCTG | /5Phos/GTTGCAGAGCGCAACAGAGCGCAA |
| TTGCTGCAGCTTGCTGCAGC | /5Phos/TCCCTTGCTGCAGCTTGCTGCAGC | /5Phos/GTTGGCTGCAGCAAGCTGCAGCAA |
| TTGGCGTCTGTTGGCGTCTG | /5Phos/TCCCTTGGCGTCTGTTGGCGTCTG | /5Phos/GTTGCAGACGCCAACAGACGCCAA |
| TTGGTCCTTCTTGGTCCTTC | /5Phos/TCCCTTGGTCCTTCTTGGTCCTTC | /5Phos/GTTGGAAGGACCAAGAAGGACCAA |
| TTGTCGAGAGTTGTCGAGAG | /5Phos/TCCCTTGTCGAGAGTTGTCGAGAG | /5Phos/GTTGCTCTCGACAACTCTCGACAA |
| TTGTCTGTACTTGTCTGTAC | /5Phos/TCCCTTGTCTGTACTTGTCTGTAC | /5Phos/GTTGGTACAGACAAGTACAGACAA |
| TTGTTCTCTCTTGTTCTCTC | /5Phos/TCCCTTGTTCTCTCTTGTTCTCTC | /5Phos/GTTGGAGAGAACAAGAGAGAACAA |
| AACACACGTTAACACACGTT | /5Phos/TCCCAACACACGTTAACACACGTT | /5Phos/GTTGAACGTGTGTTAACGTGTGTT |
| AACATCGAGTAACATCGAGT | /5Phos/TCCCAACATCGAGTAACATCGAGT | /5Phos/GTTGACTCGATGTTACTCGATGTT |
| AACCGAGGACAACCGAGGAC | /5Phos/TCCCAACCGAGGACAACCGAGGAC | /5Phos/GTTGGTCCTCGGTTGTCCTCGGTT |
| AACCTAGTAGAACCTAGTAG | /5Phos/TCCCAACCTAGTAGAACCTAGTAG | /5Phos/GTTGCTACTAGGTTCTACTAGGTT |
| AACGCATACTAACGCATACT | /5Phos/TCCCAACGCATACTAACGCATACT | /5Phos/GTTGAGTATGCGTTAGTATGCGTT |
| AACTAACCTCAACTAACCTC | /5Phos/TCCCAACTAACCTCAACTAACCTC | /5Phos/GTTGGAGGTTAGTTGAGGTTAGTT |
| AACTAAGGAGAACTAAGGAG | /5Phos/TCCCAACTAAGGAGAACTAAGGAG | /5Phos/GTTGCTCCTTAGTTCTCCTTAGTT |
| AACTCGTTCTAACTCGTTCT | /5Phos/TCCCAACTCGTTCTAACTCGTTCT | /5Phos/GTTGAGAACGAGTTAGAACGAGTT |
| AACTGCCGCTAACTGCCGCT | /5Phos/TCCCAACTGCCGCTAACTGCCGCT | /5Phos/GTTGAGCGGCAGTTAGCGGCAGTT |

Each unique label may comprise two or more detectable oligonucleotide tags. The two or more tags may be three or more tags, four or more tags, or five or more tags. In some embodiments, a unique label may comprise 2, 3, 4, 5, 6, 7, 8, 9, 10, 15, 20, 30, 40, 50, 100 or more detectable tags.

The tags are typically bound to each other, typically in a directional manner. Methods for sequentially attaching nucleic acids such as oligonucleotides to each other are known in the art and include, but are not limited to, ligation and polymerization, or a combination of both (see, e.g., Green and Sambrook. Molecular Cloning: A Laboratory Manual, Fourth Edition, 2012). Ligation reactions include blunt end ligation and cohesive overhang ligation. In some instances, ligation may comprise both blunt end and cohesive overhang ligation. A "cohesive overhang" (also referred to as a "cohesive end" or an "overhang") is a single stranded end sequence (attached to a double stranded sequence) capable of binding to another single stranded sequence thereby forming a double stranded sequence. A cohesive overhang may be generated by a polymerase, a restriction endonuclease, a combination of a polymerase and a restriction endonuclease, or a Uracil-Specific Excision Reagent (USER™) enzyme (New England BioLabs Inc., Ipswich, Mass.) or a combination of a Uracil DNA glycosylase enzyme and a DNA glycosylase-lyase Exonuclease VIII enzyme. A "cohesive overhang" may be a thymidine tail. Polymerization reactions include enzyme-mediated polymerization such as a polymerase-mediated fill-reaction.

Methods for detecting and analyzing unique labels are known in the art. In some embodiments, detection may comprise determining the presence, number, and/or order of detectable tags that may comprise a unique label. For example, if the unique label may comprise detectable moieties, as described herein, fluorometry, mass spectrometry, or other detection methodology can be used for detection. In another example, if the unique label may comprise unique nucleotide sequences, a sequencing methodology can be used for detection. If the unique label may comprise both unique sequences and detectable moieties, a combination of detection methods may be appropriate, e.g., fluorometry and a sequencing reaction.

Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem. 136:192 (1984); and Elgen and Rigler, Proc. Natl. Acad. Sci. USA 91(13):5740 (1994), all of which are expressly incorporated by reference).

Methods of detecting moieties, such as but not limited to fluorophores, are known in the art. (see, e.g., WO199641011; WO2000006770; WO2002072892; WO2007123744; Leroi V. DeSouza, K. W. Michael Siu, Ronald E. Pearlman. Mass. Spectrometry: An Outsourcing Guide. Current Protocols Essential Laboratory Techniques. 2:12.2.1-12.1.18. 2009; Domon, B. and Aebersold, R. Mass spectrometry and protein analysis. Science 312:212-217. 2006.; Current Protocols in Imaging and Microscopy, and Current Protocols in Cell Biology, the entirety of which are incorporated herein by reference). In some embodiments, fluorophores such as nanocrystal quantum dots can be used to dynamically create unique combinations of labels. Quantum dots are nanometer-sized particles which may be comprised of semiconductor material that, when excited with ultraviolet light, emit specific wavelengths of light depending on the size of the nanocrystal. The emission wavelength from a given quantum dot is narrow and symmetric, thus minimizing overlap with other wavelengths and facilitating the detection of discrete quantum dots in a mixed solution. Quantum dots can be coupled to various biomolecules including, but not limited to, proteins, nucleic acids and other small molecules. Such bioconjugated quantum dots can be used to deliver fluorophores to the target molecules by various methods including, but not limited to, nucleic acid ligation, oligonucleotide annealing and protein-ligand interaction. For example, quantum dots could be bioconjugated to short double stranded nucleic acid sequences that could then be ligated to the ends of DNA molecules or bioconjugated to specific nucleic acid sequences that could anneal (hybridize) to a target or targets of interest. Discrete populations of dsDNA-quantum dot conjugates could be prepared, physically separated into either well-plates or emulsion droplets and systematically added to the ends of DNA molecules as described above. Similarly, a solid-support particle (e.g., a bead) could be attached to the ends of a population of nucleic acids. The solid-support particle would be capable of capturing bioconjugated quantum dots through protein-ligand interactions. In any of these examples, quantum dots would be added to the target molecules in a controlled manner such that the maximum population of target molecules would not exceed the number of unique combinations that could be created by the number of quantum dots available. The same exponential relationship between the number of "tags" (i.e., quantum dots) and the iterations of tag addition applies here such that the maximum number of combinations is $X^Y$ where X is the number of quantum dots and Y is the number of iterations of tag addition. In any of these examples, standard methods for fluorescence detection including, but not limited to, fluorescence activated cell/particle sorting, hybridization to a fixed array of oligonucleotides, etc., could be used to detect the "signature" of a single molecule or population of molecules. In some embodiments, it may be desirable to analyze a large population of emulsion droplets to determine the unique emission wavelengths contained in a given droplet on a droplet-by-droplet basis.

Generation of Unique Labels

In some aspects, the invention provides methods for generating unique labels. The methods typically use a plurality of detectable tags to generate unique labels. In some embodiments, a unique label is produced by sequentially attaching two or more detectable oligonucleotide tags to each other. The detectable tags may be present or provided in a plurality of detectable tags. The same or a different plurality of tags may be used as the source of each detectable tag which may be comprised in a unique label. In other words, a plurality of tags may be subdivided into subsets and single subsets may be used as the source for each tag. This is exemplified in at least FIG. 1.

A plurality of tags may comprise 2, 3, 4, 5, 6, 7, 8, 9, 10, $10^2$, $10^3$, $10^4$, $10^5$, or $10^6$, or more tags. Typically, the tags within a plurality are unique relative to each other.

The methods of the invention allow an end user to generate a unique label for a plurality of agents using a number of tags that are less (and in some instances far less) than the number of agents to be labeled. The number of tags may be up to or about 10-fold, $10^2$-fold, $10^3$-fold, or $10^4$-fold less than the number of agents. The number of agents to be labeled will depend on the particular application. The invention contemplates uniquely labeling at least $10^3$, $10^4$, $10^5$, $10^6$, $10^7$, $10^8$, $10^9$, or $10^{10}$ or more agents. In some embodiments, the agent may comprise a plurality of nucleic acids. In some embodiments, the plurality of nucleic acids may comprise at least $10^3$, $10^4$, $10^5$, $10^6$, $10^7$, $10^8$, $10^9$, or $10^{10}$ nucleic acids.

In certain methods of the invention, agents, detectable tags, and resultant unique labels are all present in a contained volume and are thus physically separate from other agents, detectable tags, and resultant unique labels. In some instances, the contained volume is on the order of picoliters, nanoliters, or microliters. The contained volume may be a droplet such as an emulsion droplet, a well of a multiwall plate, a tube or other container.

In some embodiments a subset of the plurality of agents is present in the same container during attachment of a detectable label. In some embodiments, the plurality of agents is separated such that each agent in the plurality is in a separate container, e.g., a well of a multiwell plate.

In some embodiments, the process of pooling and subsequently separating the plurality of agents is performed n number of times, wherein n is the number of times required to generate $(m_1)(m_2)(m_3) \ldots (m_n)$ number of combinations of detectable oligonucleotide tags, wherein $(m_1)(m_2)(m_3) \ldots (m_n)$ number of combinations of detectable oligonucleotide tags is greater than the number of the plurality of agents.

The invention provides a method which may comprise
(a) labeling two or more first subsets of agents with a detectable oligonucleotide tag to produce agents within a subset that are identically labeled relative to each other and uniquely labeled relative to agents in other subsets;
(b) combining two or more subsets of uniquely-labeled agents to form a pool of agents, wherein the pool may comprise two or more second subsets of agents that are distinct from the two or more first subsets of agents;
(c) identically labeling two or more second subsets of agents with a second detectable oligonucleotide tag to produce agents within a second subset that are uniquely labeled relative to agents in the same or different second subsets; and
(d) repeating steps (b) and (c) until a number of unique labels is generated that exceeds the number of starting agents, wherein each unique label may comprise at least two detectable oligonucleotide tags.

The invention provides another method which may comprise
(a) providing a pool of agents;
(b) separating the pool of agents into sub-pools of agents;
(c) labeling agents in each sub-pool of with one of $m_1$ unique detectable oligonucleotide tags thereby producing sub-pools of labeled agents, wherein agents in a sub-pool are identically labeled to each other;
(d) combining sub-pools of labeled agents to create a pool of labeled agents;
(e) separating the pool of labeled agents into second sub-pools of agents;
(f) repeating steps (c) to (e) n times to produce agents labeled with n unique detectable oligonucleotide tags, wherein the pool in (a) consists of a number of agents that is less than $(m_1)(m_2)(m_3) \ldots (m_a)$.

The invention provides another method which may comprise
(a) providing a population of library droplets which may comprise agents, wherein each droplet may comprise an agent;
(b) fusing each individual library droplet with a single detectable oligonucleotide tag droplet from a plurality of $m_1$ detectable oligonucleotide tag droplets, each detectable oligonucleotide tag droplet which may comprise a plurality of identical detectable oligonucleotide tag;
(c) labeling the agent with the detectable oligonucleotide tag in a fused droplet;
(d) harvesting labeled agents from the fused droplets and generating another population of library droplets which may comprise labeled agents; and
(e) repeating steps (b) to (d) n times to produce agents labeled with a unique label which may comprise n detectable oligonucleotides tags, wherein the n detectable oligonucleotide tags generate an $(m_1)(m_2)(m_3) \ldots (m_n)$ number of combinations that is greater than the number of starting agents.

The invention provides another method which may comprise
(a) providing a population of library droplets which may comprise agents, wherein each droplet may comprise more than one agent;
(b) fusing each individual library droplet with a single detectable oligonucleotide tag droplet from a plurality of $m_1$ detectable oligonucleotide tag droplets, each detectable oligonucleotide tag droplet which may comprise a plurality of identical detectable oligonucleotide tag;
(c) labeling the more than one agents with the detectable oligonucleotide tag in a fused droplet;
(d) harvesting labeled agents from the fused droplets and generating another population of library droplets which may comprise labeled agents, wherein each droplet may comprise more than one agent; and
(e) repeating steps (b) to (d) n times to produce agents labeled with a unique label which may comprise n detectable oligonucleotides tags, wherein the n detectable oligonucleotide tags generate an $(m_1)(m_2)(m_3) \ldots (m_n)$ number of combinations that is greater than the number of starting agents and optionally wherein the agents within the same droplet are labeled identically.

In some embodiments, the unique oligonucleotide label is attached to a solid support. In some embodiments, the solid support is a bead or polymer. In some embodiments, the fill-in reaction is a polymerase chain reaction.

In another embodiment, the method may comprise:
sequentially end-labeling nucleic acids in a plurality, at their 5' and 3' ends, with a random combination of n detectable oligonucleotide tags,
wherein each end-labeled nucleic acid is
(a) identically labeled at its 5' and 3' ends, and
(b) uniquely labeled relative to other nucleic acids in the plurality,
wherein each detectable oligonucleotide tags is randomly and independently selected from a number of detectable oligonucleotide tags that is less than the number of nucleic acids, and n is the number of oligonucleotides attached to an end of a nucleic acid.

In some embodiments, the further may comprise fragmenting end-labeled nucleic acids into at least a 5' fragment which may comprise the 5' end of the nucleic acid attached to the random combination of n detectable oligonucleotide tags and into a 3' fragment which may comprise the 3' end of the nucleic acid attached to the random combination of n detectable oligonucleotide tags. In some embodiments, the 5' and 3' fragments are about 10-1000 bases (base pairs) in length, or about 10-500 bases in length, or about 10-200 bases in length. In some embodiments, the method further may comprise sequencing the 5' and 3' fragments.

In another embodiment, the method may comprise:
sequencing a pair of genomic nucleic acid fragments, wherein the genomic nucleic acid fragments are attached to identical unique labels at one of their ends that indicates the genomic nucleic acid fragments were separated by a known distance in a genome prior to fragmentation.

In some embodiments, the pair of nucleic acid fragments were separated by greater than 10 kb in the genome prior to fragmentation. In another embodiment, the pair of nucleic acid fragments were separated by greater than 40 kb in the genome prior to fragmentation. In some embodiments, the method further may comprise generating the pair of genomic nucleic acid fragments by fragmenting nucleic acids which may comprise genomic sequence and identical non-genomic sequence at their 5' and 3' ends.

In another aspect, the invention provides compositions. In one embodiment, the composition may comprise:
a plurality of paired nucleic acid fragments attached to unique labels at one end, wherein paired nucleic acid fragments:
(a) share an identical unique label at one end that is unique in the plurality, and
(b) were separated from each other in a genome by a known distance prior to fragmentation.

In some embodiments, paired nucleic acid fragments were separated by greater than 10 kb in the genome prior to fragmentation. In another embodiment, the paired nucleic acid fragments were separated by greater than 40 kb in the genome prior to fragmentation. In some embodiments, the composition is produced using any of the methods described herein.

Examples of nucleic acids include, but are not limited to, genomic DNA, cDNA, PCR products, mRNA, total RNA, plasmids, or fragments thereof. In some embodiments, the nucleic acids are genomic DNA, cDNA, PCR products, or fragments thereof. Nucleic acids can be fragmented using methods described herein.

In some embodiments, the nucleic acids are attached to a solid support. Examples of suitable solid supports include, but are not limited to, polymers, beads, glass, nanoparticles, hydrogels or peptides. In some embodiments, the solid support is a polymer or a bead. In some embodiments, the nucleic acids are attached to the solid support with a cleavable linker as described herein.

In some embodiments, the method further may comprise fragmenting uniquely end-labeled nucleic acids. Fragmenting of nucleic acids can be accomplished by methods described herein and those well-known in the art.

In one embodiment, the method may comprise sequencing a pair of genomic nucleic acid fragments, wherein the genomic nucleic acid fragments are attached to identical unique labels at one of their ends that indicates the genomic nucleic acid fragments were separated by a known distance in a genome prior to fragmentation. In some embodiments, the known distance is greater than 5, 10, 15, 20, 30, 40, 50, 100 kb or greater separation. Genomic nucleic acid fragments can come from any organismal genomic DNA, for example, human, mammalian, bacterial, fungal or plant genomic DNA. Genomic nucleic acid fragments can be generated by fragmentation methods known in the art (see, e.g., Green and Sambrook. Molecular Cloning: A Laboratory Manual, Fourth Edition, 2012). Examples of fragmentation include, but are not limited to, enzymatic (such as a nuclease), chemical (such as a DNA nicking agent) or mechanical (such as sonication) fragmentation. Fragmentation can be random, e.g., sequence and size unspecific, or ordered, e.g., sequence dependent and/or size-restricted. The fragments generated following label addition can be tailored to the limitations of the desired detection technology. For example, the fragments can be hundreds, thousands, millions or potentially billions of base pairs in length depending on the technology used to sequence the DNA.

Fragment Amplification

Figure 37B:
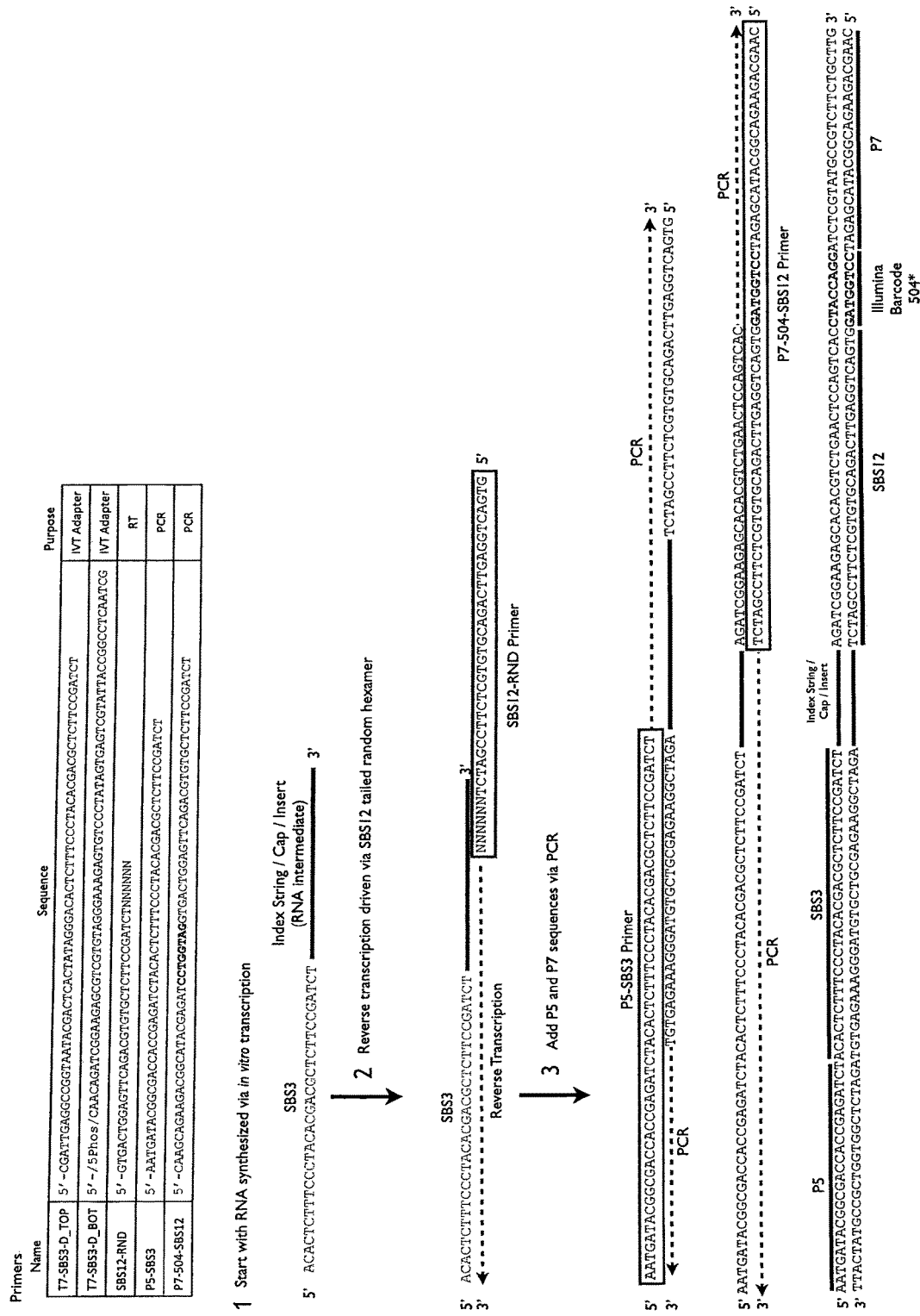

Fragments can be amplified to increase the number of read pairs properly mated via their unique index combination. Amplification methods can be used to maximize fragment end recovery. These methods utilize the fragment preparation and indexing techniques described above, but vary in their approach to recovering and amplifying fragment ends within the library construction process. In one embodiment, the amplification method involves transposome-based selection and amplification. This method is shown in FIG. 36 and described in the Examples below. In another embodiment, the amplification method involves enrichment of ends via in vitro transcription. This method is illustrated in FIGS. 37a and 37b and also described in the Examples below. In a further embodiment, the amplification method involves anchored PCR. FIG. 38 shows this method and is also exemplified in the below Examples.

Additional Applications Using Unique Labeling Approaches

The invention further contemplates use of the dynamic labeling techniques described herein for a variety of other applications including but not limited to microbiological/pathogen diagnostic applications and cellular tracking, including in vivo cellular tracking, applications. Various applications that are amenable to the unique labeling methods of the invention are described in published PCT application WO2011/106536, published on Sep. 1, 2011, the entire contents of which are incorporated by reference herein.

Diagnostic/Pathogen Signature Applications

Thus, in one aspect, the methods and compositions provided herein may be used to generate molecular signatures for pathogens such as but not limited to bacteria, fungi and viruses, and may impart information about whether the bacteria have been exposed to one or more agents and if so the identity of such agent(s). In some embodiments, the agents may be anti-bacterials such as antibiotics, anti-viral, or antifungals.

Certain methods directed to pathogen identification may involve obtaining a sample known or suspected of containing a pathogen, concentrating and lysing any pathogens from the sample, and harvesting and detecting nucleic acids from the sample, wherein the nucleic acids are indicative of, or surrogate markers of, the pathogen(s) present in the sample. In some embodiments, the method further may comprise a step of enriching pathogens in the sample prior to concentration and lysis. The labeling methods of the invention are used to label and detect the nucleic acids from the sample, as described in greater detail below.

Certain methods directed to pathogen identification and drug susceptibility may involve obtaining a sample known or suspected of containing a pathogen, concentrating pathogens from the sample, partitioning the sample into subsets (or subpools) and exposing the subsets to different agents (e.g., antibiotics), lysing any pathogens following exposure to agent, and harvesting and detecting nucleic acids from the sample, wherein the nucleic acids are indicative of, or surrogate markers of, the pathogen(s) present in the sample. In some embodiments, the method further may comprise a step of enriching pathogens in the sample prior to concentration and lysis. In some embodiments, the sample may be cultured prior to concentration and the optionally enrichment step. The labeling methods of the invention are used to label and detect the nucleic acids from the sample, as described in greater detail below.

The foregoing methods may be carried out in microfluidic devices.

These diagnostic methods may be carried out on any number of samples including samples taken from a host (e.g., a human or an animal). These latter samples may be blood samples, urine samples, cerebrospinal fluid samples, etc.

Figure 31:
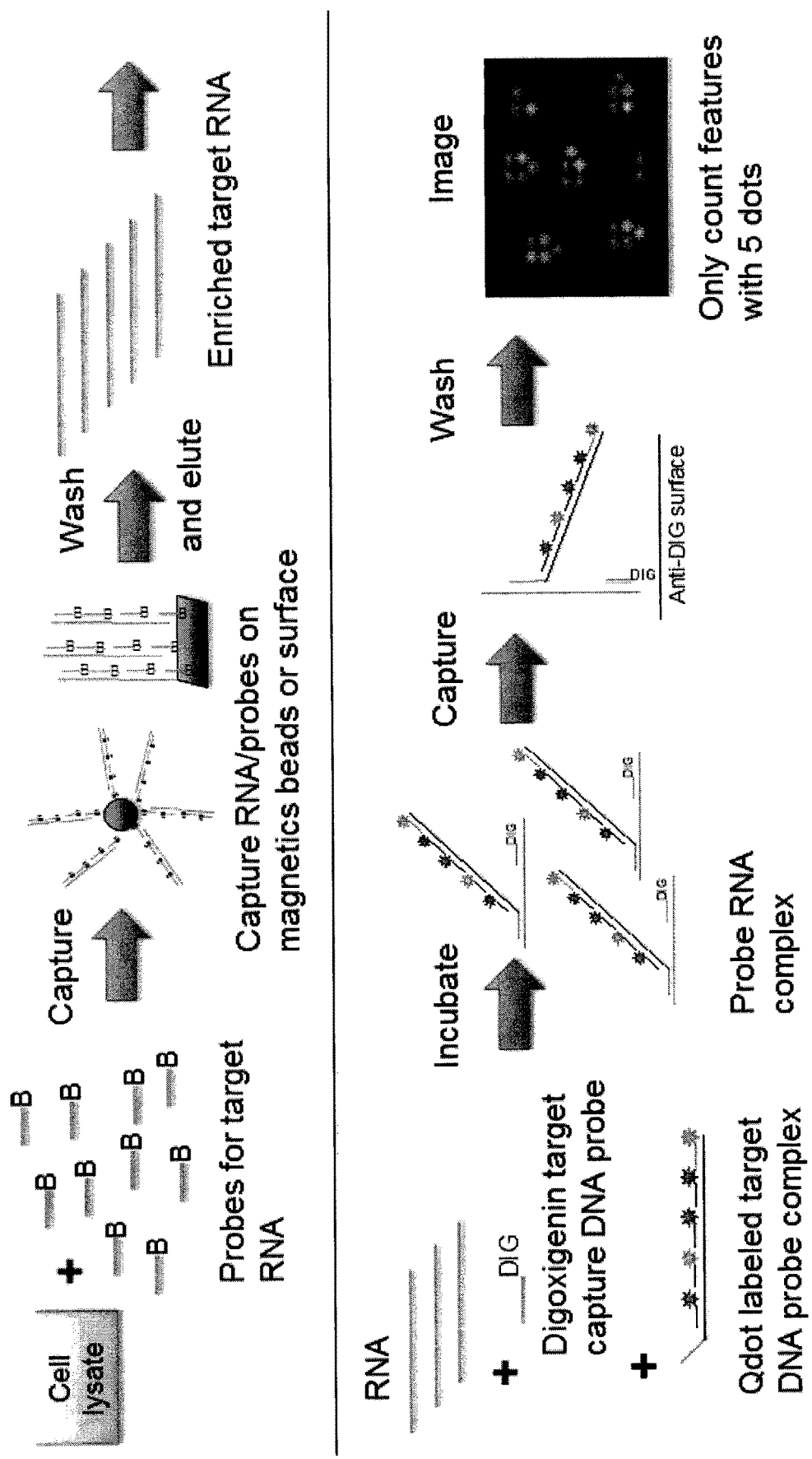
FIGS. 31-33 schematically illustrate a quantum dot RNA detection assay that can be used, inter alia, to detect and monitor pathogens.

FIG. 31 schematically illustrates a harvesting and labeling procedure that may be applied to detect the pathogen-specific nucleic acids such as those obtained through the foregoing methods. As illustrated in the Figure, a cell lysate which may comprise nucleic acid and non-nucleic acid components of a sample may be combined with a plurality of pathogen-specific nucleic acid probes. The probes may be biotinylated (shown in the Figure as "B"). The probes hybridize to their target pathogen RNA, and RNA hybridized to such probes is then physically separated from the remainder of the reaction mixture. In the Figure, the probes are biotinylated and the accordingly the probe/RNA hybrids are extracted using streptavidin (or avidin) coated beads. One of ordinary skill in the art will understand that the method may be performed using binding pairs other than biotin-avidin and using solid supports other than beads. In some instances, the RNA is mRNA.

Once the RNA is extracted, it may be initially labeled with a universal probe (i.e., a probe that hybridizes to all the RNA species). The universal probe will typically be detectably labeled (e.g., with a quantum dot or other fluorescent label or with an oligonucleotide label of the invention). This initial universal probe may indicate whether the sample was exposed to an agent, and optionally the agent type or identity. The use of this type of universal probe is not illustrated in the Figure. The Figure however does illustrate the use of another universal probe that is conjugated to digoxigenin (DIG) and that is used as a capture probe for all the harvested RNA. It is to be understood that the DIG label is exemplary and that other capture moieties may be used in its place including the oligonucleotide labels of the invention. RNA is bound to DIG-labeled universal probes and to RNA-specific, non-universal, probes that are differentially labeled. As an example, the Figure shows probes that are labeled with a set of five quantum dots ("Qdots") but it is to be understood that they may be labeled in any manner that results in a sufficient number of unique labels, including the nucleic acid-based labels of the invention. After hybridization, pathogen RNA molecules will be bound to the capture probe (e.g., the DIG-probe) and RNA-specific (e.g., Qdot-probe). The pathogen RNAs labeled in this manner are then captured on a solid support. The RNAs are captured to the solid support via interaction of DIG and anti-DIG antibody on the solid support. It will be understood that binding pairs other than DIG and anti-DIG antibody can be used. The RNAs are then imaged. If the detected moiety is a Qdot or other fluorescent moiety, then the image detects emissions from such moieties individually (as illustrated) or in some instances in combination. The image illustrates that each RNA is detected by a region of five distinct signals. Regions having less than five signals are disregarded. The combination of particular signals within each region indicate the identity of the RNA and thus act as the signature for the RNA. Assuming that 10 different detectable moieties are used (e.g., 10 Qdots) and 5 detectable moieties are used per probe, then 252 combinations are available for labeling (i.e., there are 252 unique labels available and therefore 252 different RNA species that may be distinguished from each other). If the method further included the use of another universal probe, the region of interest might contain yet another signal corresponding to the second universal probe.

Figure 32:
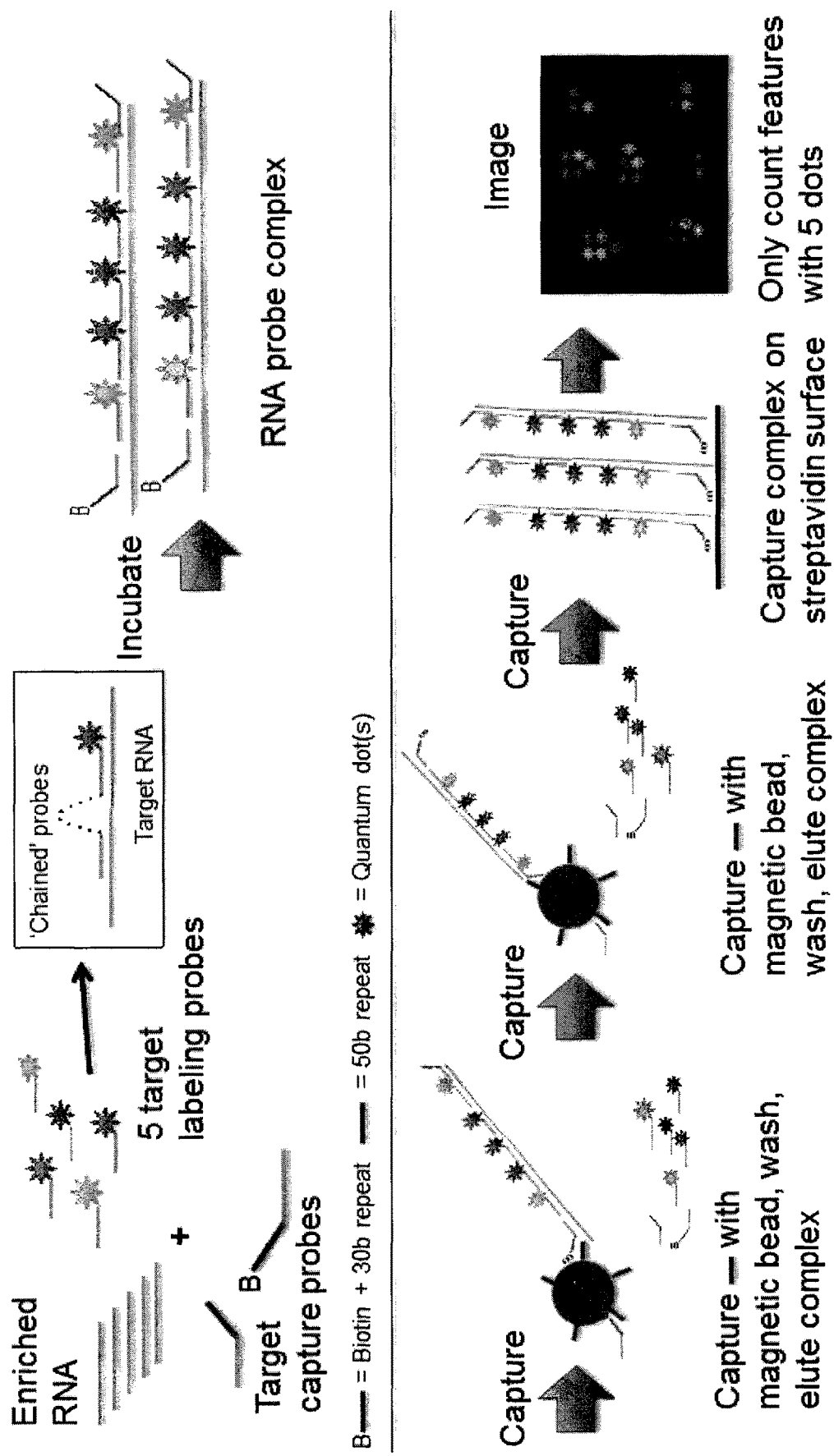
Figure 33:
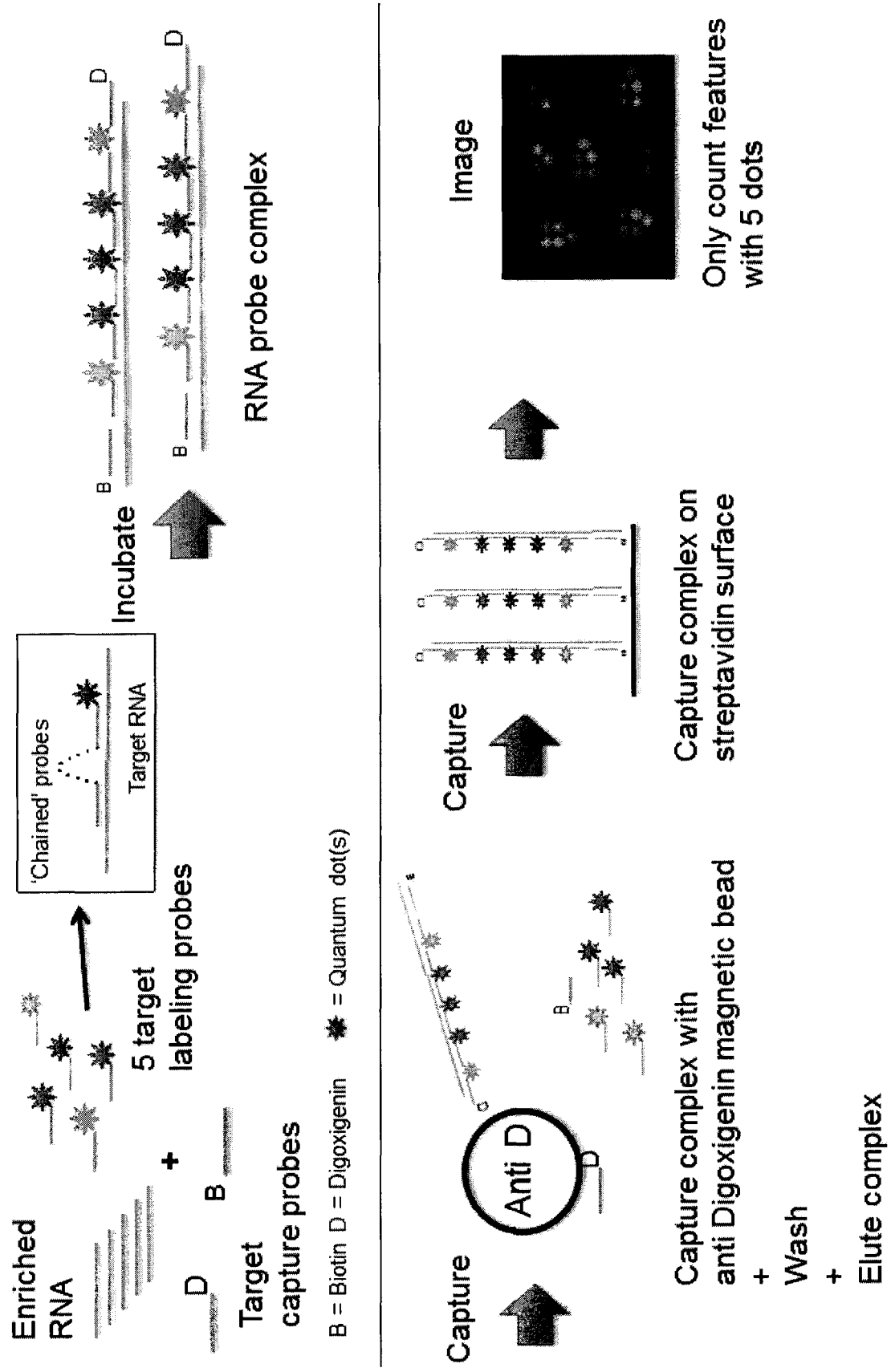
Figure 34:
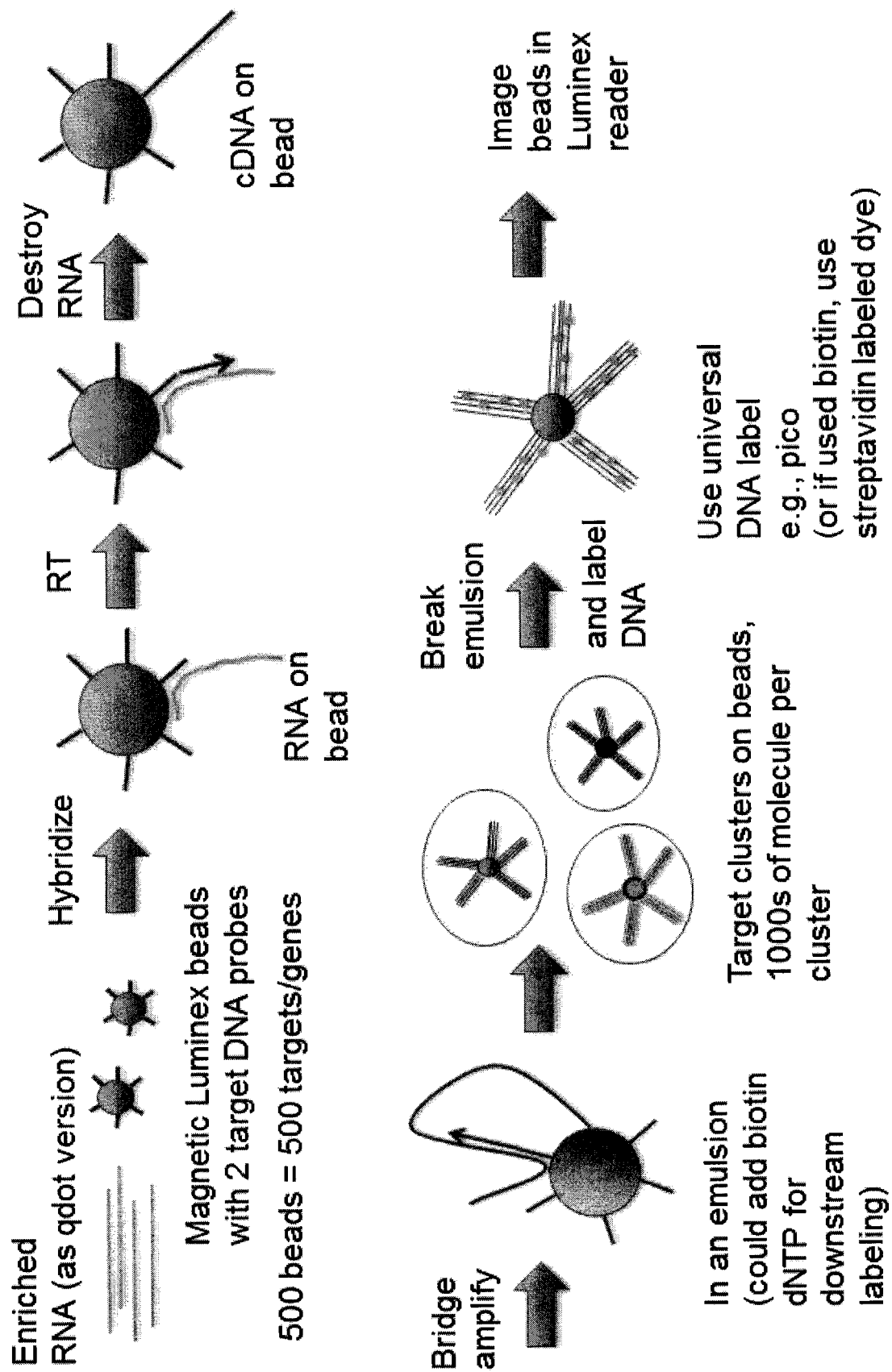
FIG. 34 is a schematic illustrating a luminex bead based RNA detection assay that can be used, inter alia, to detect and monitor pathogens.

Other labeling methods are provided in FIGS. 32-34. In FIG. 32, the enriched RNA is labeled with universal capture probes (that in this Figure are either 30 base sequences that are biotinylated, as denoted by "B", or are 50 base sequences) and with RNA-specific "labeling" probes (that in this Figure are each conjugated with a single quantum dot, but which may otherwise be labeled using the nucleic acid based labels of the invention). The configuration of the probes bound to the target RNAs is shown in the Figure, with the capture probes at the ends and the labeling probes at the internal region, thereby generating an RNA-probe complex. These complexes are then physically separated from other components of the labeling reaction mixture using streptavidin solid supports (such as beads or other surfaces) whereby the biotinylated RNAs are captured. This is followed by capture based on hybridization of the 50-mer sequence at the other end of the RNA using solid supports (such as beads or other surfaces) bound to complements of the 50-mer sequence. The RNAs are then detached from the second solid support and again captured on another streptavidin support and then imaged.

It is to be understood that the imaging methods illustrated in these Figures typically require that the RNAs are physically separated from each other and non-overlapping on a solid support. Accordingly, solid supports such as planar surfaces are suitable for such purposes.

A similar method is illustrated in FIG. 33. In this method, the capture probes are biotinylated probes and DIG-labeled probes. The initial capture step, to separate the RNA from other components in the labeling reaction mixture, uses the DIG labeled capture probe, and the final capture step, to separate RNAs from each other on a solid support (such as planar surface) uses the biotinylated capture probe.

Another method is illustrated in FIG. 34.

It is to be understood that any of the foregoing methods may be performed using a nucleic acid labeling approach as described herein rather than a fluorophore based labeling approach.

Accordingly, in some aspects, the invention provides methods of determining the sensitivity of a pathogen, e.g., a disease-causing organism such as a bacterium, fungus, virus, or parasite, to one or more agents. The agent may be a chemical agent such as a drug (e.g., antibiotic, anti-fungal, or anti-viral), or it may be a physical agent such as radiation. The methods include providing a sample known or suspected of having a pathogen and contacting the sample with one or more test agents, e.g., for less than four hours, to provide a test sample. The test sample then is treated under conditions that release RNA, such as mRNA, from the pathogen, and such RNA is exposed a plurality of nucleic acid probes. The probes may be represented by a plurality of subsets. The probes may be specific for RNA from pathogens known or suspected of being in the sample (i.e., pathogen-specific probes). Such probes may be used to determine if a particular pathogen is present and to quantitate the level of such pathogen. The probes may be pathogen-non-specific and thus able to bind to RNA from more than one pathogen. Such probes may be used to determine overall pathogen load in the sample. Such probes may also be used to identify and/or analyze pathogens that are resistant and pathogens that are susceptible to an agent. An example of such an assay is described below.

In one approach, the probes bind specifically to a target RNA, such as an mRNA, that is differentially expressed in pathogens that are sensitive to an agent as compared to pathogens that are resistant to the agent. Exposure of the target RNA and the probes occurs for a time and under conditions in which binding between the probe and target RNA can occur. The method may comprise determining a level of binding between the probe and target RNA, thereby determining a level of the target RNA, and comparing the level of the target RNA from a sample exposed to the in the presence of the test compound to a reference level, e.g., the level of the target mRNA in the absence of the test compound, wherein a difference in the level of target mRNA relative to the reference level of target mRNA indicates whether the pathogen is sensitive or resistant to the test compound.

The probes, including the pathogen-specific probes, may be labeled dynamically and/or statically, using for example the nucleic acid labeling techniques of the invention.

The pathogen may be known, e.g., an identified pathogen, or it may be an unknown pathogen, e.g., a yet to be identified pathogen. In the latter instance, the methods of the invention are used to detect a previously known pathogen.

The sample which may comprise the pathogen may be contacted with two or more agents, e.g., simultaneously or in the same sample, e.g., contacted with known or potential treatment agents, e.g., antibiotics, antifungals, antivirals, and antiparasitics. A number of these compounds are known in the art, e.g., isoniazid, rifampicin, pyrazinamide, ethambutol streptomycin, amikacin, kanamycin, capreomycin, viomycin, enviomycin, ciprofloxacin, levofloxacin, moxifloxacin, ethionamide, prothionamide, cycloserine, p-aminosalicylic acid, rifabutin, clarithromycin, linezolid, thioacetazone, thioridazine, arginine, vitamin D, R207910, ofloxacin, novobiocin, tetracycline, merepenem, gentamicin, neomycin, netilmicin, streptomycin, tobramycin, paromomycin, geldanamycin, herbimycin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, methicillin, nafcillin, oxacillin, penicillin, piperacillin, ticarcillin, bacitracin, colistin, polymyxin B, enoxacin, gatifloxacin, lomefloxacin, norfloxacin, trovafloxacin, grepafloxacin, sparfloxacin, mafenide, prontosil, sulfacetamide, sulfamethizole, sulfanilimide, sulfasalazine, sulfisoxazole, trimethoprim, trimethoprim-sulfamethoxazole (co-trimoxazole), demeclocycline, doxycycline, minocycline, oxytetracycline, arsphenamine, chloramphenicol, clindamycin, lincomycin, ethambutol, fosfomycin, fusidic acid, furazolidone, metronidazole, mupirocin, nitrofurantoin, platensimycin, quinupristin/dalfopristin, rifampin, thiamphenicol, imidazole, cephalosporin, teicoplatin, augmentin, cephalexin, rifamycin, rifaximin, cephamandole, ketoconazole, latamoxef, or cefmenoxime.

Samples may be contacted with agents for a range of times including but not limited to 24 hours, 12 hours, 6 hours, 4 hours, less than four hours, e.g., less than three hours, less than two hours, less than one hour, less than 30 minutes, less than 20 minutes, less than 10 minutes, less than five minutes, less than two minutes, less than one minute.

These methods can be used to identify an infectious disease pathogen, e.g., a bacterium, fungus, virus, or parasite, e.g., *Mycobacterium tuberculosis*, e.g., detecting the presence of the pathogen in a sample, e.g., a clinical sample.

The methods include providing a test sample from a subject suspected of being infected with a pathogen, treating the test sample under conditions that release RNA such as mRNA, exposing the test sample to a plurality of nucleic acid probes, which may comprise a plurality of subsets of probes, wherein each subset may comprise one or more probes that bind specifically to a target RNA that uniquely identifies a pathogen, wherein the exposure occurs for a time and under conditions in which binding between the probe and the target mRNA can occur, and determining a level of binding between the probe and target RNA, thereby determining a level of target RNA. An increase in the target RNA of the test sample, relative to a reference sample, indicates the identity of the pathogen in the test sample. Each probe may be uniquely labeled using any of the labeling techniques of the invention, including the nucleic acid based labeling techniques.

It is to be understood that RNA may be labeled in a static manner, in a dynamic manner, or in a combination of static and dynamic manners. As used herein, static labeling refers to the generation of a unique label and affixing of the prepared unique label to a target of interest such as a single mRNA. As used herein, dynamic labeling refers to the unique labeling of a target by affixing to the target individual detectable moieties such as oligonucleotide tags or fluorescent moieties one at a time to generate a unique label. In a dynamic labeling approach, a label affixed to the target may represent information about the target. In these diagnostic methods, the label may represent whether the sample has been exposed to an agent and optionally the identity of the agent. Some labels may be used to distinguish RNA from each other. Other labels may be used to denote particular information about the RNA such as whether it came from a sample from a particular subject or from a sample treated in a particular manner. The invention contemplates that virtually any organism may be traced, identified and monitored using the methods of the invention.

The sample may be or may comprise sputum, blood, urine, stool, joint fluid, cerebrospinal fluid, and cervical/vaginal swab. Such samples may include a plurality of other organisms (e.g., one or more non-disease causing bacteria, fungi, viruses, or parasites) and/or pathogens. In some embodiments, the sample is a clinical sample, e.g., a sample from a patient or person who is or may be undergoing a medical treatment by a health care provider.

The RNA may be crude, e.g., not purified, before contact with the probes and/or may not be amplified. The cells may be lysed enzymatically, chemically, and/or mechanically. The methods may comprise use of a microfluidic device.

The methods may be used to monitor pathogen infection, e.g., incidence, prevalence, for public health surveillance of an outbreak of a pathogen, e.g., a sudden rise in numbers of a pathogen within a particular area.

The sample may be obtained from a subject such as but not limited to humans and animals, such as laboratory animals, e.g., mice, rats, rabbits, or monkeys, or domesticated and farm animals, e.g., cats, dogs, goats, sheep, pigs, cows, horses, and birds, e.g., chickens.

The methods may further comprise determining and/or selecting a treatment for the subject and optionally administering the treatment to the subject, based on the outcome of an diagnostic assay as described herein.

In another general aspect, the invention features methods of selecting a treatment for a subject. The methods include optionally identifying an infectious disease pathogen (e.g., detecting the presence and/or identity of a specific pathogen in a sample), e.g., using a method described herein, determining the drug sensitivity of the pathogen using the methods described herein, and selecting a drug to which the pathogen is sensitive for use in treating the subject.

In yet another aspect, the invention provides methods for monitoring an infection with a pathogen in a subject. The methods include obtaining a first sample which may comprise the pathogen at a first time, determining the drug sensitivity of the pathogen in the first sample using the method described herein, optionally selecting a treatment to which the pathogen is sensitive and administering the selected treatment to the subject, obtaining a second sample which may comprise the pathogen at a second time, determining the drug sensitivity of the pathogen in the second sample using the method described herein, and comparing the drug sensitivity of the pathogen in the first sample and the second sample, thereby monitoring the infection in the subject. In some embodiments of the methods described herein, the subject is immune compromised.

In some embodiments of the methods described herein, the methods include selecting a treatment to which the pathogen is sensitive and administering the selected treatment to the subject, and a change in the drug sensitivity of the pathogen indicates that the pathogen is or is becoming resistant to the treatment, e.g., the methods include determining the drug sensitivity of the pathogen to the treatment being administered. In some embodiments, a change in the drug sensitivity of the pathogen indicates that the pathogen is or is becoming resistant to the treatment, and the method further may comprise administering a different treatment to the subject.

In yet another aspect, the invention features methods of monitoring an infection with a pathogen in a population of subjects. The methods include obtaining a first plurality of samples from subjects in the population at a first time, determining the drug sensitivity of pathogens in the first plurality of samples using the method described herein, and optionally identifying an infectious disease pathogen in the first plurality of samples using the method described herein, optionally administering a treatment to the subjects, obtaining a second plurality of samples from subjects in the population at a second time, determining the drug sensitivity of pathogens in the second plurality of samples using the method described herein, and optionally identifying an infectious disease pathogen in the first plurality of samples using the method described herein, comparing the drug sensitivity of the pathogens, and optionally the identity of the pathogens, in the first plurality of samples and the second plurality of samples, thereby monitoring the infection in the population of subject.

"Infectious diseases" also known as communicable diseases or transmissible diseases, comprise clinically evident illness (i.e., characteristic medical signs and/or symptoms of disease) resulting from the infection, presence, and growth of pathogenic biological agents in a subject (Ryan and Ray (eds.) (2004). Sherris Medical Microbiology (4th ed.). McGraw Hill). A diagnosis of an infectious disease can confirmed by a physician through, e.g., diagnostic tests (e.g., blood tests), chart review, and a review of clinical history. In certain cases, infectious diseases may be asymptomatic for some or all of their course. Infectious pathogens can include viruses, bacteria, fungi, protozoa, multicellular parasites, and prions. One of skill in the art would recognize that transmission of a pathogen can occur through different routes, including without exception physical contact, contaminated food, body fluids, objects, airborne inhalation, and through vector organisms. Infectious diseases that are especially infective are sometimes referred to as contagious and can be transmitted by contact with an ill person or their secretions.

As used herein, the term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" as used herein refers to an oligonucleotide that binds specifically to a target such as a nucleic acid such as mRNA. A probe can be single stranded at the time of hybridization to a target.

16S Amplicon Tagging

In another embodiment, the labeling methods described herein can be used to characterize pathogen populations by labeling nucleic acid regions of interest. For example, the 16S region in a bacterium can be used to identify and distinguish species of bacteria present in a sample. The 16S region is the target of numerous studies that seek to characterize the microbial community present in a given sample (e.g., human microbiome studies). The prokaryotic 16S ribosomal RNA is composed of 4 different subunits spanning approximately 1,500 base pairs in length. Current sequencing technologies make it difficult and in some cases impossible to accurately characterize the 16S region due to either prohibitively high error rates or long read lengths. To overcome these problems, the 16S region may be analyzed by PCR using primers designed to amplify each of the 4 subunits separately. The method described herein is unique in that it allows for tagging amplicons from a large population of individual cells such that an explicit and identifiable association can be made among all 4 amplicons on a cell-by-cell basis. Once tagged, all downstream sample processing can be performed in bulk, which allows for both workflow streamlining and cost reduction. Importantly, additional tagging information can be added to these samples downstream allowing for the capture of additional layers of sample history information.

Figure 35:
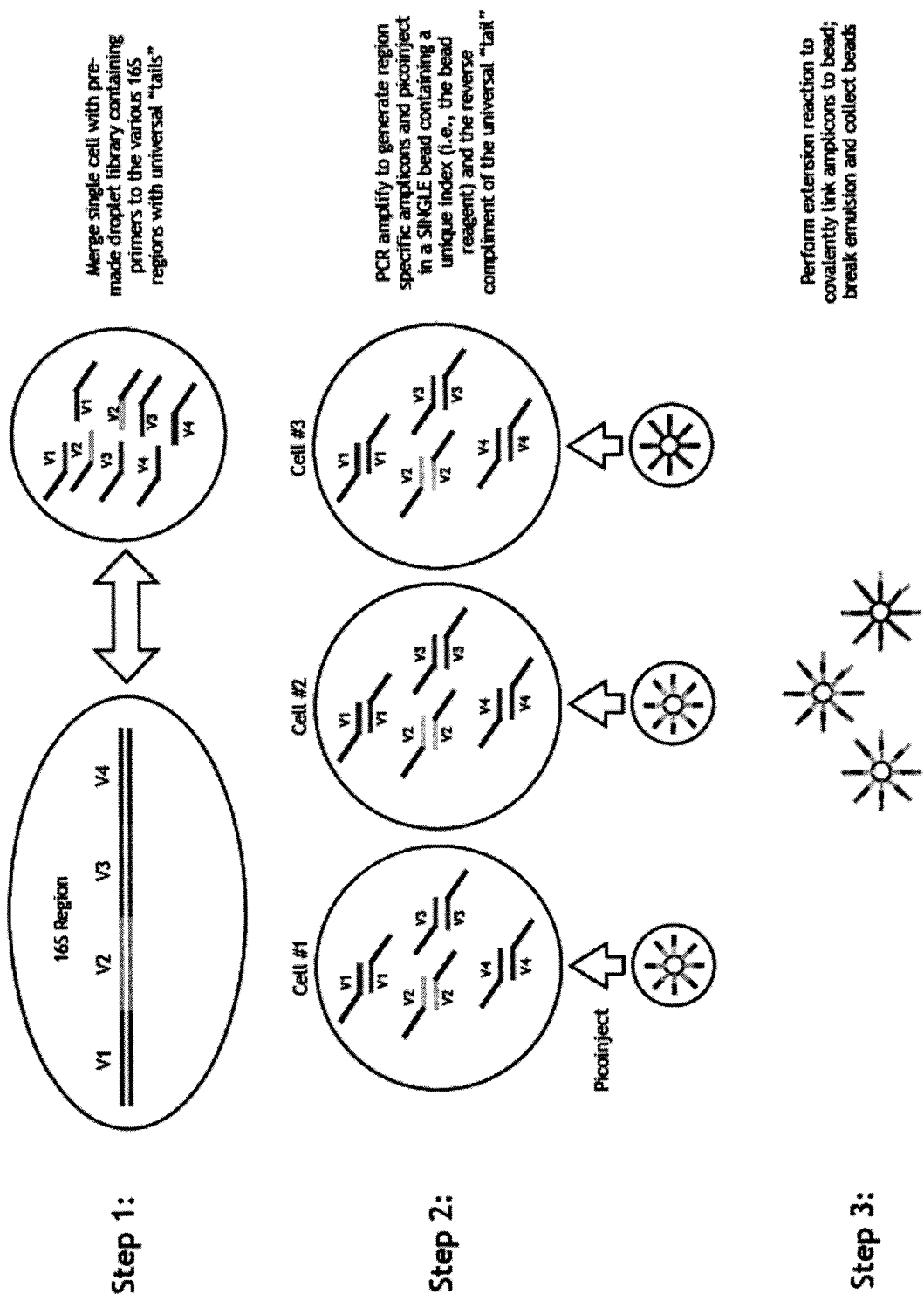
FIG. 35 is a schematic illustrating 16S amplicon tagging that can be used, inter alia, to distinguish different species of bacteria.

FIG. 35 is a schematic showing an exemplary technique for amplifying and tracking 16S regions using the methods and labels described herein. For this technique, cells are distributed into an emulsion such that each droplet only contains a single cell. The single cell emulsion is then merged to a previously constructed droplet library containing PCR primers designed to amplify each of the four 16S regions. Although each primer is designed to amplify a specific region, every primer carries a common (universal) tailing sequence. Cells may be lysed either prior to droplet merging or during PCR amplification of the 16S amplicons. Following PCR, a single bead carrying a unique index sequence (e.g., a detectable oligonucleotide tag created using the methods described herein) is added to each droplet through droplet merging, picoinjection, etc. Although each bead carries a unique index sequence, it also carries a common sequence complimentary to the universal tail present on the PCR primers. Following annealing of the amplicons to the beads via the universal tail sequence, the amplicons become covalently linked to the bead via a polymerization (extension) reaction. Once attached to the beads, the emulsion can be broken and all downstream processing can be performed in bulk.

Any desirable solid support can be used in place of beads, e.g., polymers, glass, nanoparticles, hydrogels or peptides. Alternatively, labeling can be performed in the absence of a solid support (e.g., in an emulsion). Agents other than 16S ribosome amplicons can be labeled, e.g., a nucleic acid such as a portion of a genome, a gene, a promoter, a coding sequence of a gene, a cDNA, or an RNA. Use of emulsion droplets can be replaced with separation of agents, e.g., using microwells or tubes. This technique is useful generally for assessing any sample (e.g., a cell, a genome, a transcriptome, a sample containing multiple organisms or cells) where prohibitively high error rates and/or long read lengths are an issue.

RNA Extraction and Analysis

RNA can be extracted from cells in a sample, e.g., a pathogen cell or clinical sample, by treating the sample enzymatically, chemically, or mechanically to lyse cells the sample and release mRNA. It will be understood by skilled practitioners that other disruption methods may be used in the process.

The use of enzymatic methods to remove cell walls is well-established in the art. The enzymes are generally commercially available and, in most cases, were originally isolated from biological sources. Enzymes commonly used include lysozyme, lysostaphin, zymolase, mutanolysin, glycanases, proteases, and mannose.

Chemicals, e.g., detergents, disrupt the lipid barrier surrounding cells by disrupting lipid-lipid, lipid-protein and protein-protein interactions. The ideal detergent for cell lysis depends on cell type and source. Bacteria and yeast have differing requirements for optimal lysis due to the nature of their cell wall. In general, nonionic and zwitterionic detergents are milder. The Triton X series of nonionic detergents and 3-[(3-Cholamidopropyl)dimethylammonio]-1-propane-sulfonate (CHAPS), a zwitterionic detergent, are commonly used for these purposes. In contrast, ionic detergents are strong solubilizing agents and tend to denature proteins, thereby destroying protein activity and function. SDS, an ionic detergent that binds to and denatures proteins, is used extensively in the art to disrupt cells.

Physical disruption of cells may entail sonication, French press, electroporation, or a microfluidic device which may comprise fabricated structures can be used to mechanically disrupt a cell. These methods are known in the art.

RNA extraction can be coupled with the labeling methods described herein in order to characterize transcripts present in a single cell or population of cells. Currently available platforms/techniques such as the Fluidigm C1 instrument enable the study of the transcriptomes at the single cell level. The throughput of such instruments, however, is comparatively low. The C1 instrument, for example, allows for the parallel processing of up to 96 cells. The methods described herein allows for scalable, massively parallel processing of single cells in numbers that are orders of magnitude beyond any currently available platforms.

Labeling for Quantitative Analysis of Agents

Also contemplated herein is a method of labeling agents such that quantitative information about the agents can be extracted. Quantitative information includes the number or level of an agent present in a sample or cell. Examples include transcript expression levels in a cell or a sample, chromosome copy numbers in a cell or a sample, and number of PCR amplicons in a sample. This method can be used, inter alia, to quantify relative number or level of a transcript in a cell or tissue, or relative number or level of a cell such as bacteria in a sample.

In an exemplary method, a solid support, such as a bead or polymer, carries a plurality of nucleic acid labels. The nucleic acid labels on a bead contain common sequences (i.e., sequences present on all the labels on a single solid support) and unique sequences (i.e., sequences that distinguish each label from other labels on the solid support). The common sequences include a capture sequence such as a poly(dT) sequence. Common capture sequences may be common throughout all solid supports used in a particular analysis (e.g., if all solid supports are used to capture transcripts, then all labels may comprise a common poly(dT) sequence. The common sequences also include a first detectable oligonucleotide sequence or tag (which may be comprised of one or more index sequences). This first detectable oligonucleotide sequence or tag is unique to the solid support (i.e., it distinguishes the solid support from other solid supports, and thus distinguishes the plurality of transcripts bound to the solid support from other pluralities of transcripts bound to other solid supports). In this way, transcripts from a single cell may be identified as such. The nucleic acid label may also contain a unique sequence. This unique sequence is referred to as the second detectable oligonucleotide sequence or tag and it may be comprised of one or more index sequences). This sequence differs between labels on a single solid support so that each label may comprise a unique sequence. The first and second detectable oligonucleotide sequences may be generated using the methods described herein.

The detectable oligonucleotide sequences may be generated apart from the solid support and then attached to it. Alternatively, the sequences may be generated while attached to the support. As an example, the first detectable oligonucleotide sequence may be first generated and then attached to the solid support, following which the second detectable oligonucleotide sequence is generated directly on the support. In some embodiments, the second sequence is attached to the first sequence by combining an excess of the second sequences to the first sequences (which may or may not be attached to the solid support). Attachment may occur e.g., by ligation or polymerase-mediated attachment. The ensures that the solid support is exposed to a very large number of second sequences, much larger than the number of first sequences present on the solid support, such that each nucleic acid label on the solid support contains a unique second sequence. The labeling of the solid support could thus be performed as a bulk reaction with a large number of the previously first-sequence-labeled solid supports present in the same reaction. Alternatively, the first and second sequences are generated to form the nucleic acid label and then attached to the solid support.

As another alternative, nucleic acid labels appropriate for quantitative analysis are generated and used in the absence of a solid support (e.g., in an emulsion). The nucleic acid labels, either present on a solid support or alone, are then associated with one or more agents. A population of agents (e.g., RNA transcripts from a single cell) are uniquely labeled compared to other populations of agents using the first sequence (i.e., the common but not capture sequence) of the nucleic acid label. Subgroups of agents or individual agents (e.g., a single RNA transcript in a pool of RNA transcripts from a single cell) are uniquely labeled compared to other subgroups of agents or other individual agents in the same population using the second nucleic acid (i.e., the unique sequence) of the nucleic acid label. Thus, the number of subgroups or individual agents present in a population can be quantified.

In the example of quantitative transcriptome analysis, a sample containing multiple cells is processed and put into an emulsion such that droplets are formed. Cells are lysed either immediately prior to droplet formation (e.g., hypotonic lysis) or once they have already been encapsulated in an emulsion (e.g., freeze-thaw cycling), releasing the mRNA from the cell into the droplet. A single bead containing nucleic acid labels generated as described above is then introduced into the droplet (e.g., by droplet merging or picoinjection). Each nucleic acid label contains, in addition to the first (common) and second (unique) sequences, an oligo(dT) capture sequence that binds to the polyA tail present on each mRNA transcript. Each nucleic acid label captures one mRNA and is processed through a first strand cDNA synthesis reaction to create a copy of the RNA sequence that is covalently linked to the labeled solid support. Each copy of the mRNA sequence will then contain the first sequence of the nucleic acid label, which is common to every mRNA on the same solid support, and the second sequence of the nucleic acid label, which is unique to every individual mRNA in the same solid support. This allows for the number of original mRNA molecules to be quantified, as each original individual mRNA will have a unique sequence that is carried through further processing and/or amplification.

Cell Tracking Applications

In still other aspects, the invention provides methods of tracking cells by uniquely labeling such cells using methods of the invention and/or variations thereof. For example, the invention contemplates that cells may be uniquely labeled using viruses that stably integrate into the genome at random positions. Such cells may be administered to a subject and the effect of such cells monitored. Such cells may be further labeled using the same or different viruses that stably integrate into the genome. It is to be understood that in some instances the unique labeling of the cells using such viruses results not from the virus itself, since the same viral sequence will integrate into a plurality of cells, but rather from the particular location of integration of the virus. If the virus is engineered to carry and integrate a primer sequence (along with the viral sequence), then it and its neighboring sequence at the site of integration can be amplified and sequenced, and thereby distinguished from other integration events.

The invention contemplates that a cell may be infected with a virus, including a different virus, per condition to which it is exposed. For example, a population of cells may be initially infected with virus A and then subsequently infected with virus B upon exposure to condition B. Viruses A and B are able to stably integrate into the genome of the host subject and their particular integration patterns will differ from and likely be unique compared to the integration patterns in another cell. In this way, cells may be uniquely labeled, including labeled in a dynamic manner to reveal information about the cell such as prior history of the cell.

Reference can be made to Lu et al. Nature Biotechnology, 2011, 29(10):928-934, the entire teachings of which are incorporated by reference herein.

Tagging Epigenetics Constructs

In a further embodiment, the solid supports including beads have been labeled using the combinatorial split-pool synthesis methods to generate a population of identically labeled oligos attached to the solid support. These oligos may be cleavable such that they can be released into, for example, a multi-well plate or a droplet and ligated onto the free ends of DNA bound by chromatin or any other nucleic acids in the cell. These released oligos contain the barcode generated by split pool synthesis and a T7 promoter such that only the nucleic acids ligated by the oligos are amplified in an in vitro transcription reaction following emulsion breaking. This allows for the single cell labeling of Chromatin states as described in PCT/US2013/029123 and published as WO 2013/134261, the entire contents of which are incorporated by reference herein.

Labeling Nucleic Acid-Protein Complexes

The methods described above can also be used to label various nucleic acid-protein complexes. Methods such as chromatin immunoprecipitation (e.g., ChIP and ChIA-PET), chromosome conformation capture (e.g., 3C and Hi-C) and various RNA-protein pull-down methods are designed to associate (crosslink) nucleic acids to various proteins.

The three-dimensional (3D) conformation of chromosomes is involved in compartmentalizing the nucleus and bringing widely separated functional elements into close spatial proximity. Understanding how chromosomes fold can provide insight into the complex relationships between chromatin structure, gene activity, and the functional state of the cell. Long-range interactions between specific pairs of loci can be evaluated with chromosome conformation capture (3C), using spatially constrained ligation followed by locus-specific polymerase chain reaction (PCR). Adaptations of 3C have extended the process with the use of inverse PCR (4C) or multiplexed ligation-mediated amplification (5C). Still, these techniques require choosing a set of target loci and do not allow unbiased genome wide analysis. The method Hi-C adapts the above approach to enable purification of ligation products followed by massively parallel sequencing. Hi-C allows unbiased identification of chromatin interactions across an entire genome. Aspects of the method include cells being crosslinked with formaldehyde; DNA being digested with a restriction enzyme that leaves a 5' overhang; the 5' overhang is filled, including a biotinylated residue; and the resulting blunt-end fragments are ligated under dilute conditions that favor ligation events between the cross-linked DNA fragments. The resulting DNA sample contains ligation products having fragments that were originally in close spatial proximity in the nucleus, marked with biotin at the junction. A Hi-C library may then be created by shearing the DNA and selecting the biotin-containing fragments with streptavidin beads. The library is then analyzed by using massively parallel DNA sequencing, producing a catalog of interacting fragments. This is further described in Lieberman-Aiden E et al., Comprehensive mapping of long-range interactions reveals folding principles of the human genome, *Science*. 2009 Oct. 9; 326 (5950):289-93, the contents of which are incorporated herein in their entirety. Thus, instead of using processes such as circularization to covalently link nucleic acids together within a given complex, the labeling methods described above can be leveraged in order to uniquely label the components of each complex.

EXAMPLES

The following Examples are meant for illustrative purposes, and are not meant to be exclusive or limiting. Each Example illustrates a method for labeling a specific type of construct (e.g., genomic DNA or a solid support), but it is to be understood that these methods also apply to any type of constructs that can be attached to an oligonucleotide by some means. For example, covalent attachment of a nucleotide adapter to a non-nucleotide-based construct, e.g. a protein, a cell, or a chemical, would allow for addition of unique oligonucleotide labels to a non-nucleotide-based constructs.

Example 1: Polymerase-Mediated Bioinformatic Association of Nucleic Acid Ends for Mate-Pair Analysis Generation of End-Labeled Genomic DNA Fragments A method for bioinformatically associating the ends of genomic DNA is outlined in FIG. 1. Genomic DNA is fragmented and size selected to a known size using techniques known in the art (e.g., sonication, cavitation, point-sink or mechanical shearing, or a DNA fragmenting enzyme and size-exclusion columns or gel purification). The genomic DNA is then A-tailed and ligated to a biotinylated, T-tailed asymmetric oligonucleotide adapter using methods known in the art (see, e.g. Maniatis, Molecular Cloning). Klenow exo-enzyme is commonly used to add a single nucleotide to the 3' termini of DNA fragments). The adapter is a partial duplex to allow for annealing of the single-stranded oligonucleotide indexes described below.

One or more index libraries (preferably 1-4 libraries) are created such that each library contains approximately >1000 unique single-stranded oligonucleotide indexes, thus approximately 2000-4000 unique indexes are used. Index libraries may be created in droplets using standard flow focusing techniques (ref) or placed in the wells of standard laboratory plasticware (e.g., 384-well or 1152-well plates). For a given library, each droplet/well will contain many copies of one unique single-stranded index. Droplets/wells may contain some or all of the key components of a polymerase fill-in reaction (e.g., $MgCl_2$, dNTP, and Polymerase). Each unique single-stranded oligonucleotide index contains 3 distinct regions: sequence complimentary to the adapter (Ad) or to a previously added index sequence (B or C), a unique index sequence (Idx), and a sequence used to "capture" the next index oligonucleotide index which contains one or more dUTP nucleotides (B'/C').

Fragmented genomic DNA ligated to an adapter is diluted to a desired concentration to control the number of molecules per droplet/well (e.g., a single DNA molecule per droplet/well or more than a single DNA molecule per droplet/well) and merged with (see above references for droplet merging)/added to the first index library (Library "A" in FIG. 1).

The Ad region of each unique single-stranded oligonucleotide index binds to the adapter on each end of the fragmented genomic DNA molecule. A polymerase-mediated fill-in reaction is performed in each droplet, creating the complement to the index and capture regions on the each unique single-stranded oligonucleotide index a, and thus generating unique double-stranded oligonucleotide indexes.

If emulsion droplets are utilized, they are then broken using various mechanical or chemical reagents depending on the oil/surfactant utilized in the emulsion, resulting in the combination and mixing of the DNA from each droplet. If standard plastic labware is used, samples in all wells are pooled together, resulting in the combination and mixing of the DNA from each well. Mixed DNA is the treated with USER™ enzyme (Uracil-Specific Excision Reagent, New England BioLabs Inc., Ipswich, Mass.), causing the capture portion of the double-stranded oligonucleotide index to be digested due to the presence of one or more dUTP nucleotides. This digestion reveals the nascent strand, which is complementary to a sequence contained in the next library of indexes (Library "B" in FIG. 1).

The process of fragmented genomic DNA dilution, merging with a droplet library or mixing in standard labware, polymerase fill-in, breaking the droplets or pooling the wells, and treatment with USER™ enzyme is repeated for the desired number of cycles, each time adding one new unique oligonucleotide index sequence to both ends of the fragmented genomic DNA.

Figure 3A:
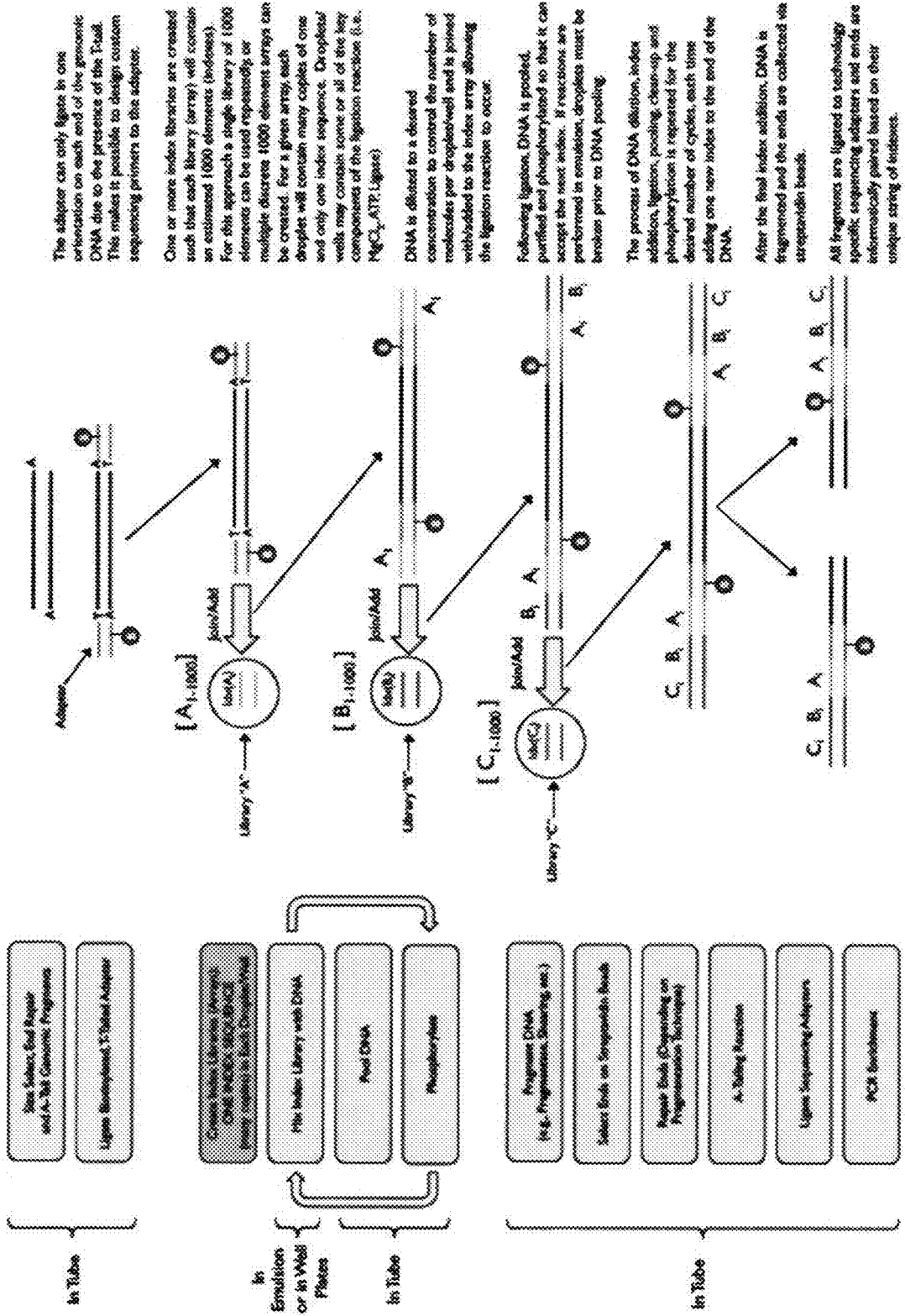
FIG. 3A is a schematic of a mate pair synthesis using droplets or multi-well plates and oligonucleotides tags which may comprise unique sequences (such unique sequences referred to as "index sequences" or "Idx"). The oligonucleotide tags are attached to each other, to form a unique label by virtue of the index sequences, using ligation.
Figure 3B:
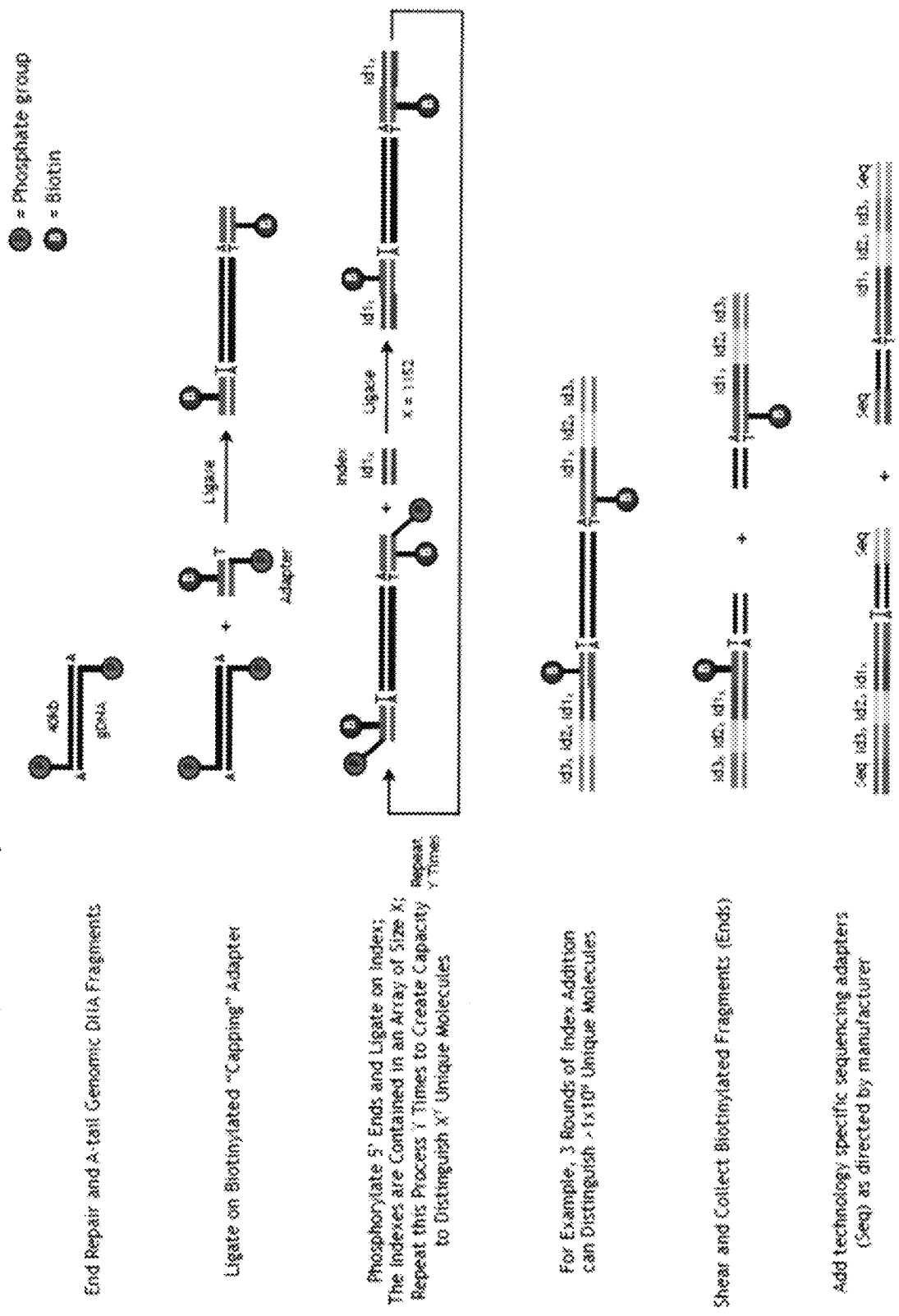
FIG. 3B is a schematic illustrating a recursive indexing strategy of the invention.
Figure 3D:
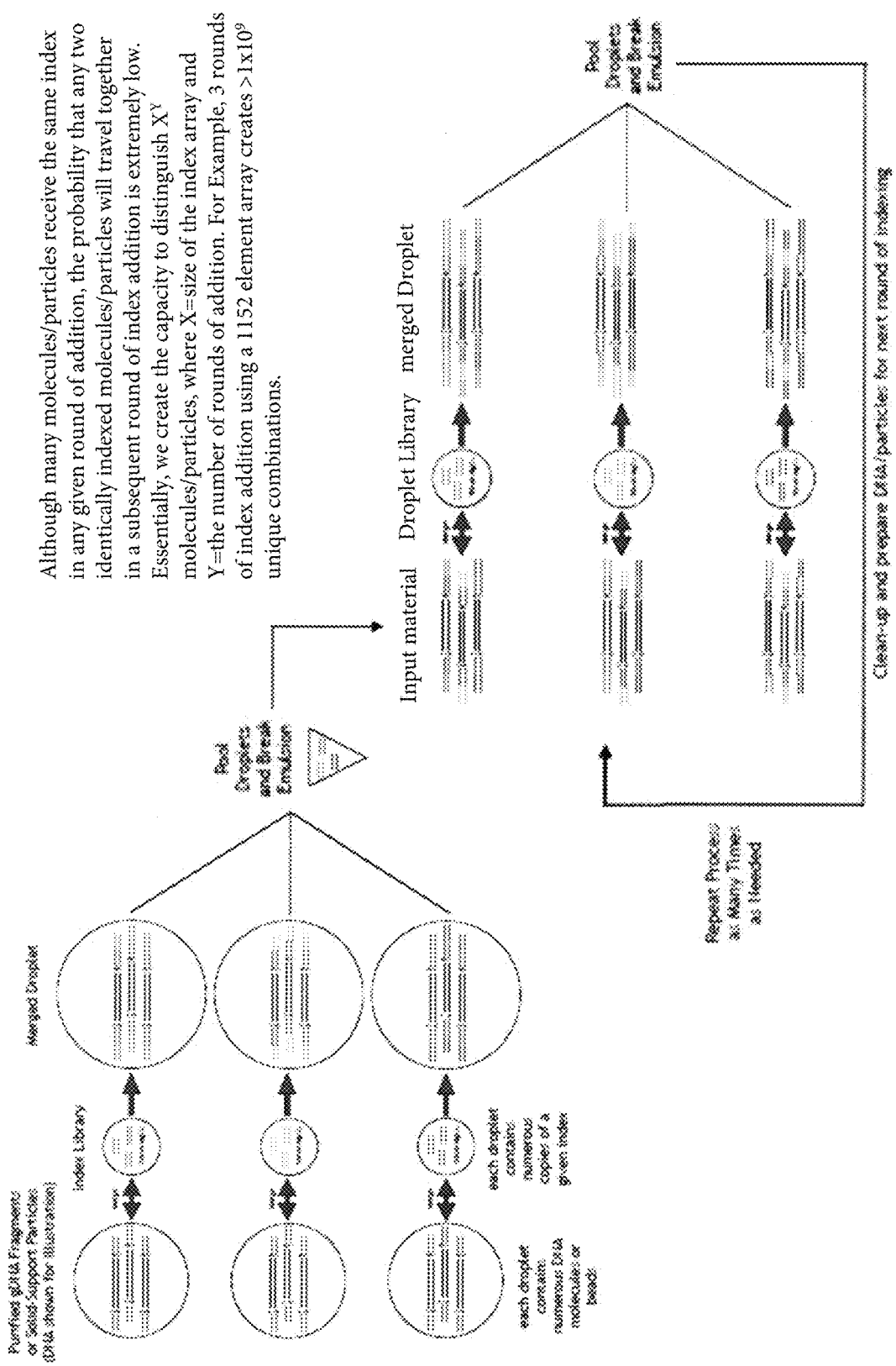
FIG. 3D is a schematic illustrating index addition to either beads or DNA using droplets.
Figure 3E:
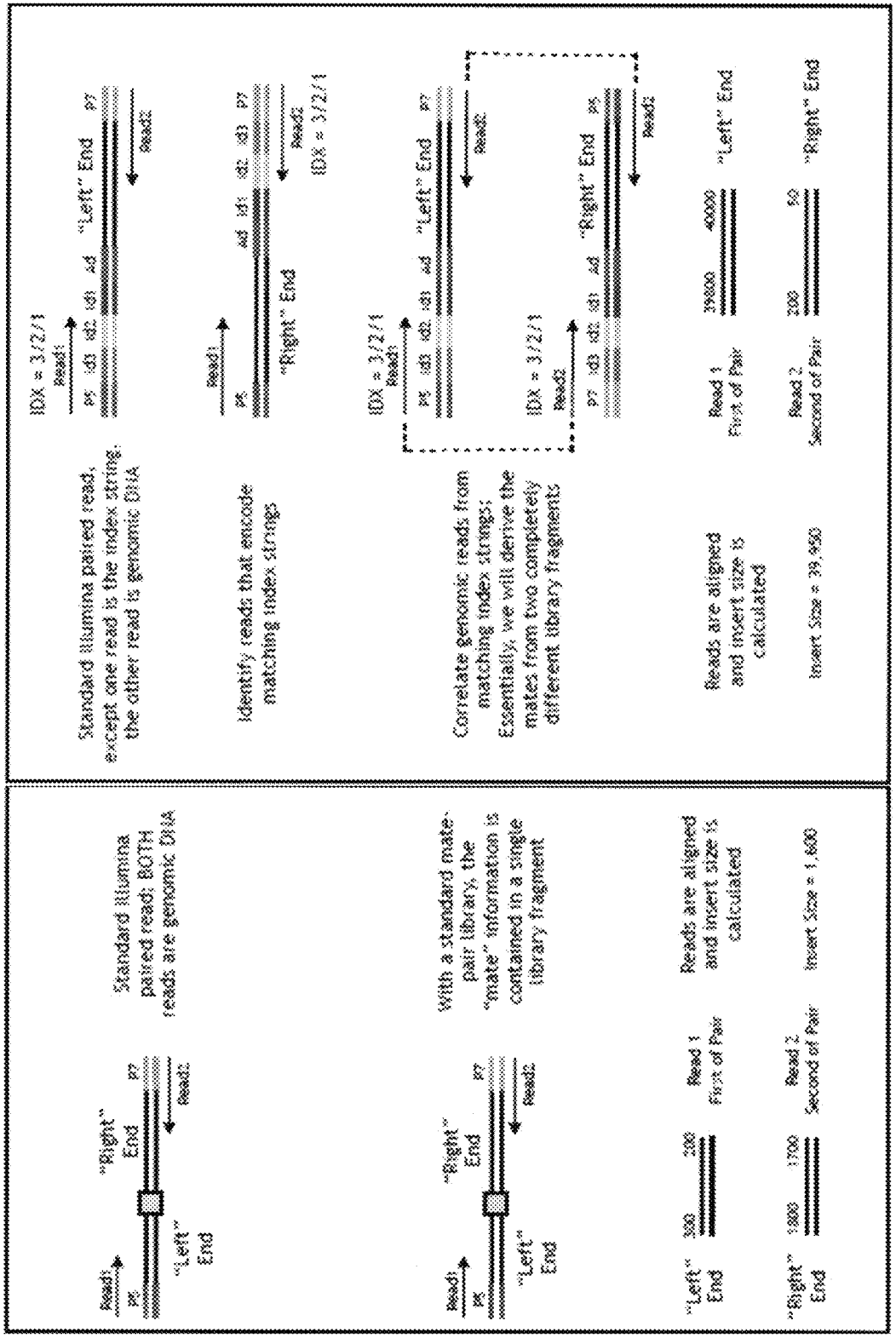
FIG. 3E is a schematic illustrating an approach to informatically associate mate pairs in accordance with the invention.

After the final index addition, the result is fragmented genomic DNA uniquely end-labeled on both the 5' and 3' end with a unique label made up of many oligonucleotide indexes. The uniquely end-labeled fragmented genomic is then fragmented and the ends are collected via streptavidin beads, which recognized the biotin label on the adapter. Fragments can be ligated to technology specific sequencing adapters (e.g., Illumina adapters) and sequenced. Ends are informatically paired by matching the unique label on one fragment of DNA with the same unique label on the other fragment of DNA (see FIG. 3E).

This method of bioinformatics association can also be used with other types of nucleic acids, such as RNA, cDNA, or PCR-amplified DNA, or any other type of construct where such a labeling scheme is required. This method can also be performed in well plates instead of emulsion droplets. To accomplish this, arrays of oligonucleotide indexes are prepared in 384-well (or 1536-well) plates. 1 to 4 index arrays are created, each containing 1000 unique indexes for a total of 1000-4000 unique indexes. Fragmented genomic DNA is aliquoted into at least one index array 384-well (or 1536-well) plate at a desired density. After the index is attached to the fragmented genomic DNA, the index-labeled fragmented genomic DNA is optionally purified and then pooled together with the other index-labeled fragmented genomic DNA molecules. The index-labeled fragmented genomic DNA molecules are then redistributed to a second set of index arrays either containing the same set of unique indexes previously used or new unique indexes. The pooling of the index-labeled fragmented genomic DNA molecules causes mixing or shuffling such that redistribution to a second set of indexes is random, minimizing the possibility that multiple index-labeled fragmented genomic DNA molecules contain the same series of indexes that make up the unique label.

Example 2: Ligation-Mediated Bioinformatic Association of Nucleic Acid Ends in Emulsions for Mate-Pair Analysis Validation of Ligation in Emulsions A 34 bp adapter was designed. The adapter was biotinylated and A-tailed to force directionality of ligation. Ligation was performed in an tube or an emulsion using 50 ng of lambda DNA and 50 ng of adapter. Lambda DNA was used as it is unlikely to form circles. Droplets were created by standard techniques (e.g., flow focusing at a T-junction using a PDMS-based microfluidic chip). Channel 1 contained DNA in ligase buffer (500 microliters) and channel 2 contained Quick Ligase in ligase buffer (500 microliters). PCR primers were designed to amplify internally within the lambda DNA (ligation-independent) or to amplify a portion of the adapter and the 5' or 3' end of the lambda DNA (ligation-dependent). Negative controls were performed in tubes to ensure ligation was ligase-dependent.

Figure 2:
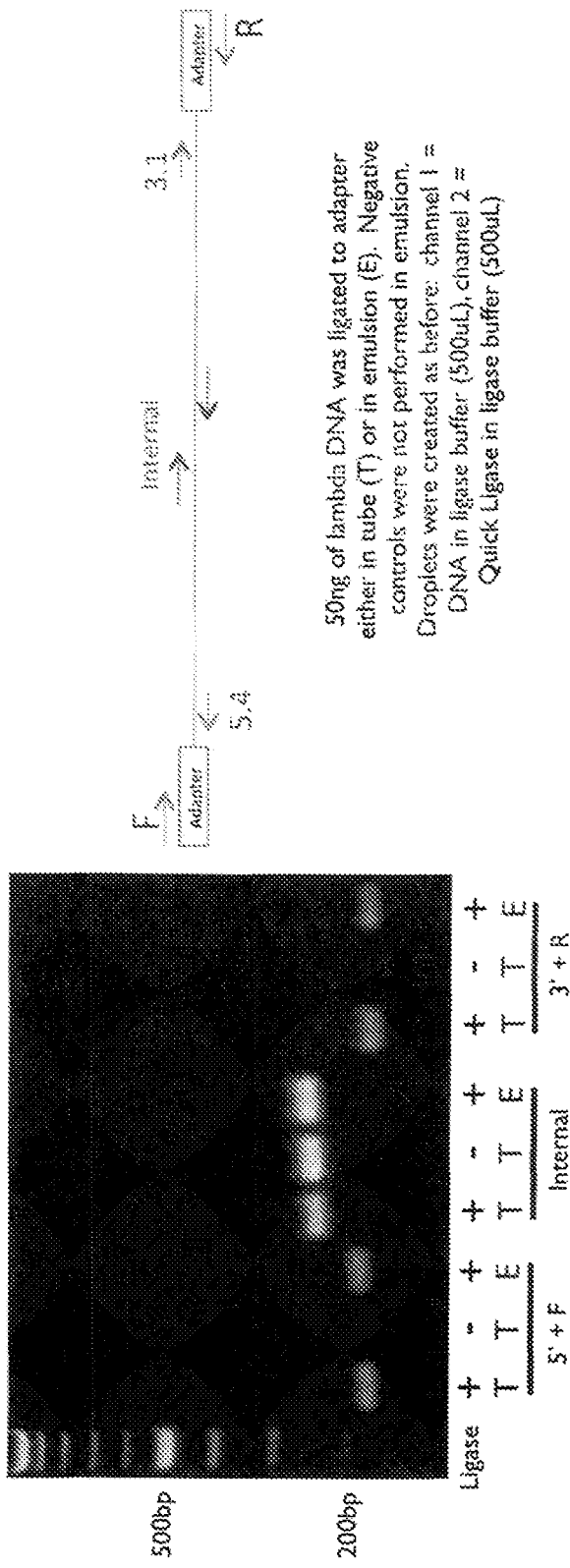
FIG. 2 is a gel electrophoresis showing ligation of an adapter sequence in either a tube (T) or an emulsion droplet (E).

FIG. 2 shows that ligation was achieved in both tubes and emulsion droplets, although ligation can also be achieved in other methods involving, for example, high-throughput plates. The forward primer for the adapter and the 5' primer for the lambda DNA only amplified in the presence of ligase, indicating that the adapter and the 5' end of the lambda DNA had ligated together in both tubes and emulsion droplets. The same result was achieved using the reverse primer for the adapter and the 3' primer for the lambda DNA, indicating that the adapter and the 3' end of the lambda DNA had ligated together in both tubes and emulsion droplets. These results demonstrate that ligation can be successfully performed in both tubes and emulsion droplets.

Generation of End-Labeled Genomic DNA Fragments

A method for bioinformatically associating the ends of genomic DNA is outlined in FIG. 3. Genomic DNA is fragmented and size selected to a known size using techniques known in the art as described in Example 1. The genomic DNA is then A-tailed and ligated to a biotinylated, T-tailed asymmetric oligonucleotide adapter using methods well known in the art as described in Example 1.

Multiple droplet libraries (preferably 2-4 libraries) are created such that each library contains approximately 1000 unique double-stranded oligonucleotide indexes, thus approximately 2000-4000 unique indexes are used. For a given library, each droplet will contain many copies of one unique double-stranded index. Droplets may contain some or all of the key components of a ligation reaction (e.g., $MgCl_2$, ATP, Ligase).

Fragmented genomic DNA ligated to an adapter is diluted to a desired concentration to control the number of molecules per droplet (e.g., a single DNA molecule per droplet or more than a single DNA molecule per droplet) and merged with the first index droplet library (Droplet Library "A" in FIG. 3).

A ligation reaction is performed in each droplet, joining each unique double-stranded oligonucleotide index to the adapter on each end of the genomic DNA. The emulsion is then broken and the DNA is phosphorylated so that a second index can be ligated to the end of the first index.

The process of fragmented genomic DNA dilution, merging with a droplet library (e.g. Droplet Library "B" or "C" in FIG. 3), ligation, breaking the droplets, and phosphorylation is repeated for the desired number of cycles, each time adding one new unique oligonucleotide index sequence to both ends of the fragmented genomic DNA.

After the final index addition, the result is fragmented genomic DNA uniquely end-labeled on both the 5' and 3' end with a unique label made up of many oligonucleotide indexes. The uniquely end-labeled fragmented genomic is then further fragmented and the ends are collected via streptavidin beads, which recognized the biotin label on the adapter. Fragments can be ligated to technology specific sequencing adapters (e.g., Illumina adapters) and sequenced. Ends are informatically paired by matching the unique label on one fragment of DNA with the same unique label on the other fragment of DNA as described in Example 1.

As with Example 1, this method can be used for other types of nucleic acids, such as RNA, cDNA, or PCR-amplified DNA, or any other type of construct where such a labeling scheme is required. Also as with Example 1, this method can be performed in well plates instead of emulsion droplets.

Validation of Ligation-Mediated End-Labeling

Three libraries were created "in bulk" in microcentrifuge tubes from fragmented, end-repaired, A-tailed *E. coli* genomic DNA. For all three libraries, an initial ligation reaction was performed to add on a generic adapter to the ends of the *E. coli* genomic DNA. Genomic DNA libraries were then subjected to 1 (Library 1), 2 (Library 2), or 3 (Library 3) rounds of index ligation. Index ligation was performed by joining unique double-stranded oligonucleotide indexes to the adapter on each end of the genomic DNA. If required, the DNA was phosphorylated so that a second index could ligated to the end of the first index (two rounds of index ligation) or a third index could be ligated to the end of a second index (three rounds of index ligation). For round 1 and round 3 of index ligation, the same library/pool of indexes was used (pool A). For round 2, a library/pool of different indexes was used (pool B). As a final step, Illumina indexed adapters were ligated to all three genomic DNA libraries. Libraries were then pooled and sequence on an Illumina MiSeq (Illumina, San Diego, Calif.) using standard Illumina sequencing primers. Paired reads were identified and analyzed en masse (i.e. data from read 1 (3' end read) and read 2 (5' end read) was analyzed together as a single population). Sequencing data was analyzed by breaking up the reads into four separate, linear 8-mer populations (i.e. positions 1 through 4 in the read), since the indexes were each 8 bp in length. For each position, the number of reads containing index or adapter were measured.

Figure 4:
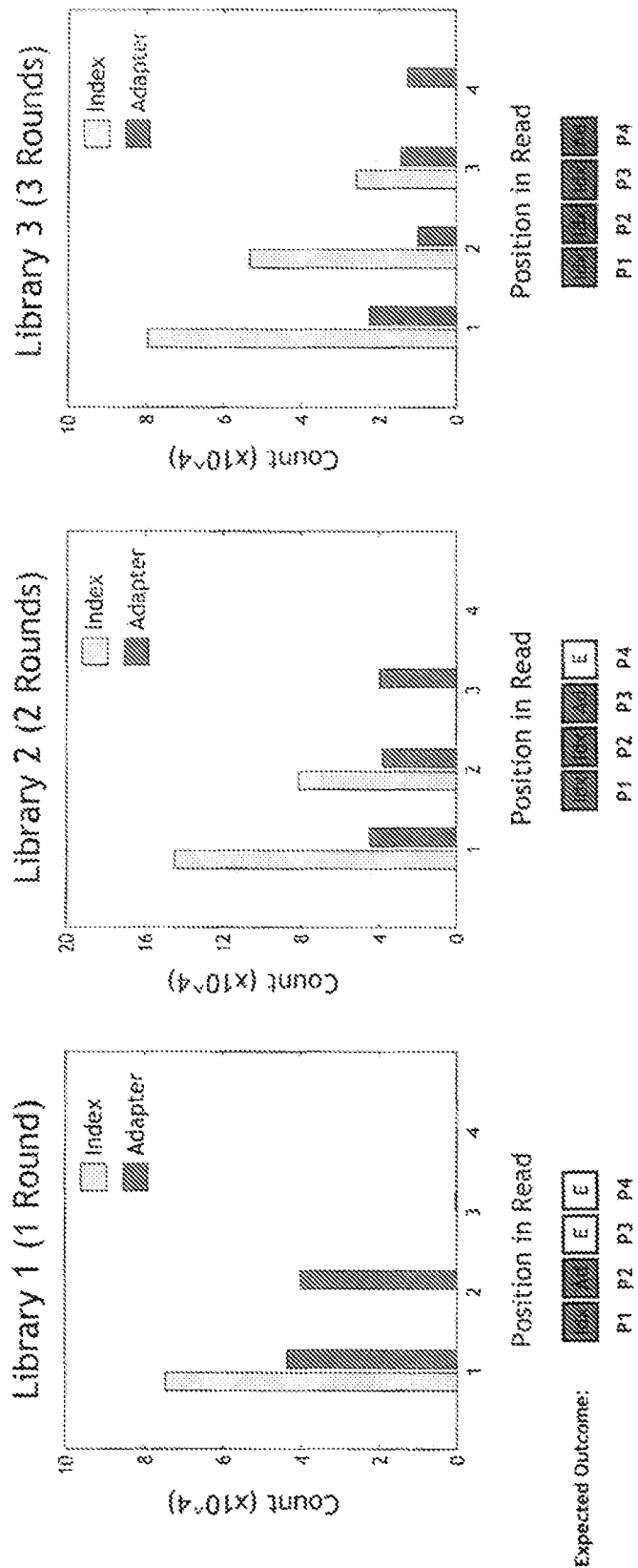
FIG. 4 provides bar graphs showing the results of 2-4 rounds of oligonucleotide tag attachment to demonstrate ligation efficiency.

FIG. 4 depicts the results of the total read population analysis (i.e. en masse analysis) of the index ligation method. Library 1, which underwent 1 round of index ligation, had an expected outcome of an index read in position 1 and an adapter read in position 2. Library 2, which underwent 2 rounds of index ligation, had an expected outcome of an index read in position 1 and 2 and an adapter read in position 3. Library 3, which underwent 3 rounds of index ligation, had an expected outcome of an index read in position 1 to 3 and an adapter read in position 4.

Figure 5:
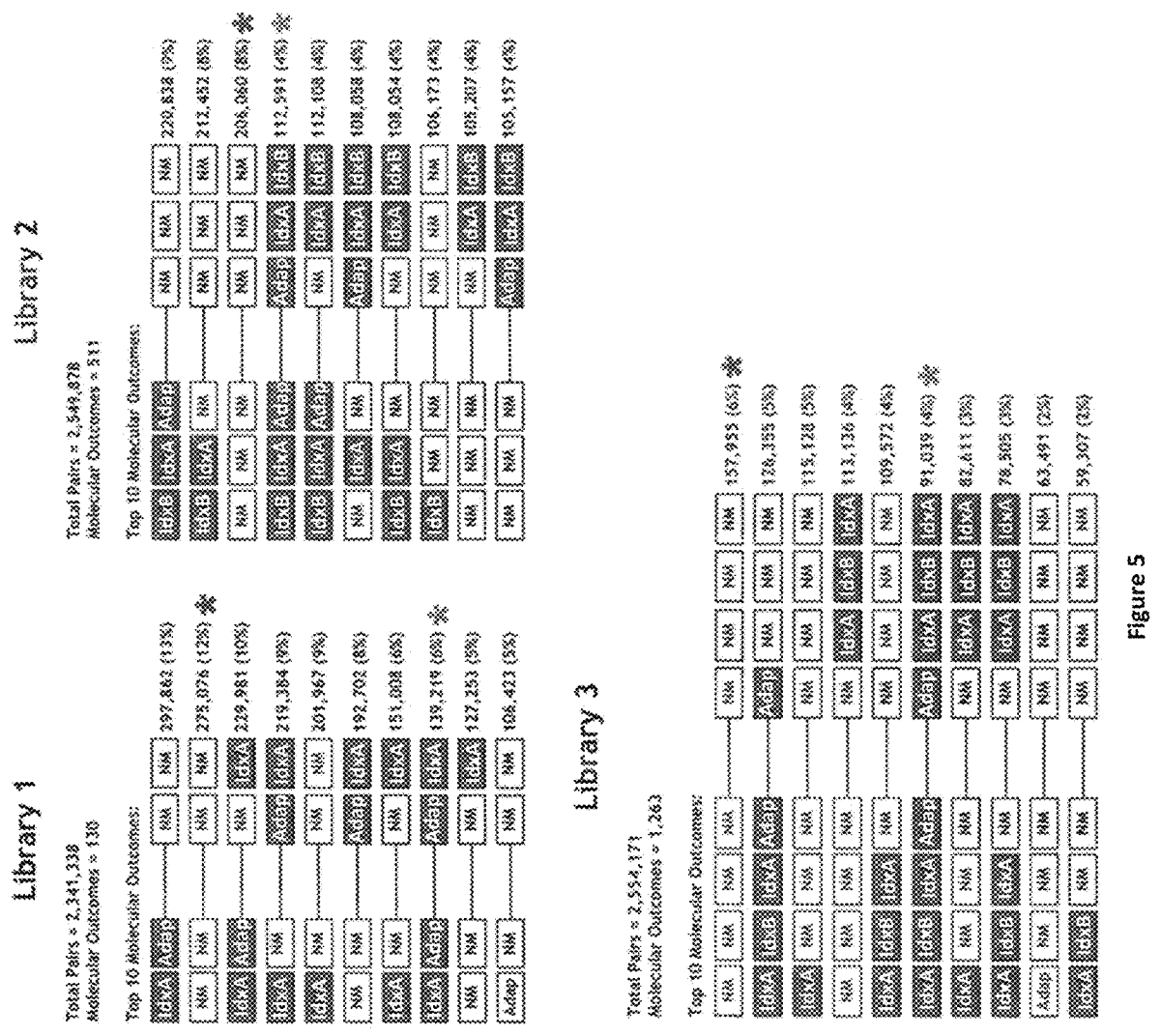

FIG. 5 depicts the results of read pair analysis of individual molecules that underwent the index ligation method. Instead of analyzing the data from read 1 (3' end read) and read 2 (5' end read) together, reads were paired so that a molecule-by-molecule analysis was performed. First, reads were paired based on their unique read identifier. Each read was then broken down into 4 positions (8-mers) per read as described above. For each library, the total number of read pairs and the total number of unique molecular outcomes were determined and are shown in FIG. 5. The composition of the top 10 most prevalent molecular outcomes and the number of pairs for each outcome are also shown in FIG. 5. It was determined that the most desired outcome (the correct expected outcome) occurred 6% of the time in Library 1, 4% of the time in Library 2, and 4% of the time in Library 3.

Thus, FIGS. 4 and 5 show that the expected outcome was achieved and thus index ligation is a valid method of generating a unique label.

Figure 6:
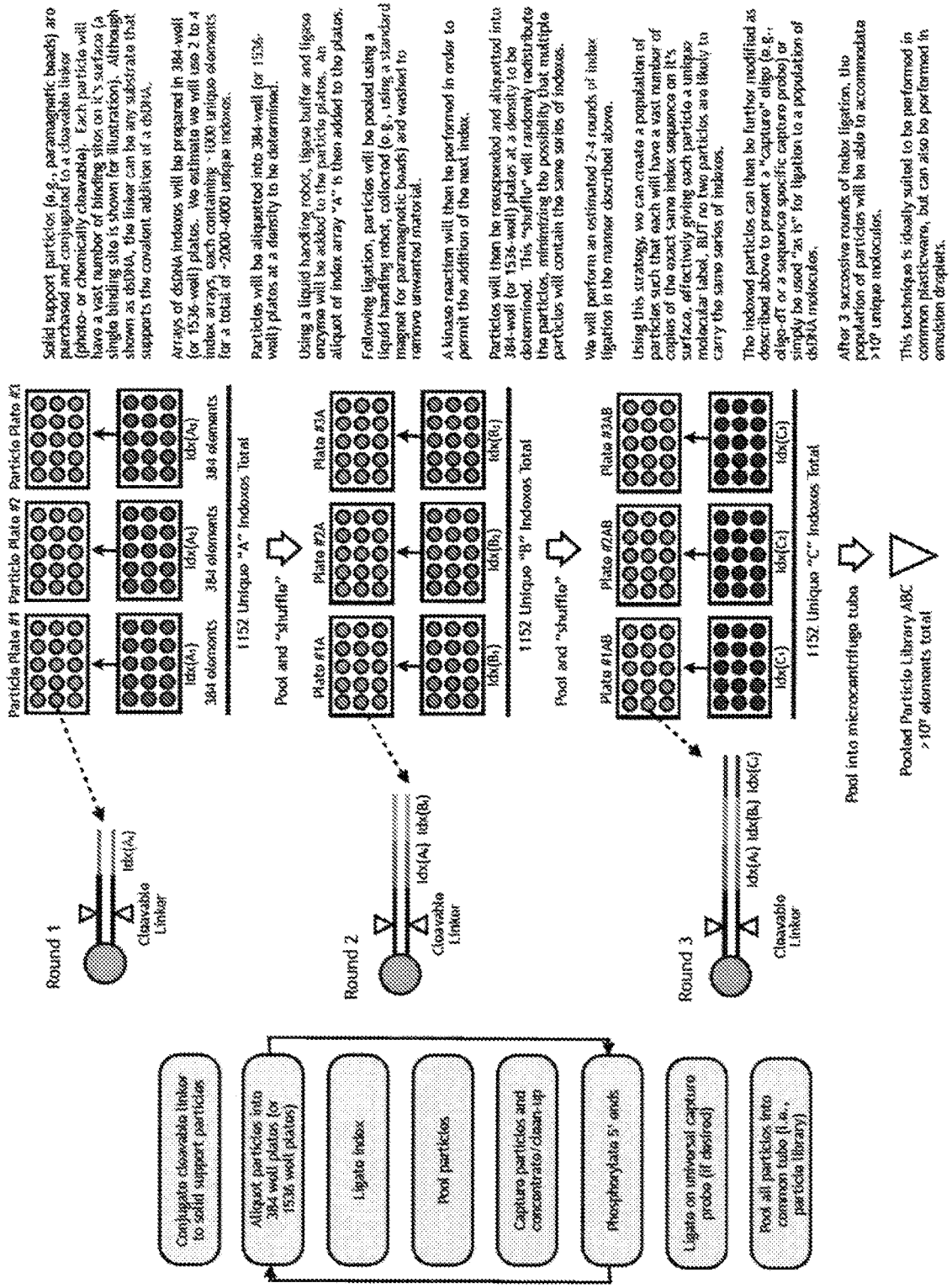
FIG. 6 is a schematic of a plate-based approach to the generation of unique index combinations (labels). The unique labels are generated on particles or directly on nucleic acids (e.g., genomic DNA and cDNA). Oligonucleotide tags are present in the wells of multiwell plates. It is to be understood that a well may typically comprise an oligonucleotide tag of a single type, although it does contain multiple copies of the same oligonucleotide tag. Each well may comprise, at any given time, one or more beads or nucleic acid fragments.

Example 3: Ligation-Mediated Oligonucleotide-Based Unique Labels Attached to Solid Supports Solid support particles (e.g. beads or a polymer) are purchased or provided and conjugated to a cleavable linker (photo- or chemically cleavable). Each solid support has a vast number of binding sites on its surface. FIG. 6 shows a single binding site on a bead for illustrative purposes. The cleavable linker in FIG. 6 shows a double-stranded DNA (dsDNA) linker, but the cleavable linker can be any substrate that supports the covalent addition of a dsDNA.

Arrays of dsDNA oligonucleotide indexes are prepared in 384-well (or 1536-well) plates. 2 to 4 index arrays are created, each containing ~1000 unique indexes for a total of ~2000-4000 unique indexes.

Solid supports are aliquoted into 384-well (or 1536-well) plates at a desired density. Using a liquid handling robot, ligase buffer and ligase enzyme are added to the solid support plates. An aliquot of index array "A" is then added to the plates (FIG. 6).

Following ligation of the "A" index to the solid supports, solid supports are pooled using a liquid handling robot, collected (e.g., using a standard magnet for paramagnetic beads or a centrifuge for beads or polymers), and washed to remove unwanted material.

A kinase reaction is then performed in order to permit the addition of the next index.

Solid supports are then resuspended and aliquoted into 384-well (or 1536-well) plates at a desired density. This mixing or shuffling randomly redistributes the solid supports, minimizing the possibility that multiple solid supports contain the same series of indexes that make up the unique label.

Index ligation is repeated 2-4 times. For example, the above steps are repeated with index array "B" and then again with index array "C" as illustrated in FIG. 6. Upon completion of this method, uniquely-labeled solid supports are generated, wherein each solid support has multiple copies of the same unique label made up of an index A sequence, an index B sequence, and an index C sequence but has a different unique label than other solid supports. The mixing and redistribution of the solid supports after each addition of an index sequence makes it unlikely that two solid supports will carry the same unique label. To illustrate this, after 3 successive rounds of index ligation, the population of solid supports can accommodate >$10^9$ unique labels.

The uniquely-labeled solid supports can then be further modified to include a capture oligo (e.g., oligo-dT or a sequence specific capture probe). Alternatively, the uniquely-labeled solid supports can be used "as is" for ligation or binding of agents (e.g., DNA, RNA, cells, polymers, proteins, etc.).

This method, for example, can be performed in common plastic ware (e.g. well plates) or emulsion droplets.

Figure 7:
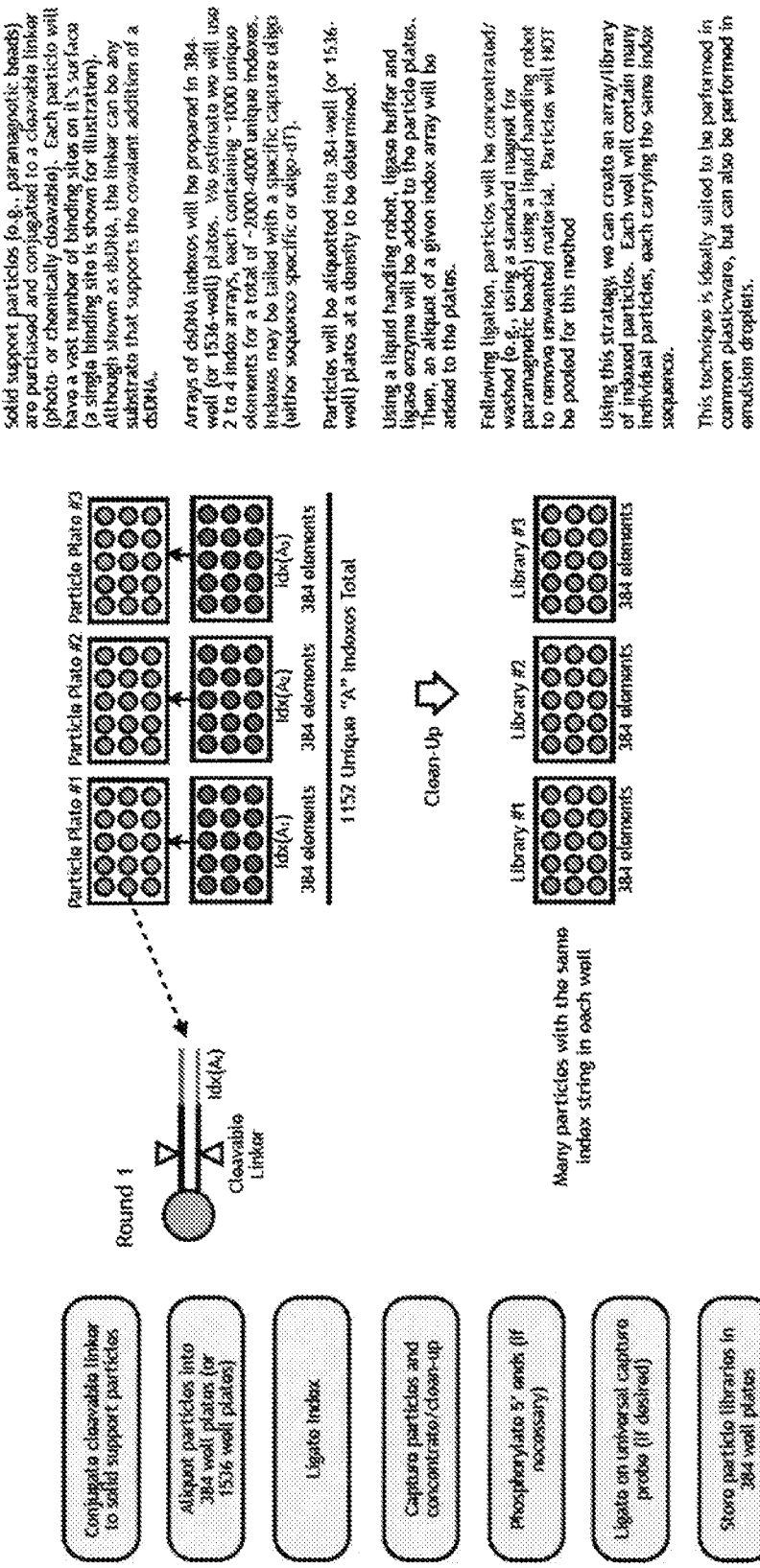
FIG. 7 is a schematic of a plate-based approach to the generation of several pluralities of particles, wherein all the particles within a plurality are identically labeled.

This method can be also adapted to create discrete libraries of uniquely labeled solid supports as shown in FIG. 7. Indexes and solid supports aliquoted into well plates as described above. Index array "A" is added to each plate of solid supports and ligated to the solid supports. A liquid handling robot is used to wash the solid supports and remove unwanted material. Solid supports are not pooled, but instead are kept separate. Index array "B" is then added to each plate of solid supports and ligated to the solid supports. This is repeated with Index array "C". This method generates many solid supports with the same unique label contained within the same well. This method, for example, can be performed in common plastic ware (e.g. well plates) or emulsion droplets.

Example 4: Microbiome Typing Using Unique Labels

Figure 8:
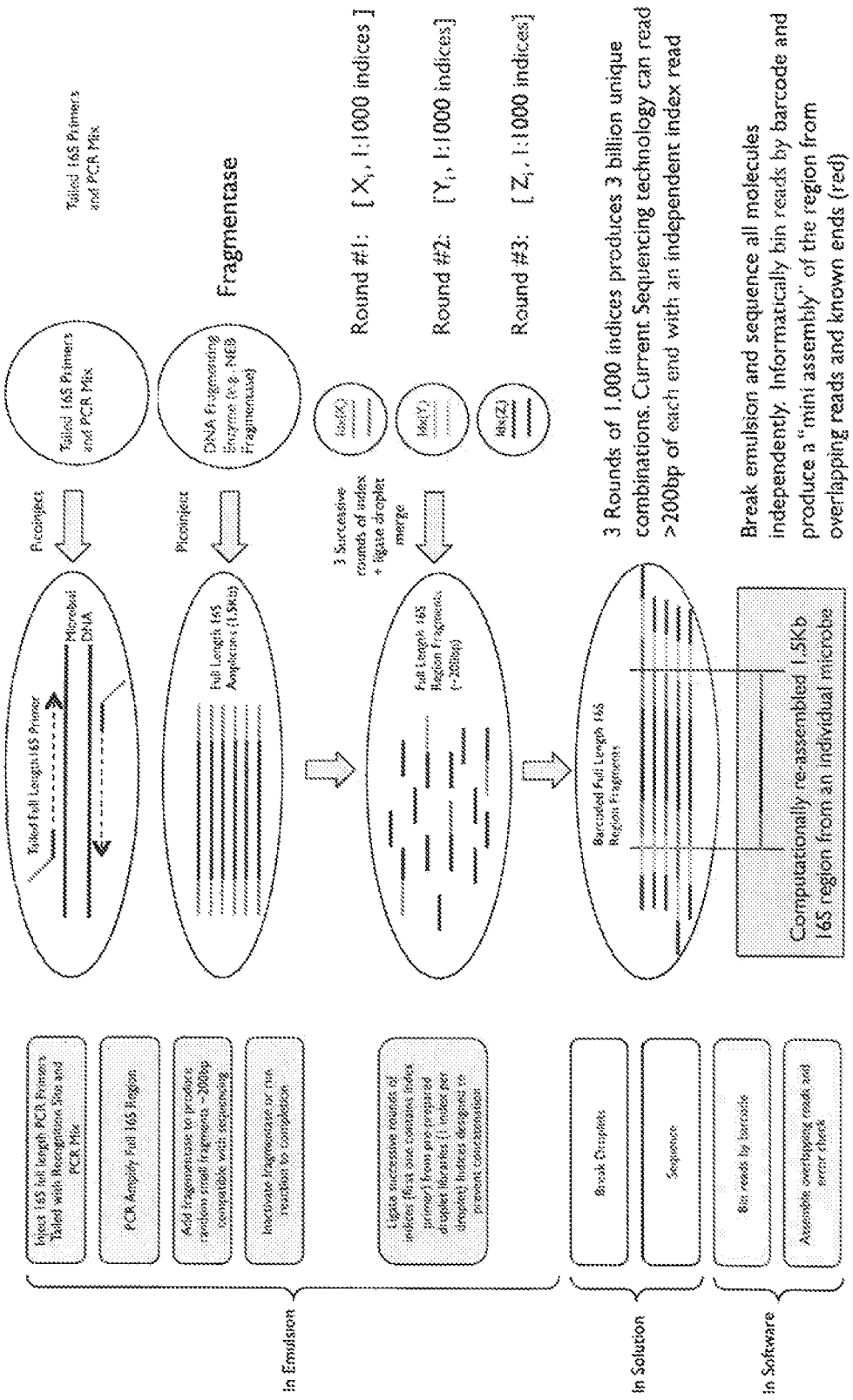
FIG. 8 is a schematic illustrating application of the labeling strategies of the invention to amplified fragments from the 16S region of a microbe.

FIG. 8 depicts an exemplary method for identifying multiple species of bacteria contained within a microbiome. A microbiome sample is isolated (e.g. from the gut of an animal or from a sample in the environment such as a water source) as is known in the art. Individual cells are suspended in emulsions and lysed by methods known in the art (e.g., chemical lysis).

16S rRNA primers tailed with a recognition site (in order to identify the ends of the 16S rRNA gene after sequencing) and PCR mix are picoinjected into each emulsion droplet in order to amplify the full-length 16S rRNA gene. The 16S rRNA gene has been used previously for phylogenetic studies as it is highly conserved between different species of bacteria and archaea. Universal primers are used to amplify the 16S rRNA gene from different species (e.g. 27F and 1492R or 27F and 534R from Weisburg, Barns, Pelletier and Lane. 16S ribosomal DNA amplification for phylogenetic study. J. Bacteriol. January 1991 vol. 173 no. 2 697-703). 16S rRNA gene sequences contain hypervariable regions that provide species-specific signature sequences useful for bacterial identification. After amplification, a DNA fragmenting agent (e.g., Fragmentase® from New England BioLabs Inc., Ipswich, Mass.) is added to produce random small fragments compatible with current sequencing technology (e.g., approximately 200 bp). Fragmentase® is inactivated by addition of 0.5 M EDTA, by heat inactivation, or by allowing the reaction to run to completion.

3 rounds of index ligation are performed as described in Example 2 to label all of the 16S fragments contained within a single emulsion droplet with the same label containing 3 indexes. In this method, each all of the fragments in each droplet will be identically labeled compared to each other but uniquely labeled compared to fragments contained in other droplet.

After completion of the index ligation, the emulsion droplets are broken and the 16S fragments pooled. The 16S fragments from multiple different microbes can then be sequenced at the same time. Sequencing is performed on standard commercial machines as is known in the art, e.g., Illumina Sequencing (Illumina, San Diego, Calif.).

The sequencing reads are then binned according to the common unique label "barcode" and a "mini-assembly" of the region from overlapping regions and known ends (from the recognition site on the primers) is performed. Thus, a computational re-assembly of the 1.5 Kb 16S region is performed from individual microbes.

Example 5: Other Methods of Generating Unique End-Labeled Nucleic Acids

The following methods describe addition of one or two index sequences to create a unique end-labeled nucleic acid. It is to be understood that more than one or two index sequences can be added by repeating the steps required to add an additional index sequence. As a result, a unique end-labeled nucleic acid could have three or more index sequences per unique label.

Figure 9:
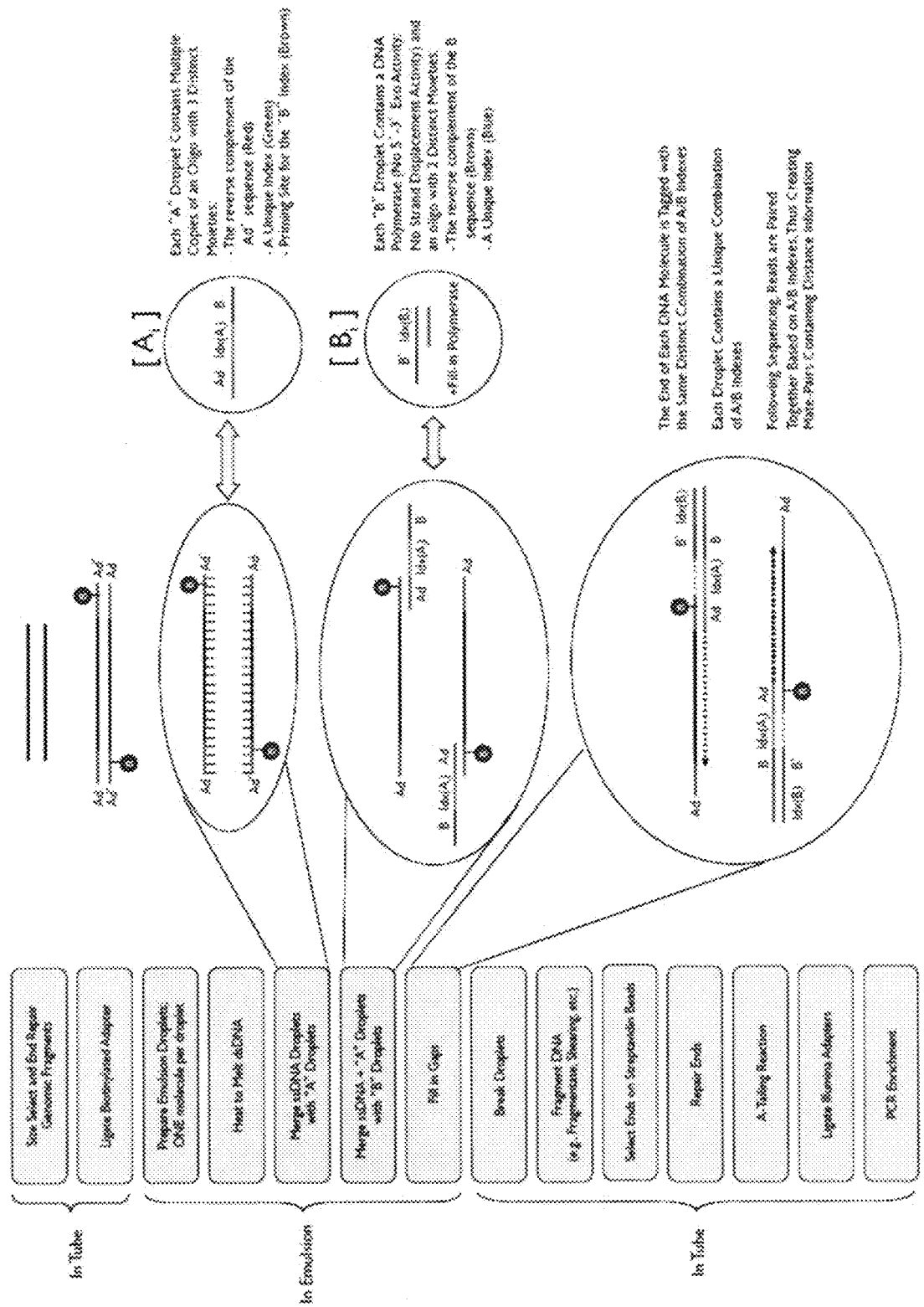
FIG. 9 is a schematic of a mate pair synthesis process using single stranded genomic DNA as the agent. Each droplet may comprise both strands of the genomic fragment. As shown in the Figure, the strands are identically labeled at one end.

FIG. 9 depicts a method using polymerase and single-stranded index oligo sequences. Genomic fragments, size selected are generated and ligated to an adapter as described in Example 1. Emulsion droplets are prepared with one genomic fragment ligated to an adapter per droplet. The genomic fragment is melted (e.g., by heating the double stranded fragment to produce two single stranded fragments) and each droplet is merged with an "A" droplet that contains multiple copies of a single stranded oligonucleotide index "$A_i$". Each "$A_i$" single stranded index includes three distinct sequence moieties: 1) the reverse complement of the adapter sequence, 2) a unique index sequence, and 3) a priming site for the next single stranded oligonucleotide index. The single stranded oligonucleotide index "$A_i$" hybridizes to the adapter attached to the genomic fragment in each merged droplet. Each merged droplet is then merged with a "B" droplet that contains multiple copies of a single stranded oligonucleotide index "$B_i$". Each "$B_i$" single stranded index includes two distinct sequence moieties: 1) the reverse complement of the priming site in "$A_i$" and 2) a unique index sequence. Each "B" droplet also contains a polymerase, preferably one without 5'-3' exonuclease activity and without strand displacement activity. The single stranded oligonucleotide index "$B_i$" hybridizes to the "$A_i$" index attached to the genomic fragment in each doubly merged droplet. The polymerase is then used to fill in the gaps to create double stranded genomic fragments, wherein the end of each genomic fragment is tagged with the same distinct combination of A/B indexes and wherein each droplet contains a unique combination of A/B indexes compared to other droplets. The uniquely end-labeled fragmented genomic DNA is then further fragmented and the ends are collected via streptavidin beads, which recognized the biotin label on the adapter. Fragments can be ligated to technology specific sequencing adapters (e.g., Illumina adapters) and sequenced. Ends are informatically paired by matching the unique label on one fragment of DNA with the same unique label on the other fragment of DNA as described in Examples 1 and 2.

Some methods of the invention use picoinjection of single molecules of fragmented genomic DNA into droplet that contain index sequences. Genomic DNA is fragmented, size selected and ligated to a biotinylated adapter as described in Example 1 and diluted sufficiently to allow picoinjection of a single genomic fragment by picoinjection. An emulsion droplet library "A" is created as described above. Each "A" droplet contains a ligase plus multiple copies of an "A" index oligonucleotide. Each "A" index oligonucleotide contains a unique index sequence and a single-stranded priming site for a "B" index oligonucleotide. Each "A" droplet is picoinjected with a single molecule of fragmented genomic DNA using methods known in the art (see, e.g., High-Throughput Injection with Microfluidics Using Picoinjectors. A. R. Abate, T. Hung, P. Mary, J. J. Agresti, and D. A. Weitz. PNAS 107, 19163-19166 (2010)). The "A" index oligonucleotide is ligated to the adapter on each fragmented genomic DNA molecule. The droplets are then broken as described in Example 1 and diluted sufficiently to allow picoinjection of a single genomic fragment molecule attached to an "A" index into the next emulsion droplet library. An emulsion droplet library "B" is created. Each "B" droplet contains a ligase plus multiple copies of a singled stranded "B" index oligonucleotide. Each "B" index contains the reverse complement to the priming site on the "A" index and a unique index sequence. Each "B" droplet is picoinjected with a single genomic fragment molecule attached to an "A" index. The "B" index is then ligated to the "A" index. The droplets are then broken and the ends are filled in using a polymerase. The result is uniquely end-labeled fragmented genomic DNA, wherein each end is labeled with the same "A" and "B" index. The uniquely end-labeled fragmented genomic DNA is then further fragmented and the ends are collected via streptavidin beads, which recognized the biotin label on the adapter. Fragments can be ligated to technology specific sequencing adapters (e.g., Illumina adapters) and sequenced. Ends are informatically paired by matching the unique label on one fragment of DNA with the same unique label on the other fragment of DNA as described in Examples 1 and 2.

Figure 10:
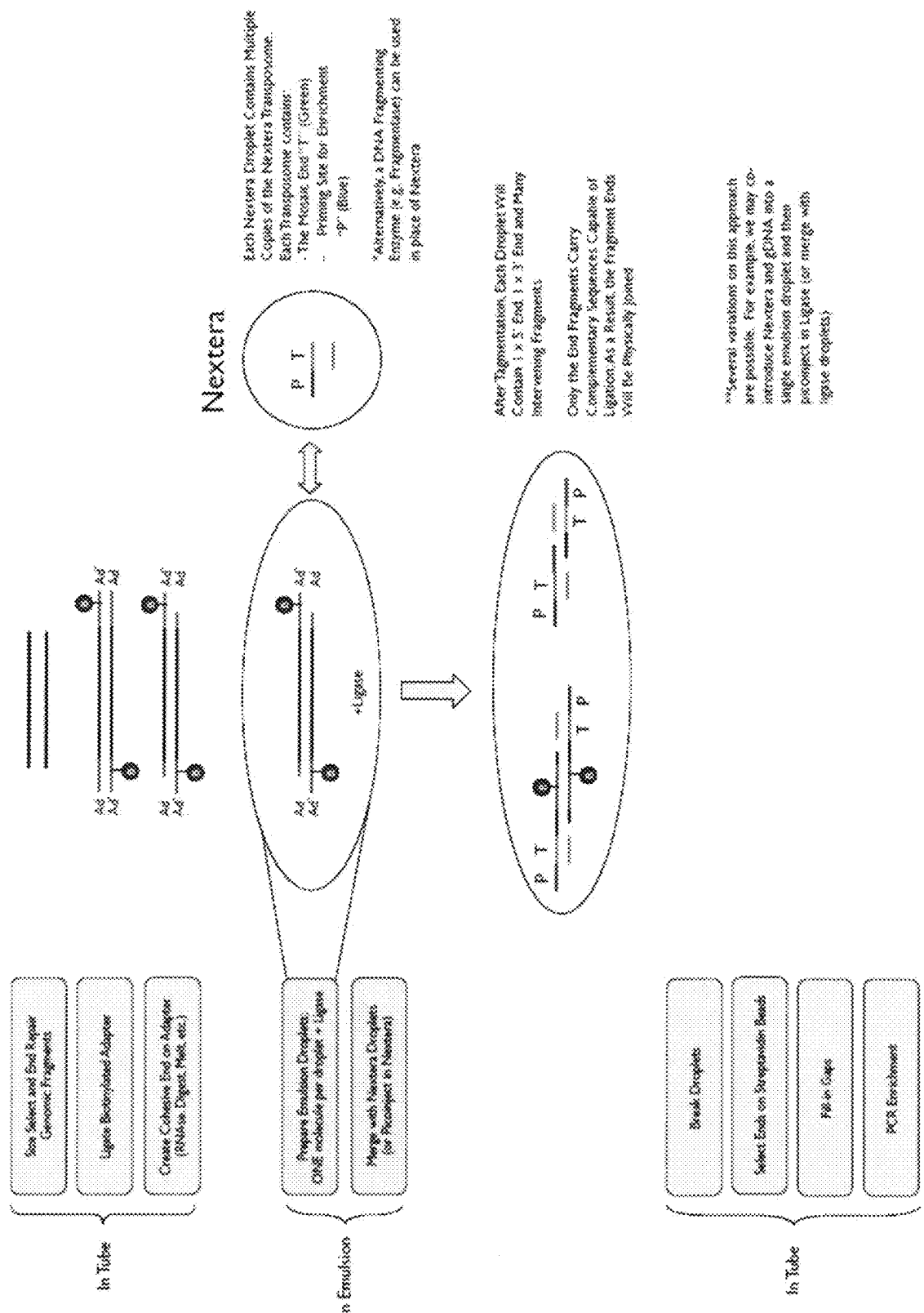
FIG. 10 is a schematic of a mate pair synthesis using droplets and Nextera transposomes as detectable tags.

FIG. 10 describes a method using a DNA fragmenting enzyme or a transposome (e.g., Nextera™ from Illumina, San Diego, Calif.). Genomic DNA is fragmented, size selected and ligated to a biotinylated adapter as described in Example 1. A cohesive end is produced on the adapter using methods known in the art (e.g., a nuclease or a restriction enzyme) such that the two adapters on each genomic fragment can be ligated together. Emulsion droplets are prepared as described in Example 1. Each droplet contains ligase and one molecule of fragmented genomic DNA. These emulsion droplets are then merged with Nextera™ droplets (or alternatively picoinjected with Nextera™). Nextera™ is a transposome that contains a modified transposase that simultaneously fragments DNA and tags the fragmented DNA with an oligonucleotide (referred to as "tagmentation"). The oligonucleotide can be an index oligonucleotide that contains a unique index sequence and a priming site. The priming site can be used either for enrichment after tagmentation or for attaching an additional index sequence after tagmentation. Following tagmentation, each droplet contains a 5' genomic fragment attached to a biotionylated adapter and an index oligonucleotide, a 3' genomic fragment attached to a biotinylated adapter and an index oligonucleotide, and several intervening fragments attached to index oligonucleotides. Only the fragments carrying the adapters can ligate to each other, so only the 5' and 3' genomic fragments will ligate together. The ligated 5' and 3' genomic fragments are then be purified away from the intervening fragments using selection on streptavidin beads. The ligated 5' and 3' genomic fragments can then be amplified using the priming site or further index oligonucleotides can be added as described in the above examples in order to create ligated 5' and 3' genomic fragments that are uniquely labeled with multiple index sequences. Fragments can be ligated to technology specific sequencing adapters (e.g., Illumina adapters) and sequenced. Ends are informatically paired by matching the unique label on one fragment of DNA with the same unique label on the other fragment of DNA as described in Examples 1 and 2. This method can also be carried out using fragmentase, index oligonucleotides, and ligase in place of Nextera™.

Example 6: Forked Adapters

Figure 11:
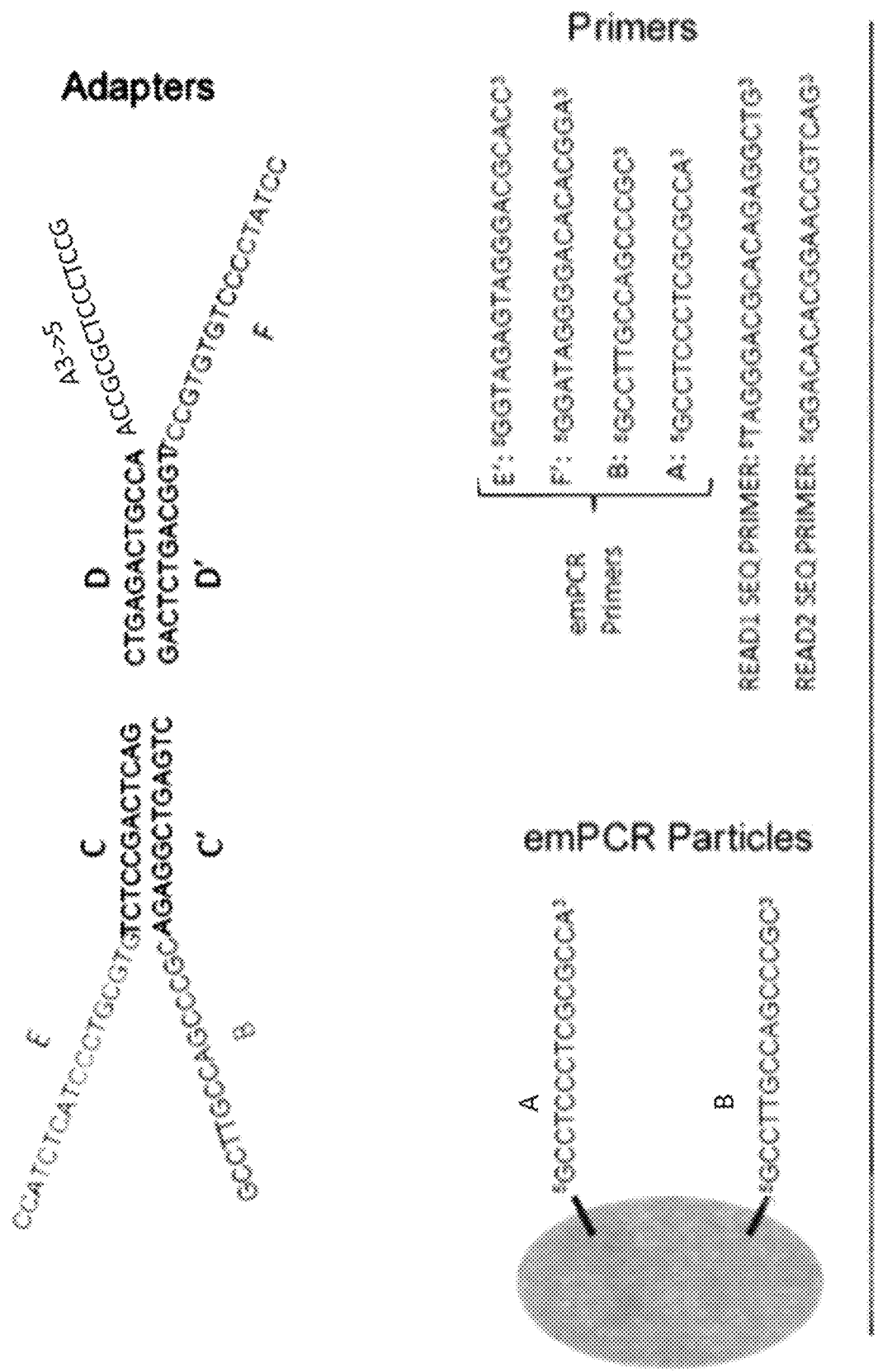
FIG. 11 is a schematic illustrating the use of forked adapters.
Figure 11:
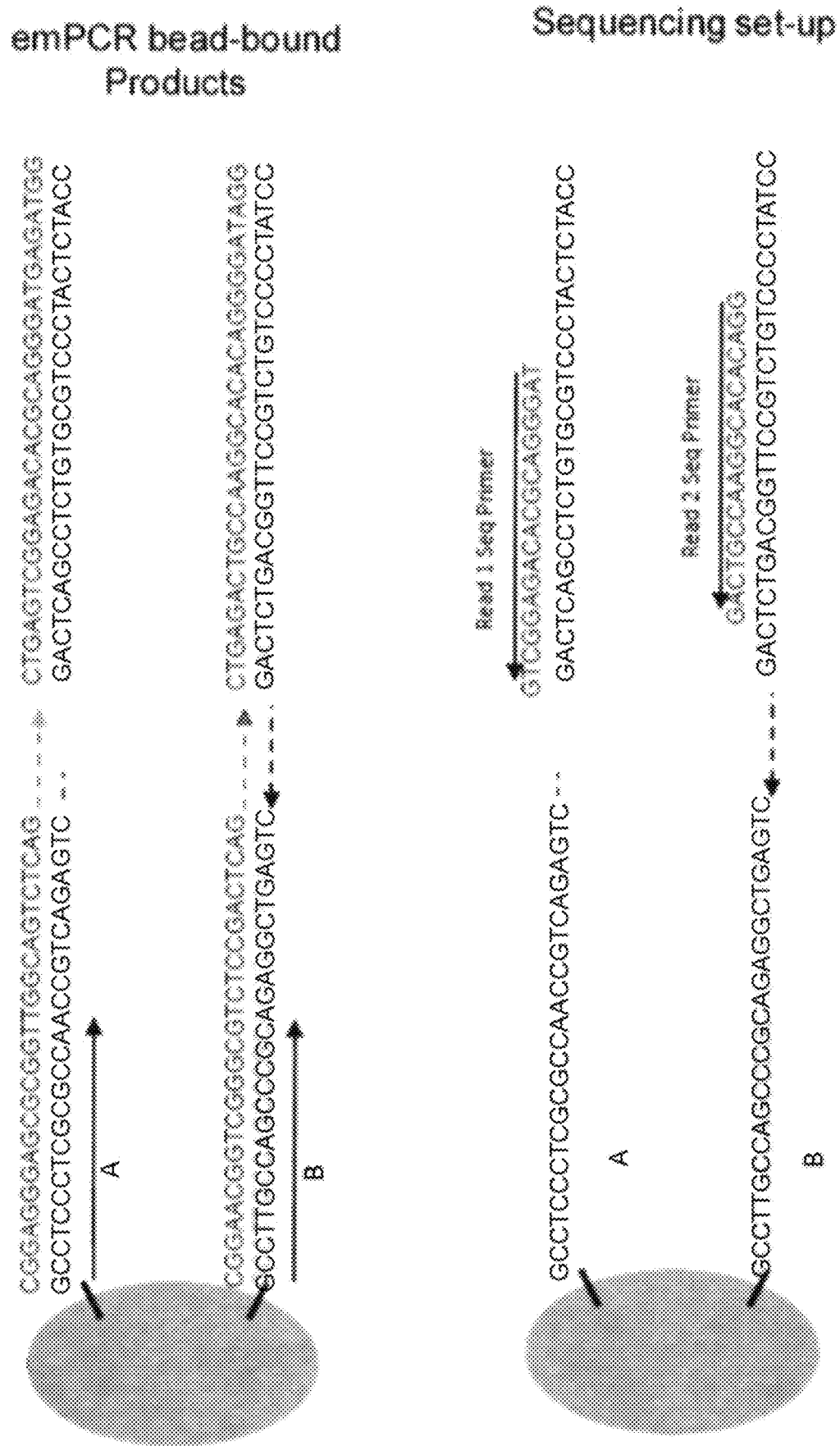

FIG. 11 depicts a pair of forked adapters for use in the invention or in other unrelated applications. The ability to produce sequence reads from distal ends of a single DNA fragment (paired-end sequencing) is extremely useful for many downstream analyses. Currently there are no commercially available methods for effective paired-end sequencing from beads on any of the established bead-based sequencing technologies (e.g., AB Solid, Roche/454 and Ion Torrent).

The method outlined briefly herein uses a pair of specially designed forked oligonucleotide adapters to tail a double-stranded DNA fragment such that once amplified in emulsion PCR, each strand of the original fragment is amplified on to the surface of the bead. Once both strands of DNA are present on the bead two distinct sequencing reactions can be performed to read the sequence at either end of the fragment.

Figure 12:
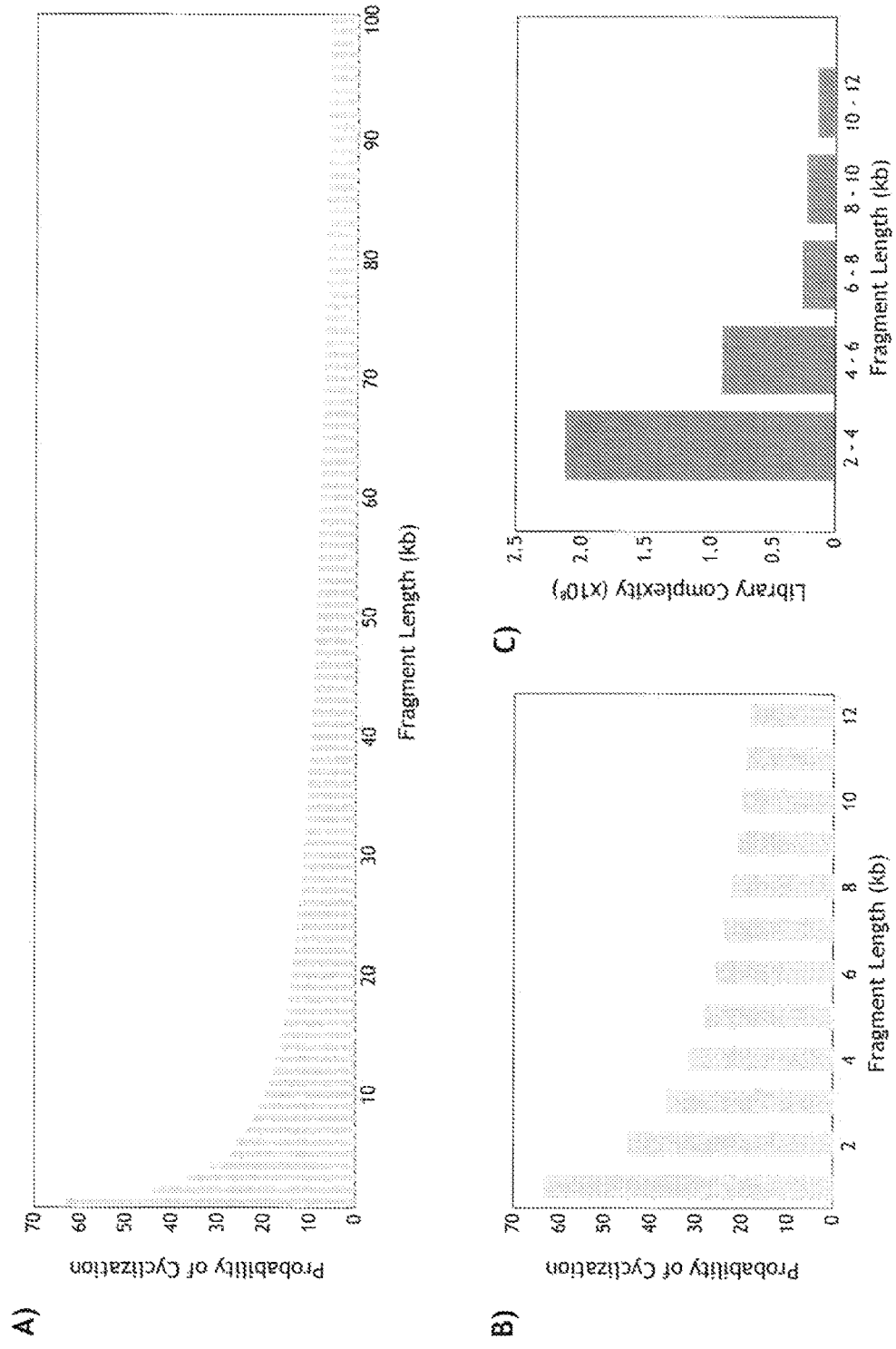
FIG. 12 shows that the efficiency of DNA circularization (cyclization) decreases as fragment length increases.
Figure 13:
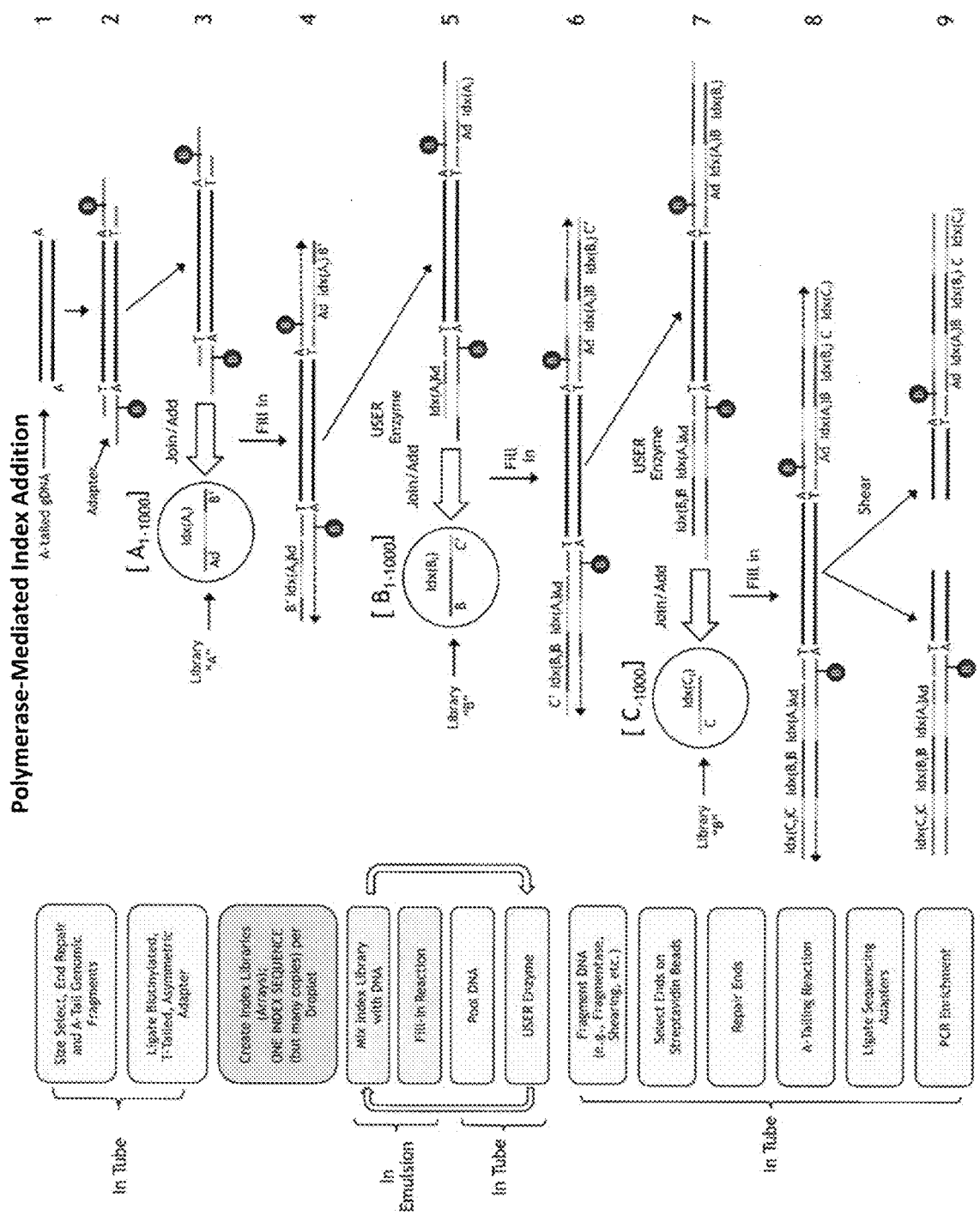
FIG. 13 is a schematic depicting the technique for polymerase mediated index addition.
Figure 14:
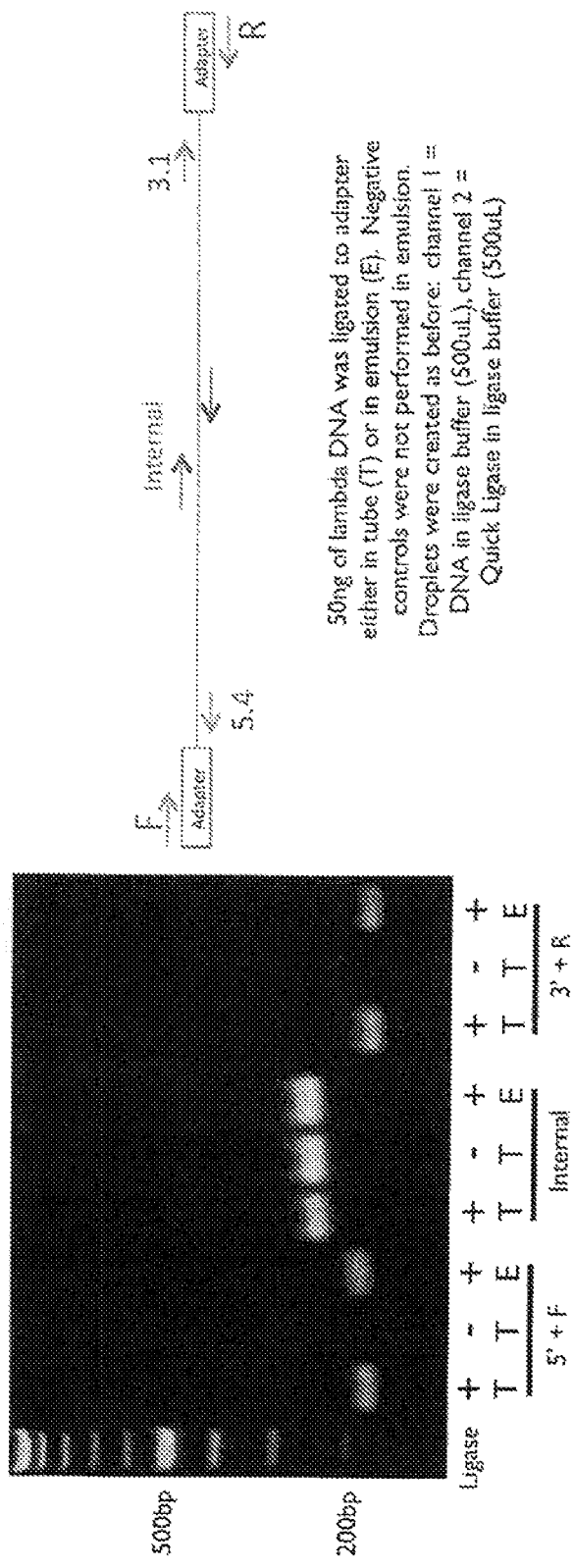
FIG. 14 is a gel electrophoresis showing ligation of an adapter sequence in either a tube (T) or an emulsion droplet (E).
Figure 15:
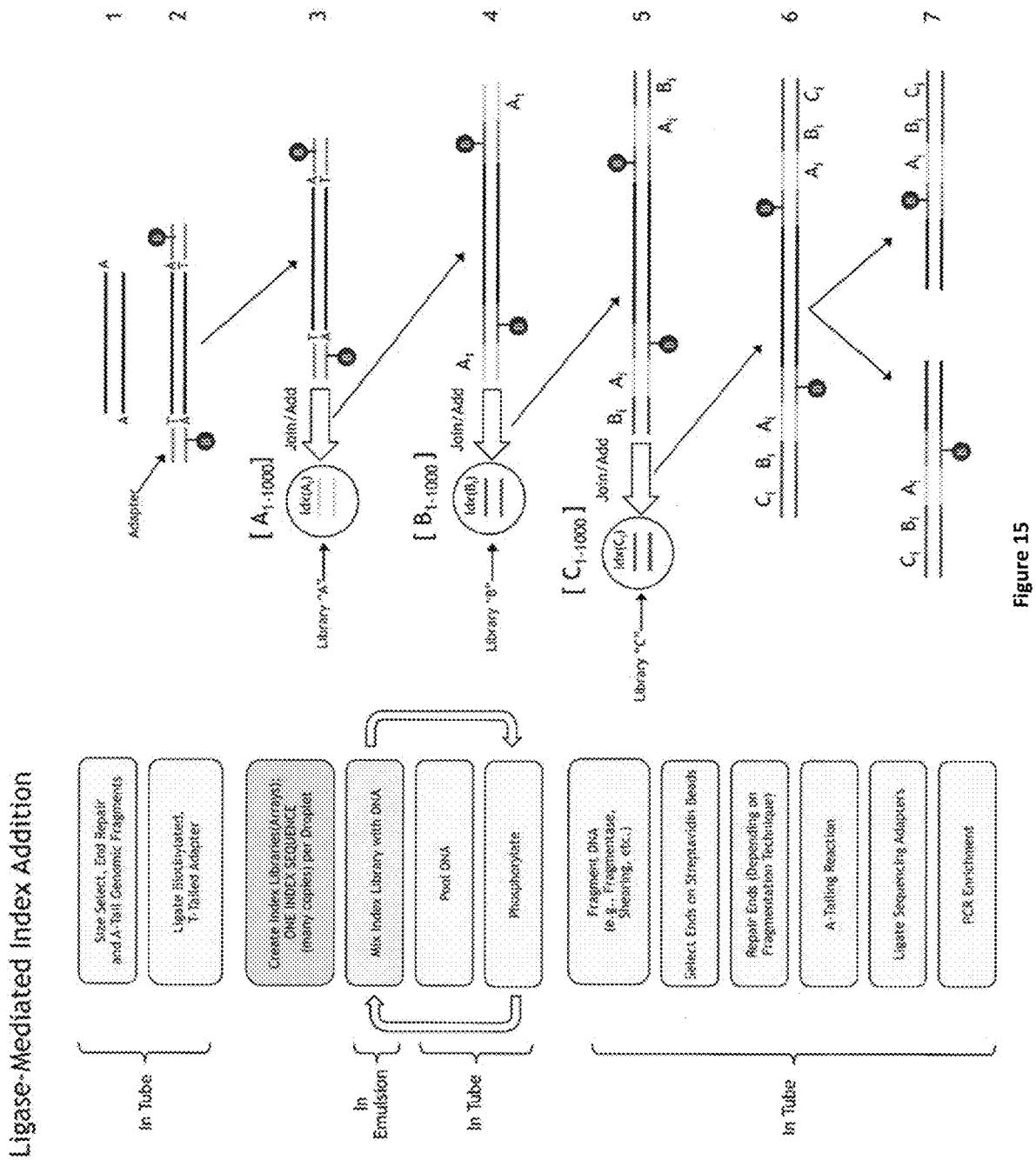
FIG. 15 is a schematic depicting the technique for ligation mediated index addition.
Figure 16:
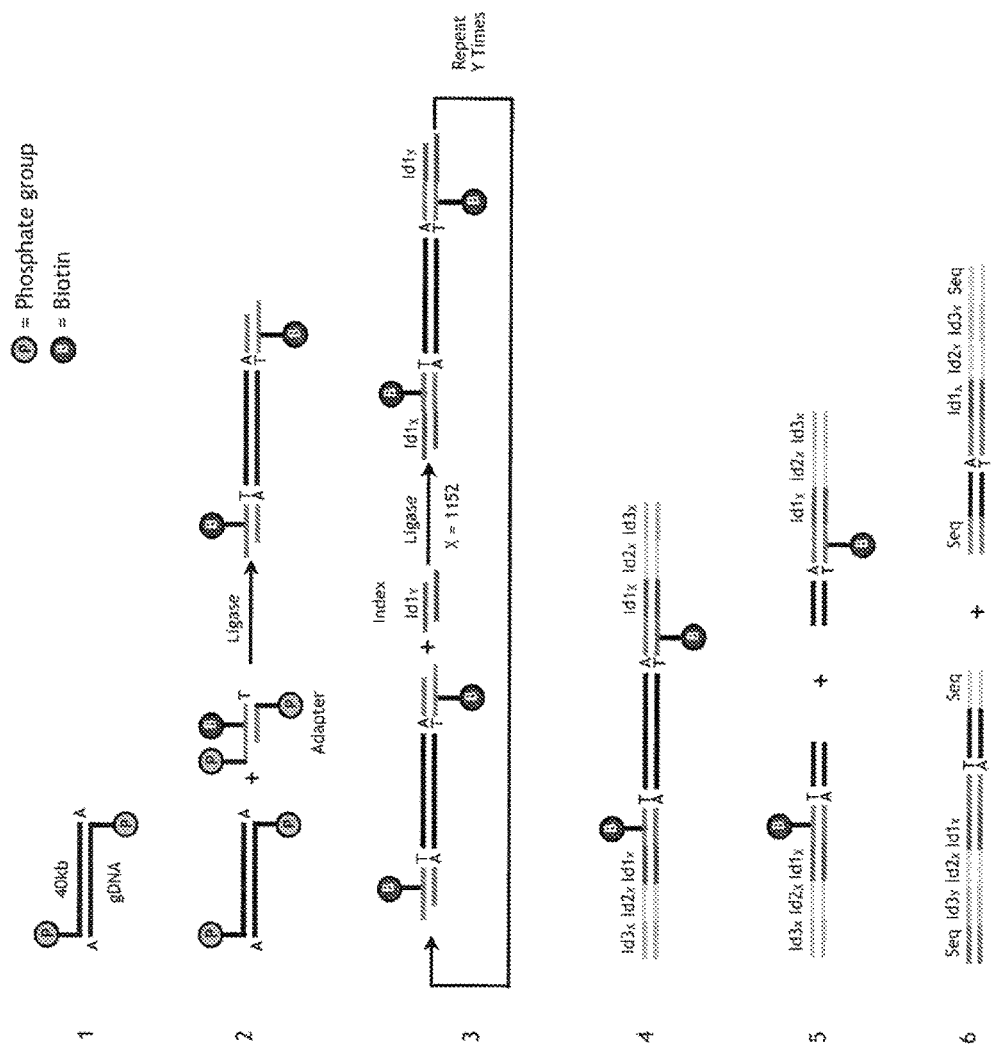
FIG. 16 is a schematic depicting the technique for symmetric ligation-mediated index addition.
Figure 17:
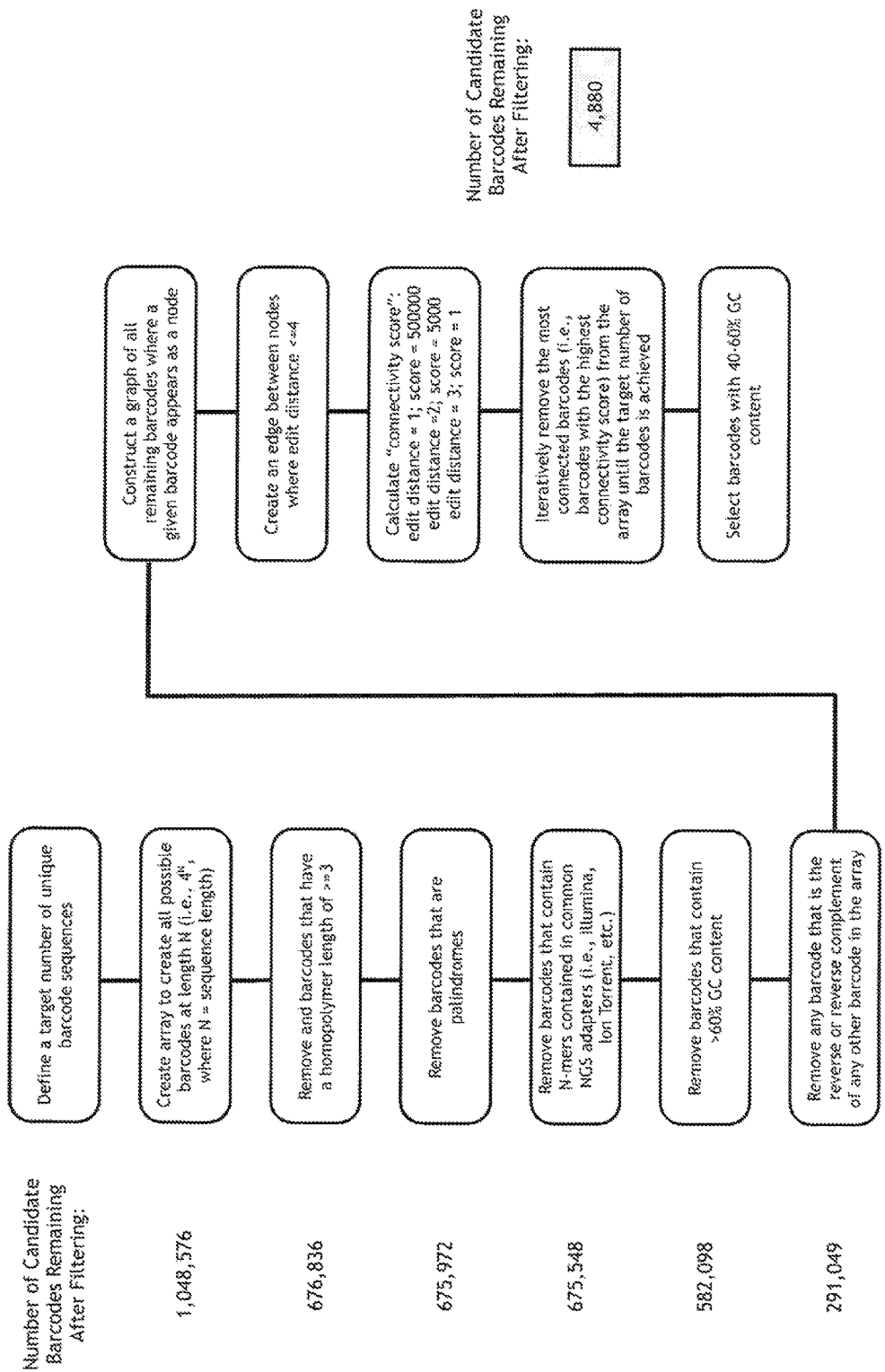
FIG. 17 is a flowchart detailing the criteria for barcode sequence selection.
Figure 18:
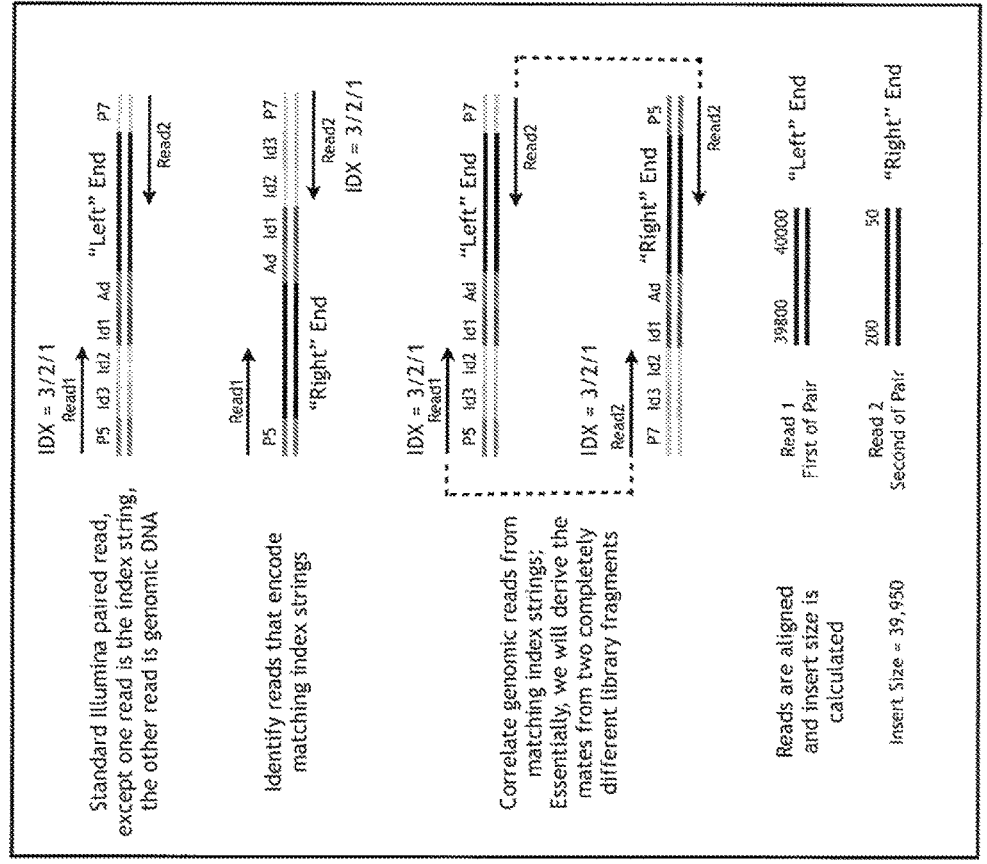
FIG. 18 is a schematic depicting the methodology for informatically deriving mate pairs.
Figure 18:
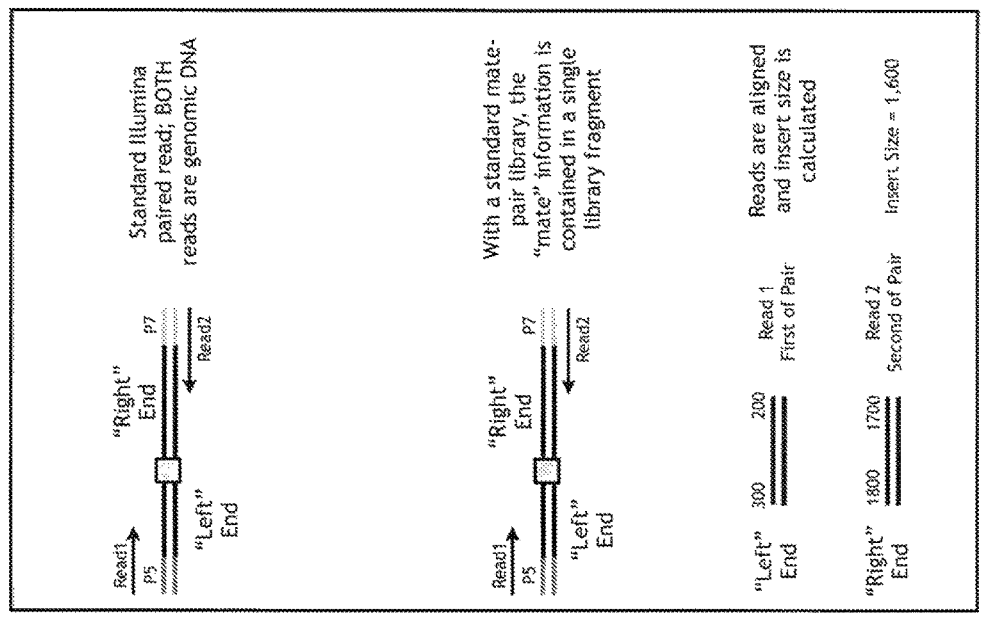
Figure 19:
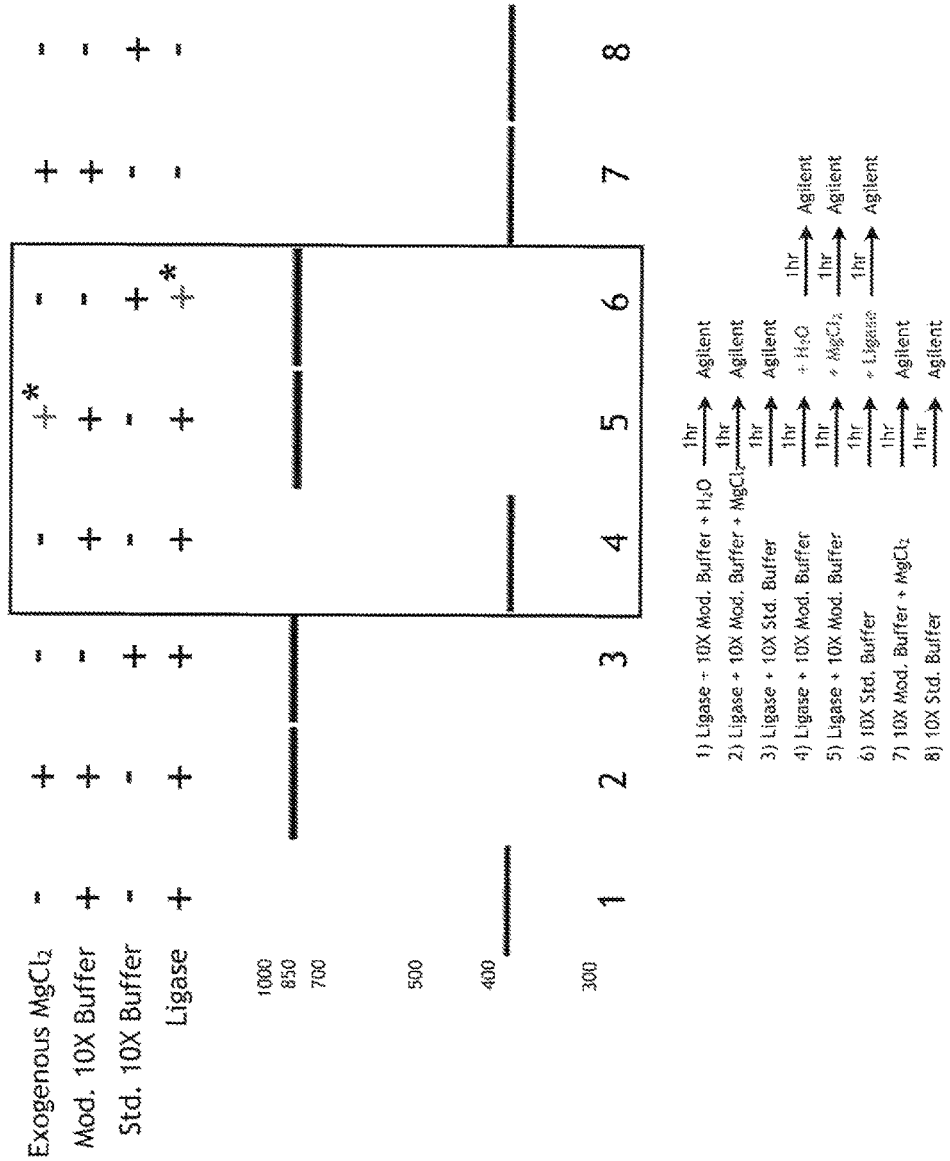
FIG. 19 shows catalyzing ligation by the controlled addition of $MgCl_2$.
Figure 20:
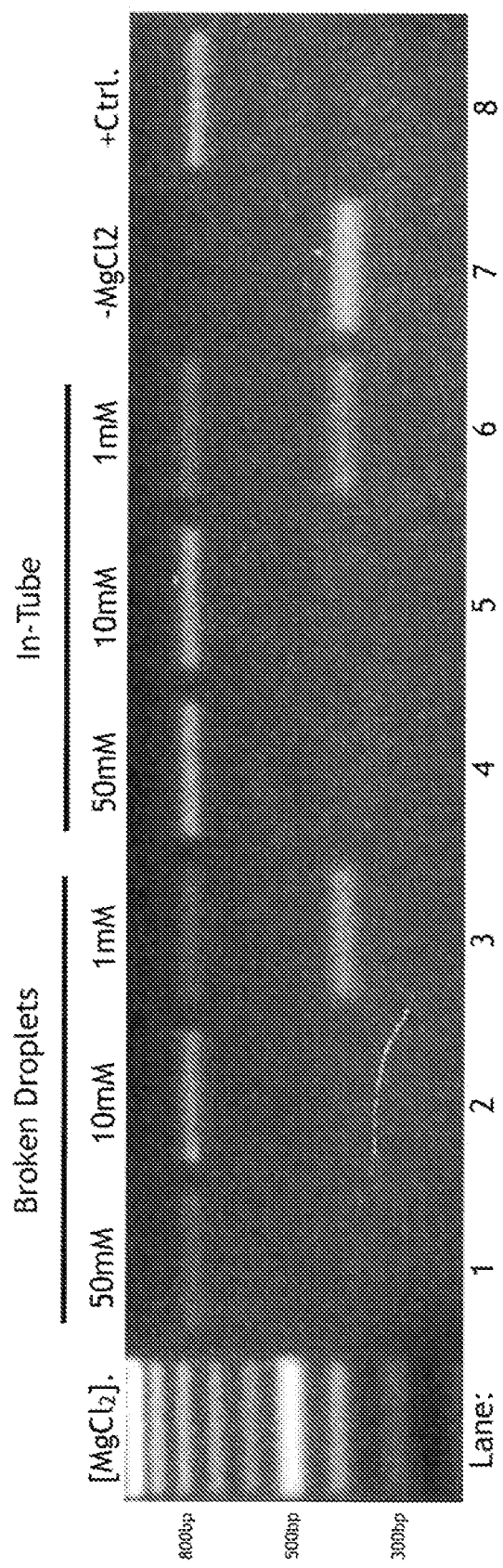
FIG. 20 shows a stability determination of $MgCl_2$ in droplets.
Figure 22:
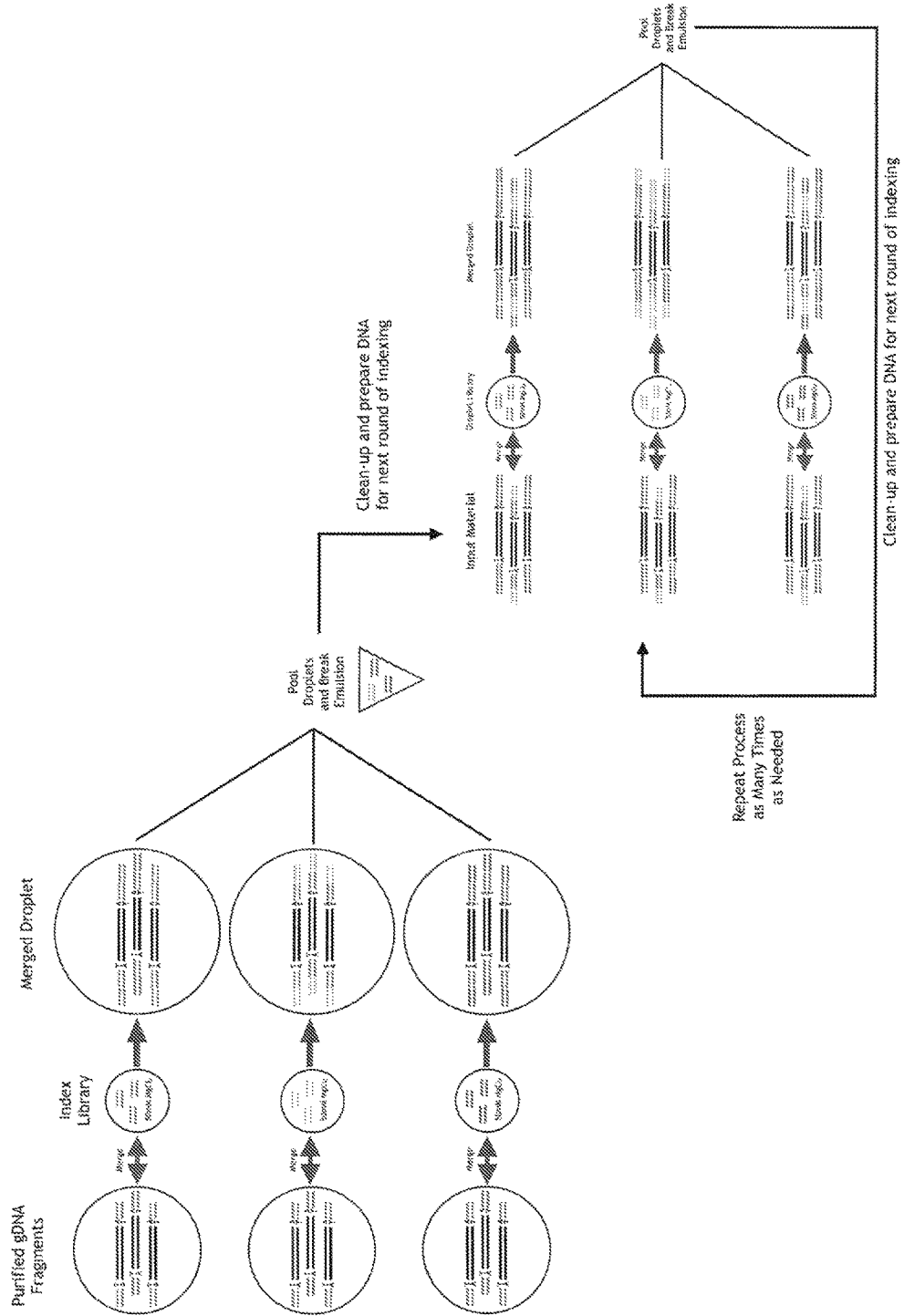
FIG. 22 is a schematic depicting the process of symmetric indexing in emulsion.
Figure 23:
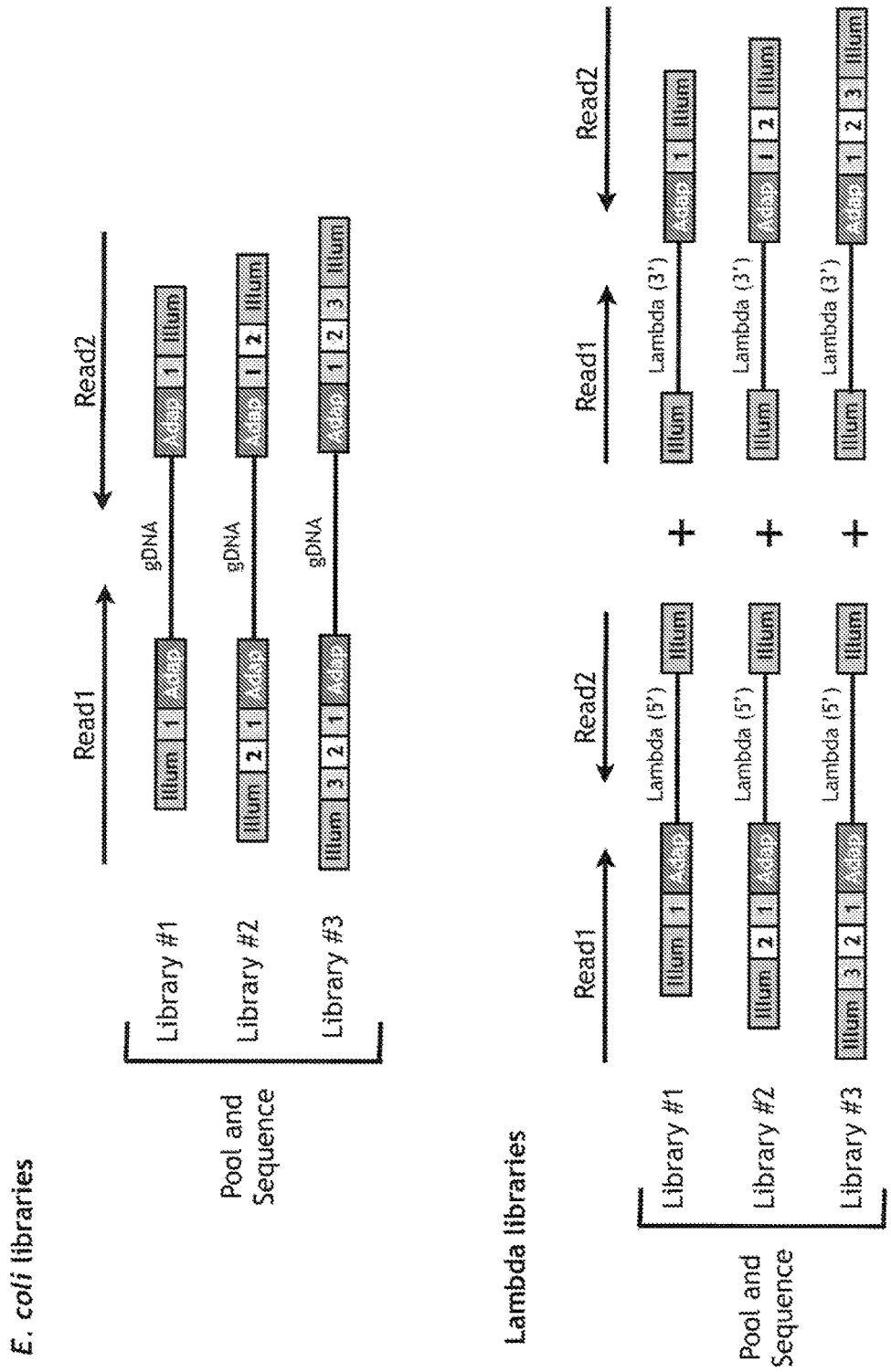
FIG. 23 shows a proof of concept experiment.
Figure 24:
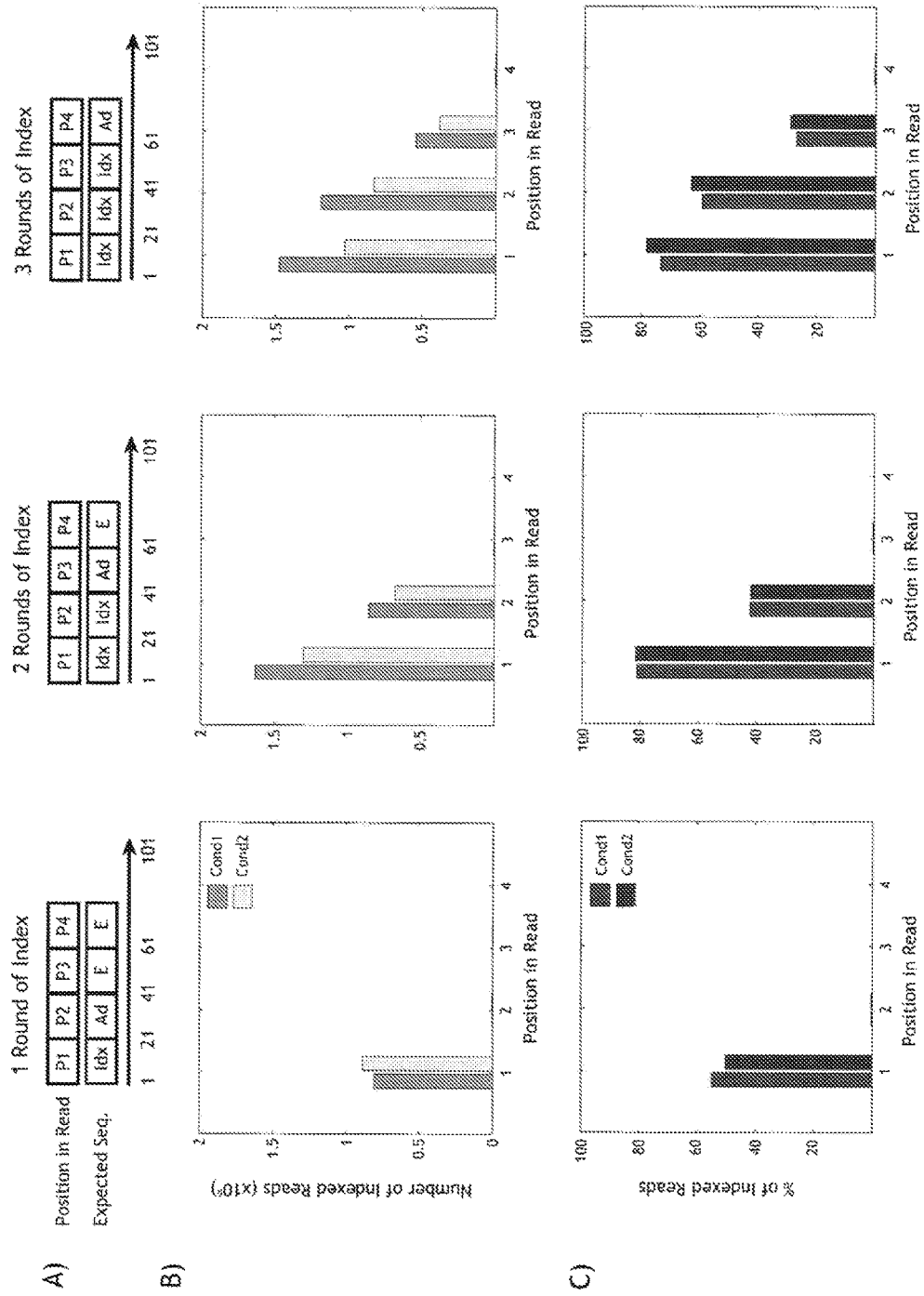
FIG. 24 shows an analysis of E. coli proof of concept libraries.
Figure 25:
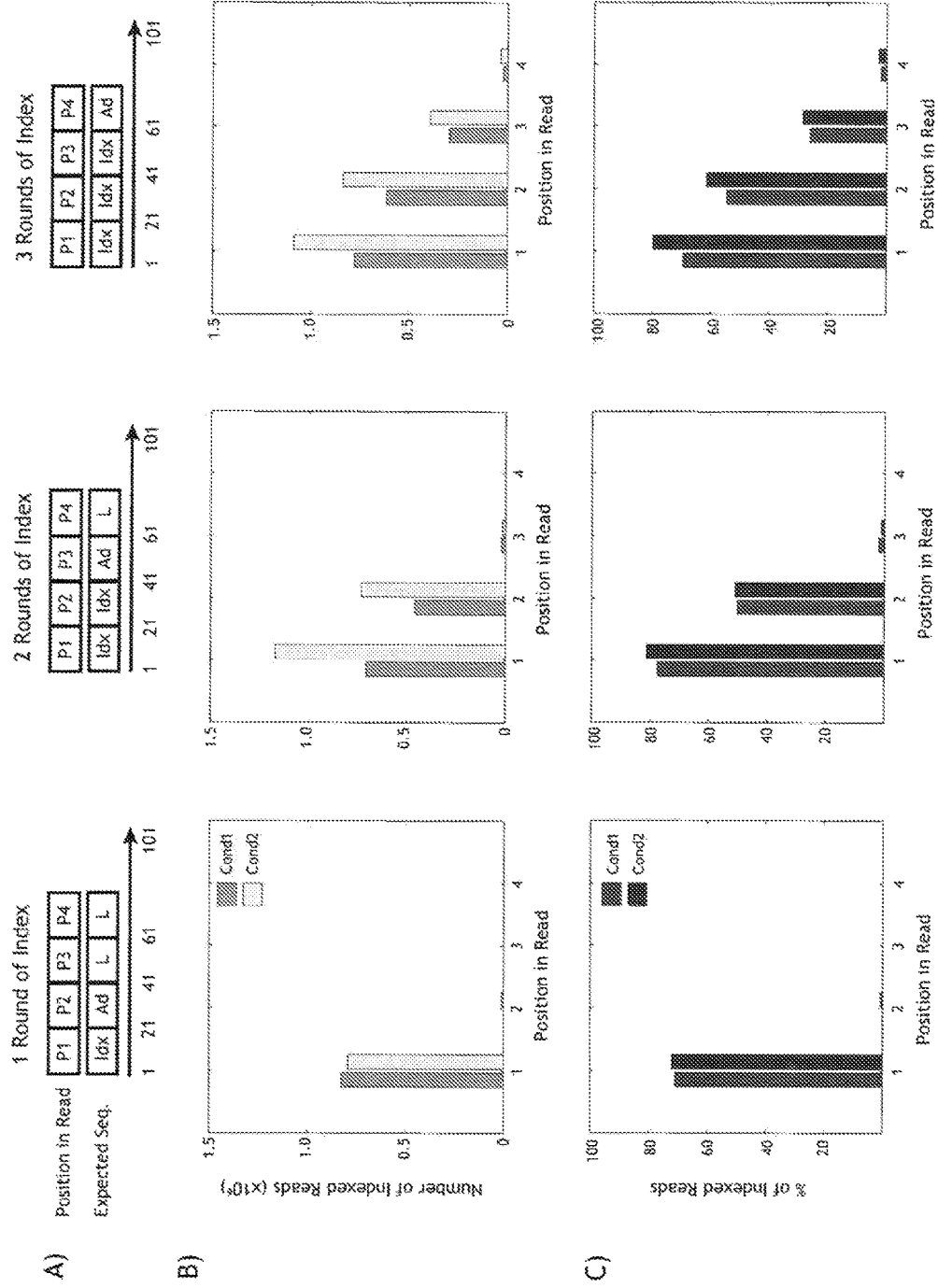
FIG. 25 shows an analysis of lambda proof of concept libraries.
Figure 26:
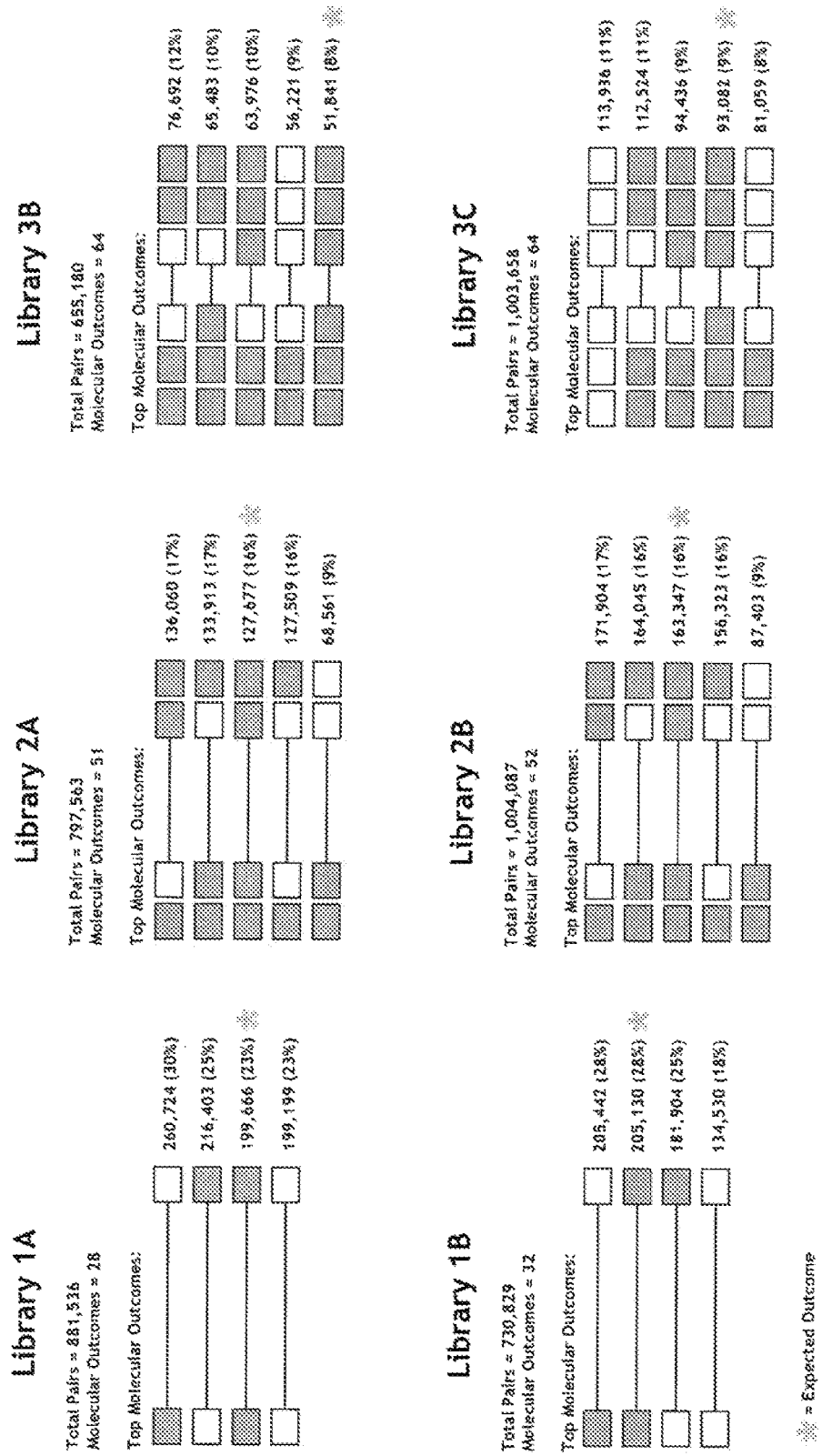
FIG. 26 shows a determination of symmetry of indexing in E. coli proof of concept libraries.
Figure 27:
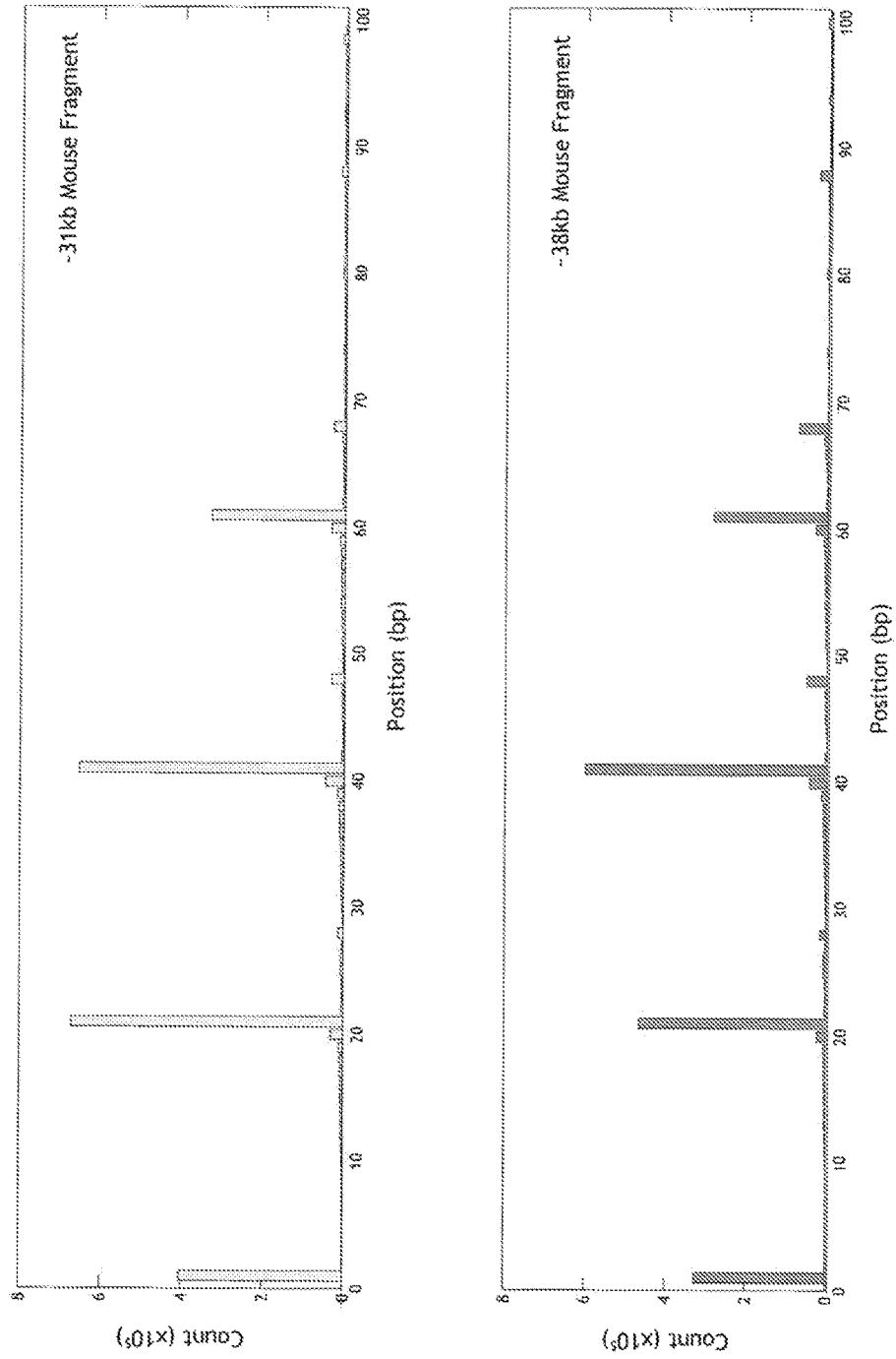
FIG. 27 shows the determination of uniformity of blunt-ended indexing.
Figure 28:
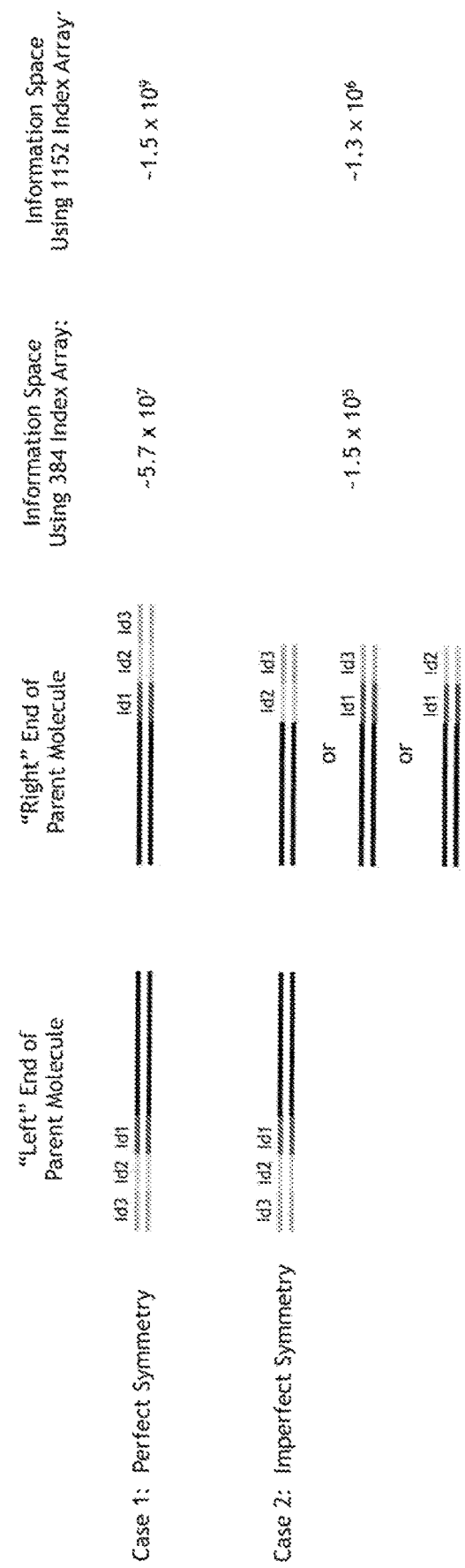
FIG. 28 shows impact of ligation efficiency on bioinformatics end association.
Figure 29:
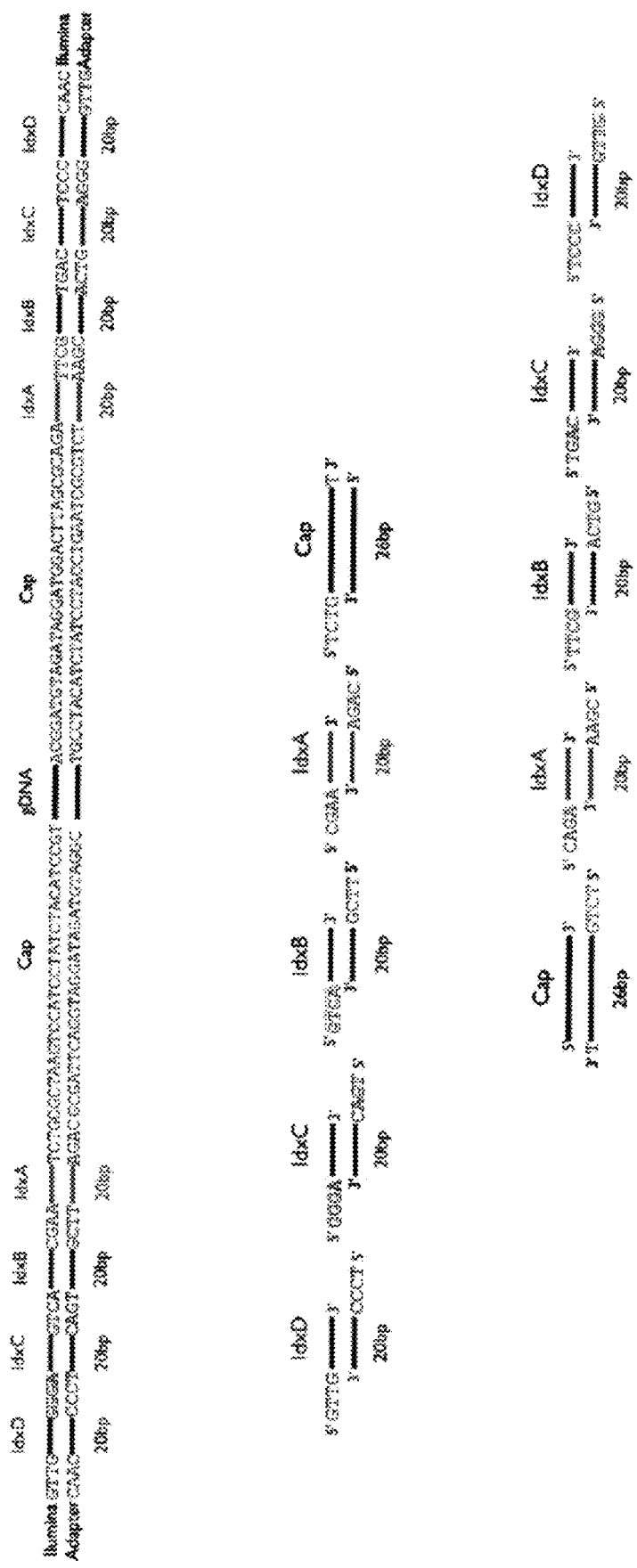
FIG. 29 shows a redesign of index sequences.
Figure 30:
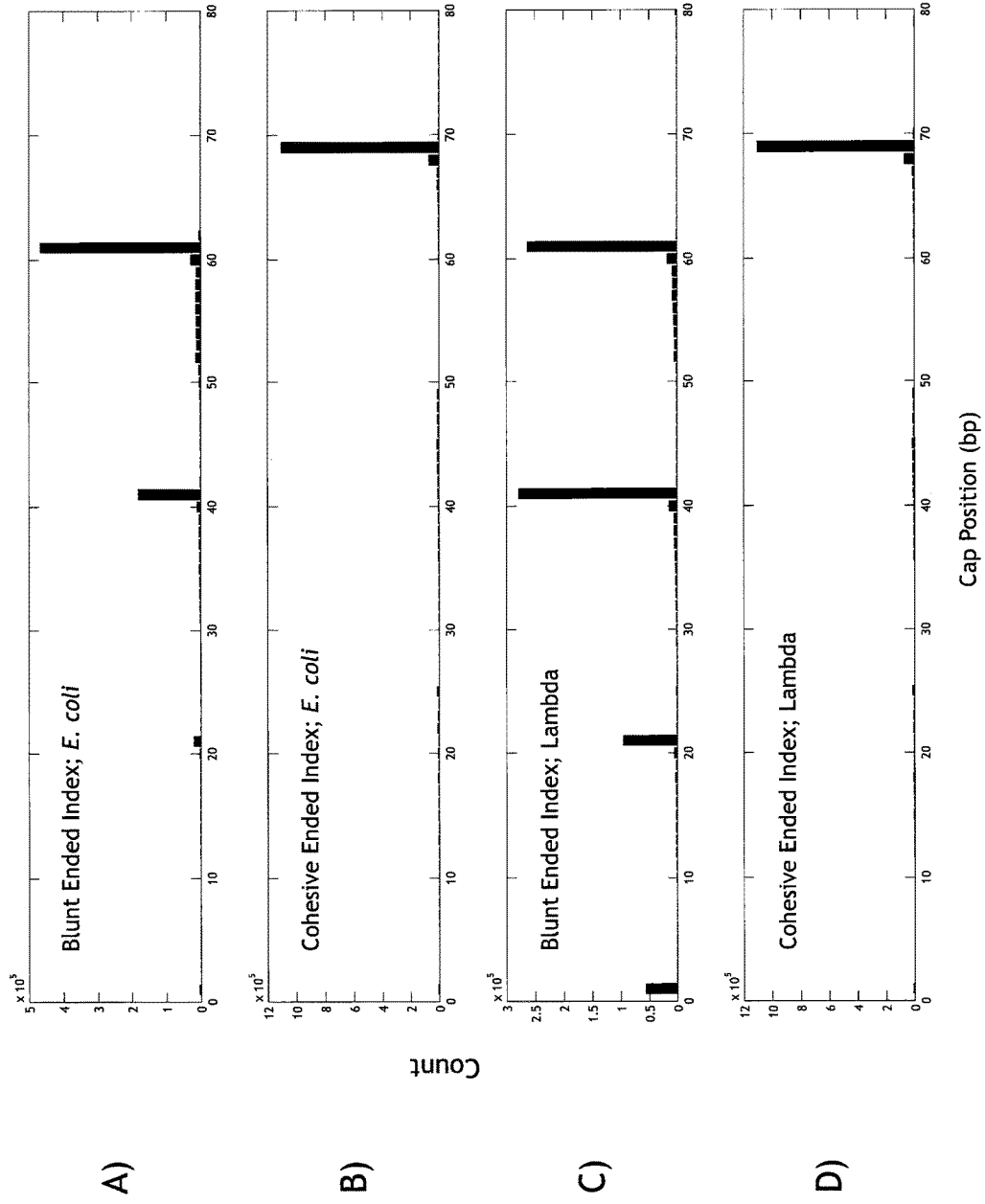
FIG. 30 shows uniformity of indexing.

As a proof of principle, streptavidin-coated magnetic particles (M280 Dynal beads, Invitrogen) were coated with two species of biotinylated oligos (A and B, see FIG. 12). A DNA library was created with the forked adapters and was amplified onto beads in an emulsion PCR containing solution phase primers and coated beads. Fluorescently labeled primers (Read Seq 1 and Read Seq 2) were annealed and beads were visualized to confirm the presence of both molecules on a single bead. Both molecules were shown to be present on a single bead.

Example 7: Blunt End Ligation

Initial attempts at preparing symmetrically indexed libraries utilized a single array of 20 bp blunt ended index sequences. To evaluate the technique, libraries were prepared from either Lambda genomic DNA (~48 kb) or E. coli genomic DNA sheared to approximately 500 bp. Lambda and E. coli samples were then subjected to three rounds of index ligation. Lambda samples were then sheared to an appropriate size using standard techniques (i.e., Covaris shearing). It was not necessary to shear the E. coli libraries after index ligation as they were already the correct size for Illumina sequencing. All samples were incubated with M-280 streptavidin beads to select molecules carrying the biotinylated cap adapter and were prepared as Illumina paired-end libraries according to standard techniques.

Analysis of these libraries revealed a mixed population of indexed reads where some contained only a single index, while other reads contained either two or three indexes. While this clearly indicated that not all molecules received the same number of indexes, it raised the possibility that molecules were not receiving the same number of molecules on both ends. Further analysis of the E. coli libraries determined that a large population of DNA fragments were asymmetrically indexed where one end harbored N number of indexes and the other end often carried N–1 (or N–2)

indexes (data not shown). This raised a significant challenge at the analysis level since the mate-pairing algorithm was intended to pair reads based on their unique index combinations and the informative content of a given index "string" decreases as the number of indexes decreases. Although there are provisions in the algorithm to attempt pairing of less than perfectly matched ends, such pairings occur at a significantly lower confidence level.

Example 8: Cohesive Overhang Ligation

In an attempt to increase the symmetry of indexing from blunt end ligation (Example 3), all indexes were redesigned to contain a 4 bp (cohesive) overhang on each oligo. Specifically, three unique populations of indexes were created with each population containing a specific overhang on either end of the index. Thus, only members of the Index "A" population ligated only to the adapter (in a single orientation). Similarly, members of the Index "B" population ligated only to Index A, and members of Index "C" ligated only to Index B. To determine the effectiveness of this new strategy, Lambda and *E. coli* samples were prepared as before, but using the new cohesive ended indexes as described in more detail below.

Materials and Methods

Genomic DNA Preparation

*E. coli* genomic DNA was sheared to an average size of 400-600 bp in a Covaris microTube using a Covaris S2 instrument with the following settings: duty cycle=20%, intensity=8, cycles per burst=200, time=50 seconds. Lambda DNA (New England Biolabs, NEB) was not sheared prior to cap ligation and indexing to maintain an ~48 kb genomic DNA fragment.

Cap Ligation 5 ug of either sheared *E. coli* or Lambda DNA was end-repaired to create blunt ended fragments as follows: Samples were incubated in a reaction containing 1× Phosphorylation Buffer (NEB), 0.5 mM dNTP mix (NEB), 50 U T4 Polynucleotide Kinase (NEB), 15 U T4 DNA Polymerase (NEB) and 10 U DNA Polymerase I Large Fragment (Klenow). Reactions were incubated at 20° C. for 30 minutes. Each sample was then purified by adding 1.8× volumes of AMPure XP beads as described in the manufacturer's recommended protocol (Beckman Coulter). Samples were then A-tailed at their 3' ends by incubating for 30 min. at 30° C. in 1× NEBuffer 2 (NEB), 0.2 mM dATP (NEB) and 25 U Klenow Fragment (3' 4 5' exo-) (NEB). Samples were then purified by adding 1.8× volumes of AMPure XP beads as described above. Samples were then ligated to the Cap_v6_C adapter (duplexed DNA composed of: 5'-/5Phos/CGGATGTAGATAGGA/iBiodT/GGACTTAGCG-3' and 5'-/5Phos/TCTGCGCTAAGTCCATCCTATCTACATCCG*T-3' (*=phosphorothioate bond, /iBiodT/=biotinylated thymidine, /5Phos/=phosphorylated 5' base) (Integrated DNA Technologies, I D T) as follows. Samples were mixed with Cap_v6_C at a molar ratio of 1:100 (gDNA:Cap_v6_C) in a solution of customized ligation buffer containing 66 mM Tris-HCl, 10 mM MgCl2, 1 mM DTT, 1 mM ATP and 15% PEG 6000 (w/v) along with 10,000 U T4 DNA ligase (NEB). Reactions were incubated at room temperature for 20 minutes and purified using 1.8× volumes of AMPure XP beads as described above.

Index Ligation

Cap_v6_C ligated DNA (Lambda or *E. coli*) was subjected to three rounds of index ligation. Three separate pools of index were prepared (round 1=pool "A", round 2=pool "B" and round 3=pool "C") with each pool containing four different index sequences (IDT, see attached for duplex sequences). For each round of index ligation, "template" DNA (i.e., Cap_v6_C ligated DNA) was mixed with the appropriate pool of index at a 1:100 molar ratio (template:index) and incubated for 20 minutes at room temperature in a reaction containing customized ligation buffer (see above) with 10,000 U T4 DNA ligase (NEB). After each round of index ligation, samples were purified by adding 1.8× volumes of AMPure XP beads as described above.

Library Preparation

Following index ligation, Lambda samples were sheared to ~400-600 bp in length in a Covaris microTube using a Covaris S2 instrument with the following settings: duty cycle=20%, intensity=8, cycles per burst=200, time=50 seconds. *E. coli* samples were not sheared following index ligation. In order to select only the ends of the DNA fragments (i.e., fragments carrying biotinylated Cap_v6_C), samples were then mixed with 50 uL of M-280 streptavidin beads that had been prepared according to the manufacturer's recommended protocol (Life Technologies). Samples were then end repaired and A-tailed in the reaction mixes described above and ligated to standard Illumina indexed adapters (Illumina) in a reaction containing 1× NEB Quick Ligation Reaction Buffer and 10,000 U of Quick T4 DNA Ligase (NEB). After each of the enzymatic reactions (i.e., end repair, A-tailing and Ilumina adapter ligation), beads were washed three times in 1× library wash buffer (5 mM Tris-HCl pH7.5, 0.5 mM EDTA, 0.5M NaCl, 0.1% Tween-20). Following adapter ligation, tubes were placed on a magnet for 1 minute and the supernatant was discarded. Beads were then resuspended in a reaction containing 1× Phusion HF PCR Master Mix (NEB) and Illumina PCR Primers (PE 1.0/2.0). Library amplification was performed using the following conditions: 98° C. for 30 sec., 18 cycles of {98° C. for 10 sec.; 65° C. for 30 sec.; 72° C. for 30 sec.}, 72° C. for 5 min. Tubes were then placed on a magnet for 1 minute and the supernatant transferred to a new tube. Samples were the purified by adding 0.75× volumes of AMPure XP beads as described above. The concentration and size distribution of each library was confirmed on an Agilent Bioanalyzer using a DNA 7500 Kit according to the manufacturer's recommended protocol (Agilent Technologies).

Sequencing

Illumina sequencing libraries were quantified using quantitative PCR (KAPA Biosystems). Based on qPCR quantification, libraries were normalized to 2 nM and then denatured using 0.1 N NaOH using Perkin-Elmer's MiniJanus liquid handling platform. Cluster amplification of denatured templates was performed according to the manufacturer's protocol (Illumina) using HiSeq v3 cluster chemistry and flowcells. Flowcells were sequenced, using 101-bp paired end reads, on HiSeq 2000 using HiSeq v3 Sequencing-by-Synthesis Kits, then analyzed using the latest version of RTA.

Data Analysis

Unaligned sequence data was analyzed using a series of AWK commands designed to identify sequences that are a perfect match for a 20 bp region of the Cap_v6_C sequence (TCTGCGCTAAGTCCATCCTA). The position of the Cap_v6_C sequence in a given read was recorded and tallied to determine the total number of reads containing Cap_v6_C sequence at a given position.

| Index Sequences | | | |
|---|---|---|---|
| Pool | Duplex Name | Oligo Name | Sequence (5'→3') |
| A | IDX_A5_C | IDX_A5_Top | /5Phos/CAGAGGATATCTGTGGATATCTGT |
| A | | IDX_A5_Bot | /5Phos/CGAAACAGATATCCACAGATATCC |
| A | IDX_A6_C | IDX_A6_Top | /5Phos/CAGAGGCTGCCATAGGCTGCCATA |
| A | | IDX_A6_Bot | /5Phos/CGAATATGGCAGCCTATGGCAGCC |
| A | IDX_A7_C | IDX_A7_Top | /5Phos/CAGAGGTATGTCAAGGTATGTCAA |
| A | | IDX_A7_Bot | /5Phos/CGAATTGACATACCTTGACATACC |
| A | IDX_A8_C | IDX_A8_Top | /5Phos/CAGAGGTGAAGGACGGTGAAGGAC |
| A | | IDX_A8_Bot | /5Phos/CGAAGTCCTTCACCGTCCTTCACC |
| B | IDX_B5_C | IDX_B5_Top | /5Phos/TTCGGTACCAGCATGTACCAGCAT |
| B | | IDX_B5_Bot | /5Phos/GTCAATGCTGGTACATGCTGGTAC |
| B | IDX_B6_C | IDX_B6_Top | /5Phos/TTCGGTATACATCCGTATACATCC |
| B | | IDX_B6_Bot | /5Phos/GTCAGGATGTATACGGATGTATAC |
| B | IDX_B7_C | IDX_B7_Top | /5Phos/TTCGGTATCGCTCAGTATCGCTCA |
| B | | IDX_B7_Bot | /5Phos/GTCATGAGCGATACTGAGCGATAC |
| B | IDX_B8_C | IDX_B8_Top | /5Phos/TTCGGTCCGATGGAGTCCGATGGA |
| B | | IDX_B8_Bot | /5Phos/GTCATCCATCGGACTCCATCGGAC |
| C | IDX_C5_C | IDX_C5_Top | /5Phos/TGACGTGTGGAATTGTGTGGAATT |
| C | | IDX_C5_Bot | AATTCCACACAATTCCACAC |
| C | IDX_C6_C | IDX_C6_Top | /5Phos/TGACGTGTGGCAGAGTGTGGCAGA |
| C | | IDX_C6_Bot | TCTGCCACACTCTGCCACAC |
| C | IDX_C7_C | IDX_C7_Top | /5Phos/TGACGTTACGGTGAGTTACGGTGA |
| C | | IDX_C7_Bot | TCACCGTAACTCACCGTAAC |
| C | IDX_C8_C | IDX_C8_Top | /5Phos/TGACGTTCGTACATGTTCGTACAT |
| C | | IDX_C8_Bot | ATGTACGAACATGTACGAAC |

Upon analysis of the sequencing data, a clear improvement in the consistency of indexing was observed; instead of observing a highly mixed population of reads with 1, 2, or 3 indexes, the predominant population of reads contained 3 indexes.

Example 9: Kits

A kit is made which may comprise indexed labels, such as beads, on a probe that hybridizes with a region of gene as described herein and can be used to detect a pathogen. The kit includes one or more other elements including: instructions for use; and other reagents, e.g., a label, or an agent useful for attaching a label to the probe. Instructions for use includes instructions for diagnostic applications of the probe for predicting response to treatment in a method described herein. Other instructions can include instructions for attaching a label to the probe, instructions for performing analysis with the probe, and/or instructions for obtaining a sample to be analyzed from a subject. The kit can include a label, e.g., a fluorophore, biotin, digoxygenin, and radioactive isotopes such as 32P and 3H.

Example 10: Fragment Amplification

Transposome-Based Selection and Amplification of Ends

As shown in FIG. 36, DNA samples are sheared to a desired size then the "Cap" and random combinations of index sequences are symmetrically attached to the fragment ends via ligation. Following the final round of index ligation, a new adapter containing an Illumina sequencing primer (SP1) adjacent to the Illumina P7 sequence is attached to the ends of the molecules via ligation as described above. The population of molecules is then incubated in the presence of a transposome carrying a different Illumina sequencing primer (SP2) adjacent to the Illumina P5 sequence. This reaction creates many fragments where both ends are flanked by the Illumina P5 sequence, but only two fragments per molecule that carry both the Illumina P7 and P5 sequences. PCR amplification using primers to P5/P7 is performed in order to enrich/select the fragment ends.

Enrichment of Ends Via In Vitro Transcription

As seen in FIGS. 37a and 37b, DNA samples are sheared to a desired size then the Cap and random combinations of index sequences are symmetrically attached to the fragment ends via ligation. Following the final round of index ligation, a new adapter sequence containing an Illumina sequencing primer (SP1) adjacent to an optimized T7 RNA polymerase promoter is attached to the ends of the molecules via ligation as described above. In vitro transcription (IVT) via T7 RNA polymerase is then performed in order to amplify both ends of a given molecule. Following IVT, a primer containing a random nucleotide sequence of a set length (i.e., pentamer, hexamer, etc.) flanked by a different Illumina sequencing primer (SP2) is utilized as the primer in a reverse transcription reaction. Alternatively, RNA molecules may be trimmed to a desired size range and ligated to the Illumina sequencing primer (SP2) via standard techniques. Illumina P5 and P7 sites are then added to the cDNA via PCR using primers carrying Illumina P5-SP1 and P7-SP2 sequences.

Amplification of Ends Via Anchored PCR

As shown in FIG. 38, DNA samples are sheared to a desired size then the Cap and random combinations of index sequences are symmetrically attached to the fragment ends via ligation. Following the final round of index ligation, a new adapter containing an Illumina sequencing primer (SP1) adjacent to the Illumina P7 sequence is attached to the ends of the molecules via ligation as described above. The population of molecules is then incubated in the presence of Fragmentase or a cocktail of restriction endonucleases to liberate the ends of the molecules. Fragments are then tailed at the 3' end using terminal transferase to attach a set number of specific nucleotides to the fragment ends, effectively creating a common priming sequence on the ends of all molecules. Alternatively, priming sequences may be ligated to the 3' of the molecules using standard techniques. The fragments are then amplified via PCR using SP2-P7 and SP1-P5 primers where the SP1-P5 primer contains a tail complementary to the priming site attached in the previous step.

Example 11: Creating Multi-Kilobase Fragment Reads from Indexed DNA Ends

The indexed jump method of the invention also enables multi-kilobase reads/jumps on the Illumina platform that allows for the assembly and analysis of extremely challenging genomes. As described in FIG. 39, DNA samples are sheared to a desired size then the Cap and random combinations of index sequences are symmetrically attached to the fragment ends via ligation. Following the final round of index ligation, a new adapter sequence containing an Illumina sequencing primer (SP1) adjacent to an optimized T7 RNA polymerase promoter is attached to the ends of the molecules via ligation as described above. In vitro transcription (IVT) via T7 RNA polymerase is then performed in order to amplify both ends of a given molecule. Next, cDNA is prepared via random (or directed) priming and molecules are circularized and prepared for Illumina sequencing using standard jumping library construction methods. For each parent fragment (distinguished via the unique index combination), a population of reads located varying distances from the end are generated. The reads are grouped and assembled into a contiguous fragment, effectively creating a multi-kilobase read. Additionally, multi-kilobase contigs can be paired via their unique index combination to define a jump that is equal to the distance of the starting (parent) DNA fragment. This is a powerful combination of sequence and physical coverage that can enable the assembly of extremely challenging genomes (e.g., plant genomes).

The invention will be further described by the following numbered paragraphs:

1. A method for labeling an agent with a unique label, comprising the steps of:
   a) providing a pool of agents; and
   b) sequentially end-labeling said agents with a random combination of n detectable oligonucleotide tags, each of said oligonucleotide tags optionally comprising a cohesive overhang of x base pairs in length,
      wherein each detectable oligonucleotide tag is randomly and independently selected from a number of detectable oligonucleotide tags that is less than the number of agents, and n is the number of oligonucleotides attached to an end of said agent.

2. The method according to paragraph 1, wherein said agent is a nucleic acid, a solid support or a protein.

3. The method according to paragraph 1, wherein the agent is a nucleic acid.

4. The method according to paragraph 1, wherein x is greater than about two base pairs.

5. The method according to paragraph 1, wherein x is from about two to about ten base pairs.

6. The method according to paragraph 1, wherein x is about four base pairs.

7. The method according to paragraph 1, wherein said detectable oligonucleotide tag is from about 10 to about 20 base pairs in length.

8. The method according to paragraph 5, wherein said oligonucleotide tag is selected from a tag in Table 1.

9. The method according to paragraph 1, wherein n is 2, 3, 4, 5, 6, 7, 8, 9, 10, $10^2$, $10^3$, $10^4$, $10^5$, or $10^6$ or more detectable oligonucleotide tags.

10. The method according to paragraph 1, wherein said method is performed in a multi-well plate.

11. The method according to paragraph 1, wherein said method is performed with a robotic liquid-handler.

12. A library of uniquely labeled nucleic acids, comprising sequentially end-labeled nucleic acids with a random combination of n detectable oligonucleotide tags, each of said oligonucleotide tags comprising an cohesive overhang of x base pairs in length, wherein each detectable oligonucleotide tag is randomly and independently selected from a number of detectable oligonucleotide tags that is less than the number of nucleic acids, and n is the number of oligonucleotides attached to an end of said nucleic acid.

13. The library according to paragraph 12, wherein x is greater than about two base pairs.

14. The library according to paragraph 12, wherein x is from about two to about ten base pairs.

15. The library according to paragraph 12, wherein x is about four base pairs.

16. The library according to paragraph 12, wherein n is 2, 3, 4, 5, 6, 7, 8, 9, 10, $10^2$, $10^3$, $10^4$, $10^5$, or $10^6$ or more detectable oligonucleotide tags.

17. A method comprising
   sequentially end-labeling nucleic acids in a plurality, at their 5' and 3' ends, with a random combination of n detectable oligonucleotide tags,
   wherein each end-labeled nucleic acid is
   (a) identically labeled at its 5' and 3' ends, and
   (b) uniquely labeled relative to other nucleic acids in the plurality,
   wherein each detectable oligonucleotide tags is randomly and independently selected from a number of detectable oligonucleotide tags that is less than the number of nucleic acids, and n is the number of oligonucleotides attached to an end of a nucleic acid.

18. The method of paragraph 17, wherein the number of oligonucleotides is 10-fold, 100-fold, 1000-fold, or 10000-fold less than the number of nucleic acids.

19. The method of paragraph 17, further comprising fragmenting end-labeled nucleic acids into at least a 5' fragment comprising the 5' end of the nucleic acid attached to the random combination of n oligonucleotide tags and into a 3' fragment comprising the 3' end of the nucleic acid attached to the random combination of n oligonucleotide tags.

20. The method of paragraph 19, wherein the 5' and 3' fragments are about 10-1000 bases (base pairs) in length, or about 10-500 bases in length, or about 10-200 bases in length.

21. The method of paragraph 17, further comprising sequencing the 5' and 3' fragments.

22. The method according to paragraph 17, wherein said method is performed in a multi-well plate.

23. The method according to paragraph 17, wherein said method is performed with a robotic liquid-handler.

24. A method, comprising:
(a) end-labeling two or more first subsets of nucleic acids with a detectable oligonucleotide tag to produce nucleic acids within a subset that are identically end-labeled relative to each other and uniquely end-labeled relative to nucleic acids in other subsets;
(b) combining two or more subsets of uniquely end-labeled nucleic acids to form a pool of nucleic acids, wherein the pool comprises two or more second subsets of nucleic acids that are distinct from the two or more first subsets of nucleic acids;
(c) identically end-labeling two or more second subsets of nucleic acids with a second detectable oligonucleotide tag to produce nucleic acids within a second subset that are uniquely labeled relative to nucleic acids in the same or different second subsets; and
(d) repeating steps (b) and (c) until a number of unique end-label combinations is generated that exceeds the number of starting nucleic acids.

25. The method according to paragraph 24, wherein said method is performed in a multi-well plate.

26. The method according to paragraph 24, wherein said method is performed with a robotic liquid-handler.

27. A method, comprising:
(a) providing a pool of nucleic acids;
(b) separating the pool of nucleic acids into sub-pools of nucleic acids;
(c) end-labeling nucleic acids in each sub-pool of with one of $m_1$ detectable oligonucleotide tags thereby producing sub-pools of labeled nucleic acids, wherein nucleic acids in a sub-pool are identically end-labeled to each other;
(d) combining sub-pools of labeled nucleic acids to create a pool of labeled nucleic acids;
(e) separating the pool of labeled nucleic acid molecules into second sub-pools of labeled nucleic acids;
(f) repeating steps (c) to (e) n times to produce nucleic acids end-labeled with n detectable oligonucleotide tags wherein the pool in (a) consists of a number of nucleic acids that is less than $(m_1)(m_2)(m_3) \ldots (m_a)$.

28. The method according to paragraph 27, wherein said method is performed in a multi-well plate.

29. The method according to paragraph 27, wherein said method is performed with a robotic liquid-handler.

30. A method, comprising:
combining a plurality of first nucleic acids, every first nucleic acid in the plurality comprising a common sequence, and a plurality of second nucleic acids, each second nucleic acid region comprising a sequence different from all other second nucleic acids,
wherein the number of second nucleic acids in the plurality of second nucleic acids is greater than the number of first nucleic acids in the plurality of first nucleic acids; and
attaching a first nucleic acid to a second nucleic acid, thereby producing a plurality of nucleic acid labels, wherein every nucleic acid label contains a common first nucleic acid and a different second nucleic acid region.

31. The method according to paragraph 30, wherein said method is performed in a multi-well plate.

32. The method according to paragraph 30, wherein said method is performed with a robotic liquid-handler.

33. A plurality of nucleic acid labels obtainable by the method of paragraph 30.

34. A labeled nucleic acid obtainable by the method of paragraph 1.

35. A method for labeling nucleic acid with a unique label, comprising the steps of:
(a) providing a pool of nucleic acids;
(b) sequentially end-labeling said nucleic acids with a random combination of n detectable oligonucleotide tags, each of said oligonucleotide tags optionally comprising a cohesive overhang of x base pairs in length; and
(c) amplifying the end-labeled nucleic acid formed in step (b) wherein each detectable oligonucleotide tag is randomly and independently selected from a number of detectable oligonucleotide tags that is less than the number of agents, and n is the number of oligonucleotides attached to an end of said agent.

36. The method of paragraph 35, wherein amplification step (f) comprises the steps of:
(i) attaching an adapter comprising a first sequencing primer to said nucleic acid;
(ii) incubating said nucleic acid in the presence of a transposome comprising a second sequencing primer; and
(iii) performing PCR amplification so as to amplify the ends of said nucleic acid.

37. The method of paragraph 35, wherein amplification step (f) comprises the steps of:
(i) attaching an adapter comprising a first sequencing primer to said nucleic acid;
(ii) performing in vitro transcription using a RNA polymerase;
(iii) performing a reverse transcription using a primer comprising a random nucleotide sequence of a given length flanked by a second sequencing primer or performing a reverse transcription using a primer comprising a nucleotide sequence attached to the 3' end of the nucleic acid; and
(iv) performing PCR amplification so as to amplify the ends of said nucleic acid.

38. The method of paragraph 35, wherein amplification step (f) comprises the steps of:
(i) attaching an adapter comprising a first sequencing primer to said nucleic acid;
(ii) incubating said nucleic acid in fragmentase or a combination of one or more restriction endonucleases so as to liberate the ends of said nucleic acid thereby forming fragments;
(iii) attaching a given number of specific nucleotides to the ends of said fragments; and
(iv) performing PCR amplification on the fragments formed in step (iii) using a second sequencing primer.

39. The method according to paragraph 35, wherein said method is performed in a multi-well plate.

40. The method according to paragraph 35, wherein said method is performed with a robotic liquid-handler.

41. A method of determining the drug sensitivity of a pathogen, the method comprising:
providing a sample comprising a pathogen;
contacting the sample with one or more, or two or more, test compounds, to provide a test sample;
treating the test sample under conditions that release messenger ribonucleic acid (mRNA) from the pathogen into the test sample;
exposing the test sample to a plurality of nucleic acid probes, comprising a plurality of subsets of probes, wherein each subset comprises one or more probes that bind specifically to a target mRNA that is differentially expressed in organisms that are sensitive to a test compound as compared to organisms that are resistant, wherein the exposure occurs for a time and under conditions in which binding between the probe and target mRNA can occur;

determining a level of binding between the probe and target mRNA, thereby determining a level of the target mRNA; and comparing the level of the target mRNA in the presence of the test compound to a reference level, wherein a difference in the level of target mRNA relative to the reference level of target mRNA indicates whether the pathogen is sensitive or resistant to the test compound, wherein the probe is uniquely labeled with a detectable oligonucleotide tag, wherein the detectable oligonucleotides tag is comprised of oligonucleotides each having a unique nucleotide sequence, oligonucleotides each comprising a non-nucleic acid detectable moiety, or oligonucleotides each comprising a unique nucleotide sequence and a non-nucleic acid detectable moiety.

42. A method of selecting a treatment for a subject, the method comprising:

optionally identifying a pathogen in a sample obtained from the subject, in a method comprising:

providing a test sample from a subject suspected of being infected with a pathogen;

treating the test sample under conditions that release messenger ribonucleic acid (mRNA);

exposing the test sample to a plurality of nucleic acid probes, comprising a plurality of subsets of probes, wherein each subset comprises one or more probes that bind specifically to a target mRNA that uniquely identifies a pathogen, wherein the exposure occurs for a time and under conditions in which binding between the probe and the target mRNA can occur; and determining a level of binding between the probe and target mRNA, thereby determining a level of target mRNA;

wherein an increase in the target mRNA of the test sample, relative to a reference sample, indicates the identity of the pathogen in the test sample;

determining the drug sensitivity of the pathogen using the method of paragraph 41; and selecting a drug to which the pathogen is sensitive for use in treating the subject.

43. A method of monitoring an infection with a pathogen in a subject, the method comprising:

providing a first sample obtained from a subject comprising the pathogen at a first time;

determining the drug sensitivity of the pathogen in the first sample using the method of paragraph 41;

optionally selecting a treatment to which the pathogen is sensitive and administering the selected treatment to the subject;

providing a second sample obtained from a subject comprising the pathogen at a second time;

determining the drug sensitivity of the pathogen in the second sample using the method of paragraph 41; and comparing the drug sensitivity of the pathogen in the first sample and the second sample, thereby monitoring the infection in the subject.

44. A method of monitoring an infection with a pathogen in a population of subjects, the method comprising:

providing a first plurality of samples obtained from subjects in the population at a first time;

determining the drug sensitivity of pathogens in the first plurality of samples using the method of paragraph 41, and optionally identifying an infectious disease pathogen in the first plurality of samples in a method comprising:

providing a test sample obtained from a subject suspected of being infected with a pathogen;

treating the test sample under conditions that release messenger ribonucleic acid (mRNA);

exposing the test sample to a plurality of nucleic acid probes, comprising a plurality of subsets of probes, wherein each subset comprises one or more probes that bind specifically to a target mRNA that uniquely identifies a pathogen, wherein the exposure occurs for a time and under conditions in which binding between the probe and the target mRNA can occur; and determining a level of binding between the probe and target mRNA, thereby determining a level of target mRNA;

wherein an increase in the target mRNA of the test sample, relative to a reference sample, indicates the identity of the pathogen in the test sample;

providing a second plurality of samples obtained from subjects in the population at a second time, optionally after administration of a treatment to the subjects;

determining the drug sensitivity of pathogens in the second plurality of samples using the method of paragraph 41, and optionally identifying an infectious disease pathogen in the first plurality of samples in a method comprising:

providing a test sample obtained from a subject suspected of being infected with a pathogen;

treating the test sample under conditions that release messenger ribonucleic acid (mRNA);

exposing the test sample to a plurality of nucleic acid probes, comprising a plurality of subsets of probes, wherein each subset comprises one or more probes that bind specifically to a target mRNA that uniquely identifies a pathogen, wherein the exposure occurs for a time and under conditions in which binding between the probe and the target mRNA can occur; and determining a level of binding between the probe and target mRNA, thereby determining a level of target mRNA;

wherein an increase in the target mRNA of the test sample, relative to a reference sample, indicates the identity of the pathogen in the test sample;

comparing the drug sensitivity of the pathogens, and optionally the identity of the pathogens, in the first plurality of samples and the second plurality of samples, thereby monitoring the infection in the population of subject.

45. A method of determining a cell's epigenetic profile, comprising:

isolating the cell from a population of cells;

lysing the cell to release chromatin;

fragmenting the chromatin into DNA-histone complexes;

ligating the DNA of the DNA-histone complex to a labeled oligo wherein the labeled oligo is generated by the following steps:

(a) end-labeling two or more first subsets of nucleic acids with a detectable oligonucleotide tag to produce nucleic acids within a subset that are identically end-labeled relative to each other and uniquely end-labeled relative to nucleic acids in other subsets;

(b) combining two or more subsets of uniquely end-labeled nucleic acids to form a pool of nucleic acids, wherein the pool comprises two or more second subsets of nucleic acids that are distinct from the two or more first subsets of nucleic acids;

(c) identically end-labeling two or more second subsets of nucleic acids with a second detectable oligonucleotide tag to produce nucleic acids within a second subset that are uniquely labeled relative to nucleic acids in the same or different second subsets; and (d) repeating steps (b) and (c) until a number of unique end-label combinations is generated that exceeds the number of starting nucleic acids, amplifying the DNA ligated to the labeled oligo in an in vitro transcription reaction; and analyzing the amplified DNA, thereby determining the cell's epigenetic profile.

46. The method of paragraph 45, wherein the labeled oligo comprises a T7 promoter.

47. The method of paragraph 45, wherein the labeled oligo is generated on a solid support.

48. The method of paragraph 47, wherein the labeled oligo is cleavable from the solid support.

49. The method of paragraph 47, wherein the solid support is a bead.

50. The method of paragraph 45, wherein said method is performed in a multi-well plate.

51. The method of paragraph 45, wherein said method is performed with a robotic liquid-handler.

52. A method of identifying unbiased chromatin interactions across a genome in a cell, comprising:

crosslinking the genome;

digesting DNA of the genome with a restriction enzyme to form complexes;

labeling the complexes with a labeled oligo wherein the labeled oligo is generated by the following steps:

(a) end-labeling two or more first subsets of nucleic acids with a detectable oligonucleotide tag to produce nucleic acids within a subset that are identically end-labeled relative to each other and uniquely end-labeled relative to nucleic acids in other subsets;

(b) combining two or more subsets of uniquely end-labeled nucleic acids to form a pool of nucleic acids, wherein the pool comprises two or more second subsets of nucleic acids that are distinct from the two or more first subsets of nucleic acids;

(c) identically end-labeling two or more second subsets of nucleic acids with a second detectable oligonucleotide tag to produce nucleic acids within a second subset that are uniquely labeled relative to nucleic acids in the same or different second subsets; and (d) repeating steps (b) and (c) until a number of unique end-label combinations is generated that exceeds the number of starting nucleic acids; and analyzing the labeled complexes, thereby identifying unbiased chromatin interactions across the genome in the cell.

53. The method of paragraph 52, wherein the labeled oligo is generated on a solid support.

54. The method of paragraph 53, wherein the labeled oligo is cleavable from the solid support.

55. The method of paragraph 53, wherein the solid support is a bead.

56. The method of paragraph 52, wherein said method is performed in a multi-well plate.

57. The method of paragraph 52, wherein said method is performed with a robotic liquid-handler.

It is to be understood that the invention is not limited to the particular embodiments of the invention described above, as variations of the particular embodiments may be made and still fall within the scope of the appended claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11643650B2). An electronic copy of the "Sequence Listing" will also be available from the USPTO upon request and payment of the fee set forth in 37 CFR 1.19(b)(3).

What is claimed is:

1. A method for labeling a cell comprising the steps of:
a) providing a pool of cells;
b) separating the pool of cells into sub-pools of cells;
c) labeling each of the cells with a first detectable oligonucleotide tag, such that the cells in each sub-pool are identically end-labeled to each other but differently labeled from the cells in other sub-pools;
d) combining the sub-pools of labeled cells from step (c) to create a new pool of cells; and
e) separating the new pool of cells into new sub-pools of cells;
f) repeating steps (c)-(e) one or more times to sequentially end label the first detectable oligonucleotide tag with a random combination of additional oligonucleotide tags.

2. The method of claim 1, wherein each of the oligonucleotide tags comprises a cohesive overhang.

3. The method of claim 2, wherein the cohesive overhang is greater than two bases in length.

4. The method according to claim 3, wherein the cohesive overhang is from two to ten bases in length.

5. The method of claim 4, wherein the cohesive overhang is 4 bases in length.

6. The method of claim 1, wherein the detectable oligonucleotide tags are from 10 to 20 base pairs in length.

7. The method of claim 1, wherein the first oligonucleotide tag is indirectly attached to the cell in step (c).

8. The method of claim 7, wherein the first oligonucleotide is indirectly attached to the cell in step (c) through an adapter.

9. The method of claim 8, wherein the adapter comprises a capture entity.

10. The method of claim 9, wherein the capture entity is an antibody.

11. The method of claim 1, wherein the sub-pools comprise a single cell.

12. The method of claim 1, wherein said method is performed in a multi-well plate.

13. The method of claim 12, wherein the method is performed with a robotic liquid-handler.

14. The method of claim 1, wherein the method is performed in a droplet emulsion.

15. The method of claim 14, wherein the cells are distributed in the droplet emulsion such that each droplet contains a single cell.

16. The method of claim 1, wherein the cells comprise tumor cells.

17. The method of claim 1, wherein the first detectable oligonucleotide tag comprises a priming sequence.

* * * * *